US011414700B2

(12) United States Patent
Perera et al.

(10) Patent No.: US 11,414,700 B2
(45) Date of Patent: Aug. 16, 2022

(54) TCR/BCR PROFILING USING ENRICHMENT WITH POOLS OF CAPTURE PROBES

(71) Applicant: Tempus Labs, Inc., Chicago, IL (US)

(72) Inventors: Jason Perera, Chicago, IL (US); Taylor Harding, Chicago, IL (US); Brittany Mineo, Oak Park, IL (US); Aly A. Khan, Chicago, IL (US); Richard Blidner, Glenview, IL (US); Jenna L. Malinauskas, Chicago, IL (US)

(73) Assignee: Tempus Labs, Inc., Chicago, IL (US)

( * ) Notice: Subject to any disclaimer, the term of this patent is extended or adjusted under 35 U.S.C. 154(b) by 0 days.

(21) Appl. No.: 17/302,030

(22) Filed: Apr. 21, 2021

(65) Prior Publication Data

US 2021/0355533 A1 Nov. 18, 2021

Related U.S. Application Data

(60) Provisional application No. 63/013,130, filed on Apr. 21, 2020, provisional application No. 63/084,459, filed on Sep. 28, 2020, provisional application No. 63/201,020, filed on Apr. 8, 2021.

(51) Int. Cl.
| | |
|---|---|
| *C12P 19/34* | (2006.01) |
| *C12Q 1/6869* | (2018.01) |
| *C12Q 1/6806* | (2018.01) |
| *C12Q 1/6876* | (2018.01) |
| *C07K 14/725* | (2006.01) |
| *C12Q 1/6881* | (2018.01) |

(52) U.S. Cl.
CPC ........ *C12Q 1/6869* (2013.01); *C07K 14/7051* (2013.01); *C12Q 1/6806* (2013.01); *C12Q 1/6876* (2013.01); *C12Q 1/6881* (2013.01); *C12N 2501/515* (2013.01); *C12N 2502/1114* (2013.01); *C12Q 2600/118* (2013.01); *G01N 2800/26* (2013.01)

(58) Field of Classification Search
CPC .................................................. C12Q 1/6869
See application file for complete search history.

(56) References Cited

U.S. PATENT DOCUMENTS

| | | | |
|---|---|---|---|
| 5,635,354 A | 6/1997 | Kourilsky | |
| 6,080,840 A | 6/2000 | Slanetz | |
| 6,623,957 B2 | 9/2003 | Ward | |
| 6,927,044 B2 | 8/2005 | Stahl | |
| 7,329,731 B2 | 2/2008 | Jakobsen | |
| 10,801,064 B2 | 10/2020 | West | |
| 2012/0220466 A1* | 8/2012 | Fire | ........... C12Q 1/68 506/2 |
| 2019/0367978 A1* | 12/2019 | West | ..... C12Q 1/6874 |
| 2019/0376981 A1 | 12/2019 | Fandl | |
| 2019/0390273 A1* | 12/2019 | Pugh | ........ C40B 40/06 |
| 2020/0075169 A1 | 3/2020 | Lau | |
| 2020/0095625 A1* | 3/2020 | Gierahn | ................ C12P 19/34 |
| 2020/0098448 A1 | 3/2020 | Shah | |
| 2020/0115749 A1* | 4/2020 | Pugh | ...................... C40B 30/04 |
| 2020/0118644 A1 | 4/2020 | Khan | |
| 2020/0210852 A1 | 7/2020 | Igartua | |
| 2020/0211716 A1 | 7/2020 | Lefkofsky | |
| 2020/0255909 A1 | 8/2020 | Venkat | |
| 2020/0258223 A1 | 8/2020 | Yip | |
| 2020/0258597 A1 | 8/2020 | Perera | |
| 2020/0258601 A1 | 8/2020 | Lau | |
| 2020/0273576 A1 | 8/2020 | Lozac'hmeur | |
| 2020/0365232 A1 | 11/2020 | Jaros | |
| 2020/0365268 A1 | 11/2020 | Michuda | |
| 2020/0381087 A1 | 12/2020 | Ozeran | |
| 2020/0395097 A1 | 12/2020 | Chang | |
| 2021/0057042 A1 | 2/2021 | Beaubier | |
| 2021/0090694 A1 | 3/2021 | Colley | |
| 2021/0098078 A1 | 4/2021 | Lozac'hmeur | |
| 2021/0118526 A1 | 4/2021 | Barber | |

OTHER PUBLICATIONS

U.S. Appl. No. 62/924,515, titled "Artificial Intelligence Assisted Precision Medicine Enhancements to Standardized Laboratory Diagnostic Testing", filed Oct. 22, 2019.
U.S. Appl. No. 62/924,621, titled "Systems and Methods for Predicting Therapeutic Sensitivity", filed Oct. 22, 2019.
U.S. Appl. No. 62/943,712, titled "Systems and Methods for Automating RNA Expression Calls in a Cancer Prediction Pipeline", filed Dec. 4, 2019.
U.S. Appl. No. 62/944,292, titled "Large Scale Phenotypic Organoid Analysis", filed Dec. 5, 2019.
Van Dongen, J. J. M., et al. "Design and standardization of PCR primers and protocols for detection of clonal immunoglobulin and T-cell receptor gene recombinations in suspect lymphoproliferations: report of the BIOMED-2 Concerted Action BMH4-CT98-3936." Leukemia 17.12 (2003): 2257-2317.
Verma, V., et al. "PD-1 blockade in subprimed CD8 cells induces dysfunctional PD-1+ CD38 hi cells and anti-PD-1 resistance." Nature immunology 20.9 (2019): 1231-1243.
Weiskopf et al, Phenotype and kinetics of SARS-CoV-2-specific T cells in COVID-19 patients with acute respiratory distress syndrome. Sci. Immunol. 5, eabd2071 (2020).
Wlodarski et al. (2005) Pathologic clonal cytotoxic T-cell responses: nonrandom nature of the T-cell receptor restriction in large granular lymphocyte leukemia, Blood 106/8:2769-2780.
Wlodarski et al. (2006) Molecular strategies for detection and quantitation of clonal cytotoxic T-cell responses in aplastic anemia and myelodysplastic syndrome, Blood 108/8:2632-2641.

(Continued)

*Primary Examiner* — Kenneth R Horlick
(74) *Attorney, Agent, or Firm* — Quarles & Brady LLP

(57) ABSTRACT

Disclosed herein are systems, methods, and compositions useful for profiling T cell receptor (TCR) and B cell receptor (BCR) repertoire using next-generation sequencing (NGS) methods. In certain embodiments, the methods include enriching a sample for TCR/BCR RNA sequences, and determining the TCR/BCR profile of a subject using five different oligonucleotide pools. Also disclosed herein are systems and methods for diagnosing, treating, or predicting infection, disease, medical conditions, therapeutic outcome, or therapeutic efficacy based on the TCR/BCR profile data from a subject in need thereof.

20 Claims, 18 Drawing Sheets

Specification includes a Sequence Listing.

(56) References Cited

OTHER PUBLICATIONS

Zhang, X., et al. "Viral and host factors related to the clinical outcome of COVID-19." Nature 583.7816 (2020): 437-440.
U.S. Appl. No. 17/112,877, titled "Systems and Methods for Automating RNA Expression Calls in a Cancer Prediction Pipeline", filed Dec. 4, 2020.
U.S. Appl. No. 17/706,704, titled "Systems and Methods for Next Generation Sequencing Uniform Probe Design", filed Oct. 21, 2020.
U.S. Appl. No. 17/114,386, titled "Large Scale Phenotypic Organoid Analysis", filed Dec. 7, 2020.
Ashford, M. GenomeWeb—Thermo Fisher Liquid Biopsy, Immuno-Oncology Tools Featured in User Reports at AMP. Nov. 5, 2018. Available online at https://www.focr.org/news/genomeweb-thermo-fisher-liquid-biopsy-immuno-oncology-tools-featured-user-reports-amp.
Bolotin, D. A., et al. "Antigen receptor repertoire profiling from RNA-seq data." Nature biotechnology 35.10 (2017): 908-911.
Boria, I., et al. "Primer sets for cloning the human repertoire of T cell Receptor Variable regions." BMC immunology 9.1 (2008): 1-9.
Braun et al, Presence of SARS-CoV-2 reactive T cells in COVID-19 patients and healthy donors. medRxiv 2020.2004.2017.20061440 [Preprint]. Apr. 22, 2020;.doi:10.1101/2020.04.17.20061440.
Bray, NL et al. Near-optimal probabilistic RNA-seq quantification, Nature Biotechnology 34, 525-527 (2016).
Canzar, S., et al. "BASIC: BCR assembly from single cells." Bioinformatics 33.3 (2017): 425.
Dijkstra, J. M., et al. "Expected immune recognition of COVID-19 virus by memory from earlier infections with common coronaviruses in a large part of the world population." F1000Research 9 (2020).
Dobin et al, STAR: ultrafast universal RNA-seq aligner, Bioinformatics Jan. 2013; 29(1): 15-21.
Elinav, E., et al. "The cancer microbiome." Nature Reviews Cancer 19.7 (2019): 371-376.
Emerson, R., et al. Immunosequencing identifies signatures of cytomegalovirus exposure history and HLA-mediated effects on the T cell repertoire. Nat Genet 49, 659-665 (2017). https://doi.org/10.1038/ng.3822.
Fernandes et al. (2005) Simplified Fluorescent Multiplex PCR Method for Evaluation of the T-Cell Receptor Vβ-Chain Repertoire, Clin. Diag. Lab. Immunol. 12/4:477-483.
Gallais, F., et al. "Intrafamilial exposure to SARS-CoV-2 induces cellular immune response without seroconversion." MedRxiv (2020).
Genevée et al. (1992) An experimentally validated panel of subfamily-specific oligonucleotide primers (Va1-w29/Vβ1-w24) for the study of human T cell receptor variable V gene segment usage by polymerase chain reaction, Eur. J. Immunol. 22:1261-1269.
Glanville, J., et al. "Identifying specificity groups in the T cell receptor repertoire." Nature 547.7661 (2017): 94-98.
Gorski et al. (1994) Circulating T Cell Repertoire Complexity in Normal Individuals and Bone Marrow Recipients Analyzed by CDR3 Size Spectralyping, J. Immunol. 152:5109-5119.
Grifoni, A., et al. "Targets of T cell responses to SARS-CoV-2 coronavirus in humans with COVID-19 disease and unexposed individuals." Cell 181.7 (2020): 1489-1501.
Helmink, B. A., et al. "The microbiome, cancer, and cancer therapy." Nature medicine 25.3 (2019): 377-388.
Hinz, T. et al. (2000) Identification of the T-cell receptor alpha variable (TRAV) gene(s) in T-cell malignancies, J. Immunol. Methods 246:145-148.
Hodges et al. (2002) Diagnostic role of tests for T cell receptor (TCR) genes, J. Clin. Pathol. 56:1-11.
Hu, X., et al. "Landscape of B cell immunity and related immune evasion in human cancers." Nature genetics 51.3 (2019): 560-567.
Ijspeert, H., et al. "Antigen receptor galaxy: a user-friendly, web-based tool for analysis and visualization of T and B cell receptor repertoire data." The Journal of Immunology 198.10 (2017): 4156-4165.
Islam, S., et al. "Quantitative single-cell RNA-seq with unique molecular identifiers." Nature methods 11.2 (2014): 163.
Johnston, S. et al. (1995) A novel method for sequencing members of multi-gene families, Nucleic Acids Res. 23/15:3074-3075.
Kalendar, R. et al. "FastPCR software for PCR primer and probe design and repeat search." Genes, Genomes and Genomics 3.1 (2009): 1-14.
Kivioja, T., et al. "Counting absolute numbers of molecules using unique molecular identifiers." Nature methods 9.1 (2012): 72-74.
Laugel, B et al. (2005) Design of Soluble Recombinant T Cell Receptors for Antigen Targeting and T Cell Inhibition, J. Biol. Chem. 280:1882-1892.
Le Bert, N., et al. "SARS-CoV-2-specific T cell immunity in cases of COVID-19 and SARS, and uninfected controls." Nature 584.7821 (2020): 457-462.
Li, B., et al. "Landscape of tumor-infiltrating T cell repertoire of human cancers." Nature genetics 48.7 (2016): 725-732.
Li, Y. et al. (2005) Directed evolution of human T-cell receptors with picomolar affinities by phage display, Nature Biotech. 23/3:349-354.
Mateus, J., et al. "Selective and cross-reactive SARS-CoV-2 T cell epitopes in unexposed humans." Science 370.6512 (2020): 89-94.
Mathew, D., et al. "Deep immune profiling of COVID-19 patients reveals distinct immunotypes with therapeutic implications." Science 369.6508 (2020).
Meckiff et al, Single-cell transcriptomic analysis of SARS-CoV-2 reactive CD4 + T cells. bioRxiv 2020.06.12.148916 (2020).
Migalska, M. et al. "Profiling of the TCRβ repertoire in non-model species using high-throughput sequencing." Scientific reports 8.1 (2018): 1-14.
Moysey, R. et al. (2004) Amplification and one-step expression cloning of human T cell receptor genes, Anal. Biochem. 326:284-286.
Ni, Q., et al. "VisTCR: An Interactive Software for T Cell Repertoire Sequencing Data Analysis." Frontiers in genetics 11 (2020): 771.
Nolan, S., et al. "A large-scale database of T-cell receptor beta (TCRβ) sequences and binding associations from natural and synthetic exposure to SARS-CoV-2." (2020).
Pannetier et al. (1995) T-cell repertoire diversity and clonal expansions in normal and clinical samples, Immunology Today 16/4:176-181.
Peng et al, Broad and strong memory CD4 +and CD8 + T cells induced by SARS-CoV-2 in UK convalescent COVID-19 patients. bioRxiv2020.06.05.134551 (2020).
Pennock, N. D., et al. "RNA-seq from archival FFPE breast cancer samples: molecular pathway fidelity and novel discovery." BMC Medical Genomics 12 (2019) 195.
Personalis. ImmunoID NeXT webpage. Version accessed on Dec. 30. 2019. Available online at https://web.archive.org/web/20191230002014/https://www.personalis.com/immunoid-next-platform/.
Reiman, D., et al. "Integrating RNA expression and visual features for immune infiltrate prediction." PSB. 2019.
Richman, S. et al. (2007) Display, engineering, and applications of antigen-specific T cell receptors, Biomolecular Engineering 24:361-373.
Robbiani, DF et al. "Convergent Antibody Responses to SARS-CoV-2 Infection in Convalescent Individuals." bioRxiv (2020). https://www.biorxiv.org/content/10.1101/2020.05.13.092619v2.
Schultheiss, C., et al. "Next-generation sequencing of T and B cell receptor repertoires from COVID-19 patients showed signatures associated with severity of disease." Immunity 53.2 (2020): 442-455.
Sekine, T., et al. "Robust T cell immunity in convalescent individuals with asymptomatic or mild COVID-19." Cell 183.1 (2020): 158-168.
Stubbington, MJT, et al. "Simultaneously inferring T cell fate and clonality from single cell transcriptomes." bioRxiv (2015): 025676.
Tran, E., et al. "T-cell transfer therapy targeting mutant KRAS in cancer." New England Journal of Medicine 375.23 (2016): 2255-2262.
U.S. Appl. No. 16/693,117, titled "Tumor Organoid Culture Compositions, Systems, and Methods", filed Nov. 22, 2019.

(56) References Cited

OTHER PUBLICATIONS

U.S. Appl. No. 62/804,509, titled "Comprehensive Evaluation of RNA Immune System for the identification of Patients with an Immunologically Active Tumor Microenvironment", filed Feb. 12, 2019.
U.S. Appl. No. 62/924,073, titled "Systems and Methods for Next Generation Sequencing Probe Design", filed Oct. 21, 2019.
U.S. Appl. No. 62/978,067, titled "Systems and Methods for Detecting Viral DNA from Sequencing", filed Feb. 18, 2020.
10X Genomics. Webpage. Multiomic Profiling of Immune Diversity, Cell by Cell. Version dated Jun. 28, 2020. Accessed online at http://web.archive.org/web/20200628153640/https://www.10xgenomics.com/products/single-cell-immune-profiling/.
10X Genomics. Webpage. Single Cell V(D)J Demonstrated Protocol Compatibility Table. Version dated Aug. 4, 2020. Accessed online at http://web.archive.org/web/20200804084223/https:///support.10xgenomics.com/single-cell-vdj/sample-prep/doc/demonstrated-protocol-single-cell-vdj-demonstrated-protocol-compatibility-table.
Adaptive Technologies. Press Release. Adaptive Biotechnologies Launches immunoSEQ T-MAP COVID, First Molecular T Cell Monitoring Tool for SARS-CoV-2. Aug. 4, 2020. Accessed online at https://www.globenewswire.com/news-release/2020/08/04/2072593/0/en/Adaptive-Biotechnologies-Launches-immunoSEQ-T-MAP-COVID-First-Molecular-T-Cell-Monitoring-Tool-for-SARS-CoV-2.html. 6 pages.
Bolotin, D. A., et al. "MiTCR: software for T-cell receptor sequencing data analysis." Nature methods 10.9 (2013): 813.
Bolotin, D. A., et al. "MiXCR: software for comprehensive adaptive immunity profiling." Nature methods 12.5 (2015): 380-381.
Bolotin, D. A., et al. "Reply to"Evaluation of immune repertoire inference methods from RNA-seq data"." Nature biotechnology 36.11 (2018): 1035-1036.
Gkazi, A. S., et al. "Clinical T cell receptor repertoire deep sequencing and analysis: an application to monitor immune reconstitution following cord blood transplantation." Frontiers in immunology 9 (2018): 2547.
Helmink, B. A., et al. "B cells and tertiary lymphoid structures promote immunotherapy response." Nature 577.7791 (2020): 549-555.
Hu, X., et al. "Evaluation of immune repertoire inference methods from RNA-seq data." Nature biotechnology 36.11 (2018): 1034-1034.
Liu, C. C., et al. "Computational approaches for characterizing the tumor immune microenvironment." Immunology 158.2 (2019): 70-84.
Mulder, D. T., et al. "CapTCR-seq: hybrid capture for T-cell receptor repertoire profiling." Blood advances 2.23 (2018): 3506-3514.
Olson, B. J., et al. "sumrep: a summary statistic framework for immune receptor repertoire comparison and model validation." Frontiers in immunology 10 (2019): 2533.
Ostmeyer, J., et al. "Biophysicochemical motifs in T-cell receptor sequences distinguish repertoires from tumor-infiltrating lymphocyte and adjacent healthy tissue." Cancer research 79.7 (2019): 1671-1680.
Pogorelyy, M. V., et al. "A framework for annotation of antigen specificities in high-throughput T-cell repertoire sequencing studies." Frontiers in immunology 10 (2019): 2159.
Repseq. Webpage. Immune Repertoire Analysis. Version dated May 25, 2020. Accessed online at http://web.archive.org/web/20200525194546/https://irepertoirecom/repseq/.
Reuben, A., et al. "Comprehensive T cell repertoire characterization of non-small cell lung cancer." Nature communications 11.1 (2020): 1-13.
Riaz, N., et al. "Tumor and microenvironment evolution during immunotherapy with nivolumab." Cell 171.4 (2017): 934-949.
Rosati, E., et al. "Overview of methodologies for T-cell receptor repertoire analysis." BMC biotechnology 17.1 (2017): 1-16.
Sepulveda, N., et al. "Estimation of T-cell repertoire diversity and clonal size distribution by Poisson abundance models." Journal of immunological methods 353.1-2 (2010): 124-137.
Sevy, A. M. "ErrorX: automated error correction for immune repertoire sequencing datasets." bioRxiv (2020).
Sharonov, G. V., et al. "B cells, plasma cells and antibody repertoires in the tumour microenvironment." Nature Reviews Immunology 20 5 (2020): 294-307.
Tickotsky-Moskovitz, N., et al. "CDR3 and V genes show distinct reconstitution patterns in T cell repertoire post-allogeneic bone marrow transplantation." Immunogenetics 73.2 (2021): 163-173. First available Sep. 1, 2020.
Venturi, V., et al. "Methods for comparing the diversity of samples of the T cell receptor repertoire." Journal of immunological methods 321.1-2 (2007): 182-195.
Zhang, H., et al. "Investigation of antigen-specific T-cell receptor clusters in human cancers." Clinical Cancer Research 26.6 (2020): 1359-1371.
Zhang, J., et al. "Immune receptor repertoires in pediatric and adult acute myeloid leukemia." Genome medicine 11.1 (2019): 1-11.
Zhang, Y., et al. "Tools for fundamental analysis functions of TCR repertoires: a systematic comparison." Briefings in bioinformatics 21.5 (2020): 1706-1716.

* cited by examiner

FIG. 3

| | |
|---|---|
| TCR non-constant region probes | 650 probes |
| TCR constant region probes | 18 probes |
| BCR non-constant region probes | 894 probes |
| BCR constant region probes | 45 probes |

FIG. 15

| TABLE 1: COMPLETE ALLELE SET | |
|---|---:|
| GROUP | COVERAGE.LENGHT |
| IGHC | 61,128 |
| IGHD | 1,071 |
| IGHJ | 922 |
| IGHV | 103,881 |
| IGKC | 1,605 |
| IGKJ | 346 |
| IGKV | 31,416 |
| IGLC | 4,196 |
| IGLJ | 380 |
| IGLV | 27,109 |
| TRAC | 423 |
| TRAJ | 4,147 |
| TRAV | 28,796 |
| TRBC | 1,605 |
| TRBD | 44 |
| TRBJ | 794 |
| TRBV | 40,923 |
| TRDC | 466 |
| TRDD | 30 |
| TRDJ | 212 |
| TRDV | 5,968 |
| TRGC | 3,704 |
| TRGJ | 332 |
| TRGV | 5,434 |
| TOTAL | 324,932 |

| TABLE 2: COMPLETE ALLELE SET | |
|---|---:|
| GROUP | COVERAGE.LENGHT |
| IGHC | 9,954 |
| IGHD | 913 |
| IGHJ | 536 |
| IGHV | 31,738 |
| IGKC | 321 |
| IGKJ | 230 |
| IGKV | 20,958 |
| IGLC | 2,575 |
| IGLJ | 304 |
| IGLV | 13,668 |
| TRAC | 423 |
| TRAJ | 3,779 |
| TRAV | 13,387 |
| TRBC | 1,068 |
| TRBD | 44 |
| TRBJ | 694 |
| TRBV | 19,003 |
| TRDC | 466 |
| TRDD | 30 |
| TRDJ | 212 |
| TRDV | 865 |
| TRGC | 868 |
| TRGJ | 332 |
| TRGV | 3,308 |
| TOTAL | 125,676 |

FIG. 17

TCR/BCR PROFILING USING ENRICHMENT WITH POOLS OF CAPTURE PROBES

CROSS-REFERENCE TO RELATED PATENT APPLICATIONS

This application claims the benefit of priority under 35 U.S.C. § 119(e) to U.S. Provisional Application No. 63/013,130 filed Apr. 21, 2020, U.S. Provisional Application No. 63/084,459, filed on Sep. 28, 2020 and U.S. Provisional Application No. 63/201,020 filed Apr. 8, 2021. The content of each provisional application is incorporated herein by reference in its entirety.

SEQUENCE LISTING

The instant application contains a Sequence Listing which has been submitted electronically in ASCII format and is hereby incorporated by reference in its entirety. Said ASCII copy, created on Jun. 14, 2021, is named 166619_00127_SL.txt and is 79,307 bytes in size.

FIELD

This present disclosure relates to systems, methods, and compositions useful for profiling T cell receptor (TCR) and B cell receptor (BCR) repertoire using next-generation sequencing (NGS) methods. The present disclosure also relates to systems and methods for diagnosing, treating, or predicting infection, disease, conditions, or therapeutic outcome, or efficacy based on the TCR/BCR profile data from a subject in need thereof. In some embodiments, the methods comprise detecting SARS-CoV-2 exposure.

BACKGROUND

The vertebrate immune system is comprised of two main arms: the innate arm and the adaptive arm. The innate arm of the immune system has evolved to quickly and effectively respond to foreign antigens or danger signals. However, in many cases an innate immune response is not sufficient to provide sterilizing immunity. In addition, the adaptive arm of the immune system has no capacity for "memory," meaning that a more effective response to a pathogen cannot be made upon subsequent challenges by the same pathogen or a similar pathogen. Therefore, the innate arm of the immune system (and/or non-immune cells, for example, infected cells) presents antigens to the adaptive immune system, which can then begin the process of selection of antigen-specific immune cells, T lymphocytes (T cells) and B lymphocytes (B cells). This process is facilitated by the presence of an incredible diversity of antigen-specific cells to be available to respond to any antigenic challenge.

SUMMARY

In some embodiments, a method of determining the TCR/BCR profile of a patient who has COVID-19 or another disease, is provided. In some embodiments, the method comprise a) isolating RNA from a sample from the patient; b) enriching the isolated RNA for TCR/BCR genes using a set of TCR/BCR hybrid-capture probes and enriching for a targeted whole transcriptome panel using a set of whole transcriptome hybrid-capture probes; c) determining the sequence of the RNA of (b) to generate sequencing data; and d) analyzing the sequencing data to determine the TCR/BCR profile of the patient, wherein the set of TCR/BCR hybrid-capture probes comprises a first pool comprising TCR constant region probes, a second pool comprising TCR non-constant region probes, a third pool comprising BCR constant region probes, a fourth pool comprising BCR non-constant region probes, and a fifth pool comprising transcriptome hybrid-capture probes.

In some embodiments, the ratio of the first pool, second pool, third pool, and fourth pool within the set is 1:2.5:100:100. In some embodiments, the ratio of the first pool, second pool, third pool, fourth pool, and fifth pool within the set is 1:2.5:100:100:10. In some embodiments, 2% or less of the reads in the sequencing data map to TCR/BCR genes. In some embodiments, the sample is a blood sample. In some embodiments, the patient's TCR/BCR profile is compared to a SARS-CoV-2 TCR/BCR positive control profile, and in some embodiments, a determination of whether the patient has been exposed to SARS CoV-2 is made. In some embodiments, the subject is treated if the determining indicates exposure to SARS-CoV-2.

In some embodiments, a method of determining SARS CoV-2 exposure in a patient is provided. In some embodiments, the method comprises a) isolating RNA from a sample from the patient; b) enriching the isolated RNA for TCR/BCR genes using a set of TCR/BCR hybrid-capture probes and enriching for a targeted whole transcriptome panel using a set of transcriptome hybrid-capture probes; c) determining the sequence of the RNA of (b) to generate sequencing data; and d) analyzing the sequencing data to determine the TCR/BCR profile of the patient; and e) comparing the TCR/BCR profile of the patient to a positive control to determine SARS-CoV-2 exposure; wherein the set of TCR/BCR hybrid-capture probes comprises a first pool comprising TCR constant region probes, a second pool comprising TCR non-constant region probes, a third pool comprising BCR constant region probes, and a fourth pool comprising BCR non-constant region probes, and fifth pool comprising transcriptome hybrid-capture probes.

In some embodiments, the ratio of the first pool, second pool, third pool, and fourth pool within the set is 1:2.5:100:100. In some embodiments, the ratio of the first pool, second pool, third pool, fourth pool, and fifth pool within the set is 1:2.5:100:100:10. In some embodiments, 2% or less of the reads in the sequencing data map to TCR/BCR genes. In some embodiments the sample is a blood sample. In some embodiments, the patient has been exposed to or is suspected to have been exposed to SARS-CoV-2. In some embodiments, the patient is experiencing flu-like symptoms or symptoms associated with a respiratory disease. In some embodiments, the method comprises treating the patient for SARS-CoV-2 exposure, if the patient is determined to have been exposed to SARS-CoV-2.

In some embodiments of any of the above-described methods, step (c) comprises whole-transcriptome sequencing or short-read sequencing.

In some embodiments, a method comprising identifying TCR/BCR non-constant region sequences that are enriched in a cohort of patients with SARS-CoV-2 is provide. In some embodiments, the method includes a) isolating RNA from a sample from each patient in the cohort; b) enriching the isolated RNA for TCR/BCR genes using a set of TCR/BCR hybrid-capture probes and enriching for a targeted whole transcriptome panel using a set of transcriptome hybrid-capture probes; c) determining the sequence of the RNA of (b) to generate sequencing data; d) analyzing the sequencing data to determine the TCR/BCR profile of the patients in the cohort; and e) identifying TCR/BCR non-constant region sequences that are enriched in the cohort as compared to a control group without the disease or condition, wherein the set of hybrid-capture probes comprises a first pool of TCR constant region probes, a second pool of TCR non-constant region probes, a third pool of BCR constant region probes, and a fourth pool of BCR non-constant region probes, and a fifth pool of transcriptome hybrid-capture probes.

In some embodiments, the ratio of the first pool, second pool, third pool, and fourth pool within the set is 1:2.5:100:100. In some embodiments, the ratio of the first pool, second pool, third pool, fourth pool, and fifth pool within the set is 1:2.5:100:100:10. In some embodiments, 2% or less of the reads in the sequencing data map to TCR/BCR genes. In some embodiments, the sample is a blood sample.

In some embodiments, a method of determining a TCR/BCR profile of a patient is provided. In some embodiments, the methods comprise a) isolating RNA from a sample from the patient; b) enriching the isolated RNA for TCR/BCR genes using a set of TCR/BCR hybrid-capture probes and enriching for a targeted whole transcriptome panel using a set of transcriptome hybrid-capture probes; c) determining the sequence of the RNA of (b) to generate sequencing data; and d) analyzing the sequencing data to determine the TCR/BCR profile of the patient, wherein the set of TCR/BCR hybrid-capture probes comprises a first pool of BCR constant region probes, a second pool of BCR non-constant region probes, a third pool of TCR constant region probes, a fourth pool of TCR non-constant region probes, and a fifth pool comprising transcriptome hybrid-capture probes. In some embodiments, the ratio of the first pool, second pool, third pool, and fourth pool within the set is 1:2.5:100:100. In some embodiments, the ratio of the first pool, second pool, third pool, fourth pool, and fifth pool within the set is 1:2.5:100:100:10. In some embodiments, 2% or less of the reads in the sequencing data map to TCR/BCR genes. In some embodiments, step (d) comprises identifying a plurality of TCR/BCR clones in the sample. In some embodiments, step (d) comprises identifying the most abundant TCR/BCR clones in the sample. In some embodiments, step (d) comprises identifying the most abundant non-constant region sequences in the sample. In some embodiments, the sample is a blood sample or a solid tumor sample.

In some embodiments, the patient's BCR/TCR profile is compared with a control TCR/BCR profile and the patient is identified as having a disease or medical condition based on the comparison. In some embodiments, the disease or condition is an infectious disease, a cancer, an autoimmune disease, or an allergy. In some embodiments, the cancer or infectious disease is one or more provided in the list in embodiment 114. In some embodiments, the infectious disease comprises exposure to SARS-CoV-2. In some embodiments, the subject is suspected of having or has been diagnosed with COVID-19. In some embodiments, the disease is cancer. In some embodiments, analyzing comprises determining the presence or extent of tumor lymphocyte infiltration. In some embodiments, the methods comprises treating the patient with a therapy. In some embodiments, the therapy comprises an immunotherapeutic agent. In some embodiments, the immunotherapeutic agent is a vaccine. In some embodiments, the immunotherapeutic agent is a chimeric antigen receptor (CAR) T cell.

BRIEF DESCRIPTION OF THE FIGURES

FIG. 3. Is a table demonstrating an exemplary embodiment of the novel hybrid-capture approach to immune profiling with the number of each individual probes (right column) per general target (left column).

FIG. 15 illustrates an example of aligned TCR reference sequences. FIG. 15 discloses SEQ ID NOS 179-185, respectively, in order of appearance.

FIG. 17 shows the difference in total desired coverage length (in base pairs) when using (Table 1) the complete set of IG and TCR allele sequences (upper bound) and (Table 2) when using gene-level consensus sequences.

DETAILED DESCRIPTION

Figure 1A:
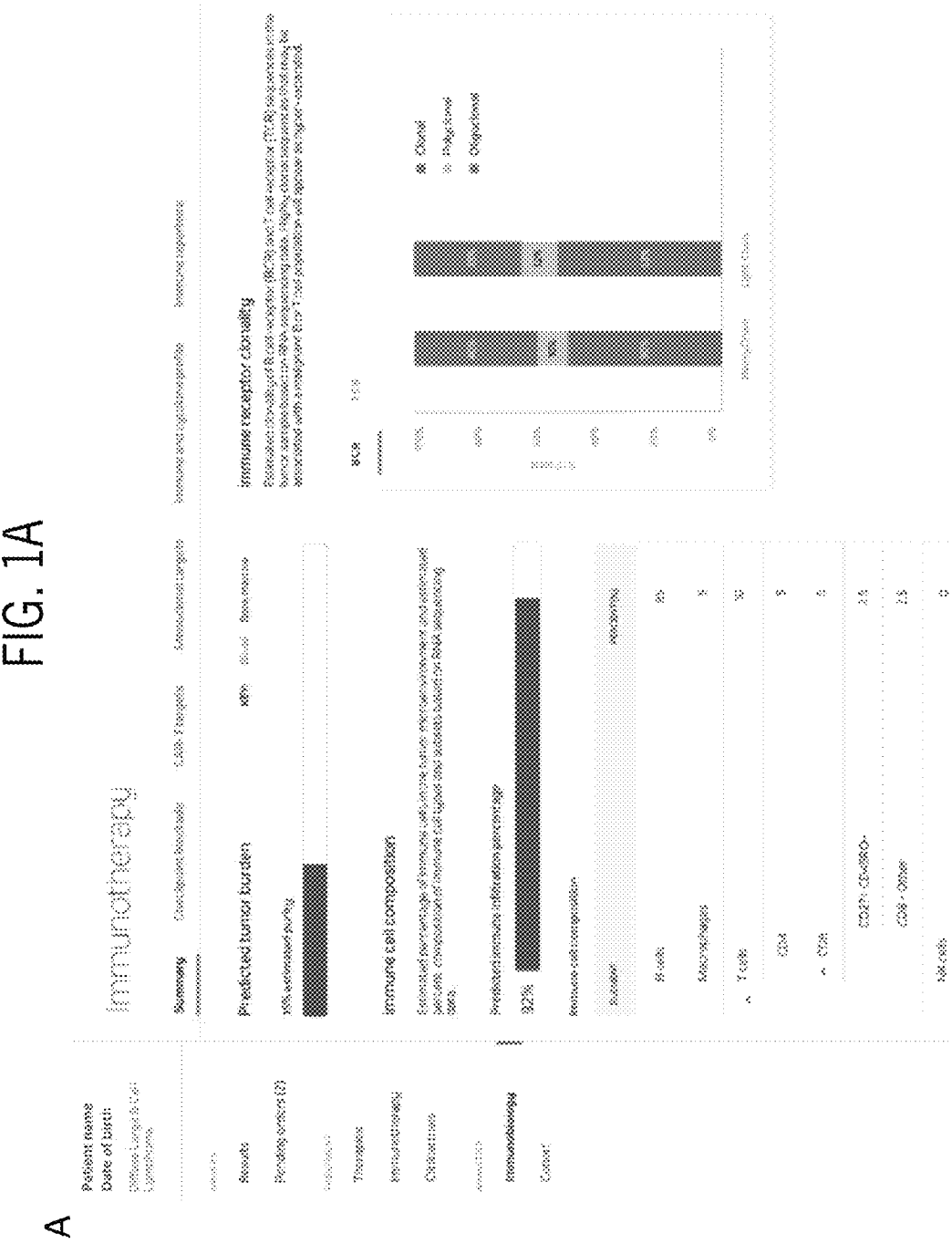
FIG. 1A-B. (A) presents an exemplary TCR/BCR immune repertoire display (report) illustrating additional or alternative fields for review by a physician. (B) An example TCR/BCR immune repertoire display (report), showing patient clonality after analysis with novel hybrid-capture approach, in this case related to BCR clonality. Fid. 1B discloses SEQ ID NOS 172-175, respectively, in order of appearance.

The various aspects of the subject disclosure are now described with reference to the drawings, wherein like reference numerals correspond to similar elements throughout the several views. It should be understood, however, that the drawings and detailed description hereafter relating thereto are not intended to limit the claimed subject matter to the particular form disclosed. Rather, the intention is to cover all modifications, equivalents, and alternatives falling within the spirit and scope of the claimed subject matter.

In the following detailed description, reference is made to the accompanying drawings which form a part hereof, and in which is shown by way of illustration, specific embodiments in which the disclosure may be practiced. These embodiments are described in sufficient detail to enable those of ordinary skill in the art to practice the disclosure. It should be understood, however, that the detailed description and the specific examples, while indicating examples of embodiments of the disclosure, are given by way of illustration only and not by way of limitation. From this disclosure, various substitutions, modifications, additions rearrangements, or combinations thereof within the scope of the disclosure may be made and will become apparent to those of ordinary skill in the art.

In accordance with common practice, the various features illustrated in the drawings may not be drawn to scale. The illustrations presented herein are not meant to be actual views of any particular method, device, or system, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or method. In addition, like reference numerals may be used to denote like features throughout the specification and figures.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof. Some drawings may illustrate signals as a single signal for clarity of presentation and description. It will be understood by a person of ordinary skill in the art that the signal may represent a bus of signals, wherein the bus may have a variety of bit widths and the disclosure may be implemented on any number of data signals including a single data signal.

The various illustrative logical blocks, modules, circuits, and algorithm acts described in connection with embodiments disclosed herein may be implemented as electronic hardware, computer software, or combinations of both. To clearly illustrate this interchangeability of hardware and software, various illustrative components, blocks, modules, circuits, and acts are described generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the embodiments of the disclosure described herein.

In addition, it is noted that the embodiments may be described in terms of a process that is depicted as a flowchart, a flow diagram, a structure diagram, or a block diagram. Although a flowchart may describe operational acts as a sequential process, many of these acts can be performed in another sequence, in parallel, or substantially concurrently. In addition, the order of the acts may be re-arranged. A process may correspond to a method, a function, a procedure, a subroutine, a subprogram, etc. Furthermore, the methods disclosed herein may be implemented in hardware, software, or both. If implemented in software, the functions may be stored or transmitted as one or more instructions or code on a computer-readable medium. Computer-readable media includes both computer storage media and communication media including any medium that facilitates transfer of a computer program from one place to another.

It should be understood that any reference to an element herein using a designation such as "first," "second," and so forth does not limit the quantity or order of those elements, unless such limitation is explicitly stated. Rather, these designations may be used herein as a convenient method of distinguishing between two or more elements or instances of an element. Thus, a reference to first and second elements does not mean that only two elements may be employed there or that the first element must precede the second element in some manner. Also, unless stated otherwise a set of elements may comprise one or more elements Definitions As used in this specification and the claims, the singular forms "a," "an," and "the" include plural forms unless the context clearly dictates otherwise. For example, the term "a polypeptide fragment" should be interpreted to mean "one or more a polypeptide fragment" unless the context clearly dictates otherwise. As used herein, the term "plurality" means "two or more."

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

As used herein, the term "subject" may be used interchangeably with the term "patient" or "individual" and may include an "animal" and in particular a "mammal." Mammalian subjects may include humans and other primates, domestic animals, farm animals, and companion animals such as dogs, cats, guinea pigs, rabbits, rats, mice, horses, cattle, cows, and the like.

As used herein a "subject sample" or a "biological sample" from the subject refers to a sample taken from the subject, such as, but not limited to a tissue sample (for example fat, muscle, skin, neurological, tumor, biopsy (e.g., solid tumor biopsy), lymph node, etc.) or fluid sample (for example, saliva, mucus, blood, serum, plasma, lymph, urine, stool, cerebrospinal fluid, etc.), and or cells, cultured cells (for example, organoids) or sub-cellular structures such as vesicles and exosomes.

"BCR" or "B-cell receptor", depending on the context in which it is used herein, refers to immunoglobulin molecules that form a receptor protein usually located on the outer surface of a lymphocyte type known as a "B cell". In some contexts, the term BCR or b-cell receptor refers to at least a part of the region(s) of a genome responsible for the development of B-cell receptor(s).

"Comprehensive genomic profiling panel" as used herein, refers to a genomic profiling panel comprising more than 10 genes.

"Contig" refers to a set of overlapping DNA segments that together represent a consensus region of DNA.

"IgM" refers to the immunoglobulin M antibody and its isotypes.

"IgD" refers to the immunoglobulin D antibody and its isotypes.

"IgG" refers to the immunoglobulin G antibody and its isotypes.

"IgA" refers to the immunoglobulin A antibody and its isotypes.

"IgE" refers to the immunoglobulin E antibody and its isotypes.

"NGS" refers to next-generation sequencing technologies.

"Profiling" refers to any one of various methods that may be used to learn about the genes in a person or in a specific cell type, and/or the way those genes interact with each other and/or with the environment.

"RNAseq" or "rna-seq" as used herein is an abbreviation of "RNA sequencing" and refers to a sequencing technique which uses NGS, to reveal the presence and quantity of RNA in a biological sample. RNA-seq can be used in the analysis of whole transcriptome, whole exome, targeted panel analysis, and combinations thereof.

"Clonal" as used herein, refers to a population of cells derived from a single cell. For example, a single T cell undergoes several successive rounds of mitosis and generates many T cells with identical T cell receptors. This population of T cells would be considered to be clonal.

"Oligoclonal" as used herein, refers to a population of cells derived from more than one, but less than many single cells. For example, a population of T cells derived from the expansion by mitosis of 2, 3, 4, 5, 6, 7, 8, 9, or 10 distinct T cell clones would be considered to be oligoclonal.

"Polyclonal" as used herein, refers to a population of cells derived from many single clones. For example, a population of T cells derived from the expansion by mitosis of 11, 20, 50, 100 or more distinct T cell clones would be considered to be polyclonal.

"TCR" or "t-cell receptor," depending on the context in which it is used herein, refers to a protein complex found on the surface of T cells, or T lymphocytes, that is responsible for recognizing fragments of antigen as peptides bound to major histocompatibility complex (MEW) molecules. In some contexts, the term TCR or t-cell receptor refers to at least a part of the region(s) of a genome responsible for the development of t-cell receptor(s).

As used herein, the term "repertoire" refers to the totality of information (including, but not limited to presence, absence, expression level, variants), derived from nucleic acid sequencing, such as NGS methods, related a particular class of molecules, such as receptors, for example B-cell receptors and/or T-cell receptors, or a collection of molecules within a system, such as an immune repertoire, which could include B-cell receptor information, T-cell receptor information and information about other immune-related genes, such as MHC genes.

As used herein, the term "TCR/BCR repertoire" refers to the totality of information derived from nucleic acid sequencing (such as by NGS methods) of a sample isolated from a subject, using the hybrid capture probes, comprising a TCR/BCR probe set (probe panel) alone, or in combination with a targeted exome panel. If a targeted whole transcriptome or targeted whole exome panel is used, the TCR/BCR repertoire does not include the remaining (non-TCR/BCR) transcriptome data. A TCR/BCR repertoire includes information, for example in the form of sequence data, about gene targets in the TCR/BCR panel. Such information can be analyzed by methods known in the art to determine receptor types (for example, TCR types $\alpha:\beta$ or $\gamma:\delta$; BCR types IgD, IgM, IgA, IgG, or IgE) receptor identity (for example based on non-constant region sequences), and specific receptor abundance, to derive a TCR/BCR profile.

As used herein, a "TCR/BCR profile" refers to a subset of the information of the TCR/BCR repertoire that allows the prediction or identification of an insight into the status or state of a medical condition, disease, effect of a therapy, tumor infiltration, etc., of a subject or a cohort. In some embodiments, the TCR/BCR profile includes a clinically actionable insight. By way of example, a TCR/BCR patient profile is typically derived by analysis, such as statistical analysis, of NGS sequencing data (e.g., from a TCR/BCR repertoire or an immune repertoire) and the results of such analysis may be provided or output in any form, such as a report or other visual representation, a summary, a listing, display, etc. Exemplary information provided in a TCR/BCR profile may include, but is not limited to one or more of a plurality of TCR/BCR receptor sequences (clones), the abundance of receptors (e.g., showing clonal abundance), the most abundant receptors, the abundance of a specific receptor or receptors, the degree of variety of receptors (clonality), receptor types, abundance of non-constant regions, and any combination of the above. By way of example only, a TCR/BCR profile may include the identity of the top 10 most abundant receptors (see, for example, Example 3); the clonality within repertoires in various cancers (see, for example, Example 7), or the identification of receptors common to a cohort database (see, for example, Example 9).

"TCR/BCR profiling" refers to the profiling of at least a part of the regions of the genome responsible for the development of T cell receptors or B cell receptors.

"V(D)J recombination" refers to the nearly random rearrangement of variable (V), joining (J), and in some cases, diversity (D) gene segments, resulting in a variety of amino acid sequences in the antigen-binding regions of immunoglobulins and TCRs that allow for the recognition of antigens from pathogens including bacteria, viruses, fungus, parasites, and worms, as well as some cancer cells.

"V region" refers to a BCR or TCR variable gene segment or gene product thereof.

"D region" refers to a BCR or TCR diversity gene segment or gene product thereof.

"J region" refers to a BCR or TCR joining gene segment or gene product thereof.

"C region" refers to a BCR or TCR constant gene segment or gene product thereof.

As used herein "transcriptome" refers to the full range of messenger RNA molecules expressed by an organism, a particular tissue, or a particular cell. A transcriptome can be defined at a particular point in time, for example, at a particular developmental stage, in a particular disease stage, etc.

"Whole transcriptome" refers to the coding and non-coding RNA expressed in cells, tissues, organs and/or an entire body.

"Whole transcriptome sequencing" or "whole transcriptome profile" refers to the measurement of the complete complement of transcripts in a sample at a given time. Whole transcriptome sequencing captures both coding (mRNA) and non-coding transcripts (such as miRNA, tRNA, rRNA, if rRNA is of interest), and provides a "snapshot" of expression levels, exons, introns, and variants. In some embodiments, whole transcriptome sequencing starts with the removal of rRNA from the sample (rRNA typically takes up a majority of the sequencing reads). In some embodiments, whole transcriptome sequencing is performed comprising a transcriptome enrichment step, using a targeting panel to enrich for certain RNA sequences, and/or to remove or reduce the presence of others (for example, by using species-specific rRNA probes to remove abundant RNA species). By way of example, whole transcriptome targeting panels to enrich for certain RNA sequences can include probes to enrich 5,000, 10,000, 20,000 RNA targets or more. In some embodiments, a whole transcriptome targeting panel, comprising transcriptome hybrid capture probes, can comprise a whole exome panel, for example, Integrated DNA Technologies xGen Exome Research Panel v2.

"Exome," as used herein refers to the part of the genome composed of exons, the sequences which, when transcribed, remain within the mature RNA after introns are removed by RNA splicing and contribute to the final protein product encoded by that gene.

As used herein "whole exome sequencing" refers to sequencing the protein-coding regions of the genome, typically using NGS sequencing methods. The human exome represents less than 2% of the genome, but contains ~85% of known disease-related variants, making this method a cost-effective alternative to whole-genome sequencing. In some embodiments, whole exome sequencing is performed comprising an exome enrichment step, using an exome targeting panel to enrich for exome sequences (and to omit non-coding sequences, for example). Such panels are commercially available, and typically include probes to enrich 5,000, 10,000, 20,000 genes or more. By way of example, a non-limiting exome panel is Integrated DNA Technologies xGen Exome Research Panel v2.

The terms "targeted panel" and "targeted gene sequencing panel" or "targeting panel" are used interchangeably herein to refer to a probe set directed to a select set of genes or gene regions of interest. Targeted panels are useful tools for detecting a set of specific sequences in a given sample. In some embodiments, a targeted panel produces a smaller, more manageable data set (e.g., TCR/BCR profile) as compared to broader approaches such as whole-genome sequencing. In some embodiments, a targeted panel comprises a whole exome panel, or a whole transcriptome panel, and encompasses 5,000, 10,000, 20,000, or more targets. In some embodiments, a targeted panel comprises hybrid capture probes.

"Hybridization-capture probes," or "hybrid-capture probes," as used herein refer to biotinylated oligonucleotides that contain a region of complementary to nucleic acid sequences of interest sufficient to bind (hybridize to) the nucleic acid sequences of interest and provide a means for their enrichment through the use of streptavidin linked capture moieties linked to a solid support structure, e.g. beads. In various embodiments, other capture moieties may be used instead of streptavidin and biotinylation. Examples of binding moieties include but are not limited to biotin: streptavidin, biotin: avidin, biotin: haba: streptavidin, antibody: antigen, antibody: antibody, covalent chemical linkage (ex. click chemistry).

As used herein, the terms "probe pool" or "probe set" and "panel" refer to a collection of probes useful for enrichment of a nucleic acid target prior to sequencing. In some embodiments, a probe set and a probe panel are used interchangeably. In some embodiments, a panel may be described as a probe set comprising a collection of probe pools. In some embodiments, additional probe pools are provided in combination with a TCR/BCR panel to enrich for additional target genes or sequences of interest. By way of example, probe pools directed to cancer-specific sequences (for example, sequences that serve as diagnostic, prognostic, and/or therapeutic biomarkers) may be included with a BCR/TCR panel, instead of a whole transcriptome panel, a whole exome panel, or in addition to a whole transcriptome panel or a whole exome panel.

The terms "polynucleotide", "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. Sequenced nucleotides may be of any form of nucleic acid, including, but not limited to RNA, DNA and cfDNA molecules. These terms also refer to complementary DNA (cDNA), which is DNA synthesized from a single-stranded RNA (e.g., messenger RNA (mRNA) or microRNA (miRNA)) template in a reaction catalyzed by the enzyme reverse transcriptase. The term "polynucleotide" includes, without limitation, single- and double-stranded polynucleotide.

As used herein, the term "gene" refers to a nucleic acid sequence that encodes a gene product, either a polypeptide or functional RNA molecule. The term "gene" is to be interpreted broadly herein, encompassing both the genomic DNA form of a gene (i.e., a particular portion of a particular chromosome), and mRNA and cDNA forms of the gene produced therefrom. During gene expression, genomic DNA is transcribed into RNA, which can be immediately functional or can be translated into a polypeptide that performs a function. In addition to a coding region (i.e., the sequence that encodes the gene product), a gene comprises "noncoding regions". Noncoding regions may be immediately adjacent to the coding region (e.g., 5' and 3' noncoding regions that flank the coding region) or may be far removed from the coding region (e.g., many kilobases upstream or downstream). Some noncoding regions are transcribed into RNA but not translated, including "introns" (i.e., regions that are removed via RNA splicing before translation) and translational regulatory elements (e.g., ribosome binding sites, terminators, and start and stop codons). Other noncoding regions are not transcribed, including essential transcriptional regulatory regions. Genes require a "promoter," a sequence that is recognized and bound by proteins (i.e., transcription factors) that recruit and help RNA polymerase bind and initiate transcription. A gene can have more than one promoter, resulting in messenger RNAs (mRNA) that differ in how far they extend on the 5' end. As used herein, genes may also comprise more distally located transcriptional regulatory elements (i.e., "enhancers" and "silencers") that can be looped into proximity of the promoter, allowing proteins (i.e., "transcription factors") bound to these distal regulatory sites to influence transcription. For example, an "enhancer" increases transcription by binding an activator protein that helps to recruit RNA polymerase or initiate transcription. Conversely, "silencers" bind repressor proteins that make the DNA less accessible to RNA polymerase or otherwise inhibit transcription. Genes may also comprise "insulator" elements that protect promoters from inappropriate regulation. Insulators may function by either blocking interaction with an enhancer or silencer or by acting as a barrier that prevents the spreading of condensed chromatin. While enhancers and silencers are generally not considered to be part of a gene per se (given that a single enhancer or silencer may regulate the expression of multiple genes), as used herein, the term gene encompasses those distal elements that influence its expression.

As used herein, the term "promoter" refers to a DNA sequence capable of controlling the expression of a coding sequence or functional RNA. In general, a coding sequence is located 3' to a promoter sequence. Promoters may be derived in their entirety from a native gene or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Artificial promoters that cause a gene to be expressed in most cell types at most times are commonly referred to as "constitutive promoters". Artificial promoters that allow the selective expression of a gene in most cell types are referred to as "inducible promoters".

The terms "genetic sequence" and "sequence" are used herein to refer to the series of nucleotides present in a DNA, RNA or cDNA molecule. In the context of the present invention, sequences are determined by sequencing nucleic acids present in a biological specimen.

The term "read" refers to a DNA sequence of sufficient length (e.g., at least about 30 bp) that can be used to identify a larger sequence or region, e.g., by aligning it with a chromosome, genomic region, or gene. A read may be a paired-end or single-end read.

As used herein, the term "reference genome" refers to any particular known genome sequence, whether partial or complete, of any organism or virus which may be used to reference identified sequences from a subject. Many reference genomes are provided by the National Center for Biotechnology Information at www.ncbi.nlm.nih.gov. A "genome" refers to the complete genetic information of an organism or virus, expressed in nucleic acid sequences.

As used herein, the terms "aligned", "alignment", or "aligning" refer to a process used to identify regions of similarity. In the context of the present disclosure, alignment refers to matching sequences with positions in a reference genome based on the order of their nucleotides in these sequences. Alignment can be performed manually or by a computer algorithm, for example, using the Efficient Local Alignment of Nucleotide Data (ELAND) computer program distributed as part of the Illumina Genomics Analysis pipeline. Alignment can refer to a either a 100% sequence match or a match that is less than 100% (non-perfect match). In various examples, alignment includes pseudo-alignment.

The terms "library" and "sequencing library" are used herein to refer to a pool of DNA fragments with adapters attached. Adapters are commonly designed to interact with a specific sequencing platform, e.g., the surface of a flowcell (Illumina) or beads (Ion Torrent), to facilitate a sequencing reaction.

The term "sequencing probe" or "sequencing primer" is used herein to refer to a short oligonucleotide that is used to sequence nucleic acids (i.e., cDNA or DNA). The sequencing probe may hybridize with a target sequence within the nucleic acids, or it may hybridize to an adapter sequence that has been attached to the nucleic acids to allow for nonspecific amplification and sequencing.

The term "RNA read count" is used herein to refer to the number of sequencing reads generated from a genetic analyzer. The term "RNA read count" is often used to refer to the number of reads overlapping a given feature (e.g., a gene or chromosome).

The term "genetic profile" is used herein to refer to information about specific genes in an individual or in a particular type of tissue. This information may include genetic variations (e.g., single nucleotide polymorphisms), gene expression data, other genetic characteristics, or epigenetic characteristics (e.g., DNA methylation patterns) determined by, for example, the analysis of next-generation sequencing data.

The term "variant" is used herein to mean a difference in a genetic sequence or genetic profile, as compared to a reference genome or reference genetic profile.

The term "expression level" is used herein to describe the number of copies of a particular RNA or protein molecule, which may or may not be normalized using standard methods (e.g., counts per million, finding the base 10 logarithm of the raw read count) generated by a gene or other genetic regulatory region (e.g. long non-coding RNAs, enhancers), which may be defined by a chromosomal location or other genetic mapping indicator.

The term "gene product" is used herein to mean a protein or RNA molecule generated by the expression (i.e., transcription, translation, post-translational modification, etc.) of a gene or other genetic regulatory region.

The terms "extracted", "recovered," "isolated," and "separated," refer to a compound, (e.g., a protein, cell, nucleic acid or amino acid) that has been removed from at least one component with which it is naturally associated and found in nature.

The terms "enriched" or "enrichment" as used herein in conjunction with nucleic acid sample preparation, for example for NGS sequencing methods, refer to the process of enhancing the amount of one or more nucleic acid species in a sample. Exemplary enrichment methods may include chemical and/or mechanical means, and may also include amplifying nucleic acids contained in a sample. By way of example, enrichment may include the use of hybrid-capture probes, and the polymerase chain reaction (PCR). Enrichment can be sequence specific (for example using hybrid-capture probes or target-specific PCR primers) or nonspecific (i.e., involving any of the nucleic acids present in a sample). "Enriched" as used herein with reference to a level or an amount of one or more biomolecules in a sample, refers to an increased level or amount of the one or more biomolecules, such as nucleic acid or protein, as compared to a control level, or as compared to the other biomolecules in the sample (as a relative amount). In a data science context, "enrichment" refers to statistical enrichment.

As used herein, "cancer" refers to any one or more of a wide range of benign or malignant tumors, including those that are capable of invasive growth and metastases through a human or animal body or a part thereof, such as, for example, via the lymphatic system and/or the blood stream. As used herein, the term "tumor" includes both benign and malignant tumors and solid growths. Typical cancers include but are not limited to carcinomas, lymphomas, or sarcomas, such as, for example, ovarian cancer, colon cancer, breast cancer, pancreatic cancer, lung cancer, prostate cancer, urinary tract cancer, uterine cancer, acute lymphatic leukemia, Hodgkin's disease, small cell carcinoma of the lung, melanoma, neuroblastoma, glioma, and soft tissue sarcoma of humans.

In the context of the present disclosure, the term "biomarker" shall be taken to mean any genetic variant or molecule or set of molecules, or characteristic of a molecule (such as location, expression level, etc.) that is indicative of or correlated with a characteristic of interest, for example, the existence of an infection, a medical condition or disease, such as cancer, or of a susceptibility to an infection, conditions, or disease in the subject, the likelihood that the infection, medical condition or disease is one subtype vs. another, the probability that a patient will or will not respond to a particular therapy or class of therapy, the degree of the positive response that would be expected for a therapy or class of therapies (e.g., survival and/or progression-free survival, which may be quantified as an interval of time), whether a patient is responding to a therapy, or the likelihood that an infection, medical condition, or disease has progressed or will progress, or has or will progress beyond its site of origin (i.e., metastasize). In some embodiments, a biomarker comprises a TCR/BCR profile.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be susceptible to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. The subject therapy will desirably be administered during the symptomatic stage of the disease, and in some cases after the symptomatic stage of the disease.

The term "effective amount" refers to an amount of an active agent that is sufficient to exhibit a detectable therapeutic effect without excessive adverse side effects (such as toxicity, irritation, and allergic response) commensurate with a reasonable benefit/risk ratio when used in the manner of the present disclosure. The effective amount for a patient will depend upon the type of patient, the patient's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on knowledge in the art and the information provided herein. The optimum dosing regimen can be determined by one skilled in the art without undue experimentation.

Overview

The diversity of lymphocyte receptors (T cell receptors, "TCRs" and B cell receptors "BCRs") is achieved by the process of recombination, producing a theoretical diversity of about $10^{18}$ unique receptors. Therefore, upon antigenic challenge and antigen presentation by innate immune cells, lymphocytes that bear receptors with high affinity to antigen, or antigen bound to major histocompatibility complex I or II (MHCI or II), are activated and clonally expand. Importantly, lymphocytes that have been activated and have differentiated to become "effector" cells persist in an individual for some time. In addition, after resolution of infection or clearance of a pathogen, "memory" cells may persist for the lifetime of the host. The particular variety of lymphocyte receptors that are present in an individual subject are termed the "repertoire." Therefore, the repertoire of lymphocyte receptors in an individual subject contains a fingerprint of their response to antigenic challenges, including to diseases such as cancer, and provides a record of pathogens they have encountered. By way of example, for blood cancers, the repertoire can be monitored for the "tumor" or cancer cells, and for solid cancers, the repertoire can be used to study why the immune system is not recognizing/eliminating the cancer cells as non-self cells. For at least these reasons, there is great interest in the profile of an individual subject's lymphocyte receptors.

The field of immune profiling leverages technology known as Next Generation Sequencing (NGS) to accurately sequence the immune receptor repertoire in an individual subject. NGS is capable of producing millions of sequencing "reads" which are then aligned to a reference genome or transcriptome to give a relatively complete picture of an individual's genome or a sample's transcriptome. The technical and computational challenges, however, in assembling and analyzing reads to detect and assess T and B cell receptors are significant. High quality sequencing data depends on two factors known as breadth and depth of sequencing. The breadth of sequencing refers to the number of genome bases that are covered by the sequencing, or the percentage of total, while the depth of sequencing refers to roughly how many times a particular base or region is covered by the sequencing run. However, in a given sample the presence of transcripts encoding lymphocyte receptors, or in some cases lymphocytes at all, can be very limited. Therefore, obtaining deep sequencing results that accurately represent the individual subject's T and B cell repertoire, without directly enriching or selecting for the non-constant regions of TCRs and BCRs, can be challenging.

T and B cell receptors are made up of discrete genes that are rearranged to form the large repertoire present in an individual. Thus, any strategy to selectively enrich T and B cell receptor transcripts must be tailored to combat the low abundance of transcripts encoding lymphocyte receptors, and the variety of different genes that are assembled to encode recombined antigen receptors. Additionally, sequencing reads mapping to TCRs and BCRs may not be balanced, causing a bias toward the detection of either TCR or BCR clones in a sample. Furthermore, the most critical information for immune profiling lies in the hypervariable (non-constant) regions, and not in the constant regions. Thus, sequences for hypervariable regions may require enrichment. In some cases sample volume and/or quality can be limiting because it is derived from biopsies or other precious samples. Therefore, there is a need in the art for a method that can extract both high-quality RNA sequencing and also provide deep and accurate immune profiling at scale, from a single sample or sequencing run. The methods and systems of the present disclosure address this need in the art.

Targeted sequencing of T cells and B cells can be a powerful tool for mapping the immune system ("immunome") in cancer and other conditions, such as auto-immune disease, infectious disease, and transplantation. Each non-clonal T cell and B cell is unique at the DNA level, and in particular, they differ at the T cell receptor (TCR) gene or B cell receptor (BCR) gene that determines the pathogen or antigen the cell will respond to. By assembling (determining) the sequences of TCR and BCR genes via RNAseq, as disclosed herein, the immune system can be more accurately mapped, and a new class of immune-specific features can be generated to, for example, predict immune responses; diagnose or confirm diseases, conditions, or pathogen exposure; determine disease severity; measure or confirm therapeutic effect and efficacy; determine minimal residual disease (MRD); and provide the information necessary to produce specific therapies such as chimeric antigen receptor (CAR) T cells (CAR-T cells), NK cells (CAR-NK cells), macrophages (CAR-M cells), or another cell type engineered to express a CAR, Immune mobilizing monoclonal T-cell receptors Against Cancer (ImmTAC), another adoptive cell therapy, and vaccines.

Determining a TCR/BCR Profile

Disclosed herein are methods, systems, and compositions for determining the TCR/BCR profile of a subject. In some embodiments, the methods comprise (a) isolating RNA from a sample from the patient; (b) enriching the isolated RNA for TCR/BCR genes using a set of TCR/BCR hybrid-capture probes; (c) determining the sequence of the RNA of (b) to generate sequencing data; and (d) analyzing the sequencing data to determine the TCR/BCR profile of the patient. In some embodiments, the set of hybrid-capture probes comprises a first pool comprising BCR constant region probes, a second pool comprising BCR non-constant region probes, a third pool comprising TCR constant region probes, and a fourth pool comprising TCR non-constant region probes. In some embodiments, a TCR/BCR probe set is used that is obtained according to the methods of example 1.

In some embodiments, TCR/BCR profiling may be performed as a standalone assay. In some embodiments, the TCR/BCR profiling methods and systems as disclosed herein may be configured for use within the context of a broader RNAseq whole transcriptome or whole exome RNA panel, thereby providing a novel and valuable method to conserve precious patient samples, speed time to diagnosis or therapy recommendation, and obtain, in addition to gene expression data and related genetic data (such as but not limited to alternative splicing events, fusions, and genetic variants), specific information about the subject's immune profile. When incorporated into an RNAseq platform, TCR/BCR profiling may have expanded utility and an even more unique and valuable resource for insight generation. By way of example but not by way of limitation, TCR/BCR profiling may be used to profile and track multiple disease states and related immune responses, including cancer, infectious disease, transplantation, allergic diseases (triggered by airway, food, or other allergens), and autoimmunity. Allergic diseases may include contact dermatitis, asthma, anaphylaxis, non-IgE-mediated food allergies related to atopic dermatitis, etc. Autoimmune diseases may include type 1 diabetes, rheumatoid arthritis, lupus, celiac disease, Sjögren's syndrome, multiple sclerosis, polymyalgia rheumatica, ankylosing spondylitis, alopecia areata, vasculitis, temporal arteritis, etc. TCR/BCR profiling may include allele typing and may be used for biomarker discovery, for predicting immune response, health outcomes, and/or disease severity.

Accordingly, in some embodiments, the TCR/BCR profiling methods disclosed herein are performed using a sequencing technique, such next-generation sequencing. In some embodiments, bulk (multiple cell) sequencing, using short-read RNA sequencing may be used. The resulting reads may then be used, for instance, to assemble contigs from TCR/BCR gene regions. In some embodiments a fifth pool of probes, comprising for example, an exon targeting panel, is provided.

As noted above, one exemplary benefit of the present methods, compositions, and systems, is that TCR/BCR profiling may be included within the context of a broader RNAseq whole transcriptome panel. In an oncology or a more general profiling environment, TCR/BCR profiling may be added to other analysis on the rest of the transcriptome, such as cytokine expression, immune cell composition, potential viral/bacterial signals, and inflammatory signatures. Whole transcriptome analysis allows for the capture of that data while also providing a TCR/BCR snapshot.

An exemplary method for sample preparation useful for TCR/BCR profiling, NGS, and related methods is provided below. The present technology is not intended to be limited by the sample preparation methods, and the skilled artisan will understand that substitutions, alternative reagents, and alternative processing steps, may be used.

RNA Extraction

Transcriptome analysis, the study of the complete set of RNA transcripts that are produced by a cell (i.e., the transcriptome), and exome analysis, the study of RNAs that encode a protein product, offers a promising means to identify genetic variants that are correlated with disease state and disease progression. For example, to identify genetic variants that are associated with cancer, transcriptome and/or exome analysis may be performed on a sample collected from a patient that contains cancer cells. Suitable patient samples include tissue samples, tumors (e.g., a solid tumor), biopsies, lymph nodes, and bodily fluids (e.g., blood, serum, plasma, lymph, sputum, lavage fluid, cerebrospinal fluid, urine, semen, sweat, tears, saliva). Alternatively, transcriptome and/or exome analysis may be performed on an organoid that was generated from a human cancer specimen (i.e., a "tumor organoid"). Sequencing may be performed on a single cell specimen or on a multi-cell specimen.

While RNA sequencing (RNA-seq) can be performed on any patient sample that contains RNA, those of skill in the art will appreciate that the sequencing protocol should be tailored to the particular sample in use. For instance, RNA tends to be highly degraded in tissue samples that have been processed for histology (e.g., formalin fixed, paraffin embedded (FFPE) tissue sections). Accordingly, investigators will modify several key steps in the RNA-seq protocol to mitigate sequencing artifacts (see, e.g., BMC Medical Genomics 12, 195 (2019)).

Today, transcriptome and exome analysis is predominantly performed using high-throughput RNA sequencing (RNA-Seq), which detects the RNA transcripts in a sample using a next-generation sequencer. The first step in performing RNA-seq is to extract RNA from the sample.

Cell Lysis

The first step in extracting RNA from a sample is often to lyse the cells present in that sample. Several physical disruption methods are commonly used to lyse cells, including, for example, mechanical disruption (e.g., using a blender or tissue homogenizer), liquid homogenization (e.g., using a dounce or French press), high frequency sound waves (e.g., using a sonicator), freeze/thaw cycles, heating, manual grinding (e.g., using a mortar and pestle), and bead-beating (e.g., using a Mini-beadbeater-96 from BioSpec). Cells are also commonly lysed using reagents that contain a detergent, many of which are commercially available (e.g., QIAzol Lysis Reagent from QIAGEN, FastBreak™ Cell Lysis Reagent from Promega). Often, physical disruption methods are performed in a "homogenization buffer" that contains, for example, lysis reagents such as detergents or proteases (e.g., proteinase K) that increase the efficiency of lysis. Homogenization buffers may also include anti-foaming agents and/or RNase inhibitors to protect RNA from degradation. Those of skill in the art will appreciate that different cell lysis techniques may be required to obtain the best possible yield from different tissues. Techniques that minimize the degradation of the released RNA and that avoid the release of nuclear chromatin are preferred.

RNA Isolation

After the cells have been lysed, RNA can be separated from other cellular components. Total RNA is commonly isolated using guanidinium thiocyanate-phenol-chloroform extraction (e.g., using TRIzol) or by performing trichloroacetic acid/acetone precipitation followed by phenol extraction. However, there are also many commercially available column-based systems for extracting RNA (e.g., PureLink RNA Mini Kit by Invitrogen and Direct-zol Miniprep kit by Zymo Research).

Ideally, the isolated RNA will contain very little DNA and enzymatic contamination. To this end, the isolation method may utilize agents that eliminate DNA (e.g., TURBO DNase-I), and/or remove enzymatic proteins from the sample (e.g., Agencourt® RNAClean® XP beads from Beckman Coulter).

In some cases, whole transcriptome sequencing is used to analyze all of the transcripts present in a cell, including messenger RNA (mRNA) as well as all non-coding RNAs. By looking at the whole transcriptome, researchers are able to map exons and introns and to identify splicing variants. Notably, most whole transcription library preparation protocols include a step to remove ribosomal RNA (rRNA), which would otherwise take up the majority of the sequencing reads. Depletion of rRNA is commonly accomplished using a kit, e.g., Ribo-Zero Plus rRNA Depletion Kit from Illumina and Seq RiboFree Total RNA Library Kit from Zymo.

In other cases, a more targeted RNA-Seq protocol is used to look at a specific type of RNA. For example, mRNA-seq is commonly used to selectively study the "coding" part of the genome, which accounts for only 1-2% of the entire transcriptome. Enriching a sample for mRNA increases the sequencing depth achieved for coding genes, enabling identification of rare transcripts and variants. Polyadenylated mRNAs are commonly enriched for using oligo dT beads (e.g., Dynabeads™ from Invitrogen). This enrichment step can be performed either on isolated total RNA or on crude cellular lysate.

Targeted approaches have also been developed for the analysis of microRNAs (miRNAs) and small interfering RNAs (siRNAs). These RNAs are commonly isolated using kits that have been designed to efficiently recover small RNAs (e.g., mirVana™ miRNA Isolation Kit from Invitrogen).

Library Preparation

After RNA has been extracted from the sample, the next major step is to convert the RNA into a form that is suitable for next-generation sequencing (NGS). Through a series of steps, the RNA is converted into a collection of DNA fragments known as a "sequencing library." After the library has been sequenced, the resulting sequencing "reads" are aligned to a reference genome or transcriptome to determine the expression profile of the analyzed cells.

In some cases, library preparation is automated to enable higher sample throughput, minimize errors, and reduce hands-on time. Fully automated library preparation can be performed, for example, using a liquid handling robot (e.g., SciClone® NGSx from PerkinElmer).

Reverse Transcription/cDNA Preparation

After RNA has been extracted from the sample, the next major step is to convert the RNA into a form that is suitable for next-generation sequencing (NGS). Through a series of steps, the RNA is converted into a collection of DNA fragments known as a "sequencing library." After the library has been sequenced, the resulting sequencing "reads" are aligned to a reference genome or transcriptome to determine the expression profile of the analyzed cells.

In some cases, library preparation is automated to enable higher sample throughput, minimize errors, and reduce hands-on time. Fully automated library preparation can be performed, for example, using a liquid handling robot (e.g., SciClone® NGSx from PerkinElmer).

For sequencing, RNA is converted to more stable, double-stranded complementary DNA (cDNA) using reverse transcription (RT). In some cases reverse transcription is performed directly on a sample lysate, prior to RNA isolation. In other cases, reverse transcription is performed on isolated RNA.

Reverse transcription is catalyzed by reverse transcriptase, an enzyme that uses an RNA template and a short primer complementary to the 3' end of the RNA to synthesize a complementary strand of cDNA. This first strand of cDNA is then made double-stranded, either by subjecting it to PCR or using a combination of DNA Polymerase I and DNA Ligase. In the latter method, an RNase (e.g., RNase H) is commonly used to digest the RNA strand, allowing the first cDNA strand to serve as a template for synthesis of the second cDNA strand.

Many reverse transcriptases are commercially available, including Avian Myeloblastosis Virus (AMV) reverse transcriptases (e.g., AMV Reverse Transcriptase from New England BioLabs) and Moloney Murine Leukemia Virus (M-MuLV, MMLV) reverse transcriptases (e.g., SMARTscribe™ from Clontech, SuperScript II™ from Life Technologies, and Maxima H Minus™ from Thermo Scientific). Notably, many of the available reverse transcriptases have been engineered for improved thermostability or efficiency (e.g., by eliminating 3→5' exonuclease activity or reducing RNase H activity).

The primers, which serve as a starting point for synthesis of the new strand, may be random primers (i.e., for RT of any RNA), oligo dT primers (i.e., for RT of mRNA), or gene-specific primers (i.e., for RT of specific target RNAs).

Following reverse transcription, an exonuclease (e.g., Exonuclease I) may be added to the samples to degrade any primers that remain from the reaction, preventing them from interfering in subsequent amplification steps.

Enrichment

For some applications, it is not necessary to sequence the entire transcriptome of a sample. Instead, "targeted sequencing" may be used to study a select set of genes or specific genomic elements. Libraries that are enriched for target sequences are commonly prepared using hybridization based methods (i.e., hybridization capture-based target enrichment). Hybridization may be performed either on a solid surface (microarray) or in solution. In the solution based method, a pool of biotinylated oligonucleotide probes that specifically hybridize with the genes or genomic elements of interest is added to the library. The probes are then captured and purified using streptavidin-coated magnetic beads, and the sequences that hybridized to these probes are subsequently amplified and sequenced. Many probe panels for library enrichment are commercially available, including those from IDT (e.g., xGen Exome Research Panel v1.0 and v2.0 probes) and Roche (e.g., SeqCap® probes). Many available probe panels can be customized, allowing investigators to design sets of capture probes that are precisely tailored to a particular application. In addition, many kits (e.g., SeqCap EZ MedExome Target Enrichment Kit from Roche) and hybridization mixes (e.g., xGen Lockdown from IDT) that facilitate target enrichment are available for purchase.

In some cases, it may be advantageous to treat the libraries with reagents that reduce off-target capture prior to performing target enrichment. For example, libraries are commonly treated with oligonucleotides that bind to adapter sequences (e.g., xGen Blocking Oligos) or to repetitive sequences (e.g., human Cot DNA) to reduce non-specific binding to the capture probes. A detailed discussion of enrichment, and an exemplary enrichment scheme for TCR/BCR gene regions is provided below.

Amplification of Library

While it may not be required for some sequencing applications, library preparation typically includes at least one amplification step to enrich for sequencing-competent DNA fragments (i.e., fragments with adapter ligated ends) and to generate a sufficient amount of library material for downstream processing. Amplification may be performed using a standard polymerase chain reaction (PCR) technique. However, when possible, care should be taken to minimize amplification bias and limit the introduction of sequencing artifacts. This is accomplished through selection of an appropriate enzyme and protocol parameters. To this end, several companies offer high-fidelity DNA polymerases (e.g., KAPA HiFi DNA Polymerase from Roche), which have been shown to produce more accurate sequencing data. Often these DNA polymerases are purchased as part of a PCR master mix (e.g., NEBNext® High-Fidelity 2× PCR Master Mix from New England BioLabs) or as part of a kit (e.g., KAPA HiFi Library Amplification kit by Roche).

Those of skill in the art will appreciate that PCR conditions must be fine-tuned for each sequencing experiment, even when a highly-optimized PCR protocol is used. For example, depending on the initial concentration of DNA in the library and on the input requirement of the sequencer to be used, it may be desirable to subject the library to anywhere from 4-14 cycles of PCR.

In some cases, library preparation protocols include multiple rounds of library amplification. For example, in some cases, an additional round of amplification followed by PCR clean-up is performed after the libraries have been pooled.

Spike-In Control

Because cells from different experimental conditions may not yield identical amounts of RNA, sequencing data may be normalized to accurately identify changes across experimental conditions. Normalization may be useful, for example, to address global changes in transcription between different experimental conditions. A "spike-in control" may be added to the sequencing libraries for normalization. In some embodiments, the spike-in control constitutes DNA sequences that are added at a known ratio to, for instance, the specimens. The control DNA can be any DNA that is readily distinguished from the experimental cDNA during data analysis. For example, control libraries commonly comprise synthetic DNA or DNA from an organism other than the organism of interest (e.g., a PhiX spike-in control may be added to a human-derived library).

Fragmentation and Size Selection

For sequencing technologies that cannot readily analyze long DNA strands, DNA is commonly fragmented into uniform pieces prior to sequencing. The optimal fragment length depends on both the sample type and the sequencing platform to be used. For example, whole genome sequencing typically works best with fragments of DNA that are ~350 bp long, while targeted sequencing using hybridization capture (see Section 2G) works best with fragments of DNA that are ~200 bp long.

In some cases, fragmentation is performed after reverse transcription (i.e., on cDNA). Suitable methods for fragmenting DNA include physical methods (e.g., using sonication, acoustics, nebulization, centrifugal force, needles, or hydrodynamics), enzymatic methods (e.g., using NEBNext dsDNA Fragmentase from New England BioLabs), and tagmentation (e.g., using the Nextera™ system from Illumina).

In other cases, fragmentation is performed prior to reverse transcription (i.e., on RNA). In addition to the fragmentation methods that are suitable to DNA, RNA may also be fragmented using heat and magnesium (e.g., using the KAPA Hyper Prep Kit from Roche).

A size selection step may subsequently be performed to enrich the library for fragments of an optimal length or range of lengths. Traditionally, size selection was accomplished by separating differentially sized fragments using agarose gel electrophoresis, cutting out the fragments of the desired sizes, and performing a gel extraction (e.g., using a MinElute Gel Extraction Kit™ from Qiagen). However, size selection is now commonly accomplished using magnetic bead-based systems (e.g., AMPure XP™ from Beckman Coulter, ProNex® Size-Selective Purification System from Promega).

Sequencing Adapter Ligation

Prior to sequencing, the cDNA fragments are ligated to sequencing adapters. Sequencing adapters are short DNA oligonucleotides that contain (1) sequences needed to amplify the cDNA fragment during the sequencing reaction, and (2) sequences that interact with the NGS platform (e.g., the surface of the Illumina flow-cell or Ion Torrent beads). Accordingly, adapters must be selected based on the sequencing platform that is to be used.

Libraries from multiple samples are commonly pooled and analyzed in a single sequencing run (see "pooling," below). To track the source of each cDNA in a pooled sample, a unique molecular barcode (or combination of multiple barcodes) is included in the adapters that are ligated to the cDNA fragments in each library. During the sequencing reaction, the sequencer reads this barcode sequence in addition to the cDNA's biological base sequence. The barcodes are then used to assign each cDNA to its sample of origin during data analysis, a process termed "demultiplexing".

The indexing strategy used for a sequencing reaction should be selected based on the number of pooled samples and the level of accuracy desired. For example, unique dual indexing, in which unique identifiers are added to both ends of the cDNA fragments, is commonly used to ensure that libraries will demultiplex with high accuracy. Adapters may also include unique molecular identifiers (UMIs), short sequences, often with degenerate bases, that incorporate a unique barcode onto each molecule within a given sample library. UMIs reduce the rate of false-positive variant calls and increase sensitivity of variant detection by allowing true variants to be distinguished from errors introduced during library preparation, target enrichment, or sequencing. Many index sequences and adapter sets are commercially available including, for example, SeqCap Dual End Adapters from Roche, xGen Dual Index UMI Adapters from IDT, and TruSeq UD Indexes from Illumina.

Library Clean-Up

Following PCR, the amplified DNA is typically purified to remove enzymes, nucleotides, primers, and buffer components that remain from the reaction. Purification is commonly accomplished using phenol-chloroform extraction followed by ethanol precipitation or using a spin column that contains a silica matrix to which DNA selectively binds in the presence of chaotropic salts. Many column-based PCR cleanup kits are commercially available including, for example, those from Qiagen (e.g., MinElute PCR Purification Kit), Zymo Research™ (DNA Clean & Concentrator™-5), and Invitrogen (e.g., PureLink™ PCR Purification Kit). Alternatively, purification may be accomplished using paramagnetic beads (e.g., Axygen™ AxyPrep Mag™ PCR Clean-up Kit).

Pooling

To keep sequencing cost-effective, clinical laboratory technicians or researchers often pool together multiple libraries, each with a unique barcode (see "sequencing adapter ligation," above), to be sequenced in a single run. The sequencer to be used and the desired sequencing depth should dictate the number of samples that are pooled. For example, for some applications it is advantageous to pool fewer than 12 libraries to achieve greater sequencing depth, whereas for other applications it may be advisable to pool more than 100 libraries.

If multiple libraries are sequenced in a single run, care should be taken to ensure that the sequencing coverage is roughly equal for each library. To this end, an equal amount of each library (based on molarity) should be pooled. Further, the total molarity of the pooled libraries must be compatible with the sequencer. Thus, it is important to accurately quantify the DNA in the libraries (e.g., using the methods discussed in "Quality Control," below) and to perform the necessary calculations before pooling the libraries. In some cases, to achieve a suitable total molarity, it may be necessary to concentrate the pooled libraries, e.g., using a vacufuge.

In various examples, pooling is performed twice. In some examples, sequencer adapter ligation and pooling (for example, pooling approximately 5-10 samples) are performed before enrichment/library amplification and a second pooling step is performed after library clean-up.

Quality Control (cDNA Library Integrity, Fragment Size)

Prior to sequencing, libraries may be evaluated to ensure that they comprise DNA of sufficient quantity and quality to generate useful sequencing results. To verify that the concentration of the library is sufficient for loading on the sequencer, the DNA may be quantified. Commonly used methods of DNA quantification include gel electrophoresis, UV spectrophotometry (e.g., NanoDrop®), fluorometry (e.g., Qubit™, Picofluor™), real-time PCR (also known as quantitative PCR), or droplet digital emulsion PCR (ddPCR). DNA quantification is often aided by the use of dyes and stains, of which an extensive assortment is commercially available (e.g., ethidium bromide, SYBR Green, RiboGreen®). Notably, given that the recommended input range is very narrow for NGS, it is preferable that a highly precise method of quantitation is used to verify that the concentration of the final library is suitable.

Additionally, the fragment size distribution of the final library should be assessed to verify that the length of the fragments is suitable for sequencing. Traditionally, fragment size distribution was determined by running out sample on an agarose gel. However, more advanced capillary electrophoretic methods (e.g., Bioanalyzer®, TapeStation®, Fragment Analyzer™, all from Agilent) that require less sample input are now more commonly employed. Conveniently, these methods can be used to analyze both the fragment size and the concentration of the DNA.

Clonal Amplification

To sequence a library, the library is applied to a device, typically a flow cell (Illumina) or chip (Ion Torrent), in which the sequencing chemistry occurs. These devices are decorated with short oligonucleotides that are complementary to the adapter sequences, allowing the cDNAs in the library to attach to the device. Prior to sequencing, the cDNAs are subjected to clonal amplification (e.g., by cluster generation (Illumina) or by microemulsion PCR (Ion Torrent)), which generates clusters of many copies of each cDNA on the surface of the device, thereby amplifying the signal produced by each cDNA during the sequencing reaction. Often clonal amplification is performed using a commercially available kit (e.g., Paired-end Cluster Kit from Illumina). Following clonal amplification, the library is ready for sequencing.

Exemplary Enrichment of TCR/BCR Gene Regions

In some embodiments, a plurality of nucleic acid probes (for example, a hybrid-capture probe set) is used to enrich one or more target sequences in a nucleic acid sample (for example, an isolated nucleic acid sample or a nucleic acid sequencing library), for example, where one or more target sequences is informative for TCR/BCR profiling. Probes may be designed and created in accordance with methods known in the art. In some embodiments, a TCR/BCR probe set is obtained according to the methods of example 1. In some embodiments, the probe set includes probes targeting one or more gene loci, e.g., exon or intron loci. In some embodiments, the probe set includes probes targeting one or more loci not encoding a protein, for example, regulatory loci, miRNA loci, and other non-coding loci, e.g., that have been found, for example, to be associated with one or more particular disease or medical conditions (for example cancer). In some embodiments, the plurality of loci include at least 25, 50, 100, 150, 200, 250, 300, 350, 400, 500, 750, 1000, 2500, 5000, or more human genomic loci.

Generally, probes for enrichment of nucleic acids (e.g., complementary DNA, cDNA, generated from nucleic acids extracted or isolated from a biological specimen, including extracted or isolated RNA) include DNA, RNA, or a modified nucleic acid structure with a base sequence that is complementary to a locus of interest. For instance, a probe designed to hybridize to a locus in a cDNA molecule can contain a sequence that is complementary to either strand, because the cDNA molecules may be double stranded. In some embodiments, each probe in the plurality of probes includes a nucleic acid sequence that is identical or complementary to at least 10, at least 11, at least 12, at least 13, at least 14, or at least 15 consecutive bases of a locus of interest. In some embodiments, each probe in the plurality of probes includes a nucleic acid sequence that is identical or complementary to at least 20, 25, 30, 40, 50, 75, 100, 150, 200, or more consecutive bases of a locus of interest.

By way of example but not by way of limitation, probe sequences may be selected in accordance with the methods set forth in FastPCR Software for PCR Primer and Probe Design and Repeat Search (Kalendar et al., 2009 Genes, Genomes, and Genomics, 3 (Special Issue 1), pp. 1-14) which is incorporated by reference herein.

Targeted-panels provide several benefits for nucleic acid sequencing. In one example, panels targeting genes with high variability among individual subjects, humans, or even cells within subjects or humans (including TCR and BCR genes) may facilitate bioinformatics processing to determine the sequences of those genes. For example, if a "whole exome" or targeted sequencing panel is not generating a sufficient number of sequencing reads mapping to the high-variable genes, probes targeting the high-variable genes may be added to the whole exome or targeted sequence panel probes to increase the number of reads mapping to high-variable genes.

In some embodiments, the gene panel is a whole-exome panel that analyzes the exomes of a biological sample. In some embodiments, the gene panel is a whole-genome panel that analyzes the genome of a specimen. In some embodiments, the gene panel is a whole-transcriptome panel that analyzes the transcriptome of a specimen. In some embodiments, the gene panel is a targeted whole-transcriptome panel that analyzes the transcriptome of a specimen. In some embodiments, the gene panel is used in conjunction with a TCR/BCR gene panel (for example, to provide clinical decision support related to immunological profiles or immunomes).

In some embodiments, the probes of a panel include additional nucleic acid sequences that do not share any homology to the loci of interest. For example, in some embodiments, the probes also include nucleic acid sequences containing an identifier sequence, e.g., a unique molecular identifier (UMI), e.g., that is unique to a particular sample or subject. Examples of identifier sequences are described, for example, in Kivioja et al., 2011, Nat. Methods 9(1), pp. 72-74 and Islam et al., 2014, Nat. Methods 11(2), pp. 163-66, which are incorporated by reference herein. Similarly, in some embodiments, the probes also include primer nucleic acid sequences useful for amplifying the nucleic acid molecule of interest, for example using the polymerase chain reaction (PCR). In some embodiments, the probes also include a capture sequence designed to hybridize to an anti-capture sequence for recovering the nucleic acid molecule of interest from the sample.

Likewise, in some embodiments, the probes each include a non-nucleic acid affinity moiety covalently attached to nucleic acid molecule that is complementary to the loci of interest, for recovering the nucleic acid molecule of interest. Non-limited examples of non-nucleic acid affinity moieties include biotin, digoxigenin, and dinitrophenol. In some embodiments, the probe is attached to a solid-state surface or particle, e.g., a dip-stick or magnetic bead, for recovering the nucleic acid of interest. In some embodiments, the methods described herein include amplifying the nucleic acids that bound to the probe set prior to further analysis, e.g., sequencing. Methods for amplifying nucleic acids, e.g., by PCR, are well known in the art.

An enrichment probe set for TCR/BCR gene regions (a TCR/BCR gene panel) may include probes targeting one or more of the TCR and/or BCR genes or gene regions. The probes may target TCR and BCR gene segments located in the V, D, J, and constant regions. The probes may target the gene segments responsible for TCR alpha, beta, gamma, and delta chains. The probes may target the gene segments responsible for BCR kappa, lambda, and heavy chains, as well as multiple B cell receptor constant region isotype variants (such as IgM, IgG, IgA, IgD and IgE).

The targets in the constant regions may be adjacent to the site of V/D/J-recombination. For example, the targets may exclude the 1200 bp region downstream of VDJ regions. For example, the probe design may be arranged so as to remove all but the most proximal probes covering each of the constant regions, for example, all but the 2, 3, 4, or 5 most proximal probes. In some embodiments, the probe design is arranged such that all but the 3 most proximal probes are removed. This arrangement provides enough signal to capture RNA fragments containing the VDJ junction, as well as identify and distinguish the different constant regions from one another, in order to determine whether the region is associated with IgG, IgM, or IgA. Annotated sequences are known in the art. See, for example, IGMT database, at http://www.imgt.org.

In some embodiments, the target genes for TCR/BCR enrichment via a TCR/BCR gene panel (e.g. a panel comprising pools of hybrid-capture probes directed to a portion of one or more TCR genes and one or more BCR genes) may include one or more of IGKV1OR1-1, IGKV2-18, IGKV3OR2-268, IGKC, IGKJ5, IGKJ4, IGKJ3, IGKJ2, IGKJ1, IGKV4-1, IGKV5-2, IGKV7-3, IGKV2-4, IGKV1-5, IGKV1-6, IGKV3-7, IGKV1-8, IGKV1-9, IGKV3-11, IGKV1-12, IGKV1-13, IGKV3-15, IGKV1-16, IGKV1-17, IGKV3-20, IGKV6-21, IGKV2-24, IGKV1-27, IGKV2-28, IGKV2-29, IGKV2-30, IGKV1-33, IGKV1-37, IGKV1-39, IGKV2-40, IGKV2D-40, IGKV1D-39, IGKV1D-37, IGKV1D-33, IGKV2D-30, IGKV2D-29, IGKV2D-28, IGKV2D-26, IGKV2D-24, IGKV6D-21, IGKV3D-20, IGKV2D-18, IGKV6D-41, IGKV1D-17, IGKV1D-16, IGKV3D-15, IGKV1D-13, IGKV1D-12, IGKV3D-11, IGKV1D-42, IGKV1D-43, IGKV1D-8, IGKV3D-7, IGKV1OR2-118, IGKV1OR2-1, IGKV1OR2-2, IGKV1OR2-3, IGKV1OR2-9, IGKV2OR2-7D, IGKV1OR2-11, IGKV1OR2-108, TRGC2, TRGJ2, TRGJP2, TRGC1, TRGJP, TRGJP1, TRGV11, TRGV10, TRGV9, TRGVA, TRGV8, TRGV5P, TRGV5, TRGV4, TRGV3, TRGV2, TRGV1, TRBV1, TRBV2, TRBV3-1, TRBV4-1, TRBV5-1, TRBV6-1, TRBV7-1, TRBV4-2, TRBV6-2, TRBV7-2, TRBV6-4, TRBV7-3, TRBV5-3, TRBV9, TRBV10-1, TRBV11-1, TRBV12-1, TRBV10-2, TRBV11-2, TRBV12-2, TRBV6-5, TRBV7-4, TRBV5-4, TRBV6-6, TRBV5-5, TRBV6-7, TRBV7-6, TRBV5-6, TRBV6-8, TRBV7-7, TRBV5-7, TRBV7-9, TRBV13, TRBV10-3, TRBV11-3, TRBV12-3, TRBV12-4, TRBV12-5, TRBV14, TRBV15, TRBV16, TRBV17, TRBV18, TRBV19, TRBV20-1, TRBV21-1, TRBV23-1, TRBV24-1, TRBV25-1, TRBV26, TRBV27, TRBV28, TRBV29-1, TRBD1, TRBJ1-1, TRBJ1-2, TRBJ1-3, TRBJ1-4, TRBJ1-5, TRBJ1-6, TRBC1, TRBJ2-1, TRBJ2-2, TRBJ2-2P, TRBJ2-3, TRBJ2-4, TRBJ2-5, TRBJ2-6, TRBJ2-7, TRBC2, TRBV30, IGLV8OR8-1, TRBV200R9-2, TRBV21OR9-2, TRBV23OR9-2, TRBV24OR9-2, TRBV26OR9-2, TRBV29OR9-2, IGKV1OR9-2, IGKV1OR-2, IGKV1OR9-1, IGKV1OR-3, IGKV1OR10-1, IGHG2, TRAV1-1, TRAV1-2, TRAV2, TRAV3, TRAV4, TRAV5, TRAV6, TRAV7, TRAV8-1, TRAV9-1, TRAV10, TRAV11, TRAV12-1, TRAV8-2, TRAV8-3, TRAV13-1, TRAV12-2, TRAV8-4, TRAV13-2, TRAV14DV4, TRAV9-2, TRAV12-3, TRAV8-6, TRAV16, TRAV17, TRAV18, TRAV19, TRAV20, TRAV21, TRAV22, TRAV23DV6, TRDV1, TRAV24, TRAV25, TRAV26-1, TRAV8-7, TRAV27, TRAV29DV5, TRAV30, TRAV26-2, TRAV34, TRAV35, TRAV36DV7, TRAV38-1, TRAV38-2DV8, TRAV39, TRAV40, TRAV41, TRDV2, TRDD1, TRDD2, TRDD3, TRDJ1, TRDJ4, TRDJ2, TRDJ3, TRDC, TRDV3, TRAJ61, TRAJ60, TRAJ59, TRAJ58, TRAJ57, TRAJ56, TRAJ55, TRAJ54, TRAJ53, TRAJ52, TRAJ51, TRAJ50, TRAJ49, TRAJ48, TRAJ47, TRAJ46, TRAJ45, TRAJ44, TRAJ43, TRAJ42, TRAJ41, TRAJ40, TRAJ39, TRAJ38, TRAJ37, TRAJ36, TRAJ35, TRAJ34, TRAJ33, TRAJ32, TRAJ31, TRAJ30, TRAJ29, TRAJ28, TRAJ27, TRAJ26, TRAJ25, TRAJ24, TRAJ23, TRAJ22, TRAJ21, TRAJ20, TRAJ19, TRAJ18, TRAJ17, TRAJ16, TRAJ14, TRAJ13, TRAJ12, TRAJ11, TRAJ10, TRAJ9, TRAJ8, TRAJ7, TRAJ6, TRAJ5, TRAJ4, TRAJ3, TRAJ2, TRAJ1, TRAC, IGHA2, IGHE, IGHG4, IGHAL IGHG1, IGHG2, IGHG3, IGHD, IGHM, IGHJ6, IGHJ3P, IGHJ5, IGHJ4, IGHJ3, IGHJ2P, IGHJ2, IGHJ1, IGHD7-27, IGHJ1P, IGHD1-26, IGHD6-25, IGHD5-24, IGHD4-23, IGHD3-22, IGHD2-21, IGHD1-20, IGHD6-19, IGHD5-18, IGHD4-17, IGHD3-16, IGHD2-15, IGHD1-14, IGHD6-13, IGHD5-12, IGHD4-11, IGHD3-10, IGHD3-9, IGHD2-8, IGHD1-7, IGHD6-6, IGHD4-4, IGHD3-3, IGHD2-2, IGHD1-1, IGHV6-1, IGHV1-2, IGHV1-3, IGHV4-4, IGHV7-4-1, IGHV2-5, IGHV3-7, IGHV3-64D, IGHV5-10-1, IGHV3-11, IGHV3-13, IGHV3-15, IGHV3-16, IGHV1-18, IGHV3-19, IGHV3-20, IGHV3-21, IGHV3-22, IGHV3-23, IGHV1-24, IGHV3-25, IGHV2-26, IGHV4-28, IGHV3-32, IGHV3-30, IGHV3-30-2, IGHV4-31, IGHV3-29, IGHV3-33, IGHV3-33-2, IGHV4-34, IGHV7-34-1, IGHV3-35, IGHV3-38, IGHV4-39, IGHV7-40, IGHV3-43, IGHV1-45, IGHV1-46, IGHV3-47, IGHV3-48, IGHV3-49, IGHV5-51, IGHV3-52, IGHV3-53, IGHV3-54, IGHV4-55, IGHV1-58, IGHV4-59, IGHV4-61, IGHV3-62, IGHV3-63, IGHV3-64, IGHV3-66, IGHV1-68, IGHV1-69, IGHV2-70D, IGHV3-69-1, IGHV1-69-2, IGHV1-69D, IGHV2-70, IGHV3-71, IGHV3-72, IGHV3-73, IGHV3-74, IGHV5-78, IGHV7-81, IGHV1OR15-9, IGHV1OR15-2, IGHV3OR15-7, IGHV1OR15-1, IGHV1OR15-3, IGHV4OR15-8, IGHV1OR15-4, IGHV3OR16-9, IGHV2OR16-5, IGHV3OR16-15, IGHV3OR16-6, IGHV3OR16-10, IGHV3OR16-8, IGHV3OR16-12, IGHV3OR16-13, IGHV3OR16-16, IGHV1OR21-1, IGKV1OR22-5, IGKV2OR22-4, IGLV4-69, IGLV10-54, IGLV1-62, IGLV8-61, IGLV4-60, IGLV6-57, IGLV11-55, IGLV5-52, IGLV1-51, IGLV1-50, IGLV9-49, IGLV5-48, IGLV1-47, IGLV7-46, IGLV5-45, IGLV1-44, IGLV7-43, IGLV1-41, IGLV1-40, IGLV5-37, IGLV1-36, IGLV2-34, IGLV2-33, IGLV3-32, IGLV3-31, IGLV3-27, IGLV3-25, IGLV2-23, IGLV3-22, IGLV3-21, IGLV3-19, IGLV2-18, IGLV3-16, IGLV2-14, IGLV3-13, IGLV3-12, IGLV2-11, IGLV3-10, IGLV3-9, IGLV2-8, IGLV2-5, IGLV4-3, IGLV3-1, IGLJ1, IGLC1, IGLJ2, IGLC2, IGLJ3, IGLC3, IGLJ4, IGLJ5, IGLJ6, IGLC6, IGLJ7, IGLC7, TRBV3-2, TRBV4-3, TRBV6-9, TRBV7-8, and TRBV5-8.

Each probe may be designed to cover only a TCR and/or BCR region, or designed to cover both a TCR and/or BCR region as well as a non-TCR/BCR region.

In some embodiments, gene regions may be expressed by gene name or by Ensembl ID. Ensembl ID may be expressed as ENSG or ENST. For example, the gene IGKV3OR2-268 may be mapped to Ensembl ID ENSG00000233999-ENSG00000233999 or ENST00000421835-ENST00000421835.

In some embodiments, probes sets for TCR/BCR profiling according to the systems and methods disclosed herein are derived according to the methods of example 1.

In some embodiments, probes may be separated into various pools (groups). In some embodiments, the pools are: 1) BCR constant region group; 2) BCR non-constant region group (VDJ); 3) TCR constant region group, 4) TCR non-constant region group (VDJ). In some embodiments, a probe set comprises at least one probe from each probe pool. In some embodiments, a probe set comprises 1-5 probes from each pool; 5-10 probes from each pool; 10-50 probes from each pool; or 100-200 probes from each pool. In some embodiments, the number of probes in each pool is different. By way of example only, in one embodiment, the probes of each group are as follows: TCR non-constant region group comprises about 100-1000 probes; the TCR constant Region group comprises about 10-50 probes; the BCR Non-constant Region group comprises about 500-2000 probes; and the BCR Constant Region group comprises about 20-100 probes. In some embodiments, a probe set comprises: a TCR non-constant region group comprising about 650 probes; a TCR constant region group comprising about 18 probes; a BCR non-constant region group comprising about 894 probes; and a BCR constant region group comprising about 45 probes.

Probe Concentration

In some embodiments, TCR/BCR hybrid capture probes may be included as part of a comprehensive genomic profiling panel. Examples include a whole exome/whole transcriptome RNAseq panel, a targeted enrichment sequencing panel, a whole-exome panel, a whole genome panel, a whole transcriptome panel, etc. In some embodiments, probes may be separated into various pools (groups). In some embodiments, the pools are: 1) BCR constant; 2) BCR non-constant (VDJ); 3) TCR constant, 4) TCR non-constant (VDJ). In some embodiments, a fifth panel, comprising a transcriptome-targeting, or other panel is included.

In some embodiments, the resulting probe set may be defined by the number of different probes in a particular pool or group of probes. By way of example, for TCR/BCR enrichments and/or profiling, probes may be grouped or pooled as TCR non-constant Region group; the TCR Constant Region group; the BCR non-constant Region group; and the BCR Constant Region group. In some embodiments, each group has the same number of probes; in other embodiments, each group has a different number of probes. In some embodiments, two or more groups have the same number of probes. By way of example only, in one embodiment, the probes of each group are as follows: TCR Non-constant Region group has 100-1000 probes; the TCR Constant Region group has 10-50 probes; the BCR Non-constant Region group has 500-2000 probes; and the BCR Constant Region group has 20-100 probes. In some embodiments, the TCR Non-constant Region group has 650 probes; the TCR Constant Region group has 18 probes; the BCR Non-constant Region group has 894 probes; and the BCR Constant Region group has 45 probes.

In some embodiments, the amount of each probe pool used in the genomic profiling panel is characterized as a ratio. For example, a first pool comprising BCR constant region probes, a second pool comprising BCR non-constant region probes, a third pool comprising TCR constant region probes, and a fourth pool comprising TCR non-constant region probes may be provided at a ratio of about 0.1-10: 0.25-25:10-1000:10-1000, or about 0.5-5:1.25-12.5:50-500: 50-500, or about 0.7-1.3:1.7-7.5:75-125:75-125, or about 1:2.5:100:100. In some embodiments, a fifth pool, comprising an exome-targeting panel is provided. In some embodiments, the ratio of the first pool, second pool, third pool, fourth pool, and fifth pool is about 0.1-10:0.25-25:10-1000: 10-1000:1-100, or about 0.5-5:1.25-12.5:50-500:50-500:5-50, or about 0.7-1.3:1.7-7.5:75-125:75-125:7-12, or about 1:2.5:100:100:10.

In some embodiments, the probe pool concentrations in the genomic profiling panel are characterized by concentrations in attomole/probe/capture (i.e. one reaction well).

By way of example, and not by way of limitation, in some embodiments, BCR constant probes=about 0.25-25, about 0.5-12.5, about 1-10, 1-5, or about 2.5 amole/probe/capture; BCR non constant probes=about 0.6-62.5, about 1-30, or about 2-20, about 5-15 or about 6.25 amole/probe/capture; TCR constant probes=about 25-500, about 30-300, about 100-300, about 200-300, or about 250 amole/probe/capture; TCR non constant probes=about 25-500, about 30-300, about 100-300, about 200-300, 250 amole/probe/capture.

By way of example, and not by way of limitation, in some embodiments, the BCR constant probes=2.5 amole/probe/ capture; the BCR non constant probes=6.25 amole/probe/ capture; the TCR constant probes=250 amole/probe/capture; and the TCR non constant probes=250 amole/probe/capture. In some embodiments, exome probes are additionally used. In some embodiments, exome probes are provided at 25 amole/probe/capture, so in some embodiments, the TCR and BCR probe pools are used at 0.1×, 0.25×, 10×, and 10× respectively, compared to the exome pool.

Reads Processing and Analysis

The sequenced reads may be processed for further analysis. In some embodiments, the processing may comprise one or more of an aligning step, an assembly step, an annotation step, and a quantification step.

In one example, the systems and methods disclosed herein receive an RNA-seq FASTQ file having raw output from the NGS sequencing pipeline, including a list of all of the reads generated by the sequencer and any quality information associated with each read.

In an optional filtering step, the systems and methods may remove amplification duplicates (for example, two or more reads derived from a PCR duplicate, the same source template, or same nucleic acid molecule). In one example, the systems and methods may utilize unique molecular identifiers (UMIs) to remove amplification duplicates. The systems and methods may remove low quality reads, or reads having a quality score below a selected threshold value.

During a TCR/BCR gene sequence assembly step, the systems and methods may provide RNA-seq FASTQ (forward read and reverse read files) to a specialized aligner and/or gene sequence assembler for repertoire-seq (rep-seq), especially a specialized aligner designed for quantifying immune receptors.

Examples of TCR and/or BCR gene sequence assembly methods are described, for example, in Landscape of tumor-infiltrating T cell repertoire of human cancers (Li et al., 2016, Nat. Genet. 48(7), pp. 725-732), Landscape of B cell immunity and related immune evasion in human cancers (Hu et al., 2019, Nat. Genet. 51(3), pp. 560-567), BASIC: BCR assembly from single cells (Canzar et al., 2017, Bioinformatics 33(3), pp. 425-427), Simultaneously inferring T cell fate and clonality from single cell transcriptomes (Stubbington et al., 2015, BioRxiv https://doi.org/10.1101/ 025676), and Antigen receptor repertoire profiling from RNA-seq data (Bolotin et al., 2017, Nat. Biotech. 35(10), pp. 908-911), which are incorporated by reference herein.

For example, paired-end reads may be aligned to a predetermined immunological receptor gene sequence or aligned to the whole genome, using identified anchor reads having a first paired end that aligns to TCR/BCR gene and a second paired end that does not. RNA-seq data in fastq files may be aligned to a reference, such as hg19, GRCh37, etc., using an alignment tool such as STAR or Kallisto. See, e.g., Nicolas L Bray, Harold Pimentel, Pall Melsted and Lior Pachter, Near-optimal probabilistic RNA-seq quantification, Nature Biotechnology 34, 525-527 (2016), doi:10.1038/nbt.3519, incorporated by reference herein; see also https://pachterlab.github.io/kallisto/(California Institute of Technology; Pasadena, Calif.). STAR, for example, may be used to prepare rna-seq data for deconvolution of immune CDR3 sequences. See Dobin et al, STAR: ultrafast universal RNA-seq aligner, Bioinformatics 2013 January; 29(1): 15-21, incorporated by reference herein.

Reads may be filtered to those mapped to BCR or TCR regions. In one example, there are three TCR regions; for the hg19 reference genome, for instance, the coordinates may include TCRα (chr. 14: 22,090,057-23,021,075), TCRβ (chr. 7: 141,998,851-142,510,972) and TCRγ (chr. 7: 38,279,625-38,407,656). The TCRδ gene region (chr. 14: 22,891,537-22,935,569) is embedded in the TCRα region, and therefore the reads for this region may be obtained along with those for TCRα. Counts of mapped reads in each non-constant gene region for the TCRα and TCRβ chains may be used to estimate the usage of different genes and PCA. In one example, there are three BCR regions; for the hg19 reference genome, for instance, the coordinates may include IGH (chr. 14: 106,032,614-107,288,051); IGK (chr. 2: 89,890,568-90,274,235); IGL (chr. 22: 22,380,474-23,265,085).

Of all the mapped reads extracted in the above step, for the subset that had unmapped mates, which were potentially generated from the CDR3 regions and could not be aligned to the reference genome, the reads in the BAM file may be screened and searched for the mate for each such read until all mapped reads in the TCR regions were paired. The unmapped reads found in this step, which may be associated with CDR3 regions, may be used for CDR3 de novo assembly.

As another example, each read may be aligned to a predetermined immunological receptor gene sequence. A plurality of anchor windows may be identified, each window being associated with a plurality of reads that exceed a threshold value. Reads that align to a region of an anchor window, called "anchor reads," may be used to generate an anchor sequence from the anchor reads. The anchor windows, the anchor sequences, and the un-aligned reads may be provided to an assembly process to generate a contig sequence. Each contig sequence may be annotated or otherwise associated with at least one immunological gene region class selected from one of V, D, J, and C. Optionally, portions of each contig sequence located outside of CDR3 region may be deleted. The number of contig sequences annotated and/or associated with each class may be quantified.

In some embodiments, to for instance, assist in the recognition of one or more antigens, at least one read that aligns to the predetermined immunological receptor gene sequence may be to a CDR3 region. At least one read that aligns to the predetermined immunological receptor gene sequence may be to a CDR3-adjacent region.

In one example, the systems and methods include an assembler that outputs unique receptor sequence non-constant regions, including immune receptor clonotypes. In various embodiments, the assembler disclosed herein outputs a list of the CDR3 sequences at their nucleotide level and also shows read quantity (for example, the number of reads associated with each CDR3 sequence). In alternative embodiments, output sequences may correspond to entire or partial CDR1, CDR2, and/or CDR3 portions of TCR and/or BCR genes. In various embodiments, the assembler may output data associated with between zero and multiple tens of thousands of different CDR3 sequences assembled from the sequencing reads. In one example, the complementarity determining region 3 (CDR3) is a region where immune genes recombine during VDJ recombination.

Specimens may have varying quantities of immune cells. Some, such as glioblastoma specimens, may have few or no immune infiltrates. For such specimens, the number of output CDR3 sequences will be very low. Other specimens or tumors will have many immune cells. In some instances, the specimen includes immune cell cancers or a specimen from a patient having an active adaptive immune response to an infection or another class of disease state. Another example would be a large immune cell population originating from a lymph node with a very diverse collection of CDR3 sequences (for example, 5,000; 10,000; 20,000; 30,000; etc. sequences).

In various embodiments, the output of the assembler is a table wherein each row is a sequence. Each sequence may have a number of nucleotides in the low hundreds or even less than a hundred nucleotides. For each sequence, the systems and methods may also output a confidence or quality metric.

In one example, each sequence may be associated with a read quantity. In various embodiments, the quantity may reflect the number of reads and/or the proportion or percentage of total reads detected in the specimen that align to that sequence.

The systems and methods return a list of genetic segment identifiers that comprise the CDR3 sequence, for example, the genetic segments that were most likely to have recombined during VDJ recombination to form a particular CDR3 sequence. In one embodiment, for each genetic segment (the V segment, the J segment, and if applicable, the D segment), the systems and methods return a list of multiple likely genetic segment identifiers, for example, identifiers for the top 3 most likely genetic segments.

In various embodiments, the systems and methods may filter sequences to remove any sequences predicted to be non-productive. Non-productive sequences may include sequences having a detected frame-shift mutation, premature stop-codon, or partially assembled clonotype.

The systems and methods may calculate secondary statistics based on the read quantities associated with the sequences in the output table or the filtered output table. In various embodiments, categories of secondary statistics may include richness (for example, how many different clonotypes or unique sequences are detected in the specimen and/or represented in the table) and evenness (for example, whether the read quantities for all of the clonotypes are approximately equal or how skewed the distribution of the read quantities are to one or a few clones). Examples of statistics include Shannon entropy, Simpson index, GINI index, etc. For an example of statistical methods that may be applied to the output table data, see Bolotin et al, Nat Biotechnol 35, 908-911 (2017). https://doi.org/10.1038/nbt.3979, which is incorporated by reference herein in its entirety.

The selection of the statistical calculation may be based on various criteria. In one example, the criteria may include: the distribution of the value calculated for multiple specimens in a database, the range of possible output values, and/or the reproducibility or similarity of the statistic for technical or biological duplicates. For example, if the value of a secondary statistic has a small distribution among multiple specimens, it may be difficult to distinguish one specimen from another. The distribution may be measured by a variety of statistical methods. In terms of possible value ranges, Shannon entropy is not bound to a range of 0-1, which may be advantageous in various embodiments. In other embodiments, a statistic that is bound to a range (for example, of 0-1), may be desired. The technical duplicates may be multiple NGS runs of the same specimen and the biological duplicates may be multiple slices of the same biopsy, and reproducibility may be calculated by comparing the value of the statistic calculated for each duplicate. The comparison may include calculating a standard deviation, standard error of the mean, etc.

The systems and methods may also determine the protein structure that is associated with each sequence. The systems and methods may cluster sequences according to the similarity of their associated protein structures. The systems and methods may also analyze the protein structure, including any antigens and/or human leukocyte antigen (HLA)/major histocompatibility complex (MEW) molecules that are predicted to bind to the TCR or BCR, especially antigens that are relevant to the patient's disease state (for example, antigens generated during infection by a specific pathogen, neoantigens generated by cancer cells, antigens or allergens that cause allergic reactions, or antigens that cause autoimmune diseases). The analysis may include combining multiple sequences or predicting pairing of two or more sequences. The sequences may be predicted to be paired sequences from the same heterodimer protein, for example, a heavy chain sequence and a light chain sequence, an alpha chain sequence and a beta chain sequence, a gamma chain sequence and a delta chain sequence, etc. In various embodiments, two sequences may be predicted to be associated with the same heterodimer protein if the read quantities associated with each sequence is approximately equal. For example, if 30% of the detected heavy chain reads are sequence A and 28% of the detected light chain reads are sequence alpha, sequences A and alpha may be predicted to be paired. These predicted pairings may be confirmed by the use of single-cell sequencing or other methods for analyzing TCR or BCR genetic sequences and/or protein sequences. For examples of analyses of TCR or BCR protein structures, see Glanville et al, Nature 547, 94-98 (2017). https://doi.org/10.1038/nature22976, which is incorporated by reference herein in its entirety.

The systems and methods may include storing TCR/BCR sequencing results in a database, and TCR and/or BCR sequences may be associated with additional molecular data (for example, HLA sequences, genomic, transcriptomic, epigenomic, proteomic, metabolomic, etc. data) and/or clinical data (for example, demographic information, diagnosis data, disease severity, immune response, phenotype, therapy response data, etc.). The systems and methods may access a similar database to determine whether TCR/BCR sequences are associated with particular molecular or clinical data characteristics (for example, the presence of a variant in genomic data or a particular response to a therapy or class or therapies, for example, immunotherapy).

The systems and methods may include discovering TCR or BCR sequences (individual sequences or groups of sequences) from pools of patients or from individual patient data that may be therapeutically effective to inform the development of therapies based on antibodies, vaccines, CAR-Ts, CAR-NKs, ImmTACs, etc.

The systems and methods may include designing experiments to test therapy responses associated with one or more detected sequences. The experiments may be biochemical assays, organoid experiments, t-cell and organoid co-culturing experiments, etc.

The systems and methods may be used for differential gene expression determination. One use of RNA-seq data, including data derived using a TCR/BCR enrichment panel, is to identify genes that are differentially expressed between two or more experimental groups. For example, RNA sequencing data can be used to identify genes that are expressed at significantly higher or lower levels in patients (for example, patients having cancer, autoimmune disease(s), an infection, allergies and/or transplantation requirement) as compared to healthy individuals. This may be accomplished by performing a statistical analysis to compare the normalized read count of each gene across the different experimental groups. The aim of this analysis is to determine whether any observed difference in read count is significant, i.e., whether it is greater than what would be expected (enriched) compared to differences caused by natural random variation.

Several data processing steps may be performed to prepare the raw sequencing data for analysis. Sequencing data is typically supplied in FASTQ format, in which each sequencing read is associated with a quality score. First, the data is processed to remove sequencing artifacts, e.g., adaptor sequences and low-complexity reads. Sequencing errors are identified based on the read quality score and are removed or corrected. Publicly available tools, such as TagDust, SeqTrim, and Quake, can be used to perform these "data grooming" steps.

During the next stage of data processing, the reads are aligned to a reference genome using an alignment tool. Several publicly available tools can be used for this step including, for example, TopHat, Cufflinks, and Scripture. These programs can be used to reconstruct transcripts, identify variants, and quantitate expression levels for each transcript and gene.

After the reads have been aligned and quantitated, a differential expression analysis may be performed. Statistical methods that are commonly used for differential expression analysis include those based on negative binomial distributions (e.g., edgeR and DESeq) and Bayesian approaches based on a negative binomial model (e.g., baySeq and EBSeq).

Reports

Figure 1B:

FIGS. 1A-B illustrate an example report.

The results of TCR/BCR profiling may be displayed to an ordering clinician or other individual. Results may be provided in a number of formats, such as a gene-by-gene or segment-by-segment basis. Results may also be aggregated. Results may include immune repertoire clonality, such as estimated clonality of BCR or TCR sequences in a specimen. One example result is displayed in the form of a report excerpt shown in FIGS. 1A-1B. The excerpt is from a report for a cancer specimen, but similar reports may be generated for other disease states, infections, or medical conditions.

Summary Tab

This section may include multiple data fields and/or conclusions related to those data fields, based on TCR/BCR sequencing data. Data fields may include estimated tumor purity (burden), estimated immune cell composition (percentage of immune cells in sample that are B cells, macrophages, T cells, CD4 T cells, CD8 T cells, CD8 T cell subtypes, NK cells, etc.), estimated immune infiltration percentage, and immune receptor clonality percentages.

Immune Repertoire Tab

This section includes a profile of the immune repertoire generated by leveraging TCR/BCR sequencing data. For hematological malignancies this profile could potentially be used to highlight and track dominant clonotypes, and this information or related conclusions may be included in the report. For patients that have received CAR therapy, this profile could also be used to track abundance of that CAR product longitudinally, and this information or related conclusions may be included in the report.

The bar chart: if the sequences detected in a specimen are mostly clonal or from one clone, that can indicate expansion of a particular V(D)J combination. In various embodiments, thresholds may be used to classify each CDR3 sequence as clonal, oligoclonal, or polyclonal. For example, CDR3 sequences associated with less than 25 reads may be classified as polyclonal, CDR3 sequences associated with 25 to 99 reads may be classified as oligoclonal, and CDR3 sequences associated with 100 or more reads may be classified as clonal. In the bar chart, the percentage associated with each category indicates the percentage of reads associated with CDR3 sequences that are classified into each category. In another example, if there is one dominant clone expected for a disease condition, that clone's CDR3 sequence may be the only sequence classified as clonal. The CDR3 sequence table: the report may include a table or list that indicates the most common VDJ or VJ combinations (in one example, there may be one/a few V(D)J combination(s) that make up the majority of the sequences detected in the specimen).

In this example, the most common heavy chain sequence accounts for approximately 40% of the detected heavy chain sequences and the most common light chain sequence accounts for approximately 35% of the detected light chain sequences. These two sequences represent a similar percentage of the total reads for their respective chain types, and may be predicted to be paired in the same protein heterodimer based on the similar percentages.

The report may include interpretations of any statistics calculated from the read quantities. For example, if the evenness is skewed such that a sequence has a proportion of reads that exceed a read threshold (for example, 10%, 20%, 50%, or more of reads), this may indicate that an immune cell population expanded. The sequence associated with a read quantity that exceeds a read threshold may indicate a TCR or BCR that recognizes or binds to an infectious pathogen (or antigen derived from a pathogen), an allergen, a neoantigen, or cancer cell. The report may include antigens and/or HLA sequences that are predicted to bind to a TCR or BCR sequence or combination of sequences and may further include any association between an antigen and genomic data associated with the specimen.

The report may include treatment(s) and/or clinical trial(s) matched to the patient (or organoid) based on the TCR/BCR profile. For example, matched treatment(s) and/or clinical trial(s) may include adoptive cell therapy, cancer vaccine, immuno-oncology drugs, immunotherapy, checkpoint blockade, immune checkpoint inhibitors, chemotherapy, a cancer specific treatment, vaccine, antivirals, antibiotics, antiparasitics, antifungals, one or more antibodies (could be monoclonal, polyclonal, etc., could be isolated from another patient after recovery from infection), anti-histamines, nasal sprays, antileukotriene, leukotriene modifier, leukotriene receptor antagonist, allergy shots or another method to induce isotype switching from an allergenic IgE to a more tolerable IgG, anti-inflammatory treatment, steroids, oral corticosteroid, prednisone, anti-rheumatic drugs (DMARDS), biologics that target common anti-inflammatory pathways, TNF pathway antagonists (including Remicade), B cell depletion (including Rituxan), immunosuppressant, insulin, bone marrow transplant, anti-inflammatory dietary restrictions, physical therapy, surgery, topical medication, and/or topical scalp medication.

The report may include conclusions related to CAR-T cell, CAR-NK cell, CAR-M cell, another CAR cell or ImmTAC monitoring (for example, whether the CAR cells are present in high numbers) in the patient, based on detected sequences. The report may include conclusions related to the status of a heme cancer (for example, a lymphoid or myeloid cancer, a lymphoma, etc.) and/or minimal or measurable residual disease (MRD), based on the expanded immune cells detected in the patient.

The report may include predicted therapy responses associated with TCR or BCR sequences detected in a specimen. For example, predicted immunotherapy response based on infiltrating lymphocytes detected or predicted to be present in a tumor specimen.

The report may exclude sequences for various reasons. For example, if a sequence is known not to be relevant to the patient's disease state, the sequence may not be included in the report.

In one example, a patient may have a genomic alteration that is a documented antigen or neoantigen. In one example, a TCR/BCR profile may be generated for a patient having colorectal cancer, a KRAS P12D alteration, and an HLA C08.02 allele known to present this altered KRAS peptide. The TCR/BCR profile may be analyzed for CDR3 sequences likely to recognize the altered KRAS peptide (see the world wide web and the NCBI NLM database nih.gov/pmc/articles/PMC5178827/).

In one example, a TCR/BCR profile may be generated for a patient having multiple myeloma and a RAS mutation. The TCR/BCR profile may be analyzed for CDR3 sequences likely to recognize the altered RAS peptide.

In one example, a patient's TCR/BCR profile indicates that the patient's repertoire is skewed (for example 90% of the sequencing reads are associated with the top clone). This patient could be monitored over time with Longitudinal testing to determine if the clone is consistent over time. In one example, the top clone is associated with 50% of sequencing reads at time x, and only 20% of sequencing reads at a later time, which could imply that therapy the patient is receiving has some efficacy. If the clone is lower than the limit of detection of the systems and methods disclosed herein, the patient's report may indicate a follow-up MRD assay with high sensitivity and may include information about confounders/confounding factors (including biopsy site, variation in sample, etc.).

The report may include various data visualizations, especially visualizations of repertoire sequencing (rep-seq) data, immunological profiling data, and/or TCR or BCR sequence data. Examples include Circos plots, heatmaps or histograms/distribution plots (for example, number of reads associated with each V, D, or J gene family, number of instances of an amino acid in a primary protein structure predicted from a TCR or BCR sequence, % of rearrangements vs. CDR3 length, subclasses of IgG/IgM/etc., etc.), box and whisker plots (for example, for diversity scores or mutation frequencies of various specimens or groups of specimens), transition tables demonstrating frequency of each possible base (nucleotide) change, plots showing genetic locations of mutations (base changes), etc. For examples of data visualizations relevant to rep-seq data, see IJSpeert et al, J Immunol 2017, 198:4156-4165, doi:

10.4049/jimmunol.1601921 and Ni Q, Zhang J, Zheng Z, Chen G, Christian L, Grönholm J, Yu H, Zhou D, Zhuang Y, Li Q-J and Wan Y (2020) VisTCR: An Interactive Software for T Cell Repertoire Sequencing Data Analysis. Front. Genet. 11:771. doi: 10.3389/fgene.2020.00771, the contents of each are incorporated herein by reference in their entirety for all purposes.

The report may include antigens or epitopes that are predicted to be recognized by the TCR or BCR sequences included in the report. These predicted antigens or epitopes may be used in vaccine development. For example, the most prevalent antigen or epitope may be included as part of a vaccine, which may further include an adjuvant.

For example, coronavirus epitopes (antigens recognized by BCRs or TCRs) may include those listed in Table 1:

TABLE 1

| T cell type | Amino acid positions | SARS-CoV-2 amino acid sequence | SARS-CoV-1 amino acid sequence |
|---|---|---|---|
| CD4 | NP 81-95 | DDQIGYYRRATRRIR | DDQIGYYRRATRRVR |
| CD4 | NP 266-280 | KAYNVTQAFGRRGPE | KQYNVTQAFGRRGPE |
| CD4 | NP 291-305 | LIRQGTDYKHWPQIA | LIRQGTDYKHWPQIA |
| CD4 | NP 301-315 | WPQIAQFAPSASAFF | WPQIAQFAPSASAFF |
| CD4 | NP 51-65 | SWFTALTQHGKEDLK | SWFTALTQHGKEELR |
| CD4 | NP 101-120 | MKDLSPRWYFYYLGT GPEAG | MKELSPRWYFYYLGT GPEAS |
| CD4/CD8 | NP 321-340 | GMEVTPSGTWLTYTG AIKLD | GMEVTPSGTWLTYHG AIKLD |
| CD4 | NSP7 21-35 | RVESSSKLWAQCVQL | RVESSSKLWAQCVQL |

In this table, each row represents a SARS-CoV-2 peptide and corresponding SARS-CoV-1 peptide that could be recognized by a T cell receptor. The table includes information about the T cell type (CD4 or CD8) of the TCR that recognizes the peptide and the protein/amino acid position of the peptide origin within the viral protein. See, Le Bert, N., Tan, A. T., Kunasegaran, K. et al. SARS-CoV-2-specific T cell immunity in cases of COVID-19 and SARS, and uninfected controls. Nature 584, 457-462 (2020). https://doi.org/10.1038/s41586-020-2550-z, the contents of which are incorporated herein by reference in their entirety for all purposes.

Table 2 includes human coronavirus peptides and corresponding amino acid positions and the source viral protein for each peptide. Peptides in the same row are homologous peptides from distinct coronaviruses. See, Mateus et al, DOI: 10.1126/science.abd3871, the contents of which are incorporated herein by reference in their entirety for all purposes. In the Table, column 1 "VP" is viral protein; column 2 "1st AA" is the position of first amino acid.

TABLE 2

| 1VP | 1st AA | SARS-CoV-2 sequence | 229E sequence | HKU1 sequence | NL63 sequence | OC43 sequence |
|---|---|---|---|---|---|---|
| insp6 | 3801 | NRYFRLTL GVYDYLV | NRFCKCTL GVYDFCV | NSVFRMPM GVYNYKI | NRFFKCTM GVYDFKV | NSLFRM PLGVYN YKI |
| nsp4 | 3151 | KHFYWFFS NYLKRRV | KSFSTFES AYMPIAD | NHVLWLFS YCRKIGV | GHFNEEFY NFLRLRG | NHAFWV FSYCRK LGT |
| nsp2 | 276 | PLNSIIKT IQPRVEK | PCPSILKV IDGGKIW | PSNSIVCR FDTRVLN | LLSSLTLT VKFVVES | PLLENI DYFNMR RAK |
| Insp12 | 5246 | LMIERFVS LAIDAYP | ILLERYVS LAIDAYP | LLIERFVS LAIDAYP | VLLERYVS LAIDAYP | |
| nsp12 | 5136 | EFYAYLRK HFSMMIL | DFYGYLQK HFSMMIL | EYYEFLCK HFSMMIL | DYYGYLRK HFSMMIL | EYYEFL NKHFSM MIL |
| nsp5 | 3326 | NHNFLVQA GNVQLRV | LHNFSIIS GTAFLGV | FYGPYRDA QVVQLPV | LHNFSVSH NGVFLGV | NDVAFV STFNVL QDV |
| nsp14 | 6001 | REEAIRHV RAWIGFD | RDFAMRHV RGWLGMD | KDEAIKRV RGWVGFD | RDFAIRNV RGWLGMD | KEEAVK RVRAWV GFD |
| ORF6 | 21 | TFKVSIWN LDYIINL | NDKITEFQ LDYSIDV | LERVSLWN YGKPINL | LFTNSILM LDKQGQL | YQKVFR VYLAYI KKL |
| nsp13 | 5881 | NVNRFNVA ITRAKVG | NANRFNVA ITRAKKG | NVNRFNVA ITRAKKG | NVNRFNLA ITRAKKG | NVNRFN VAITRA RKG |
| nsp12 | 5141 | LRKHFSMM ILSDDAV | LQKHFSMM ILSDDSV | LCKHFSMM ILSDDGV | LRKHFSMM ILSDDGV | LNKHFS MMILSD DGV |

Table 3 includes SARS-CoV-2 peptides, corresponding amino acid positions and the source viral protein for each peptide, and a compatible HLA for each peptide. See, Sekine et al, Robust T cell immunity in convalescent individuals with asymptomatic or mild COVID-19, Cell (2020), doi: https://doi.org/10.1016/j.cell.2020.08.017, the contents of which are incorporated herein by reference in their entirety for all purposes.

TABLE 3

| Compatible HLA | Peptide Sequence | Position | Viral Protein (peptide origin) |
|---|---|---|---|
| A*02:01 | YLQPRTFLL | 269 | Spike |
| A*02:01 | VLNDILSRL | 976 | Spike |
| A*02:01 | TLDSKTQSL | 109 | Spike |
| A*02:01 | KIADYNYKL | 417 | Spike |
| A*02:01 | RLDKVEAEV | 983 | Spike |
| A*02:01 | RLQSLQTYV | 1000 | Spike |
| A*02:01 | LLFNKVTLA | 821 | Spike |
| A*02:01 | HLMSFPQSA | 1048 | Spike |
| A*02:01 | VVFLHVTYV | 1060 | Spike |
| A*02:01 | FIAGLIAIV | 1220 | Spike |
| B*07:02 | SPRRARSVA | 680 | Spike |

TABLE 3-continued

| Compatible HLA | Peptide Sequence | Position | Viral Protein (peptide origin) |
|---|---|---|---|
| B*07:02 | GPKKSTNLV | 526 | Spike |
| B*07:02 | TPINLVRDL | 208 | Spike |
| B*07:02 | EPVLKGVKL | 1262 | Spike |
| B*07:02 | QPTESIVRF | 321 | Spike |
| B*07:02 | FPQSAPHGV | 1052 | Spike |
| B*07:02 | IPTNFTISV | 714 | Spike |
| B*07:02 | LPPAYTNSF | 24 | Spike |
| B*07:02 | KPFERDIST | 462 | Spike |

Additional coronavirus peptides have been described in scientific publications. For example, see Dijkstra J M and Hashimoto K. Expected immune recognition of COVID-19 virus by memory from earlier infections with common coronaviruses in a large part of the world population [version 2; peer review: 2 approved]. F1000Research 2020, 9:285 https://doi.org/10.12688/f1000research.23458.2; and Peng et al, Broad and strong memory CD4+ and CD8+ T cells induced by SARS-CoV-2 in UK convalescent COVID-19 patients. bioRxiv2020.06.05.134551 (2020). Pmid: 32577665, the contents of each are incorporated by reference herein in their entirety for all purposes.

The methods and systems described above may be utilized in combination with or as part of a digital and laboratory health care platform that is generally targeted to medical care and research. It should be understood that many uses of the methods and systems described above, in combination with such a platform, are possible. One example of such a platform is described in U.S. patent application Ser. No. 16/657,804, titled "Data Based Cancer Research and Treatment Systems and Methods", and filed Oct. 18, 2019, which is incorporated herein by reference and in its entirety for all purposes.

For example, an implementation of one or more embodiments of the methods and systems as described above may include microservices constituting a digital and laboratory health care platform supporting TCR/BCR profiling. Embodiments may include a single microservice for executing and delivering TCR/BCR profiling information or may include a plurality of microservices each having a particular role which together implement one or more of the embodiments above. In one example, a first microservice may execute TCR/BCR profiling in order to deliver profile results to a second microservice for reporting.

Where embodiments above are executed in one or more micro-services with or as part of a digital and laboratory health care platform, one or more of such micro-services may be part of an order management system that orchestrates the sequence of events as needed at the appropriate time and in the appropriate order necessary to instantiate embodiments above. A micro-services based order management system is disclosed, for example, in U.S. patent application Ser. No. 16/927,976, titled "Adaptive Order Fulfillment and Tracking Methods and Systems", filed Jul. 13, 2020, which is incorporated herein by reference and in its entirety for all purposes.

For example, continuing with the above first and second microservices, an order management system may notify the first microservice that an order for RNA sequencing has been received and is ready for processing. The first microservice may execute and notify the order management system once the delivery of RNA sequencing is ready for the second microservice. Furthermore, the order management system may identify that execution parameters (prerequisites) for the second microservice are satisfied, including that the first microservice has completed, and notify the second microservice that it may continue processing the order to provide a completed RNA report according to an embodiment, above.

Where the digital and laboratory health care platform further includes a genetic analyzer system, the genetic analyzer system may include targeted panels and/or sequencing probes. An example of a targeted panel is disclosed, for example, in U.S. patent application Ser. Nos. 16/789,288 and 15/930,234, filed Feb. 12, 2020 and May 12, 2020, respectively which are incorporated herein by reference and in its entirety for all purposes. In one example, targeted panels may enable the delivery of next generation sequencing results for genes having a high degree of sequence variability among individuals and/or cells within an individual, including immunological genes (for example, TCR and BCR genes) according to an embodiment, above. An example of the design of next-generation sequencing probes is disclosed, for example, in U.S. patent application Ser. No. 17/706,704, titled "Systems and Methods for Next Generation Sequencing Uniform Probe Design", and filed Oct. 21, 2020, which is incorporated herein by reference and in its entirety for all purposes.

Where the digital and laboratory health care platform further includes a bioinformatics pipeline, the methods and systems described above may be utilized after completion or substantial completion of the systems and methods utilized in the bioinformatics pipeline. As one example, the bioinformatics pipeline may receive next-generation genetic sequencing results and return a set of binary files, such as one or more BAM files, reflecting DNA and/or RNA read counts aligned to a reference genome. The methods and systems described above may be utilized, for example, to ingest the DNA and/or RNA read counts and produce TCR/BCR sequence profiling as a result.

When the digital and laboratory health care platform further includes an RNA data normalizer, any RNA read counts may be normalized before processing embodiments as described above. An example of an RNA data normalizer is disclosed, for example, in U.S. patent application Ser. No. 16/581,706, titled "Methods of Normalizing and Correcting RNA Expression Data", and filed Sep. 24, 2019, which is incorporated herein by reference and in its entirety for all purposes.

When the digital and laboratory health care platform further includes a genetic data deconvoluter, any system and method for deconvoluting may be utilized for analyzing genetic data associated with a specimen having two or more biological components to determine the contribution of each component to the genetic data and/or determine what genetic data would be associated with any component of the specimen if it were purified. An example of a genetic data deconvoluter is disclosed, for example, in U.S. patent application Ser. No. 16/732,229 and PCT/US19/69161, both titled "Transcriptome Deconvolution of Metastatic Tissue Samples", and filed Dec. 31, 2019, and U.S. patent application Ser. No. 17/074,984, titled "Calculating Cell-type RNA Profiles for Diagnosis and Treatment", and filed Oct.

20, 2020, which are incorporated herein by reference and in their entirety for all purposes.

When the digital and laboratory health care platform further includes an automated RNA expression caller, RNA expression levels may be adjusted to be expressed as a value relative to a reference expression level, which is often done in order to prepare multiple RNA expression data sets for analysis to avoid artifacts caused when the data sets have differences because they have not been generated by using the same methods, equipment, and/or reagents. An example of an automated RNA expression caller is disclosed, for example, in U.S. patent application Ser. No. 17/112,877, titled "Systems and Methods for Automating RNA Expression Calls in a Cancer Prediction Pipeline", and filed Dec. 4, 2020, which is incorporated herein by reference and in its entirety for all purposes.

The digital and laboratory health care platform may further include one or more insight engines to deliver information, characteristics, or determinations related to a disease state that may be based on genetic and/or clinical data associated with a patient and/or specimen. Exemplary insight engines may include a tumor of unknown origin engine, a human leukocyte antigen (HLA) loss of homozygosity (LOH) engine, a tumor mutational burden engine, a PD-L1 status engine, a homologous recombination deficiency engine, a cellular pathway activation report engine, an immune infiltration engine, a microsatellite instability engine, a pathogen infection status engine, and so forth. An example tumor of unknown origin engine is disclosed, for example, in U.S. patent application Ser. No. 15/930,234, titled "Systems and Methods for Multi-Label Cancer Classification", and filed May 12, 2020, which is incorporated herein by reference and in its entirety for all purposes. An example of an HLA LOH engine is disclosed, for example, in U.S. patent application Ser. No. 16/789,413, titled "Detection of Human Leukocyte Antigen Class I Loss of Heterozygosity in Solid Tumor Types by NGS DNA Sequencing", and filed Feb. 12, 2020, which is incorporated herein by reference and in its entirety for all purposes. An example of a tumor mutational burden (TMB) engine is disclosed, for example, in U.S. patent application Ser. No. 16/789,288, titled "Targeted-Panel Tumor Mutational Burden Calculation Systems and Methods", and filed Feb. 12, 2020, which is incorporated herein by reference and in its entirety for all purposes. An example of a PD-L1 status engine is disclosed, for example, in U.S. patent application Ser. No. 16/888,357, titled "A Pan-Cancer Model to Predict The PD-L1 Status of a Cancer Cell Sample Using RNA Expression Data and Other Patient Data", and filed May 29, 2020, which is incorporated herein by reference and in its entirety for all purposes. An additional example of a PD-L1 status engine is disclosed, for example, in U.S. patent application Ser. No. 16/830,186, titled "Determining Biomarkers from Histopathology Slide Images", and filed Mar. 25, 2020, which is incorporated herein by reference and in its entirety for all purposes. An example of a homologous recombination deficiency engine is disclosed, for example, in U.S. patent application Ser. No. 16/789,363 and PCT/US20/18002, both titled "An Integrative Machine-Learning Framework to Predict Homologous Recombination Deficiency", and filed Feb. 12, 2020, which is incorporated herein by reference and in its entirety for all purposes. An example of a cellular pathway activation report engine is disclosed, for example, in U.S. patent application Ser. No. 16/994,315, titled "Systems And Methods For Detecting Cellular Pathway Dysregulation In Cancer Specimens", and filed Aug. 14, 2020, which is incorporated herein by reference and in its entirety for all purposes. An example of an immune infiltration engine is disclosed, for example, in U.S. patent application Ser. No. 16/533,676, titled "A Multi-Modal Approach to Predicting Immune Infiltration Based on Integrated RNA Expression and Imaging Features", and filed Aug. 6, 2019, which is incorporated herein by reference and in its entirety for all purposes. An additional example of an immune infiltration engine is disclosed, for example, in U.S. Patent Application No. 62/804,509, titled "Comprehensive Evaluation of RNA Immune System for the Identification of Patients with an Immunologically Active Tumor Microenvironment", and filed Feb. 12, 2019, which is incorporated herein by reference and in its entirety for all purposes. An example of an MSI engine is disclosed, for example, in U.S. patent application Ser. No. 16/653,868, titled "Microsatellite Instability Determination System and Related Methods", and filed Oct. 15, 2019, which is incorporated herein by reference and in its entirety for all purposes. An additional example of an MSI engine is disclosed, for example, in U.S. patent application Ser. No. 16/945,588, titled "Systems and Methods for Detecting Microsatellite Instability of a Cancer Using a Liquid Biopsy", and filed Jul. 31, 2020, which is incorporated herein by reference and in its entirety for all purposes.

When the digital and laboratory health care platform further includes a report generation engine, the methods and systems described above may be utilized to create a summary report of a patient's genetic profile and the results of one or more insight engines for presentation to a physician. For instance, the report may provide to the physician information about the extent to which the specimen that was sequenced contained tumor or normal tissue from a first organ, a second organ, a third organ, and so forth. For example, the report may provide a genetic profile for each of the tissue types, tumors, or organs in the specimen. The genetic profile may represent genetic sequences present in the tissue type, tumor, or organ and may include variants, expression levels, information about gene products, or other information that could be derived from genetic analysis of a tissue, tumor, or organ. The report may include therapies and/or clinical trials matched based on a portion or all of the genetic profile or insight engine findings and summaries. For example, the clinical trials may be matched according to the systems and methods disclosed in U.S. patent application Ser. No. 16/889,779, titled "Systems and Methods of Clinical Trial Evaluation", filed Jun. 1, 2020, which is incorporated herein by reference and in its entirety for all purposes.

The report may include a comparison of the results to a database of results from many specimens. An example of methods and systems for comparing results to a database of results are disclosed in U.S. patent application Ser. No. 16/732,168 and PCT/US19/69149, both titled "A Method and Process for Predicting and Analyzing Patient Cohort Response, Progression and Survival", and filed Dec. 31, 2019, which is incorporated herein by reference and in its entirety for all purposes. The information may be used, sometimes in conjunction with similar information from additional specimens and/or clinical response information, to discover biomarkers or design a clinical trial.

When the digital and laboratory health care platform further includes application of one or more of the embodiments herein to organoids developed in connection with the platform, the methods and systems may be used to further evaluate genetic sequencing data derived from an organoid to provide information about the extent to which the organoid that was sequenced contained a first cell type, a second cell type, a third cell type, and so forth. For example, the report may provide a genetic profile for each of the cell types in the specimen. The genetic profile may represent genetic sequences present in a given cell type and may include variants, expression levels, information about gene products, or other information that could be derived from genetic analysis of a cell. The report may include therapies matched based on a portion or all of the deconvoluted information. These therapies may be tested on the organoid, derivatives of that organoid, and/or similar organoids to determine an organoid's sensitivity to those therapies. For example, organoids may be cultured and tested according to the systems and methods disclosed in U.S. patent application Ser. No. 16/693,117, titled "Tumor Organoid Culture Compositions, Systems, and Methods", filed Nov. 22, 2019; PCT/US20/56930, titled "Systems and Methods for Predicting Therapeutic Sensitivity", filed Oct. 22, 2020; and U.S. patent application Ser. No. 17/114,386, titled "Large Scale Phenotypic Organoid Analysis", filed Dec. 7, 2020, which are incorporated herein by reference and in their entirety for all purposes.

When the digital and laboratory health care platform further includes application of one or more of the above in combination with or as part of a medical device or a laboratory developed test that is generally targeted to medical care and research, such laboratory developed test or medical device results may be enhanced and personalized through the use of artificial intelligence. An example of laboratory developed tests, especially those that may be enhanced by artificial intelligence, is disclosed, for example, in U.S. Provisional Patent Application No. 62/924,515, titled "Artificial Intelligence Assisted Precision Medicine Enhancements to Standardized Laboratory Diagnostic Testing", and filed Oct. 22, 2019, which is incorporated herein by reference and in its entirety for all purposes.

It should be understood that the examples given above are illustrative and do not limit the uses of the systems and methods described herein in combination with a digital and laboratory health care platform.

Applications

The present disclosure provides methods to analyze the number of clones and distribution of clones of T cell receptors (TCRs) and B cells receptors (BCRs). Sequences encoding TCRs and BCRs contain a variety of information that is useful for medical and research applications. For example, by performing immune profiling, the clonality of the T and B cell repertoire can be determined.

In one example, T and B cells that are specific to the pathogen SARS-CoV-2 are activated and expand following infection that is accompanied by no obvious symptoms. Immune profiling of an individual in such a case would reveal the expansion of SARS-CoV-2 specific lymphocytes. Furthermore, humoral immune responses to SARS-CoV-2 have been shown to wane over time, leaving fewer SARS-CoV-2 specific antibodies in the circulation (Self W H et al. MMWR Morb Mortal Wkly Rep 2020; 69:1762-1766). This feature of SARS-CoV-2 infection (COVID-19) reduces the potential effectiveness of tests for SARS-CoV-2 exposure based on virus-specific antibody titer.

Immune profiling is also important, for example, in detecting T and B cell lymphomas, as these cancers generally have dominant clones that arise and expand as the cancer progresses. The presence of dominant T or B cell clones could be assessed in an individual that would aid in determining the extent or severity of disease.

However, missing from traditional immune profiling assays is the ability to assess the molecular phenotype of cells of interest. Therefore, the technology of the current application combines complete next generation sequencing of DNA or RNA based samples with immune profiling. Traditionally, to perform RNA or exome sequencing and immune profiling on a sample, the sample material would have to be split into two separate assays and the data combined after sequencing. The method of the present application allows for the analysis of both genomic/transcriptomic data and immune profiling in one assay without compromising the quality of the data derived from either component. Therefore, the method of the present application has superior efficiency that could be translated to provide precision medicine at a scale that would make it viable for routine use by medical practitioners for a variety of potential applications.

The method of the present disclosure leverages hybrid capture probes to enrich sequences most vital to understanding the T and B cell repertoire in an individual subject. Novel probes are designed to tile constant and non-constant regions of TCR and BCR sequences. The probe sets are designed so that sequencing is deep in critical areas of the TCR and BCR sequences so that a complete immune profile can be developed with fewer reads than traditional assays. Furthermore, the probe sets are formulated to provide productive sequences that cover both TCRs and BCRs. In addition, using the method of the present application, the formulation of probes may be further tuned to each individual application to provide maximum coverage of the immune repertoire. This novel hybrid capture approach allows immune profiling to be accomplished while dedicating less than 2% of the reads in a given sequencing run to TCR/BCR profiling. Consequently, with 98% or greater of the sequencing reads available for other applications, high quality, deep sequencing can be accomplished concurrently with immune profiling.

General

In a given tumor sample, tissue sample, or blood sample, there are hundreds, thousands, tens of thousands, or even millions of different TCR and BCR sequences. These sequences can be used to predict, for example, past infections and potentially which T cells are killing tumor cells. While standard RNAseq allows us to infer the proportion of T cells in a tumor (infiltration), TCR sequencing can tell us whether the majority of the T cells in the tumor are specific for a single neoantigen or arise from a diverse pool. By tracking TCRs and BCRs over the entirety of a patient cohort, it is possible to identify specific receptors that recur in patients with the same alterations, generating information that may be directed to TCR-based/CAR cell therapies.

In the context of past or present infections, TCR and BCR sequencing results may be useful for characterizing an infection and/or an immune response to infection. When the TCR/BCR sequencing is performed as part of a whole-exome RNAseq assay, RNA sequences and expression levels of various immune genes (for example, cytokines, checkpoint molecules, innate immune genes) may also contribute to that characterization.

By way of example, but not by way of limitation, TCR/BCR profiling results may be used to: determine whether an individual has been exposed to one or more infectious pathogens; detect whether an individual has TCR or BCR sequences associated with sterilizing immunity and/or neutralizing antibodies for a group of infectious pathogens or a specific infectious pathogen; identify an adaptive immune response to a particular pathogen or antigen; analyze and improve treatment protocols for the infectious disease for the general patient population or a patient subpopulation; identify associations between severity of disease and immune profile; categorize or predict the severity of an individual's disease (for example, see Schultheiß et al, 2020, Immunity, https://doi.org/10.1016/j.immuni.2020.06.024, which is incorporated by reference herein in its entirety), assist a physician in selecting treatment protocols, tailor a treatment protocol to an individual's immune response, develop and/or assess the efficacy of therapeutics or preventative treatments (for example, vaccines), design clinical trials or better define patient cohorts, and/or gain additional relevant information.

In some examples, serologic tests may determine whether an individual has developed antibodies that react to an infectious pathogen and/or antigen. However, it is known that not all infectious pathogens elicit a strong antibody (B cell) response or cause seroconversion in each instance of infection. These infections may be caused by pathogens with life cycles that occur mostly within the host cell (for example, listeria, etc.), viruses that do not cause viremia or are not found in high concentrations in the blood of an individual. One example of viruses that generally do not cause viremia includes coronaviruses, for example, SARS, MERS, SARS-CoV-2, etc.

In some cases, infections that do not elicit a strong B cell response may still be controlled and cleared by an individual, and one of the hypothesized mechanisms for this control in the absence of a B cell response is a T cell response (see, Gallais et al, 2020, MedRxiv https://doi.org/10.1101/2020.06.21.20132449) A number of assays (for example, ELISpot, Fluorospot, ELISA, etc.) may be used to analyze an individual's T cell response and/or memory B cells that are specific to a particular pathogen and/or antigen. However, these assays often require cell culturing techniques and/or an incubation period that limits the number of tests that can be performed each day. In various examples, TCR/BCR sequencing may be more amenable to high volume testing allowing many samples to be processed each day.

The aforementioned T cell, B cell, and antibody assays detect TCR and BCR that react to the antigens included in the assay and may not detect TCR or BCR that react to antigens generated during an infection, cancer, or other disease state that are not included in the assay. Furthermore, these assays do not automatically provide the genetic sequence (and thus, the protein structure) of the BCR or TCR molecule, which is another advantage of methods of TCR/BCR sequencing disclosed herein.

Additional, exemplary, non-limiting applications of the present technology are provided below.

Applications Related to Direct Analysis of a Patient TCR/BCR Profile

Disease Testing—Measurement/Confirmation of Cancer Diagnosis and Severity

In some embodiments, patient samples are collected including blood or tumor samples, and the severity of disease is evaluated. By way of example, but not by way of limitation, the severity of disease for hematological malignancies including T and B cell lymphoma may be evaluated by performing TCR/BCR hybrid-capture and sequencing to develop an immune profile for the patient. The immune profile provides information regarding the clonality of normal and of the malignant cells. This information can be used by a healthcare practitioner to develop an understanding of the tumor burden in the patient, and to help guide treatment decisions.

In some embodiments, a therapy is recommended or matched based on a TCR/BCR profile. The TCR/BCR profile provides information regarding the major clones that make up the malignancy. Therefore, the TCR/BCR profile may help inform treatment decisions made by a healthcare practitioner. By way of example, but not by way of limitation, therapies recommended subsequent to TCR/BCR profiling may include adoptive cell therapy/ACT, CAR-T cell therapy, chimeric antigen receptor macrophage (CAR-M) therapy, or other classes of cells engineered to express a chimeric antigen receptor (CAR). Additional therapies include, but are not limited to, cancer vaccine, immuno-oncology drugs, immunotherapy, checkpoint blockade, immune checkpoint inhibitors, chemotherapy, a cancer specific treatment, vaccine, antivirals, antibiotics, antiparasitics, antifungals, one or more antibodies (could be monoclonal, polyclonal, etc., could be isolated from another patient after recovery from infection), anti-histamines, nasal sprays, anti-leukotriene, leukotriene modifier, leukotriene receptor antagonist, allergy shots or another method to induce isotype switching from an allergenic IgE to a more tolerable IgG, anti-inflammatory treatment, steroids, oral corticosteroid, prednisone, anti-rheumatic drugs (DMARDS), biologics that target common anti-inflammatory pathways, TNF pathway antagonists (including Remicade), B cell depletion (including Rituxan), immunosuppressant, insulin, bone marrow transplant, anti-inflammatory dietary restrictions, physical therapy, surgery, topical medication, and/or topical scalp medication.

In some embodiments, the present technology is used to perform only one or several of the following functions simultaneously: evaluate the presence and extent of lymphocyte infiltration in a solid tumor sample, to measure/confirm disease severity, or detect infiltration biomarker. TCR/BCR profiles of patient samples derived from a solid tumor provide information about the frequency and clonality of tumor infiltrating lymphocytes (TILs). In some embodiments, a therapy is recommended based on the analysis of TILs made using TCR/BCR profiling. By way of example, but not by way of limitation, treatments that may be recommended following TCR/BCR profiling include: ACT, CAR-T, and/or other immune oncological (IO) modalities.

In some embodiments, TCR/BCR data is combined with other infiltration predictors (engines), and/or as a feature to refine those prediction models. An example of an immune infiltration engine is disclosed, for example, in U.S. patent application Ser. No. 16/533,676, titled "A Multi-Modal Approach to Predicting Immune Infiltration Based on Integrated RNA Expression and Imaging Features", and filed Aug. 6, 2019, which is incorporated herein by reference and in its entirety for all purposes. An additional example of an immune infiltration engine is disclosed, for example, in U.S. Patent Application No. 62/804,509, titled "Comprehensive Evaluation of RNA Immune System for the Identification of Patients with an Immunologically Active Tumor Microenvironment", and filed Feb. 12, 2019, which is incorporated herein by reference and in its entirety for all purposes.

In one example, a TCR/BCR profile may be generated for a patient having non-small cell lung cancer (NSCLC) and an EGFR mutation. This TCR/BCR profile may be analyzed with or without output from infiltration predictors used to analyze the patient's data. These results may be used to match a therapy (for example, immunotherapy, checkpoint blockade, etc.) with the patient.

Therapeutic Efficacy Testing

In some embodiments, the present technology is used to identify whether a therapeutic immune cell has infiltrated a target tumor. By way of example, but not by way of limitation, cells that are detected using TCR/BCR profiling include CAR-T cells, or cells delivered through adoptive cell transfer (ACT) therapy. By way of example, but not by way of limitation, additional probes may be added to specifically target a sequence unique to the particular therapeutic modality.

In some embodiments, the present technology can be used to perform longitudinal testing, for example, before and after administration of immune-affecting therapy, such as chemotherapy. Chemotherapeutic drugs often adversely affect a patient's immune system. By way of example, but not by way of limitation, chemotherapeutic drugs may include Anthracyclines, such as doxorubicin and epirubicin, taxanes such as paclitaxel and docetaxel, 5-fluorouracil, cyclophosphamide, or carboplatin, or other drugs used in the treatment of cell proliferative diseases. In some embodiments, the present technology can be used to monitor the extent and nature of immune repertoire adverse events or off target effects. By way of example, but not by way of limitation, the TCR/BCR profile is used to understand whether the subject is more susceptible to infection or other disease associated with being immunocompromised. In some embodiments, the TCR/BCR profile allows a physician to provide additional directed therapy in response to TCR/BCR profile analysis. By way of example, but not by way of limitation, TCR/BCR profile may lead to administration of cytokines known to positively affect the immune system, and in some embodiments, longitudinal TCR/BCR analysis provides data to determine the extent and nature of immune repertoire improvement, and to provide data to modify the treatment as necessary.

Sequence, Analyze, and Report List of Cells and/or Receptor Sequences in a Patient Sample In some embodiments, the present technology is used to determine a TCR/BCR profile for the patient or patient sample taken from, for example, malignant tissue. In some embodiments, the methods are useful to determine the presence and extent of lymphocyte infiltration in a tumor sample and identify the most abundant clones in a tumor sample. By way of example, but not by way of limitation, such profiles can allow selection of highly represented clones to be expanded for patient-specific Adoptive Cell Transfer, and/or used to identify receptor non-constant regions that are highly expressed to generate patient-specific chimeric receptors. This information provides a basis for developing a personalized medicine treatment approach using, for example, CAR-T cell therapy.

In some embodiments, the present technology is used to determine the TCR/BCR profile of a patient suffering from or suspected of having a pathogenic infection. In some embodiments, the most abundant clones in a patient sample (e.g., blood sample) are identified, to be expanded for patient-specific Adoptive Cell Transfer. In some embodiments, the receptor non-constant regions for this patient sample are identified to generate patient-specific chimeric receptors for use in CAR cell therapy.

Diagnosis or Confirmatory Diagnosis for a Patient Based on TCR/BCR Analysis

In some embodiments, the TCR/BCR data is used in combination with other pathogen detection or prediction methods and/or can be used as a feature to revise those prediction models. An example of a pathogen detection or prediction method is disclosed, for example, in U.S. patent application Ser. No. 16/802,126, filed Feb. 26, 2020, which is incorporated herein by reference and in its entirety for all purposes. Another example of a pathogen detection or prediction method is disclosed, for example, in PCT/US21/18619, filed Feb. 18, 2021, which is incorporated herein by reference and in its entirety for all purposes. In some embodiments, data could be used to predict whether a patient is protected from future infection. By way of example, but not by way of limitation, this information would be valuable for patients following vaccination or natural infection with a virus. In some embodiments, analysis could be performed longitudinally to characterize the immune response to a pathogenic organism. For oncogenic pathogens, immune profiling may be used to predict whether the patient has/had an infection and can guide treatment decisions made by a healthcare practitioner.

In some embodiments, a list of receptor sequences associated with a pathogen (see the application of the technology above) is provided. In some embodiments a large dataset with positive controls and negative controls to determine which TCR/BCR sequences are associated with, for example, a given disease, pathogen, or antigen is provided (see e.g., Example 2). By way of example, but not by way of limitation, an example of utilizing the present TCR/BCR profiling methods for a diagnostic or confirmatory diagnostic application is provided below.

SARS-CoV-2 Diagnosis

In various embodiments, BCR sequences that recognize SARS-CoV-2 antigens may include those shown in Table 4. Table 4 provides an example of positive control data for SAR-CoV-2 exposure and/or infection:

TABLE 4

| HEAVY | HEAVY | HEAVY | HEAVY | LIGHT | LIGHT | LIGHT |
|---|---|---|---|---|---|---|
| IGHV | IGHD | IGHJ | CDRH3 (amino acid) | IGLV | IGLJ | CDRL3 (amino acid) |
| IGHV1-58*01 | IGHD2-15*01 | IGHJ3*02 | AAPHCSGG SCLDAFDI | IGKV3-20*01 | IGKJ1*01 | QQYGSSPWT |
| IGHV1-58*01 | IGHD2-15*01 | IGHJ3*02 | ~~~~~~~~ ~~Y~~~~~ | IGKV3-20*01 | IGKJ1*01 | ~~~~~~~~~ |
| IGHV1-58*02 | IGHD2-15*01 | IGHJ3*02 | ~~N~~~~~ ~~Y~G~~~ | IGKV3-20*01 | IGKJ1*01 | ~~~~~~~~M |
| IGHV1-58*02 | IGHD2-15*01 | IGHJ3*02 | ~~~Y~~~~ ~~N~~~~~ | IGKV3-20*01 | IGKJ1*01 | ~~~~~~~~~ |
| IGHV1-58*01 | IGHD2-2*01 | IGHJ3*02 | ~~~~~~ST ~~F~~~~~ | IGKV3-20*01 | IGKJ1*01 | ~~~~N~~~~ |
| IGHV1-58*01 | IGHD2-15*01 | IGHJ3*02 | ~~~Y~~~~ ~~S~~~~~ | IGKV3-20*01 | IGKJ1*01 | ~~~~~~~~~ |

TABLE 4-continued

| HEAVY | HEAVY | HEAVY | HEAVY | LIGHT | LIGHT | LIGHT |
|---|---|---|---|---|---|---|
| IGHV3-30-3*01 | IGHD5-18*01 | IGHJ4*02 | ARDGIVDTAMVTWFDY | IGKV1-39*01 | IGKJ1*01 | QQSYSTPPWT |
| IGHV3-30-3*01 | IGHD5-24*01 | IGHJ4*02 | ~~~~~QGMATTY~~~~ | IGKV1-39*01 | IGKJ1*01 | ~~~~N~~~~ |
| IGHV3-30-3*01 | IGHD5-18*01 | IGHJ4*02 | ~~~~~~~~~L~~~~~~ | IGKV1-39*01 | IGKJ1*01 | ~~~~~~~~ |
| IGHV3-30-3*01 | IGHD5-18*01 | IGHJ5*01 | ~~~SD~~~S~~~~~~~ | IGKV1-39*01 | IGKJ1*01 | ~~~~~~~~ |
| IGHV3-30-3*01 | IGHD5-18*01 | IGHJ5*01 | ~~~SD~~~~~~~~~~~ | IGKV1-39*01 | IGKJ1*01 | ~~~~~~~~ |

Each row in Table 4 represents a BCR sequence, which includes a V, D, J family classification for the heavy chain and an amino acid sequence for the heavy chain CDR3, and a V and J family classification for the light chain and an amino acid sequence for the light chain CDR3. The amino acid sequence may represent a consensus sequence of the amino acids that are present in multiple CDR3 sequences when aligned and compared, and a tilde (~) may indicate a location in the sequence that does not have the same amino acid in the aligned CDR3 sequences. In various embodiments, two BCR sequences may be paired. For example, the third and fourth rows may represent two alleles that are expressed by the same cell to create a heterodimer protein BCR structure. Similarly, the fifth and sixth rows may be paired sequences, the seventh and eighth rows may be paired, the ninth and tenth rows may be paired, etc.

TABLE 5

| IGH VDJ (nucleotide) | IGH VDJ (amino acid) | IGL VJ (nucleotide) | IGL VJ (amino acid) |
|---|---|---|---|
| GAGGTGCAGCT GGTGGAGTCTG GGGGAGGCGTG GTCCAGCCTGG GAGGTCCCTGA GACTCTCCTGT GCAGCCTCTGG ATTCACCTTCA GTATCTATGGC ATGCACTGGGT CCGCCAGGCTC CAGGGCAAGGGG CTGGAGTGGGT GGCAGTTATAT CATATGATGGA AGTAATAAATA CTATGCAGACT CCGTGAAGGGC CGATTCACCAT CTCCAGAGACA ATTCCAAGAAC ACGCTGTATCT GCAAATGAACA GCCTGAGAGCT GAGGACACGGC TGTGTATTACT GTGCGAAAGAG GGGAGACCATC TGATATTGTAG TGGTGGTGGCC TTTGACTACTG GGGCCAGGGAA | EVQLVESGGGVV QPGRSLRLSCAA SGFTFSIYGMHW VRQAPGKGLEWV AVISYDGSNKYY ADSVKGRFTISR DNSKNTLYLQMN SLRAEDTAVYYC AKEGRPSDIVVV VAFDYWGQGTLV TVSS | GACATCCAGTTG ACCCAGTCTCCA TCCTCCCTGTCT GCATCTGTAGGA GACAGAGTCACC ATCACTTGCCGG GCAAGTCAGAGC ATTAGCAGCTAT TTAAATTGGTAT CAGCAGAAACCA GGGAAAGCCCCT AAGCTCCTGATC TATGCTGCATCC AGTTTGCAAAGT GGGGTCCCATCA AGGTTCAGTGGC AGTGGATCTGGG ACAGATTTCACT CTCACCATCAGC AGTCTGCAACCT GAAGATTTTGCA ACTTACTACTGT CAACAGAGTTAC AGTACCCCTCGG ACGTTCGGCCAA GGGACCAAGGTG GAAATCAAAC | DIQLTQSPSSLS ASVGDRVTITCR ASQSISSYLNWY QQKPGKAPKLLI YAASSLQSGVPS RFSGSGSGTDFT LTISSLQPEDFA TTYCQQSYSTPR TFGQGTKVEIK |

TABLE 5-continued

| IGH VDJ (nucleotide) | IGH VDJ (amino acid) | IGL VJ (nucleotide) | IGL VJ (amino acid) |
|---|---|---|---|
| CCCTGGTCACC GTCTCCTCAG | | | |
| GAGGTGCAGCT GGTGGAGTCTG GAGGAGGCTTG ATCCAGCCTGG GGGGTCCCTGA GACTCTCCTGT GCAGCCTCTGG GTTCACCGTCA GTAGCAACTAC ATGAGCTGGGT CCGCCAGGCTC CAGGGAAGGGG CTGGAGTGGGT CTCAGTTATTT ATAGCGGTGGT AGCACATACTA CGCAGACTCCG TGAAGGGCCGA TTCACCATCTC CAGAGACAATT CCAAGAACACG CTGTATCTTCA AATGAACAGCC TGAGAGCCGGG GACACGGCCGT GTATTACTGT CGAGGGATTAC GGTGACTTCTA CTTTGACTACT GGGGCCAGGGA ACCCTGGTCAC CGTCTCCTCAG | EVQLVESGGGLI QPGGSLRLSCAA SGFTVSSNYMSW VRQAPGKGLEWV SVIYSGGSTYYA DSVKGRFTISRD NSKNTLYLQMNS LRAGDTAVYYCA RDYGDFYFDYWG QGTLVTVSS | GAAATTGTGTTG ACGCAGTCTCCA GGCACCCTGTCT TTGTCTCCAGGG GAAAGAGCCACC CTCCTCCAGGG GCCAGTCAGAGT GTTAGCAGCACC TACTTAGCCTGG TACCAGCAGAAA CCTGGCCAGGCT CCCAGGCTCCTC ATCTATGGTGCA TCCAGCAGGGCC ACTGGCATCCCA GACAGGTTCAGT GGCAGTGGGTCT GGGACAGACTTC ACTCTCACCATC AGCAGACTGGAG CCTGAAGATTTT GCAGTGTATTAC TGTCAGCAGTAT GGTAGCTCACCT AGGACTTTTGGC CAGGGGACCAAG CTGGAGATCAAA C | EIVLTQSPGTLS LSPGERATLSCR ASQSVSSTYLAW YQQKPGQAPRLL IYGASSRATGIP DRFSGSGSGTDF TLTISRLEPEDF AVYYCQQYGSSP RTFGQGTKLEIK |
| CAGGTGCAGCT GGTGCAGTCTG GGGCTGAGGTG AAGAAGCCTGG GGCCTCAGTGA AGGTCTCCTGC AAGGCTTCTGG ATACACCTTCA CCGGCTACTAT ATGCACTGGGT GCGACAGGCCC CTGGACAAGGG CTTGAGTGGAT GGGATGGATCA ACCCTATCAGT GGTGGCACAAA CTATGCACAGA AGTTTCAGGGC | QVQLVQSGAEVK KPGASVKVSCKA SGYTFTGYYMHW VRQAPGQGLEWM GWINPISGGTNY AQKFQGRVTMTR ATCACTTGCCAG RFSGSGSGTDFT FTISSLQPEDIA TYYCQQYDNLPI TFGQGTRLEIK | GCCATCCGGATG ACCCAGTCTCCA TCCTCCCTGTCT GCATCTGTAGGA GACAGAGTCACC ATCACTTGCCAG GCGAGTCAGGAC ATTAGCAACTAT TTAAATTGGTAT CAGCAGAAACCA GGGAAAGCCCCT AAGCTCCTGATC TACGATGCATCC AATTTGGAAACA GGGGTCCCATCA AGGTTCAGTGGA AGTGGATCTGGG ACAGATTTTACT | AIRMTQSPSSLS ASVGDRVTITCQ ASQDISNYLNWY QQKPGKAPKLLI YDASNLETGVPS RFSGSGSGTDFT FTISSLQPEDIA TYYCQQYDNLPI TFGQGTRLEIK |

TABLE 5-continued

| IGH VDJ (nucleotide) | IGH VDJ (amino acid) | IGL VJ (nucleotide) | IGL VJ (amino acid) |
|---|---|---|---|
| AGGGTCACCAT GACCAGGGACA CGTCCATCAGC ACAGCCTACAT GGAGCTGAGCA GGCTGAGATCT GACGACACGGC CGTGTATTACT GTGCGAGCCCA GCATCACGTGG ATATAGTGGCT ACGATCATGGG TACTACTACTA CATGGACGTCT GGGGCAAAGGG ACCACGGTCAC CGTCTCCTCA | | TTCACCATCAGC AGCCTGCAGCCT GAAGATATTGCA ACATATTACTGT CAACAGTATGAT AATCTCCCTATC ACCTTCGGCCAA GGGACACGACTG GAGATTAAAC | |
| CAGGTGCAGCT GGTGCAGTCTG GGCCTGAGGTG SGFTFTSSAVQW AAGAAGCCTGG GACCTCAGTGA AGGTCTCCTGC ATTCACCTTTA CTAGCTCTGCT GTGCAGTGGGT GCGACAGGCTC GTGGACAACGC CTTGAGTGGAT AGGATGGATCG TCGTTGGCAGT GGTAACACAAA CTACGCACAGA AGTTCCAGGAA AGAGTCACCAT TACCAGGGACA TGTCCACAAGC ACAGCCTACAT GGAGCTGAGCA GCCTGAGATCC GAGGACACGGC CGTGTATTACT GTGCGGCTCCC CATTGTAGCGG TGGTAGCTGCC TTGATGCTTTT GATATCTGGGG CCAAGGGACAA TGGTCACCGTC TCTTCAG | QVQLVQSGPEVK KPGTSVKVSCKA SGFTFTSSAVQW VRQARGQRLEWI GWIVVGSGNTNY AQKFQERVTITR DMSTSTAYMELS SLRSEDTAVYYC AAPHCSGGSCLD AFDIWGQGTMVT VSS | GAAATTGTGTTG ACGCAGTCTCCA GGCACCCTGTCT TTGTCTCCAGGG GAAAGAGCCACC CTCTCCTGCAGG GCCAGTCAGAGT GTTAGAAGCAGC TACTTAGCCTGG TACCAGCAGAAA CCTGGCCAGGCT CCCAGGCTCCTC ATCTATGGTGCA TCCAGCAGGGCC ACTGGCATCCCA GACAGGTTCAGT GGCAGTGGGTCT GGGACAGACTTC ACTCTCACCATC AGCAGACTGGAG CCTGAAGATTTT GCAGTGTATTAC TGTCAGCAGTAT GGTAGCTCACCG TGGACGTTCGGC CAAGGGACCAAG GTGGAAATCAAA C | EIVLTQSPGTLS LSPGERATLSCR ASQSVRSSYLAW YQQKPGQAPRLL IYGASSRATGIP DRFSGSGSTDF TLTISRLEPEDF AVYYCQQYGSSP WTFGQGTKVEIK |
| CAGGTGCAGCT GGTGGAGTCTG GGGGAGGCTTG GTCAAGCCTGG AGGGTCCCTGA GACTCTCCTGT GCAGCCTCTGG ATTCATCTTCA GTGACTACTGC ATGAGCTGGAT CCGCCGGGCTC CAGGGAAGGGG CTGGAATGGCT TTCATATATTA GTAATAGTGGT ACCACCAGATA CTACGCAGACT CTGTGAAGGGC CGATTCACCAT CTCCAGGACA ACGGCAGGAAC TCACTGTATCT GCAAATGGACA | QVQLVESGGGLV KPGGSLRLSCAA SGFIFSDYCMSW IRRAPGKGLEWL SYISNSGTTRYY ADSVKGRFTISR DNGRNSLYLQMD ATIHFSLSAEDTAVYYC ARRGDGSSSIYY NYMDVWGKGTT VTVSS | CAGTCTGTGCTG ACTCAGCCACCC TCAGCGTCTGGG AGGGTCACCGTC AGGGTCACCGTC ACCCCCGGACAG CTTTGTTCTGGA AGCAGCTCCAAC ATCGGAAGCAAT ACTGTAAACTGG TACCAGCAGCTC CCAGGAACGGCC CCCAAACTCCTC ATCTATAGTAAT AATCAGCGGCCC TCAGGGGTCCCT GACCGATTCTCT GGCTCCAAGTCT GGCACCTCAGCC TCCCTGGCCATC AGTGGGCTCCAG TCTGAGGATGAG GCTGATTATTTC TGTGCAGCATGG | QSVLTQPPSASG TPGQRVTVSCSG SSSNIGSNTVNW YQQLPGTAPKLL IYSNNQRPSGVP DRFSGSKSGTSA SLAISGLQSEDE ADYFCAAWDDSL NGPVFGGGTKLT VL |
| GCCTGAGCGCC GAAGACACGGC CGTTTATTACT GTGCGAGAGGG GGGGACGGTAG CAGCTCGATCT ACTACTACAAC TACATGACGT CTGGGGCAAAG GGACCACGGTC ACCGTCTCCTC A | | GATGACAGCCTG AATGGTCCGGTA TTCGGCGGAGGG ACCAAGCTGACC GTCCTAG | |
| GAGGTGCAGCT GGTGGAGTCTG GGGGAGGCGTG GTCCAGCCTGG GAGGTCCCTGA GACTCTCCTGT GCAGCCTCTGG ATTCACCTTCA GTAGCTATGGC ATGCACTGGGT CCGCCAGGCTC CAGGCAAGGGG CTGGAGTGGGT GACAGTTATTT CATATGATGGA AGGAATAAATA CTATGCAGACT CCGTGAAGGGC CGATTCACCAT CTCCAGAGACA ACTCCAAGAAC ACGCTGTATCT GCAAATGAACA GCCTGAGAGCT GAGGACACGGC TGTGTATTACT GTGCGAGAGAA TTCGGTGACCC CGAGTGGTACT TTGACTACTGG GGCCAGGGAAC CCTGGTCACCG TCTCCTCAG | EVQLVESGGGVV QPGRSLRLSCAA SGFTFSSYGMHW VRQAPGKGLEWV TVISYDGRNKYY ADSVKGRFTISR DNSKNTLYLQMN SLRAEDTAVYYC AREFGDPEWYFD YWGQGTLVTVSS | GACATCCAGATG ACCCAGTCTCCT TCCACCCTGTCT GCATCTGTAGGA GACAGAGTCACC ATCACTTGCCGG GCCAATCAGAGT ATTAGTAGCTGG TTGGCCTGGTAT CAGCAGAAACCA GGGAAAGCCCCT AAGCTCCTGATC TATAAGGCGTCT AGTTTAGAAAGT GGGGTCCCATCA AGGTTCAGCGGC AGTGGATCTGGG ACAGAATTCACT CTCACCATCAGC AGCCTGCAGCCT GATGATTTTGCA ACTTATTACTGC CAACAGTATAAT AGTTATTGGACG TTCGGCCAAGGG ACCAAGGTGGAA ATCAAAC | DIQMTQSPSTLS ASVGDRVTITCR ANQSISSWLAWY QQKPGKAPKLLI YKASSLESGVPS RFSGSGSTEFT LTISSLQPDDFA TYYCQQYNSYWT FGQGTKVEIK |
| CAGGTGCAGCT GGTGCAGTCTG GGGGCTGAGGTG AAGAAGCCTGG GGCCTCAGTGA AGGTCTCCTGC ATGGCTTGCAG ATACACCTTCA ATGCACTGGGT NDYWGQGTLVTV GCGACAGGCCC CTGGACAAGGG CTTGAGTGGAT GGGATGGATCA ACCCTAACAGT GGTGGCACAAA CTATGCACAGA AGTTTCAGGGC AGGGTCACCAT GACCAGGGACA CGTCCATCAGC ACAGCCTACAT GGAGCTGAGCA GCCTGAGATCT GACGACACGGC CGTGTATTACT GTGCGAGAGAC TCCCCATTTAG TGCTTTAGGGG | QVQLVQSGAEVK KPGASVKVSCMA SGYTFTGYYMHW VRQAPGQGLEWM GWINPNSGGTNY AQKFQGRVTMTR DTSISTAYMELS RLRSDDTAVYYC ARDSPFSALGAS SS | CAGTCTGCCCTG ACTCAGCCTCCC TCCGCGTCCGGG TCCATTACTTGT AAGCTCCTGATC CTAGTCACCATC TCCTGCACTGGA ACCAGCAGTGAC GTTGGTGGTTAT AACTATGTCTCC TGGTACCAACAG CACCCAGGCAAA GCCCCCAAACTC ATGATTTATGAG GTCAGTAAGCGG CCCTCAGGGGTC CCTGATCGCTTC TCTGGCTCCAAG TCTGGCAACACG GCCTCCCTGACC GTCTCTGGGCTC CAGGCTGAGGAT GAGGCTGAGTAT TACTGCAGCTCA AACAATGGTA TTCGGCGGAGGG ACCAAGCTGACC GTCCTAG | QSALTQPPSASG SPGQSVTISCTG TSSDVGGYNYVS WYQQHPGKAPKL MIYEVSKRPSGV PDRFSGSKSGNT ASLTVSGLQAED EAEYYCSSDAGS NNVVFGGGTKLT VL |

TABLE 5-continued

| IGH VDJ (nucleotide) | IGH VDJ (amino acid) | IGL VJ (nucleotide) | IGL VJ (amino acid) |
|---|---|---|---|
| CCTCCAATGAC TACTGGGGCCA GGGAACCCTGG TCACCGTCTCC TCAG | | | |
| GAGGTGCAGCT GGTGGAGTCTG GGGGAGGCGTG GTCCAGCCTGG GAGGTCCCTGA GACTCTCCTGT GCAGCCTCTGG ATTCACCTTCA GTAGCTATGCT ATGCACTGGGT CCGCCAGGCTC CAGCCAAGGGG CTGGAGTGGGT GGCAGTTATAT TATATGATGGA AGCGGTAAATA CTACGCAGACT CCGTGAAGGGC CGATTCACCAT CTCCAGAGACA ATTCCAAGAAC ACGTTGTATCT GCAAATGAACA GCCTGAGAGCT GAGGACACGGC TGTGTATTACT GTGCGAGAGAC GGGATCGTGGA TACAGCTCTGG TTACGTGGTTT GACTACTGGGG CCAGGGAACCC TGGTCACCGTC TCCTCAG | EVQLVESGGGVV QPGRSLRLSCAA SGFTFSSYAMEI WVRQAPAKGLEW VAVILYDGSGKY YADSVKGRFTIS RDNSKNTLYLQM NSLRAEDTAVYY CARDGIVDTALV TWFDYWGQGTLV TVSS | GACATCCAGTTG ACCCAGTCTCCA TCCTCCCTGTCT GCATCTGTAGGA GACAGAGTCACC ATCACTTGCCGG GCAAGTCAGAGC ATTAGCACCTAT TTAAATTGGTAT CAGCAGAAACCA GGGAAAGCCCCT AAGCTCCTGATC TATGCTGCATCC AGTTTGCAAAGT GGGGTCCCATCA AGGTTCAGTGGC AGTGGATCTGGG ACAGATTTCACT CTCACCATCAGC AGTCTGCAACCT GAAGATTTTGCA ACTTACTACTGT CAACAGAGTTAC AGTACCCCTCCG TGGACGTTCGGC CAAGGGACCAAG GTGGAGATCAAA C | DIQLTQSPSSLS ASVGDRVTITCR ASQSISTYLNWY QQKPGKAPKLLI YAASSLQSGVPS RFSGSGSGTDFT LTISSLQPEDFA TTYYCQQSYSTPP WTFGQGTKVEIK |
| CAGGTGCAGCT GGTGCAGTCTG GGGCTGAGGTG AAGAAGCCTGG GTCCTCGGTGA AGGTCTCCTGC AAGGCTTCTGG AGGCACCTTCA GCAGCTATGCT ATCAGCTGGGT GCGACAGGCCC CTGGACAAGGG CTTGAGTGGAT GGGAGGGATCA TCCCTATCTTT GGTACAGCAAA CTACGCACAGA AGTTCCAGGGC AGAGTCACGAT TACCGCGGACG AATCCACGAGC ACAGCCTACAT GGAGCTGAGCA GCCTGAGATCT GAGGACACGGC CGTGTATTACT GTGCGAGAGGG AATGACTACT TATTGTAGTA GTACCAGCTGC TATCTAGATGC GGTTAGGCAGG GGTACTACTAC TACTACTACAT GGACGTCTGGG | QVQLVQSGAEVK KPGSSVKVSCKA SGGTFSSYAISW VRQAPGQGLEWM GGIIPIFGTANY AQKFQGRVTITA DESTSTAYMELS SLRSEDTAVYYC ARGNRLLYCSST SCYLDAVRQGYY YYYMDVWGKGT TVTSS | GAAATTGTGTTG ACACAGTCTCCA GCCACCCTGTCT TTGTCTCCAGGG GAAAGAGCCACC CTCTCCTGCAGG RFSGSGSGTDFT GCCAGTCAGAGT TTAGCCTGGTAC CAACAGAAACCT GGCCAGGCTCCC AGGCTCCTCATC TATGATGCATCC AACAGGGCCACT GGCATCCCAGCC AGGTTCAGTGGC AGTGGGTCTGGG ACAGACTTCACT CTCACCATCAGC AGCCTAGAGCCT GAAGATTTTGCA GTTTATTACTGT CAGCAGCGTAGC AACTGGCCCCTC ACTTTCGGCGGA GGGACCAAGGTG GAGATCAAAC | EIVLTQSPATLS LSPGERATLSCR ASQSVSSYLAWY QQKPGQAPRLLI YDASNRATGIPA RFSGSGSGTDFT LTISSLEPEDFA VYYCQQRSNWPL TFGGGTKVEIK |
| GAGGTGCAGCT GGTGGAGTCTG GGGGAGGCGTG GTCCAGCCTGG GAGGTCCCTGA GACTCTCCTGT GCAGCCTCTGG ATTCACCTTCA GTAGATATGGC ATGCACTGGGT CCGCCAGGCTC CAGGGAAGGGG CTGGAGTGGGT GGCAGTTATAT CATATGATGGA AGTAATAAATA CTATGCAGACT CCGTGAAGGGC CGATTCACCAT CTCCAGAGACA ATTCCAAGAAC ACGCTGTATCT GCAAATGAACA GCCTGAGAGCT GAGGACACGGC TGTGTATTACT GTGCGAAAGTG ACCGCCCCTTA TTGTAGTGGTG GTAGCTGCTAC GGAGGTAACTT TGACTACTGGG GCCAGGGAACC CTGGTCACCGT CTCCTCAG | EVQLVESGGGVV QPGRSLRLSCAA SGFTFSRYGMHW VRQAPGKGLEWV AVISYDGSNKYY ADSVKGRFTISR DNSKNTLYLQMN SLRAEDTAVYYC AKVTAPYCSGGS CYGGNFDYWGQG TLVTVSS | GCCATCCGGATG ACCCAGTCTCCA TCCTCCCTGTCT GCATCTGTAGGA GACAGAGTCACC ATCACTTGCCAG GCGAGTCAGGAC ATTAGCAACTAT TTAAATTGGTAT CAGCAGAAACCA GGGAAAGCCCCT AAGCTCCTGATC TACGATGCATCC AATTTGGAAACA GGGGTCCCATCA AGGTTCAGCGGA AGTGGATCTGGG ACAGATTTACT TTCACCATCAAC AGCCTGCAGCCT GAAGATATTGCA ACATATTACTGT CAACAGTATGAT AATCTCCCTCCT ACTTTCGGCGGA GGGACCAAGGTG GAGATCAAAC | AIRMTQSPSSLS ASVGDRVTITCQ ASQDISNYLNWY QQKPGKAPKLLI YDASNLETGVPS RFSGSGSGTDFT FTINSLQPEDIA TYYCQQYDNLPP TFGGGTKVEIK |
| GAAGTGCAGCT GGTGGAGTCTG GGGGAGGCTTG GTACAGCCTGG CAGGTCCCTGA GACTCTCCTGT GCAGCCTCTGG ATTCACCTTTG ATGATTATGCC ATGCACTGGGT CCGCCAAGCTC CAGGGAAGGGC CTGGAGTGGGT CTCAGGTATTA GTTGGAATAGT GGTACCATAGG CTATGCGGACT CTGTGAAGGGC CGATTCACCAT CTCCAGAGACA ACGCCAAGAAC TCCCTGTATCT GCAAATGAACA GTCTGAGAGCT GAGGACACGGC CTTTTATTACT GTGCAAAAGCG GGCGTAAGGGG TATAGCAGCAG CTGGTCCCGAC CTCAACTTCGA CCACTGGGGCC AGGGAACCCTG GTCACCGTCTC CTCAG | EVQLVESGGGLV QPGRSLRLSCAA SGFTFDDYAMHW VRQAPGKGLEWV SGISWNSGTIGY ADSVKGRFTISR DNAKNSLYLQMN SLRAEDTAFYYC AKGVRGIAAAG PDLNFDHWGQGT LVTVSS | GAAATTGTGTTG ACACAGTCTCCA GCCACCCTGTCT TTGTCTCCAGGG GAAAGAGCCACC CTCTCCTGCAGG GCCAGTCAGAGT GTTAGCAGCTAC TTAGCCTGGTAC CAACAGAAACCT GGCCAGGCTCCC AGGCTCCTCATC TATGATGCATCC AACAGGGCCACT GGCATCCCAGCC AGGTTCAGTGGC AGTGGGTCTGGG ACAGACTTCACT CTCACCATCAGC AGCCTAGAGCCT GAAGATTTTGCA GTTTATTACTGT CAGCAGCGTATC ACCTTCGGCCAA GGGACACGACTG GAGATTAAAC | EIVLTQSPATLS LSPGERATLSCR ASQSVSSYLAWY QQKPGQAPRLLI YDASNRATGIPA RFSGSGSGTDFT LTISSLEPEDFA VYYCQQRITFGQ GTRLEIK |

TABLE 5-continued

| IGH VDJ (nucleotide) | IGH VDJ (amino acid) | IGL VJ (nucleotide) | IGL VJ (amino acid) |
|---|---|---|---|
| GAGGTGCAGCT GGTGGAGTCTG GGGGAGGCGTG GTCCAGCCTGG GAGGTCCCTGA GACTCTCCTGT GCAGCCTCTGG ATTCACCTTCA GTAACTATGCT ATACACTGGGT CCGCCAGGCTC CAGGCAAGGGG CTGGAGTGGGT GGCAGTTATAT CATATGATGGA AGCAATAAATA CTACGCAGACT CCGTGAAGGGC CGATTCACCAT CTCCAGAGACA ATTCCAAGAAC ACGCTGTATCT GCAAATGAACA GCCTGAGAGCT GAGGACACGGC TGTGTATTACT GTGCAGAGAT TTTGACGATAG TTCGTTCTGGG CGTTTGACTAC TGGGGCCAGGG AACCCTGGTCA CCGTCTCCTCA G | EVQLVESGGVV QPGRSLRLSCAA SGFTFSNYAIHW VRQAPGKGLEWV AVISYDGSNKYY ADSVKGRFTISR DNSKNTLYLQMN SLRAEDTAVYYC ARDFDDSSFWAF DYWGQGTLVTVS S | GACATCCAGTTG ACCCAGTCTCCA TCCTCCCTGTCT GCGTCTGTAGGA GACAGAGTCACC ATCACTTGCCGG GCAAGTCAGAGC ATTCGCAGCTAT TTAAATTGGTAT CAACAGAAACCA GGGAAAGCCCCT AAGCTCCTGATC TATGCTGCATCC AGTTTGCAAAGT GGGGTCCCTTCA AGGTTCAGTGGC AGTGGATCTGGG ACAGATTTCACT CTCACCATCAGC AGTCTGCAACCT GATGATTTTGCA ACTTACTACTGT CAACAGAGTTAC AGTACCCCTCCG GCCACTTTTGGC CAGGGGACCAAG CTGGAGATCAAA C | DIQLTQSPSSLS ASVGDRVTITCR ASQSIRSYLNWY QQKPGKAPKLLI YAASSLQSGVPS RFSGSGSGTDFT LTISSLQPDDFA TYYCQQSYSTPP ATFGQGTKLEIK |
| CAGGTGCAGCT GGTGCAGTCTG GGGCTGAGGTG AAGAAGCCTGG GGCCTCAGTGA AGGTTTCCTGC AAGGCATCTGG ATACACCTTCA CCAGTTACTAT ATGCACTGGGT GCGACAGGCCC CTGGACAAGGG CTTGAGTGGAT GGGAATAATCA ACCCTAGTGGT GGTAGCACAAG CTACGCACAGA AGTTCCAGGGC AGAGTCACCAT GACCAGGGACA CGTCCACGAGC ACAGTCTACAT GGAGCTGAGCA GCCTGAGATCT GAGGACACGGC CGTGTATTACT GTGCTAGAGTG CCCCGTGAGGG GACCCCAGGGT TCGACCCCTGG GGCCAGGGAAC CCTGGTCACCG TCTCCTCAG | QVQLVQSGAEVK KPGASVKVSCKA SGYTFTSYYMHW VRQAPGQGLEWM GIINPSGGSTSY AQKFQGRVTMTR DTSTSTVYMELS SLRSEDTAVYYC ARVPREGTPGFD PWGQGTLVTVSS | TCCTATGAGCTG ACACAGCCACCC TCAGTGTCAGTG GCCCAGGAAAG ACGGCCAGGATT ACCTGTGGGGAA AACAACATTGGA AGTAAAAGTGTG CACTGGTACCAG CAGAAGCCAGGC CAGGCCCTGTG CTGGTCATCTAT TATGATAGCGAC CGGCCCTCAGGG ATCCCTGAGCGA TTCTCTGGCTCC AACTCTGGGAAC ACGGCCACCCTG ACCATCAACAGG GTCGAAGCCGGG GATGAGGCCGAC TATTACTGTCAG GTGTGGGATAGT AGTAGTGATCAT GTGGTATTCGGC GGAGGGACCAAG CTGACCGTCCTA G | SYELTQPPSVSV APGKTARITCGE NNIGSKSVHWYQ QKPGQAPVLVIY YDSDRPSGIPER FSGSNSGNTATL TINRVEAGDEAD YYCQVWDSSSDH VVFGGGTKLTVL |
| CAGGTGCAGCT GCAGGAGTCGG GCCCAGGACTG GTGAAGCCTTC ACAGACCCTGT CCCTCACCTGC ACTGTCTCTGG | QVQLQESGPGLV KPSQTLSLTCTV SGGSISSGGYYW SWIRQHPGKGLE WIGYIYYSGSTY YNPSLKSRVTIS VDTSKNQFSLKL | GATATTGTGATG ACTCAGTCTCCA CTCTCCCTGCCC GTCACCCCTGGA GAGCCGGCCTCC ATCTCCTGCAGG TCTAGTCAGAGC | DIVMTQSPLSLP VTPGEPASISCR SSQSLLHSNGYN YLDWYLQKPQS PQLLIYLGSNRA SGVPDRFSGSGS GTDFTLKISRVE |

TABLE 5-continued

| IGH VDJ (nucleotide) | IGH VDJ (amino acid) | IGL VJ (nucleotide) | IGL VJ (amino acid) |
|---|---|---|---|
| TGGCTCCATCA GCAGTGGTGGT TACTACTGGAG CTGGATCCGCC AGCACCCAGGG AAGGGCCTGGA GTGGATTGGGT ACATCTATTAC AGTGGGAGCAC CTACTACAACC CGTCCCTCAAG AGTCGAGTTAC CATATCAGTAG ACACGTCTAAG AACCAGTTCTC CCTGAAGCTGA GCTCTGTGACT GCCGCGGACAC GGCCGTGTATT ACTGTGCGAGA GTTTGGCAATA CTATGATAGTA GTGGTTCCTTT GACTACTGGGG CCAGGGAACCC TGGTCACCGTC TCCTCAG | SSVTAADTAVYY CARVWQYYDSSG SFDYWGQGTLVT VSS | CTCCTGCATAGT AATGGATACAAC TATTTGGATTGG TACCTGCAGAAG CCAGGGCAGTCT CCACAGCTCCTG ATCTATTTGGGT TCTAATCGGGCC TCCGGGGTCCCT GACAGGTTCAGT GGCAGTGGATCA GGCACAGATTTT ACACTGAAAATC AGCAGAGTGGAG GCTGAGGATGTT GGGGTTTATTAC TGCATGCAAGCT CTACAAACTCCA TTCACTTTCGGC CCTGGGACCAAA GTGGATATCAAA C | AEDVGVYYCMQA LQTPFTFGPGTK VDIK |

Each row in table 5 represents a BCR sequence, which includes a nucleotide and amino acid sequence for the VDJ regions of the heavy chain and the VJ regions of the light chain (see Robbiani et al, doi: https://doi.org/10.1101/2020.05.13.092619, the contents of which are incorporated herein by reference in their entirety for all purposes).

Characteristics and phenotypes of SARS-CoV-2 specific T cells and the viral antigens (epitopes) that they recognize have been described in scientific literature. For example, see Weiskopf et al, Phenotype and kinetics of SARS-CoV-2-specific T cells in COVID-19 patients with acute respiratory distress syndrome. Sci. Immunol. 5, eabd2071 (2020). doi: 10.1126/sciimmunol.abd2071pmid:32591408, the contents of which are incorporated herein by reference in their entirety for all purposes.

TCR and/or BCR sequences that recognize coronaviruses may further include sequences found in the iReceptor database (https://gateway.ireceptor.org/login). For an example of a database comprising data associated with 1,414 specimens, including metadata, clinical data, coronavirus infection status, sequences of over 135,000 TCRs, coronavirus peptide sequences, and peptide and TCR binding pair data, see Nolan et al, DOI: 10.21203/rs.3.rs-51964/v1, the contents of which are incorporated herein by reference in their entirety for all purposes.

Accordingly, a diagnosis, or confirmatory diagnosis of COVID, or SARS-CoV-2 exposure can be provided, based on a TCR/BCR analysis.

While the above example is directed to SARS-CoV-2, the present technology is not so limited and can be used to diagnose, confirm a diagnosis, predict, or identify other diseases, infections, or conditions. By way of example, but not by way of limitation, in some embodiments, one or more of specific cancer types, infectious disease, e.g., flu A, HIV, EBV, CMV, SARS-CoV-2, Lyme, allergy, and autoimmune (diabetes, Celiac, psoriasis, etc.) is diagnosed or exposure is confirmed by determining the TCR/BCR profile of a subject sample.

Minimal Residual Disease (MRD) Testing

In some embodiments, the present technology is used to detect a small number of remaining tumor cells in, for example, a patient being treated for a hematological malignancy. In some embodiments, the present methods detect 1 malignant TB cell clone in 1,000, 10,000, or 100,000 cells. By way of example, but not by way of limitation, the detection of 1 cell in 1,000, 10,000, or 100,000 cells may be useful to a healthcare practitioner in a decision to resume therapy or to choose a second-line therapy to treat the disease.

Applications of TCR/BCR Profiling Related to Comparison of Patient Data to Known Cohort Data Biomarkers for Disease and Therapy Development In some embodiments, many TCR/BCR profiles from a cohort of patients suffering from a particular disease, infection, or medical condition are developed and analyzed. In some embodiments, the TCR/BCR profiles from a cohort of patients suffering from a particular disease, infection, or medical condition includes positive controls, i.e. patients known to have been diagnosed with a particular disease, infection, or medical condition, and negative controls, or patients known not to have the particular disease, infection, or medical condition, are provided. By way of example, in some embodiments, TCR/BCR profiles are developed from a cohort of individuals suffering from a single type of tumor or cancer, a specific infectious disease, specific autoimmune disease, specific allergy, or specific medical condition.

In some embodiments, receptor chain pairs are identified. In some embodiments, TCR reactivity is validated with major histocompatibility complex (MEW) tetramer assay testing.

In some embodiments, the identified common TCR/BCR sequences are used for immunotherapy production e.g., CAR-T cell production for various disease states, including, but not limited to infection, autoimmune disease, allergies, and cancer.

In some embodiments, the identified common TCR/BCR sequences of a disease cohort are used for antigen prediction (e.g., for vaccine development) for diseases or conditions including but not limited to infection, autoimmune disease, allergies, and cancer. In some embodiments, the patients would be grouped by HLA type to facilitate predicting the antigen that corresponds to a common receptor sequence. In some embodiments, machine learning would be used to predict one or more antigens. In some embodiments, the antigen would be validated with, for example, wet lab experiments including but not limited to multiplex identification of antigen specific T cell (MIRA) assay and Biacore or other similar assays based on surface plasmon resonance to detect binding energies and molecular interactions.

Predictive Testing

In some embodiments, models generated from TCR/BCR profiles derived from disease cohort analyses can also be applied to individual patient data.

In some embodiments, longitudinal testing of TCR/BCR profiles is performed during a therapy, or during clinical trials to determine effectiveness/efficacy of a given therapeutic approach. Likewise, longitudinal testing of TCR/BCR profiles concurrently with vaccination in the context of, for example, cancer vaccines, can be performed to determine efficacy and estimated time to progression or time to remission, disease progression (with or without therapy), and/or therapeutic outcome or efficacy. In some embodiments, longitudinal testing of TCR/BCR profiles concurrent with immune oncology (IO) therapies provides detailed and accurate information regarding the efficacy of an immune oncological modality.

In some embodiments, a single sampling point may be sufficient to evaluate a patient's response or efficacy of an IO modality.

In some embodiments, TCR/BCR profile data is integrated with other immunotherapy response predictors to accurately evaluate the response of a patient to an immunotherapy. In some embodiments, TCR/BCR profiles can be used as additional data to refine other existing and not as yet conceived prediction models.

In some embodiments, large cohort data of individuals suffering from a particular disease or disorder includes TCR/BCR profile data and therapy outcomes.

In some embodiments, the TCR/BCR analysis predicts protective or sterilizing immunity after natural infection/pathogen exposure or vaccination. In some embodiments, a large dataset with positive and negative controls and distribution of receptor sequence enrichment levels is used to identify threshold levels for certain receptor sequence enrichment associated with infection/exposure to the pathogen is provided.

In some embodiments, the TCR/BCR analysis is used for HLA typing. In some embodiments, the TCR/BCR data is used in combination with other HLA typing methods and/or can be used as a feature to refine those prediction models. An example of an HLA typing method is disclosed, for example, in U.S. patent application Ser. No. 16/789,413, filed Aug. 20, 2019, which is incorporated herein by reference and in its entirety for all purposes.

ILLUSTRATIVE EMBODIMENTS

Disclosed herein are several non-limiting illustrative embodiments of the present technology.

Embodiment 1. In a first embodiment, a method of determining a TCR/BCR profile of a patient is provided. In some embodiments, the method comprises (a) isolating RNA from a sample from the patient; (b) enriching the isolated RNA for TCR/BCR genes using a set of TCR/BCR hybrid-capture probes; (c) determining the sequence of the RNA of (b) to generate sequencing data; and (d) analyzing the sequencing data to determine the TCR/BCR profile of the patient. In some embodiments, the set of TCR/BCR hybrid-capture probes comprises a first pool of BCR constant region probes, a second pool of BCR non-constant region probes, a third pool of TCR constant region probes, and a fourth pool of TCR non-constant region probes.

Embodiment 2. The method of embodiment 1, wherein the ratio of the first pool, second pool, third pool, and fourth pool within the set is 1:2.5:100:100.

Embodiment 3. The method of embodiment 1, wherein step (b) further comprises enriching for (1) a targeted whole transcriptome panel, (2) a targeted whole exome panel; (3) a targeted panel directed to at least 10 target sequences of interest, or (4) a combination of any of 1-3, using a fifth pool of hybrid-capture probes.

Embodiment 4. The method of embodiment 3, wherein the ratio of the first pool, second pool, third pool, fourth pool, and fifth pool within the set is 1:2.5:100:100:10.

Embodiment 5. The method of embodiment 4, wherein 2% or less of the reads in the sequencing data map to TCR/BCR genes.

Embodiment 6. The method of embodiment 1, wherein step (b) further comprises enriching for a targeted whole exome panel using a fifth pool of hybrid-capture probes.

Embodiment 7. The method of embodiment 1 wherein step (d) comprises identifying a plurality of TCR/BCR clones in the sample.

Embodiment 8. The method of embodiment 1 wherein step (d) comprises identifying the most abundant TCR/BCR clones in the sample.

Embodiment 9. The method of embodiment 1 wherein step (d) comprises identifying the most abundant non-constant region sequences in the sample.

Embodiment 10. The method of embodiment 1, wherein the sample is a blood sample or a solid tumor sample.

Embodiment 11. The method of any of the previous embodiments, further comprising diagnosing the subject with a disease or condition based on the TCR/BCR profile.

Embodiment 12. The method of embodiment 11, wherein the disease or condition comprises one or more of cancer, an infection, an autoimmune condition, allergy, or graft versus host disease.

Embodiment 13. The method of embodiment 12, wherein the cancer or infection (infectious disease) is one or more provided in the list in embodiment 114.

Embodiment 14. The method of embodiment 11, wherein the diagnosing comprises comparing the subject's TCR/BCR profile to a control, wherein if the subject's BCR/TCR profile is similar to the control (for example, the abundance, identity, and/or clonality of one or more BCR/TCR receptors is similar to or identical to the control) the subject is diagnosed as having the disease or condition.

Embodiment 15. In some methods of any of the previous embodiments, a control TCR/BCR panel for a disease (such as cancer or an infection), or medical condition is provided.

Embodiment 16. In some embodiments, a method of diagnosing a patient with a disease or condition based on the patient's TCR/BCR profile is provided. In some embodiments, the method comprises: a) isolating RNA from a sample from the patient; b) enriching the isolated RNA for TCR/BCR genes using a set of TCR/BCR hybrid-capture probes; c) determining the sequence of the RNA of (b) to generate sequencing data; d) analyzing the sequencing data to determine the TCR/BCR profile of the patient; and e) comparing the TCR/BCR profile of the patient to a set of standards to diagnose the patient with a disease or condition; wherein the set of TCR/BCR hybrid-capture probes comprises a first pool of TCR constant region probes, a second pool of TCR non-constant region probes, a third pool of BCR constant region probes, and a fourth pool of BCR non-constant region probes.

Embodiment 17. The method of embodiment 16, wherein the ratio of the first pool, second pool, third pool, and fourth pool within the set is 1:2.5:100:100.

Embodiment 18. The method of embodiment 16, wherein step (b) further comprises enriching for a targeted whole-transcriptome panel using a fifth pool of hybrid-capture probes.

Embodiment 19. The method of embodiments 18, wherein the ratio of the first pool, second pool, third pool, fourth pool, and fifth pool within the set is 1:2.5:100:100:10.

Embodiment 20. The method of embodiment 19, wherein 2% or less of the reads in the sequencing data map to TCR/BCR genes.

Embodiment 21. The method of embodiment 16, wherein step (b) further comprises enriching for a targeted whole-exome panel using a fifth pool of hybrid-capture probes.

Embodiment 22. The method of embodiment 16, wherein the disease or condition is an infectious disease, a cancer, an autoimmune disease, an allergy, or graft versus host disease.

Embodiment 23. The method of embodiment 22, wherein the cancer, infection or infectious disease is wherein the cancer or infection (infectious disease) is one or more provided in the list in embodiment 114.

Embodiment 24. The method of embodiment 23, wherein the diagnosing comprises comparing the subject's TCR/BCR profile to a control, wherein if the subject's BCR/TCR profile is similar to the control (for example, the abundance, identity, and/or clonality of one or more BCR/TCR receptors is similar to or identical to the control) the subject is diagnosed as having the disease or condition.

Embodiment 25. In some embodiments, a control TCR/BCR panel for a disease (such as cancer or an infection), or medical condition is provided.

Embodiment 26. In some embodiments, a method of evaluating the severity or progression of a disease or condition based on the TCR/BCR profile of a patient is provided. In some embodiments, the method comprises: a) isolating RNA from a sample from the patient; b) enriching the isolated RNA for TCR/BCR genes using a set of TCR/BCR hybrid-capture probes; c) determining the sequence of the RNA of (b) to generate sequencing data; d) analyzing the sequencing data to determine the TCR/BCR profile of the patient; and e) comparing the TCR/BCR profile of the patient to a set of standards to characterize the severity or progression of the disease; wherein the set of TCR/BCR hybrid-capture probes comprises a first pool of TCR constant region probes, a second pool of TCR non-constant region probes, a third pool of BCR constant region probes, and a fourth pool of BCR non-constant region probes.

Embodiment 27. The method of embodiment 26, wherein the ratio of the first pool, second pool, third pool, and fourth pool within the set is 1:2.5:100:100.

Embodiment 28. The method of embodiment 26, wherein step (b) further comprises enriching for a targeted whole transcriptome panel using a fifth pool of hybrid-capture probes.

Embodiment 29. The method of embodiment 28, wherein the ratio of the first pool, second pool, third pool, fourth pool, and fifth pool within the set is 1:2.5:100:100:10.

Embodiment 30. The method of embodiment 29, wherein 2% or less of the reads in the sequencing data map to TCR/BCR genes.

Embodiment 31. The method of embodiment 26, wherein step (b) further comprises enriching for a targeted whole exome panel using a fifth pool of hybrid-capture probes.

Embodiment 32. The method of embodiment 26, wherein the disease is an infectious disease, a cancer, an autoimmune disease, or an allergy.

Embodiment 33. The method of embodiment 29, wherein the sample is a solid tumor sample.

Embodiment 34. The method of embodiment 30, wherein step (e) comprises determining the presence or extent of tumor lymphocyte infiltration.

Embodiment 35. The method of embodiment 32, wherein the cancer or infection (infectious disease) is one or more provided in the list in embodiment 114.

Embodiment 36. The method of embodiment 35, wherein the diagnosing comprises comparing the subject's TCR/BCR profile to a control, wherein if the subject's BCR/TCR profile is similar to the control (for example, the abundance, identity, and/or clonality of one or more BCR/TCR receptors is similar to or identical to the control) the subject is diagnosed as having the disease or condition.

Embodiment 37. In some embodiments, a control TCR/BCR panel for a disease (such as cancer or an infection), or medical condition is provided.

Embodiment 38. In some embodiments, a method for treating a disease or condition of a patient based on the patient's TCR/BCR profile is provided. In some embodiments the method comprises: a) isolating RNA from a sample from the patient; b) enriching the isolated RNA for TCR/BCR genes using a set of TCR/BCR hybrid-capture probes; c) determining the sequence of the RNA of (b) to generate sequencing data; d) analyzing the sequencing data to determine the TCR/BCR profile of the patient; and e) administering a treatment based on the TCR/BCR profile of the patient; wherein the set of TCR/BCR hybrid-capture probes comprises a first pool of TCR constant region probes, a second pool of TCR non-constant region probes, a third pool of BCR constant region probes, and a fourth pool of BCR non-constant region probes.

Embodiment 39. The method of embodiment 38, wherein the ratio of the first pool, second pool, third pool, and fourth pool within the set is 1:2.5:100:100.

Embodiment 40. The method of embodiment 38, wherein step (b) further comprises enriching for a targeted whole transcriptome panel using a fifth pool of hybrid-capture probes.

Embodiment 41. The method of embodiment 40, wherein the ratio of the first pool, second pool, third pool, fourth pool, and fifth pool within the set is 1:2.5:100:100:10.

Embodiment 42. The method of embodiment 41, wherein 2% or less of the reads in the sequencing data map to TCR/BCR genes.

Embodiment 43. The method of embodiment 38, wherein step (b) further comprises enriching for a targeted whole exome panel using a fifth pool of hybrid-capture probes.

Embodiment 44. The method of embodiment 38, wherein step (d) comprises identifying the most abundant TCR/BCR clone in the sample, and wherein the treatment administered in step (e) comprises expanding the most abundant clones in vitro and re-administering the expanded cells to the patient.

Embodiment 45. The method of embodiment 38, wherein step (d) comprises identifying the most abundant TCR non-constant region sequences in the sample, and wherein the treatment administered in step (e) comprises administering a CAR-T cell therapy comprising at least one of the most abundant TCR non-constant region sequences.

Embodiment 46. The method of embodiment 38, wherein the disease or condition is an infectious disease, a cancer, an autoimmune disease, or an allergy.

Embodiment 47. The method of embodiment 46, wherein the cancer or infection (infectious disease) is one or more provided in the list in embodiment 114.

Embodiment 48. In some embodiments, a method for characterizing the effect of a therapy on the TCR/BCR profile of a patient is provided. In some embodiments the method comprises: (a) at a first time point before the therapy is administered: (i) isolating RNA from a sample from the patient; (ii) enriching the isolated RNA for TCR/BCR genes using a set of TCR/BCR hybrid-capture probes; (iii) determining the sequence of the RNA of (ii) to generate sequencing data; and (iv) analyzing the sequencing data to determine the TCR/BCR profile of the patient; and (b) at a second time point after the therapy has been administered: (i) isolating RNA from a sample from the patient; (ii) enriching the isolated RNA for TCR/BCR genes using a set of hybrid-capture probes; (iii) determining the sequence of the RNA of (ii) to generate sequencing data; and (iv) analyzing the sequencing data to determine the TCR/BCR profile of the patient; and (c) comparing the TCR/BCR profile determined in step (a) to the TCR/BCR profile determined in step (b) to characterize the effect of the therapy on the TCR/BCR profile of the patient; wherein the set of TCR/BCR hybrid-capture probes comprises a first pool of TCR constant region probes, a second pool of TCR non-constant region probes, a third pool of BCR constant region probes, and a fourth pool of BCR non-constant region probes.

Embodiment 49. The method of embodiment 48, wherein the ratio of the first pool, second pool, third pool, and fourth pool within the set is 1:2.5:100:100.

Embodiment 50. The method of embodiment 48, wherein step (b) further comprises enriching for a targeted whole transcriptome panel using a fifth pool of hybrid-capture probes.

Embodiment 51. The method of embodiment 50, wherein the ratio of the first pool, second pool, third pool, fourth pool, and fifth pool within the set is 1:2.5:100:100:10.

Embodiment 52. The method of embodiment 51, wherein 2% or less of the reads in the sequencing data map to TCR/BCR genes.

Embodiment 53. The method of embodiment 48, wherein step (b) further comprises enriching for a targeted whole exome panel using a fifth pool of hybrid-capture probes.

Embodiment 54. The method of embodiment 48, wherein the therapy is an immunotherapeutic agent.

Embodiment 55. The method of embodiment 54, wherein the immunotherapeutic agent is a vaccine.

Embodiment 56. The method of embodiment 54, wherein the immunotherapeutic agent is a chimeric antigen receptor (CAR) T cell.

Embodiment 57. The method of any one of embodiments 48-57 further comprising modifying the treatment prescribed to the patient based on the observed effect.

Embodiment 58. In some embodiments, a method of identifying TCR/BCR non-constant region sequences that are enriched in a cohort of patients that have a specific disease or condition is provided. In some embodiments the method comprises: a) isolating RNA from a sample from each patient in the cohort; b) enriching the isolated RNA for TCR/BCR genes using a set of TCR/BCR hybrid-capture probes; wherein the set of hybrid-capture probes comprises a first pool of TCR constant region probes, a second pool of TCR non-constant region probes, a third pool of BCR constant region probes, and a fourth pool of BCR non-constant region probes; c) determining the sequence of the RNA of (b) to generate sequencing data; d) analyzing the sequencing data to determine the TCR/BCR profile of the patients in the cohort; and e) identifying TCR/BCR non-constant region sequences that are enriched in the cohort as compared to a control group without the disease or condition.

Embodiment 59. The method of embodiment 58, wherein the ratio of the first pool, second pool, third pool, and fourth pool within the set is 1:2.5:100:100.

Embodiment 60. The method of embodiment 58, wherein the set of hybrid-capture probes further comprises a fifth pool of probes comprising a targeted whole transcriptome panel.

Embodiment 61. The method of embodiment 60, wherein the ratio of the first pool, second pool, third pool, fourth pool, and fifth pool within the set is 1:2.5:100:100:10.

Embodiment 62. The method of embodiment 61, wherein 2% or less of the reads in the sequencing data map to TCR/BCR genes.

Embodiment 63. The method of embodiment 58, wherein the set of hybrid-capture probes further comprises a fifth pool of probes comprising a targeted whole exome panel.

Embodiment 64. The method of embodiment 58, wherein the disease or condition is an infection, an autoimmune disease, an allergy, or cancer.

Embodiment 65. The method of embodiment 58 further comprising using the enriched TCR/BCR non-constant region sequences to identify disease-specific antigens.

Embodiment 66. The method of embodiment 65 further comprising producing a vaccine comprising the disease-specific antigens.

Embodiment 67. The method of embodiments 65 or 66, wherein the disease-specific antigens are tumor antigens.

Embodiment 68. The method of embodiment 64, wherein the cancer or infection (infectious disease) is one or more provided in the list in embodiment 114.

Embodiment 69. In some embodiments, a kit for determining the TCR/BCR profile of a patient is provided. In some embodiments, the kit comprises a set of TCR/BCR hybrid-capture probes.

Embodiment 70. In some embodiments, a method of determining the TCR/BCR profile of a patient is provided. In some embodiments, the method comprises: a) isolating RNA from a sample from the patient; b) enriching the isolated RNA for TCR/BCR genes using a set of TCR/BCR hybrid-capture probes and enriching for a targeted whole transcriptome panel using a set of hybrid-capture probes; c) determining the sequence of the RNA of (b) to generate sequencing data; and d) analyzing the sequencing data to determine the TCR/BCR profile of the patient, wherein the set of TCR/BCR hybrid-capture probes comprises a first pool of BCR constant region probes, a second pool of BCR non-constant region probes, a third pool of TCR constant region probes, and a fourth pool of TCR non-constant region probes, wherein the ratio of the whole transcriptome-targeting panel, first pool, second pool, third pool, and fourth pool within the set is 10:1:2.5:100:100, wherein 2% or less of the reads in the sequencing data map to TCR/BCR genes.

Embodiment 71. In some embodiments, a method of determining the TCR/BCR profile of a patient is provided. In some embodiments, the method comprises: a) isolating RNA from a sample from the patient; b) enriching the isolated RNA for TCR/BCR genes using a set of TCR/BCR hybrid-capture probes; c) determining the sequence of the RNA of (b) to generate sequencing data; and d) analyzing the sequencing data to determine the TCR/BCR profile of the patient, wherein the patient has been exposed to or is suspected to have been exposed to SARS-CoV-2, wherein the set of TCR/BCR hybrid-capture probes comprises a first pool of TCR constant region probes, a second pool of TCR non-constant region probes, a third pool of BCR constant region probes, and a fourth pool of BCR non-constant region probes.

Embodiment 72. The method of embodiment 71, wherein the ratio of the first pool, second pool, third pool, and fourth pool within the set is 1:2.5:100:100.

Embodiment 73. The method of embodiment 71, wherein step (b) further comprises enriching for a targeted whole-transcriptome panel using a fifth pool of hybrid-capture probes.

Embodiment 74. The method of embodiment 73, wherein the ratio of the first pool, second pool, third pool, fourth pool, and fifth pool within the set is 1:2.5:100:100:10.

Embodiment 75. The method of embodiment 74, wherein 2% or less of the reads in the sequencing data map to TCR/BCR genes.

Embodiment 76. The method of embodiment 71, wherein step (b) further comprises enriching for a whole exome targeting panel using a fifth pool of hybrid-capture probes.

Embodiment 77. The method of embodiment 71 further comprising identifying a plurality of TCR/BCR clones in the sample.

Embodiment 78. The method of embodiment 71 further comprising identifying the most abundant TCR/BCR clone in the sample.

Embodiment 79. The method of embodiment 71 further comprising identifying the most abundant non-constant region sequences in the sample.

Embodiment 80. The method of embodiment 71, wherein the sample is a blood sample or a solid tumor sample.

Embodiment 81. In some embodiments, a method of evaluating the severity or progression of COVID-19 based on the TCR/BCR profile of a patient is provided. In some embodiments, the method comprises: a) isolating RNA from a sample from the patient; b) enriching the isolated RNA for TCR/BCR genes using a set of TCR/BCR hybrid-capture probes; c) determining the sequence of the RNA of (b) to generate sequencing data; d) analyzing the sequencing data to determine the TCR/BCR profile of the patient; and e) comparing the TCR/BCR profile of the patient to a set of standards to characterize the severity or progression of the disease; wherein the set of TCR/BCR hybrid-capture probes comprises a first pool of TCR constant region probes, a second pool of TCR non-constant region probes, a third pool of BCR constant region probes, and a fourth pool of BCR non-constant region probes.

Embodiment 82. The method of claim 81, wherein the ratio of the first pool, second pool, third pool, and fourth pool within the set is 1:2.5:100:100.

Embodiment 83. The method of claim 81, wherein step (b) further comprises enriching for a targeted transcriptome panel using a fifth pool of hybrid-capture probes.

Embodiment 84. The method of claim 83, wherein the ratio of the first pool, second pool, third pool, fourth pool, and fifth pool within the set is 1:2.5:100:100:10.

Embodiment 85. The method of claim 84, wherein 2% or less of the reads in the sequencing data map to TCR/BCR genes.

Embodiment 86. The method of claim 81, wherein step (b) further comprises enriching for a targeted whole exome panel using a fifth pool of hybrid-capture probes.

Embodiment 87. In some embodiments, a method for treating COVID-19 based on the patient's TCR/BCR profile is provided. In some embodiments, the method comprises: a) isolating RNA from a sample from the patient; b) enriching the isolated RNA for TCR/BCR genes using a set of TCR/BCR hybrid-capture probes; c) determining the sequence of the RNA of (b) to generate sequencing data; d) analyzing the sequencing data to determine the TCR/BCR profile of the patient; and e) administering a treatment based on the TCR/BCR profile of the patient; wherein the set of TCR/BCR hybrid-capture probes comprises a first pool of TCR constant region probes, a second pool of TCR non-constant region probes, a third pool of BCR constant region probes, and a fourth pool of BCR non-constant region probes.

Embodiment 88. The method of embodiment 87, wherein the ratio of the first pool, second pool, third pool, and fourth pool within the set is 1:2.5:100:100.

Embodiment 89. The method of embodiment 87, wherein step (b) further comprises enriching for a targeted whole transcriptome panel using a fifth pool of hybrid-capture probes.

Embodiment 90. The method of embodiment 89, wherein the ratio of the first pool, second pool, third pool, fourth pool, and fifth pool within the set is 1:2.5:100:100:10.

Embodiment 91. The method of embodiment 90, wherein 2% or less of the reads in the sequencing data map to TCR/BCR genes.

Embodiment 92. The method of embodiment 87, wherein step (b) further comprises enriching for a targeted whole transcriptome panel using a fifth pool of hybrid-capture probes.

Embodiment 93. The method of embodiment 87, wherein step (d) comprises identifying the most abundant TCR/BCR clone in the sample, and wherein the treatment administered in step (e) comprises expanding the most abundant clones in vitro and re-administering the expanded cells to the patient.

Embodiment 94. The method of claim 1, wherein step (d) comprises identifying the most abundant TCR non-constant region sequences in the sample, and wherein the treatment administered in step (e) comprises administering a CAR-T cell therapy comprising at least one of the most abundant TCR non-constant region sequences.

Embodiment 95. In some embodiments, a method for characterizing the effect of a COVID-19 therapy on the TCR/BCR profile of a patient is provided. In some embodiments, the method comprises a) at a first time point before the therapy is administered: i. isolating RNA from a sample from the patient; ii. enriching the isolated RNA for TCR/BCR genes using a set of TCR/BCR hybrid-capture probes; iii. determining the sequence of the RNA of (aii) to generate sequencing data; and iv. analyzing the sequencing data to determine the TCR/BCR profile of the patient; and b) at a second time point after the therapy has been administered: i) isolating RNA from a sample from the patient; ii) enriching the isolated RNA for TCR/BCR genes using a set of TCR/BCR hybrid-capture probes; iii) determining the sequence of the RNA of (bii) to generate sequencing data; and iv) analyzing the sequencing data to determine the TCR/BCR profile of the patient; and c) comparing the TCR/BCR profile determined in step (a) to the TCR/BCR profile determined in step (b) to characterize the effect of the therapy on the TCR/BCR profile of the patient; wherein the set of TCR/BCR hybrid-capture probes comprises a first pool of TCR constant region probes, a second pool of TCR non-constant region probes, a third pool of BCR constant region probes, and a fourth pool of BCR non-constant region probes.

Embodiment 96. The method of embodiment 95, wherein the ratio of the first pool, second pool, third pool, and fourth pool within the set is 1:2.5:100:100.

Embodiment 97. The method of embodiment 95, wherein step (aii) and (bii) further comprises enriching for a targeted whole transcriptome panel using a fifth pool of hybrid-capture probes.

Embodiment 98. The method of embodiment 97, wherein the ratio of the first pool, second pool, third pool, fourth pool, and fifth pool within the set is 1:2.5:100:100:10.

Embodiment 99. The method of embodiment 98, wherein 2% or less of the reads in the sequencing data map to TCR/BCR genes.

Embodiment 100. The method of embodiment 95, wherein step (aii) and (bii) further comprises enriching for a targeted whole exome panel using a fifth pool of hybrid-capture probes.

Embodiment 101. The method of embodiment 95, wherein the therapy is an immunotherapeutic agent.

Embodiment 102. The method of embodiment 101, wherein the immunotherapeutic agent is a vaccine.

Embodiment 103. The method of embodiment 101, wherein the immunotherapeutic agent is a chimeric antigen receptor (CAR) T cell.

Embodiment 104. The method of any one of embodiments 95-104 further comprising modifying the treatment prescribed to the patient based on the observed effect.

Embodiment 105. In some embodiments, a method of identifying TCR/BCR non-constant region sequences that are enriched in a cohort of patients with SARS-CoV-2 is provided. In some embodiments, the method comprises: a) isolating RNA from a sample from each patient in the cohort; b) enriching the isolated RNA for TCR/BCR genes using a set of TCR/BCR hybrid-capture probes; c) determining the sequence of the RNA of (b) to generate sequencing data; d) analyzing the sequencing data to determine the TCR/BCR profile of the patients in the cohort; and e) identifying TCR/BCR non-constant region sequences that are enriched in the cohort as compared to a control group without the disease or condition, wherein the set of hybrid-capture probes comprises a first pool of TCR constant region probes, a second pool of TCR non-constant region probes, a third pool of BCR constant region probes, and a fourth pool of BCR non-constant region probes.

Embodiment 106. The method of embodiment 105, wherein the ratio of the first pool, second pool, third pool, and fourth pool within the set is 1:2.5:100:100.

Embodiment 107. The method of embodiment 105, wherein the set of hybrid-capture probes further comprises a fifth pool of probes comprising a whole transcriptome targeting panel.

Embodiment 108. The method of embodiment 107, wherein the ratio of the first pool, second pool, third pool, fourth pool, and fifth pool within the set is 1:2.5:100:100:10.

Embodiment 109. The method of embodiment 108, wherein 2% or less of the reads in the sequencing data map to TCR/BCR genes.

Embodiment 110. The method of embodiment 105, wherein the set of hybrid-capture probes further comprises a fifth pool of probes comprising a whole exome targeting panel.

Embodiment 111. The method of embodiment 105 further comprising using the enriched TCR/BCR non-constant region sequences to identify SARS-CoV-2-specific antigens.

Embodiment 112. The method of embodiment 108 further comprising producing a vaccine comprising the SARS-CoV-2-specific antigens.

Embodiment 113. In some embodiments, a kit for determining the TCR/BCR profile of a patient with COVID-19 is provided. In some embodiments, the kit comprises a set TCR/BCR hybrid capture probes. In some embodiments, the set of probes is provided as four separate pools, comprising a first pool of TCR constant region probes, a second pool of TCR non-constant region probes, a third pool of BCR constant region probes, and a fourth pool of BCR non-constant region probes. In some embodiments, the ratio of the first pool, second pool, third pool, and fourth pool within the set is 1:2.5:100:100. In some embodiments, the probe set is used in combination with one of (1) a whole transcriptome targeting panel, (2) a whole exome targeting panel; or (3) a targeted panel directed to 10-20,000 targets of interest, as a fifth pool of probes, and the ratio of the first pool, second pool, third pool, fourth pool, and fifth pool within the set is 1:2.5:100:100:10. When used in a sequencing reaction such as rna-seq, the TCR/BCR panels are configured such that 2% or less of the reads in the sequencing data map to TCR/BCR genes.

Embodiment 114. In some of the above embodiments, (a) a subject or a cohort is diagnosed with, suspected of having, or is suffering from a disease or medical condition, such as a cancer or infection (infectious disease); or (b) a method for diagnosing a disease or medical condition, such as a cancer or infection (infectious disease) is provided. By way of example, but not by way of limitation, in any of the aforementioned embodiments, the cancer may be one or more of chondrosarcoma, Ewing's sarcoma, malignant fibrous histiocytoma of bone/osteosarcoma, osteosarcoma, rhabdomyosarcoma, leiomyosarcoma, myxosarcoma, astrocytoma, brainstem glioma, pilocytic astrocytoma, ependymoma, primitive neuroectodermal tumor, cerebellar astrocytoma, cerebral astrocytoma, glioblastoma, glioma, medulloblastoma, neuroblastoma, oligodendroglioma, pineal astrocytoma, pituitary adenoma, breast cancer, invasive lobular carcinoma, tubular carcinoma, invasive cribriform carcinoma, medullary carcinoma, male breast cancer, phyllodes tumor, inflammatory breast cancer adrenocortical carcinoma, islet cell carcinoma (endocrine pancreas), multiple endocrine neoplasia syndrome, parathyroid cancer, pheochromocytoma, thyroid cancer, Merkel cell carcinoma, uveal melanoma, retinoblastoma anal cancer, appendix cancer, cholangiocarcinoma, carcinoid tumor, gastrointestinal, colon cancer, extrahepatic bile duct cancer, gallbladder cancer, gastric (stomach) cancer, gastrointestinal carcinoid tumor, gastrointestinal stromal tumor (gist), hepatocellular cancer, pancreatic cancer, islet cell, rectal cancer bladder cancer, cervical cancer, endometrial cancer, extragonadal germ cell tumor, ovarian cancer, ovarian epithelial cancer (surface epithelial-stromal tumor), ovarian germ cell tumor, penile cancer, renal cell carcinoma, renal pelvis and ureter, transitional cell cancer, prostate cancer, testicular cancer, gestational trophoblastic tumor, ureter and renal pelvis, transitional cell cancer, urethral cancer, uterine sarcoma, vaginal cancer, vulvar cancer, Wilms tumor esophageal cancer, head and neck cancer, nasopharyngeal carcinoma, oral cancer, oropharyngeal cancer, paranasal sinus and nasal cavity cancer, pharyngeal cancer, salivary gland cancer, hypopharyngeal cancer, acute biphenotypic leukemia, acute eosinophilic leukemia, acute lymphoblastic leukemia, acute myeloid leukemia, acute myeloid dendritic cell leukemia, aids-related lymphoma, anaplastic large cell lymphoma, angioimmunoblastic t-cell lymphoma, b-cell prolymphocytic leukemia, burkitt's lymphoma, chronic lymphocytic leukemia, chronic myelogenous leukemia, cutaneous t-cell lymphoma, diffuse large b-cell lymphoma, follicular lymphoma, hairy cell leukemia, hepatosplenic t-cell lymphoma, Hodgkin's lymphoma, hairy cell leukemia, intravascular large b-cell lymphoma, large granular lymphocytic leukemia, lymphoplasmacytic lymphoma, lymphomatoid granulomatosis, mantle cell lymphoma, marginal zone b-cell lymphoma, mast cell leukemia, mediastinal large b cell lymphoma, multiple myeloma/plasma cell neoplasm, myelodysplastic syndromes, mucosa-associated lymphoid tissue lymphoma, mycosis fungoides, nodal marginal zone b cell lymphoma, non-Hodgkin lymphoma, precursor b lymphoblastic leukemia, primary central nervous system lymphoma, primary cutaneous follicular lymphoma, primary cutaneous immunocytoma, primary effusion lymphoma, plasmablastic lymphoma, Sézary syndrome, splenic marginal zone lymphoma, t-cell prolymphocytic leukemia, basal cell carcinoma, squamous cell carcinoma, skin adnexal tumors (e.g. sebaceous carcinoma), melanoma, sarcomas of primary cutaneous origin (e.g. dermatofibrosarcoma protuberans), lymphomas of primary cutaneous origin, bronchial adenomas/carcinoids, small cell lung cancer, mesothelioma, non-small cell lung cancer, pleuropulmonary blastoma, laryngeal cancer, thymoma and thymic carcinoma, Kaposi sarcoma, epithelioid hemangioendothelioma (EHE), desmoplastic small round cell tumor, or liposarcoma. In any of the aforementioned embodiments, the infection (infectious disease may be one or more of: Acinetobacter infections, Actinomycosis, African sleeping sickness (African trypanosomiasis), AIDS (acquired immunodeficiency syndrome), Amoebiasis, Anaplasmosis, Angiostrongyliasis, Anisakiasis, Anthrax, Arcanobacterium haemolyticum infection, Argentine hemorrhagic fever, Ascariasis, Aspergillosis, Astrovirus infection, Babesiosis, *Bacillus cereus* infection, Bacterial meningitis, Bacterial pneumonia, Bacterial vaginosis, Bacteroides infection, Balantidiasis, Bartonellosis, Baylisascaris infection, BK virus infection, Black piedra, Blastocystosis, Blastomycosis, Bolivian hemorrhagic fever, Botulism (and Infant botulism), Brazilian hemorrhagic fever, Brucellosis, Bubonic plague, *Burkholderia* infection, Buruli ulcer, Calicivirus infection (Norovirus and Sapovirus), Campylobacteriosis, Candidiasis (Moniliasis; Thrush), Capillariasis, Carrion's disease, Cat-scratch disease, Cellulitis, Chagas disease (American trypanosomiasis), Chancroid, Chickenpox, Chikungunya, Chlamydia, *Chlamydophila pneumoniae* infection (Taiwan acute respiratory agent or TWAR), Cholera, Chromoblastomycosis, Chytridiomycosis, Clonorchiasis, *Clostridium difficile* colitis, Coccidioidomycosis, Colorado tick fever (CTF), Common cold (Acute viral rhinopharyngitis; Acute coryza), Coronavirus disease 2019 (COVID-19), Creutzfeldt-Jakob disease (CJD), Crimean-Congo hemorrhagic fever (CCHF), Cryptococcosis, Cryptosporidiosis, Cutaneous larva migrans (CLM), Cyclosporiasis, Cysticercosis, Cytomegalovirus infection, Dengue fever, *Desmodesmus* infection, Dientamoebiasis, Diphtheria, Diphyllobothriasis, Dracunculiasis, Ebola hemorrhagic fever, Echinococcosis, Ehrlichiosis, Enterobiasis (Pinworm infection), *Enterococcus* infection, Enterovirus infection, Epidemic typhus, Erythema infectiosum (Fifth disease), Exanthem subitum (Sixth disease), Fasciolasis, Fasciolopsiasis, Fatal familial insomnia (FFI), Filariasis, Food poisoning by Clostridium perfringens, Free-living amebic infection, *Fusobacterium* infection, Gas gangrene (Clostridial myonecrosis), Geotrichosis, Gerstmann-Straussler-Scheinker syndrome (GSS), Giardiasis, Glanders, Gnathostomiasis, Gonorrhea, Granuloma inguinale (Donovanosis), Group A streptococcal infection, Group B streptococcal infection, *Haemophilus influenzae* infection, "Hand, foot and mouth disease (HFMD)", Hantavirus Pulmonary Syndrome (HPS), Heartland virus disease, Helicobacter pylori infection, Hemolytic-uremic syndrome (HUS), Hemorrhagic fever with renal syndrome (HFRS), Hendra virus infection, Hepatitis A, Hepatitis B, Hepatitis C, Hepatitis D, Hepatitis E, Herpes simplex, Histoplasmosis, Hookworm infection, Human bocavirus infection, Human ewingii ehrlichiosis, Human granulocytic anaplasmosis (HGA), Human metapneumovirus infection, Human monocytic ehrlichiosis, Human papillomavirus (HPV) infection, Human parainfluenza virus infection, Hymenolepiasis, Epstein-Barr virus infectious mononucleosis (Mono), Influenza (flu), Isosporiasis, Kawasaki disease, Keratitis, *Kingella kingae* infection, Kuru, Lassa fever, Legionellosis (Legionnaires' disease), Pontiac fever, Leishmaniasis, Leprosy, Leptospirosis, Listeriosis, Lyme disease (Lyme borreliosis), Lymphatic filariasis (Elephantiasis), Lymphocytic choriomeningitis, Malaria, Marburg hemorrhagic fever (MHF), Measles, Middle East respiratory syndrome (MERS), Melioidosis (Whitmore's disease), Meningitis, Meningococcal disease, Metagonimiasis, Microsporidiosis, Molluscum contagiosum (MC), Monkeypox, Mumps, Murine typhus (Endemic typhus), Mycoplasma pneumonia, Mycoplasma genitalium infection, Mycetoma, Myiasis, Neonatal conjunctivitis (Ophthalmia neonatorum), Nipah virus infection, Norovirus, "(New) Variant Creutzfeldt-Jakob disease (vCJD, nvCJD)", Nocardiosis, Onchocerciasis (River blindness), Opisthorchiasis, Paracoccidioidomycosis (South American blastomycosis), Paragonimiasis, Pasteurellosis, *Pediculosis capitis* (Head lice), *Pediculosis corporis* (Body lice), "*Pediculosis pubis* (pubic lice, crab lice)", Pelvic inflammatory disease (PID), Pertussis (whooping cough), Plague, Pneumococcal infection, Pneumocystis pneumonia (PCP), Pneumonia, Poliomyelitis, Prevotella infection, Primary amoebic meningoencephalitis (PAM), Progressive multifocal leukoencephalopathy, Psittacosis, Q fever, Rabies, Relapsing fever, Respiratory syncytial virus infection, Rhinosporidiosis, Rhinovirus infection, Rickettsial infection, Rickettsialpox, Rift Valley fever (RVF), Rocky Mountain spotted fever (RMSF), Rotavirus infection, Rubella, Salmonellosis, Severe acute respiratory syndrome (SARS), Scabies, Scarlet fever, Schistosomiasis, Sepsis, Shigellosis (bacillary dysentery), Shingles (Herpes zoster), Smallpox (variola), Sporotrichosis, Staphylococcal food poisoning, Staphylococcal infection, Strongyloidiasis, Subacute sclerosing panencephalitis, Bejel, Syphilis, Yaws, Taeniasis, Tetanus (lockjaw), Tinea barbae (barber's itch), Tinea capitis (ringworm of the scalp), Tinea corporis (ringworm of the body), Tinea cruris (Jock itch), Tinea manum (ringworm of the hand), Tinea nigra, Tinea pedis (athlete's foot), Tinea unguium (onychomycosis), Tinea versicolor (Pityriasis versicolor), Toxic shock syndrome (TSS), Toxocariasis (ocular larva migrans (OLM)), Toxocariasis (visceral larva migrans (VLM)), Toxoplasmosis, Trachoma, Trichinosis, Trichomoniasis, Trichuriasis (whipworm infection), Tuberculosis, Tularemia, Typhoid fever, Typhus fever, Ureaplasma urealyticum infection, Valley fever, Venezuelan equine encephalitis, Venezuelan hemorrhagic fever, Vibrio vulnificus infection, Vibrio parahaemolyticus enteritis, Viral pneumonia, West Nile fever, White piedra (tinea blanca), Yersinia pseudotuberculosis infection, Yersiniosis, Yellow fever, Zeaspora, Zika fever, Zygomycosis.

Embodiment 115. A method of sequencing at least one TCR or BCR region of a specimen using a plurality of probes, wherein the probes comprise: a first pool of TCR constant region probes, a second pool of TCR non-constant region probes, a third pool of BCR constant region probes, and a fourth pool of BCR non-constant region probes, wherein the first pool has a first concentration level, the second pool has a second concentration level, the third pool has a third concentration level, and the fourth pool has a fourth concentration level.

Embodiment 116. The method of embodiment 115, wherein the first concentration level, the second concentration level, the third concentration level, and the fourth concentration level are different from each other.

Embodiment 117. The method of embodiment 115 or 116, wherein the concentration level of probes in the first pool is less than the concentration level of probes in the second pool, and wherein the concentration level of probes in the third pool is less than the concentration level of probes in the fourth pool. In some embodiments, the concentration level of probes in the first pool is about the same as the concentration level of probes in the second pool, and wherein the concentration level of probes in the third pool is less than the concentration level of probes in the fourth pool.

Embodiment 118. The method of any one of embodiments 115-117, wherein the concentration level of probes in the first and third pool are independently at least about 2-fold, at least about 5-fold, at least about 10-fold, at least about 15-fold, at least about 20-fold, at least about 30-fold, at least about 40-fold, or at least about 50-fold less the concentration level of probes in the second and fourth pools. In some embodiments, the concentration level of probes in the third and fourth pool are independently at least about 2-fold, at least about 5-fold, at least about 10-fold, at least about 15-fold, at least about 20-fold, at least about 30-fold, at least about 40-fold, or at least about 50-fold less than the concentration level of probes in the first and second pools.

Embodiment 119. A method of sequencing at least one TCR or BCR region of a specimen, comprising, selecting more than one probe from a set of probes to form a pool, wherein the more than one probes in the pool are selected to omit at least a portion of a constant region of the at least one TCR or BCR region.

Embodiment 120. The method of embodiment 119, wherein the pool comprises probes for sequencing at least a portion of the constant region of the TCR or BCR.

Embodiment 121. The method of any of embodiments 119-120, wherein the sequencing is whole-transcriptome sequencing.

Embodiment 122. The method of any of embodiments 117-121, wherein the sequencing is short-read sequencing.

Embodiment 123. The method of embodiment 115, wherein the sequencing is performed on a specimen collected from a patient and the results are used to predict the disease susceptibility of the patient.

Embodiment 124. The method of embodiment 115, wherein the TCR or BCR region is associated with a viral infection, and the specimen is collected prior to the administration to the patient of a vaccine designed to protect against the viral infection.

Embodiment 125. The method of embodiment 115, wherein the sequencing is performed on a specimen collected from a patient, wherein the patient was exposed to an infectious pathogen prior to specimen collection.

Embodiment 126. The method of embodiment 125, wherein the patient generated antibodies against the infectious pathogen.

Embodiment 127. The method of embodiment 125, wherein the patient did not generate a substantial amount of antibodies against the infectious pathogen.

Embodiment 128. The method of embodiment 125, wherein the infectious pathogen did not cause seroconversion.

Embodiment 129. The method of embodiment 125, wherein high concentrations of the infectious pathogen were not detectable in the patient's blood.

Embodiment 130. The method of embodiment 125, wherein the infectious pathogen is SARS-CoV-2.

Embodiment 131. The method of embodiment 115, wherein the sequencing is performed on a specimen collected from a patient, wherein the patient is experiencing symptoms associated with respiratory disease.

Embodiment 132. The method of embodiment 115, wherein the sequencing is performed on a specimen collected from a patient, wherein the patient is experiencing flu-like symptoms.

Embodiment 133. The method of embodiment 115, wherein the specimen is a tissue specimen.

Embodiment 134. The method of embodiment 115, wherein the specimen is a tumor specimen.

Embodiment 135. The method of embodiment 115, wherein the specimen is a blood specimen.

Embodiment 136. The method of claim 115, wherein the specimen is a saliva specimen.

Embodiment 137. The method of claim 115, wherein the specimen is a mucus specimen.

Embodiment 138. The method of claim 115, wherein the specimen is a spinal fluid specimen.

Embodiment 139. The method of claim 115, wherein the sequencing is conducted in whole-transcriptome sequencing.

Embodiment 140. A method of sequencing RNA transcriptome, comprising the method of embodiment 115.

Embodiment 141. The method of embodiment 115, further comprising identifying a plurality of TCR clones in the specimen.

Embodiment 142. The method of embodiment 141, further comprising identifying the proportion of at least one TCR clone in the plurality of TCR clones in the specimen.

Embodiment 143. The method of embodiment 115 further comprising identifying a plurality of BCR clones in the specimen.

Embodiment 144. The method of embodiment 143, further comprising identifying the proportion of at least one BCR clone in the plurality of BCR clones in the specimen.

Embodiment 145. The method of any of embodiments 115-141, wherein the set comprises at least one oligonucleotide from a TCR constant region pool, a TCR non-constant region pool, a BCR constant region pool, and a BCR non-constant region pool.

Embodiment 146. The method of any of the previous embodiments, wherein the TCR/BCR probe set is obtained as described in Example 1.

EXAMPLES

The following Examples are illustrative and should not be interpreted to limit the claimed subject matter.

Example 1

TCR/BCR Profiling Probe and Assay Development

A. Methods for Selecting or Designing the Sequences of Hybrid Capture Probes

Probes may be designed for enriching nucleic acids associated with TCR/BCR genes in a sequencing library, for example, within an RNA-seq assay.

Step 1 is the step of generating a list of reference target genetic sequences located in desired target genes.

Step 1 may include gathering the complete set of reference sequences for these genes and corresponding alleles from the database for potential probe design. In another embodiment, a portion of the set of reference sequences for these genes may be collected to generate the list. In one embodiment, a gene's reference sequence may include all exons and all introns, only a portion of exons, only a portion of introns, or no introns associated with that gene. In one example, for each gene, segments (portions) of the gene may be selected as a target genetic sequence. In one embodiment, each target genetic sequence has a length of approximately 400 bp. Each gene may have multiple alleles and each allele may have a unique reference sequence.

Figure 14:
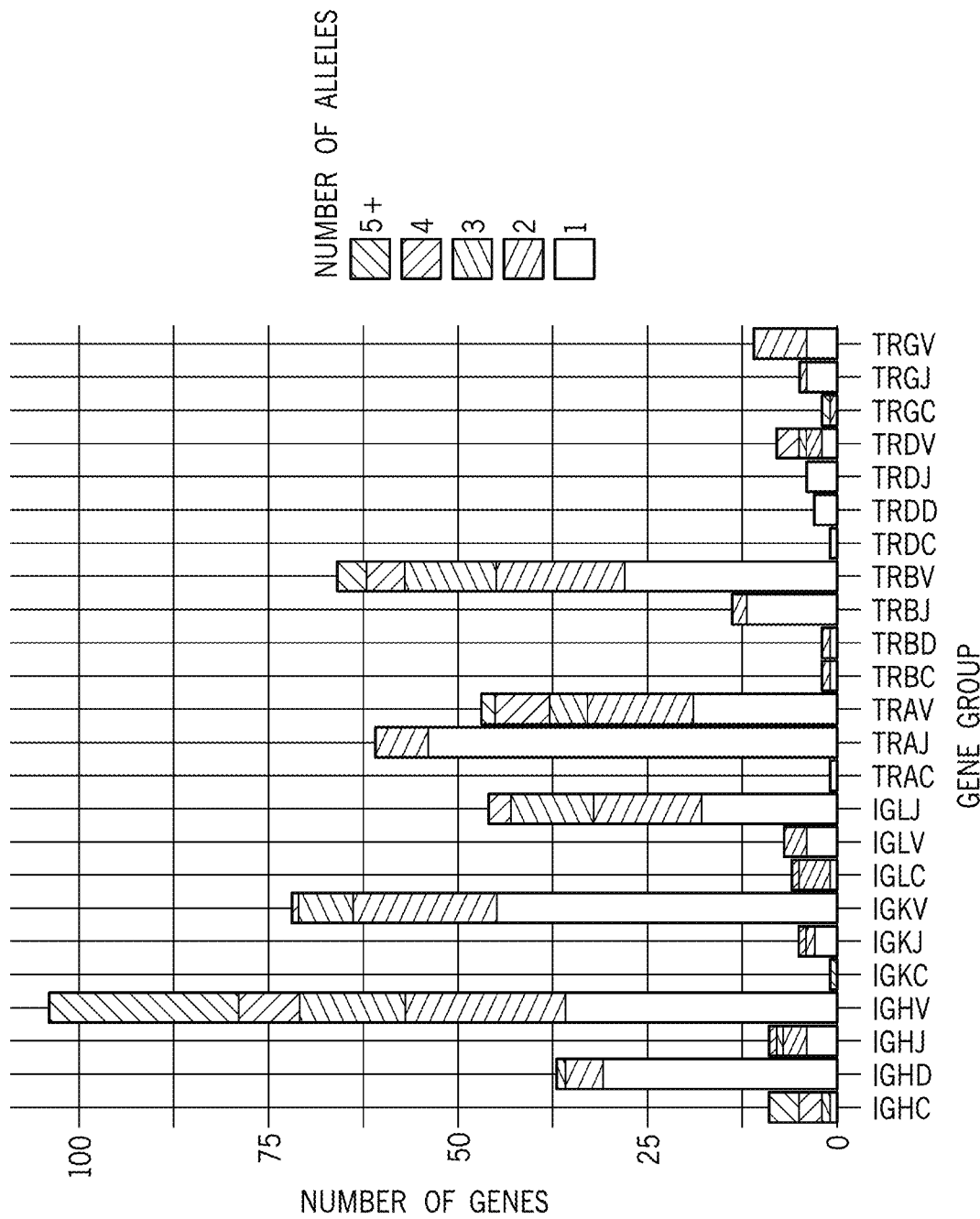
FIG. 14 illustrates the number of genes in each class of IG (BCR) or TCR genes having 1, 2, 3, 4, or 5+ alleles, demonstrating the allelic variation of these genes.

In one embodiment, step 1 comprises gathering the complete set of IG and TCR gene sequences from a genetic sequence database, for example, the IMGT database. In one example, the database has 296 IG (BCR) and 222 TCR genes which generally range from ~100-1000 bp in length. As seen in FIG. 14, approximately half of these genes have more than one annotated allele.

IG and TCR loci may contain hundreds of genes with substantial homology as well as allelic variation. FIG. 14 ("Gene and Allele Counts") illustrates the number of genes (y-axis) in each class of IG (BCR) or TCR genes having 1, 2, 3, 4, or 5+ alleles (see legend for color coding), demonstrating the allelic variation of these genes. Each class of genes is denoted along the x-axis (IGHC, IGHD, IGHJ, IGHV, IGKC, IGKJ, IGKV, IGLC, IGLJ, IGLV, TRAC, TRAJ, TRAV, TRBC, TRBD, TRBJ, TRBV, TRDC, TRDD, TRDJ, TRDV, TRGC, TRGJ, TRGV, etc.).

Step 2 is the optional set of determining a gene consensus sequence across alleles. This step may include comparing a gene's allele sequences to determine the consensus sequence.

While a probe set covering all alleles may guarantee complete coverage, it may be possible to eliminate a substantial amount of redundancy due to high sequence similarity between alleles. At a basic level, gene-level representative (consensus) target sequences may result in a probe panel that covers the majority of allelic variations.

Figure 15:
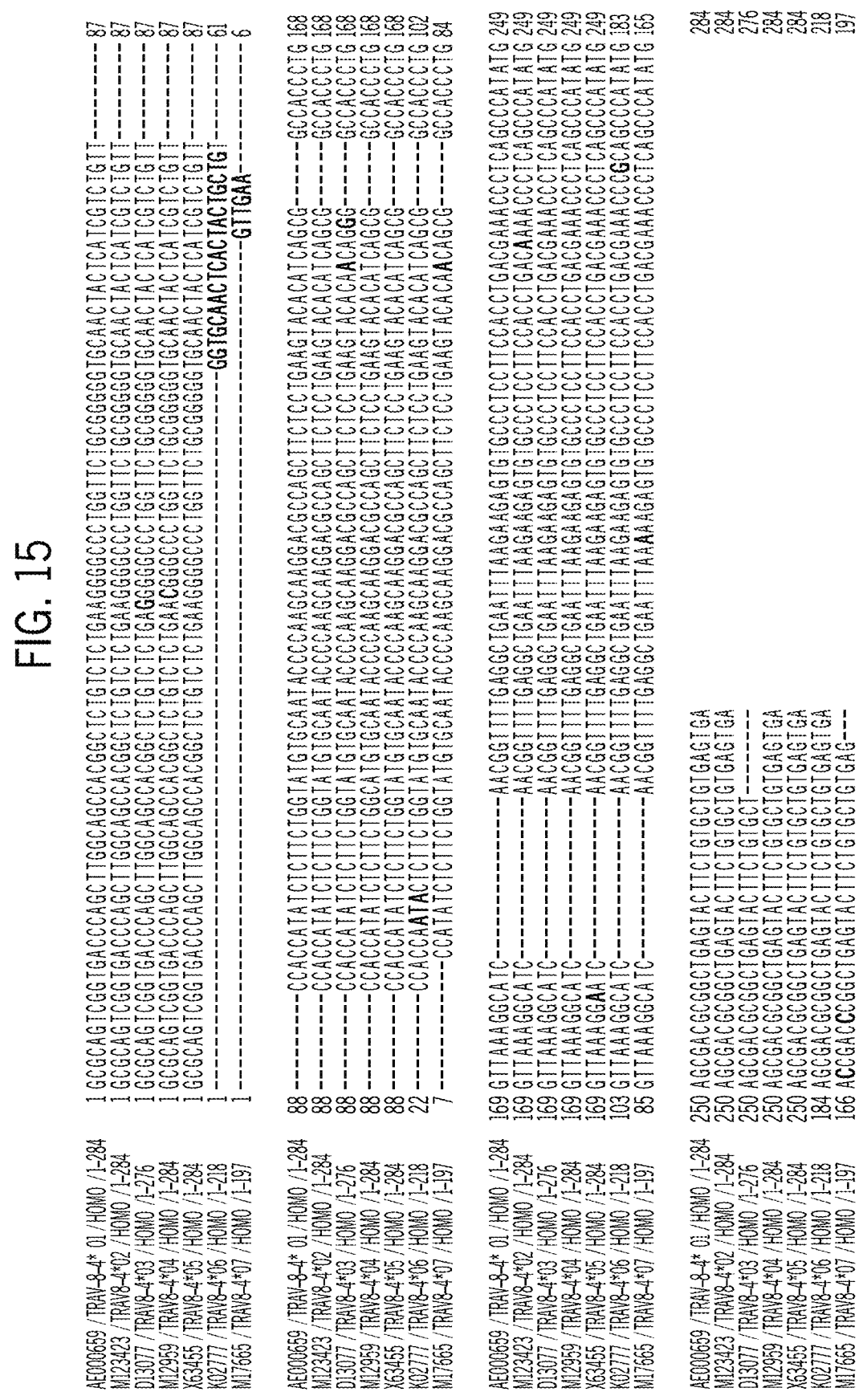

Comparing allele sequences may include filling in missing portions of reference sequences prior to comparison. In this example, IMGT provides reference sequences in a curated alignment format (IMGT gapped fasta). Unfortunately, many of these IMGT reference sequences are incompletely sequenced at the 5' or 3' ends. As a consequence, besides single nucleotide variations, there are frequently substantial truncations in raw IMGT allelic sequences. This issue is illustrated by the example TRAV 8-4 in FIG. 15 with truncations in various alleles at both the 5' and 3' ends. FIG. 15 illustrates an example of aligned TCR reference sequences.

In one example, filling in missing portions of reference sequences (converting raw IMGT references sequences to complete allele reference sequences), is done by determining the consensus sequence, based on IMGT's curated alignment (most frequent nucleotide per position) and using that consensus sequence to fill in (replace) any truncated or missing segment in each allele. In this example, this processed set of filled in reference sequences comprises the set of target sequences that the probes should cover. (See FIG. 15, "IMGT Sequence Processing")

Step 3 is the optional step of evaluating sequence similarity across alleles.

This step may use the processed IMGT reference sequences (filled in, if applicable and/or if a portion of the sequence was missing as described above) to determine if gene-level consensus sequences could cover potential allelic diversity.

Figure 16:
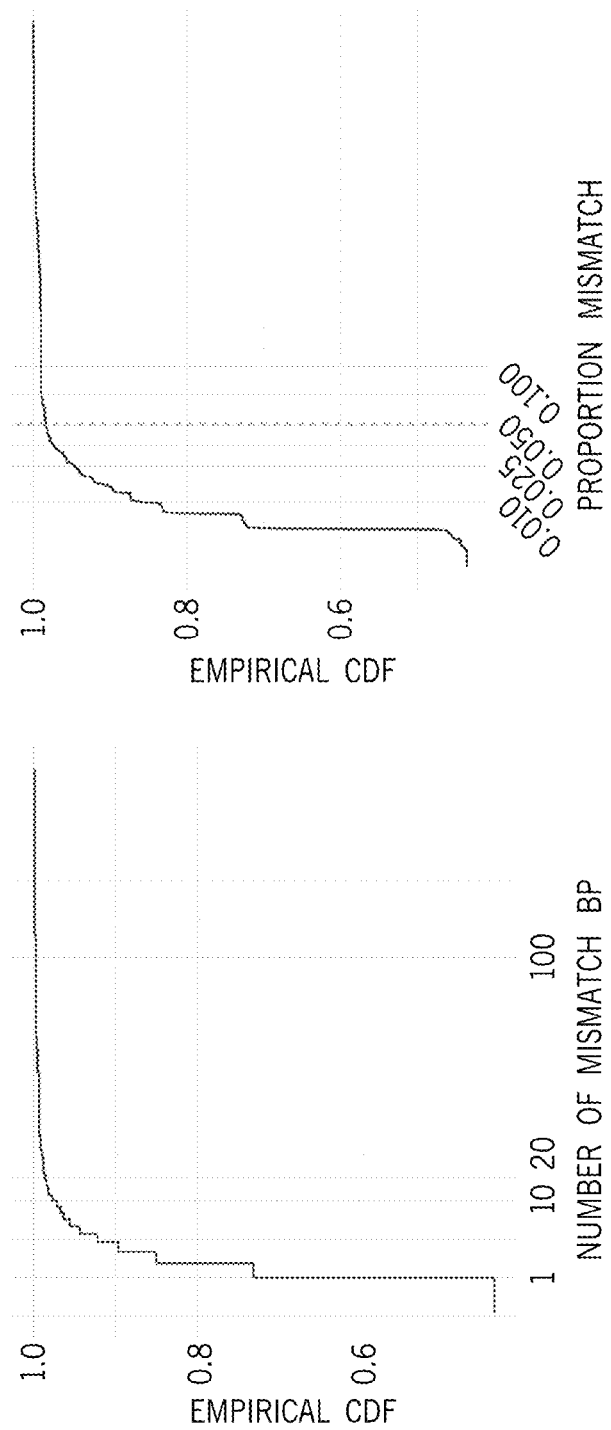
FIG. 16 shows cumulative distributions of the number of mismatched base pairs (bp), and the proportion of mismatched bp (number mismatch over gene length).

This step may include comparing each allele sequence to its corresponding gene consensus sequence. FIG. 16 shows cumulative distributions of the number of mismatched base pairs (bp), and the proportion of mismatched bp (number mismatch over gene length).

FIG. 16 ("Allele Sequence Similarity") illustrates that most alleles are very similar to their gene consensus sequence, according to an empirical cumulative distribution function (CDF).

In this example, 98.6% of all alleles have fewer than 15 bp mismatches, and 98.2% of all alleles have at least 95% identity compared to gene consensus. For the handful of alleles (<20) with low consensus sequence identity, it may be more appropriate to separately cover their sequence differences in order to design a set of probes that cover all alleles.

Step 4 is the optional step of filtering the list of genes, alleles, and/or target segments. The filtering strategies described here may be used individually, with other probe design list filtering strategies known in the art, or any combination thereof.

The list may be filtered with the goal of reducing sequencing reads from less desirable targets. In one example, constant region targets are less desirable than non-constant region targets. In this example, constant region targets may be filtered out and eliminated from the list if they are located at a distance from the non-constant region that exceeds a specified distance threshold (in bp). In another example, constant region targets may be filtered out and eliminated from the list if they are not within the 2-5 targets located most closely to the non-constant region of a gene.

The list may be filtered with the goal of reducing redundancy of targets and duplicate or substantially similar probe sequences designed based on those targets.

In one example, allele reference sequences may be eliminated from the list or replaced by their gene consensus sequence when they have at least 95% sequence identity (for example, at least 95% of their sequence has the same nucleotide as the consensus sequence, for each position in the consensus sequence and corresponding position in the allele sequence). For the 19 alleles in which 95% sequence identity is not achieved, the original allele sequence is retained. In this example, the likelihood is high that every allele sequence with at least 95% identity with this gene consensus set would be covered by the final probe set.

Step 5 is the optional step of calculating estimates for total desired probe coverage for these loci.

The tables in FIG. 17 show the difference in total desired coverage length (in base pairs) when using (Table 1 of FIG. 17) the complete set of IG and TCR allele sequences (upper bound, the unfiltered target list) and (Table 2 of FIG. 17) when using gene-level consensus sequences (the filtered target list). Using a gene-level consensus sequence strategy reduces the number of gene sequences in the set from 1098 total allele sequences to 532 total gene consensus sequences and reduces the total coverage length from 325 kb to 125 kb. It is expected this sequence set reduction to correspondingly reduce the number of probes required for coverage. In this example, using the gene-level consensus strategy reduces the number of possible target sequences/distinct 120-mers (example probe length) contained in the IG/TCR sequences from 115,920 to 68,746. Results may vary depending on selected probe length.

Step 6 is the optional step of delivering the list of targets to a probe design specialist. The list may be a list of filtered targets generated in step 4. A probe design specialist, may be a commercial vendor that designs and/or manufactures sequencing probes and/or primers. One example of such a commercial vendor is IDT.

Step 7 is the step of selecting (designing) probe sequences based on the list (for example, using probe design software). The probe sequence selection may be performed by a probe design specialist.

By way of example but not by way of limitation, probe sequences may be selected or designed in accordance with the methods set forth in FastPCR Software for PCR Primer and Probe Design and Repeat Search (Kalendar et al., 2009 Genes, Genomes, and Genomics, 3 (Special Issue 1), pp. 1-14) which is incorporated by reference herein.

B. TCR/BCR Assay Development using Probes Derived by the Method in Step A

Figure 4:
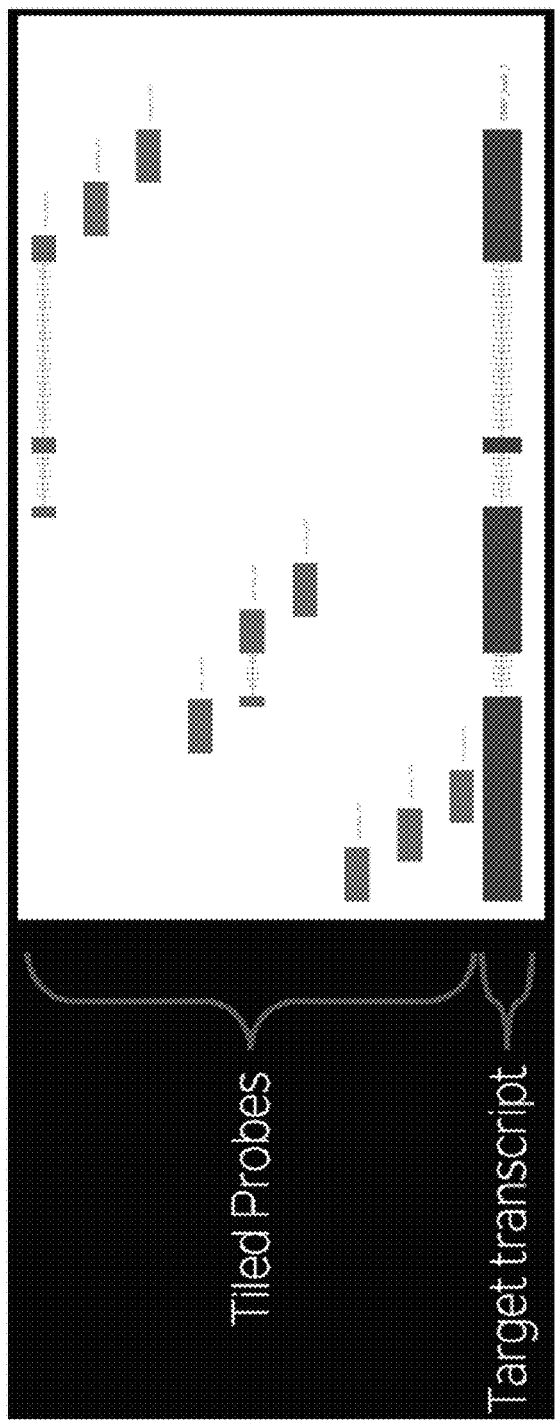
FIG. 4. Is a schematic drawing showing the probe tiling strategy for enriching TCR and BCR sequences in the novel hybrid-capture approach to immune profiling.

This Example illustrates the development of one embodiment of a TCR/BCR profiling assay. In this embodiment, TCR/BCR sequencing is performed in combination with RNAseq. The embodiment described herein tiles 7 receptors: IGH, IGK, IGL, TRA, TRB TRG and TRD. Thus, repertoire data includes annotated CDR3 hypervariable sequence quantification for IgH, IgK, IgL, TCR-alpha, TCR-beta, TCR-delta and TCR-gamma receptors. (See e.g., FIG. 4).

Figure 5:
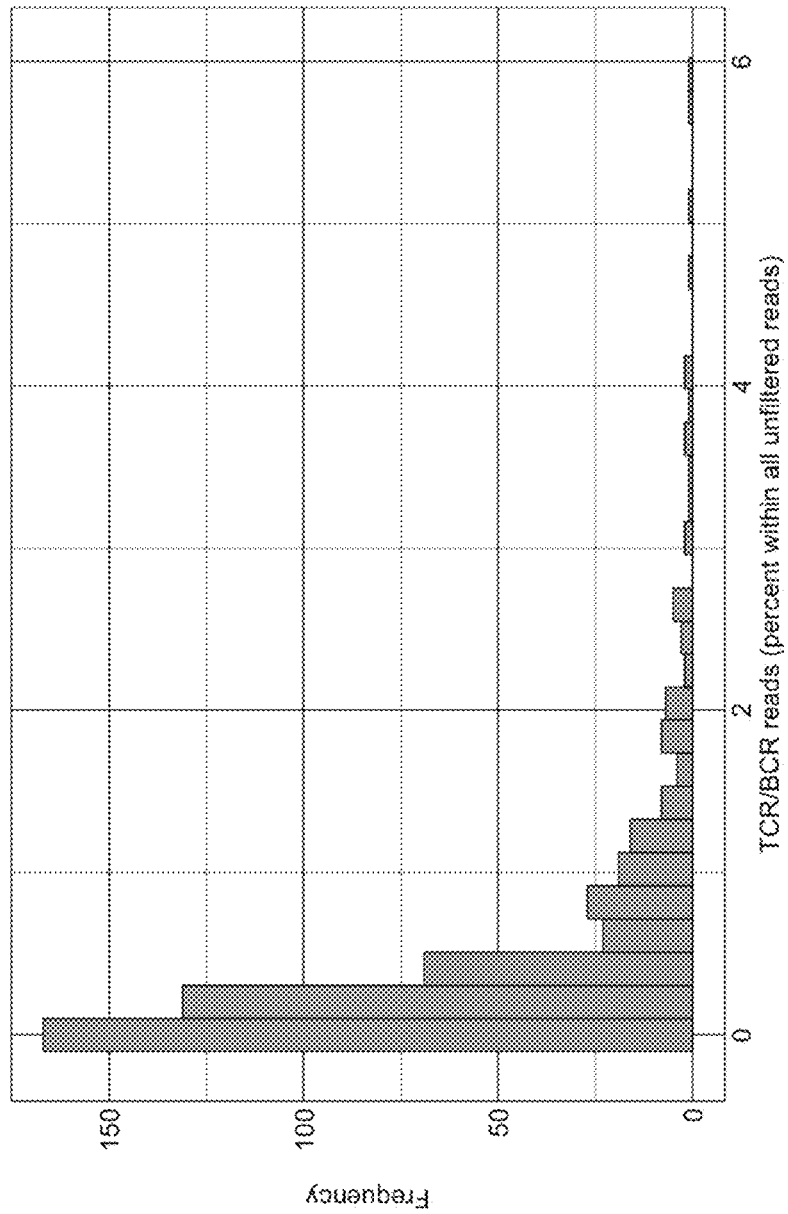
FIG. 5. Is a histogram showing the distribution of frequency of TCR/BCR reads as a percentage of all unfiltered reads in a sequencing run from using the novel hybrid-capture approach to immune profiling.
Figure 6A:
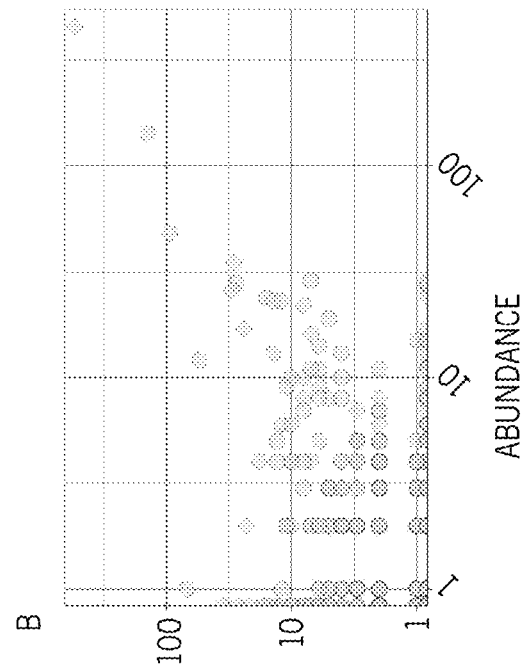
FIG. 6A-B. (A) A sample subjected to an enriched RNA-based rep-seq and a highly sensitive TCR-β receptor DNA sequencing assay. Exact TCR-β CDR3 nucleotide sequences are quantified and compared between runs in this benchmark and (B) separate RNA-based rep-seq runs. The x-axis indicates the abundance of each CDR3 nucleotide sequence in data from one run of the RNA-based rep-seq assay. The y-axis indicates the abundance of each CDR3 nucleotide sequence in data from either a highly sensitive TCR-β receptor DNA sequencing assay (A) or a second run of the RNA-based rep-seq assay (B). While enriched RNA-based rep-seq may be less sensitive than stand-alone DNA-based assays in various examples, the RNA-based rep-seq method detects and recapitulates the relative abundance of the most frequent clonotypes, even in the relatively small TCR-β repertoire displayed in FIG. 6. Consistency is also high for abundant clonotypes in inter-assay tests.
Figure 6B:
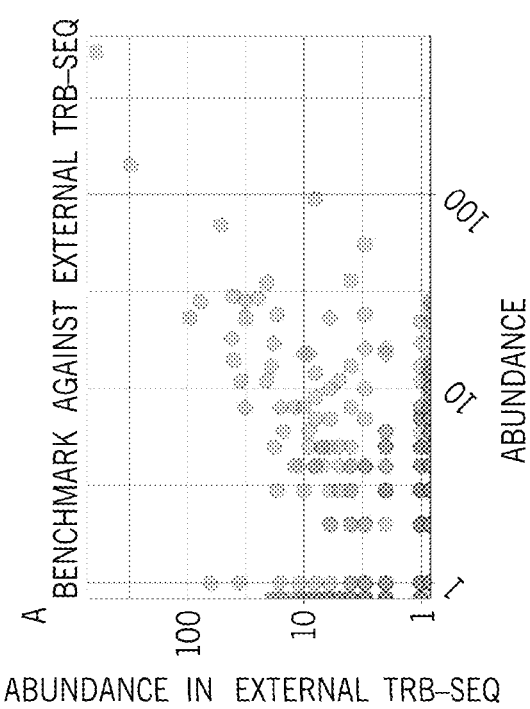

The capture method of the present embodiment has been optimized to yield RNAseq output wherein no more than 2% of all unfiltered read pairs map to TCR and BCR sequences in 95% of samples. This capture rate preserves the integrity of the transcriptome for downstream analysis while still capturing enough depth to correctly identify receptor clonotypes from the most abundant infiltrating lymphocyte clones. (See FIGS. 3 and 5).

In several early attempts to perform this analysis, some of the least informative regions (the constant regions) were taking up the majority of reads. Additionally, BCR region coverage vastly outweighed TCR region coverage. To address these problems, in some embodiments useful constant region coverage was identified and retained, while a number of constant region probes that were unlikely to generate informative TCR/BCR reads were removed. Probes were also separated into distinct pools for TCR and BCR, so that the signal from the TCR and BCR regions could be independently tuned. In some embodiments, probes were separated into TCR non-constant, TCR constant, BCR non-constant, and BCR constant probe concentration pools. By independently tuning TCR non-constant, TCR constant, BCR non-constant, and BCR constant probe concentrations more informative TCR/BCR information with many fewer reads was obtained. We also were able to ensure that the information from TCR/BCR profiling is more evenly balanced between TCR and BCR.

Figure 2:
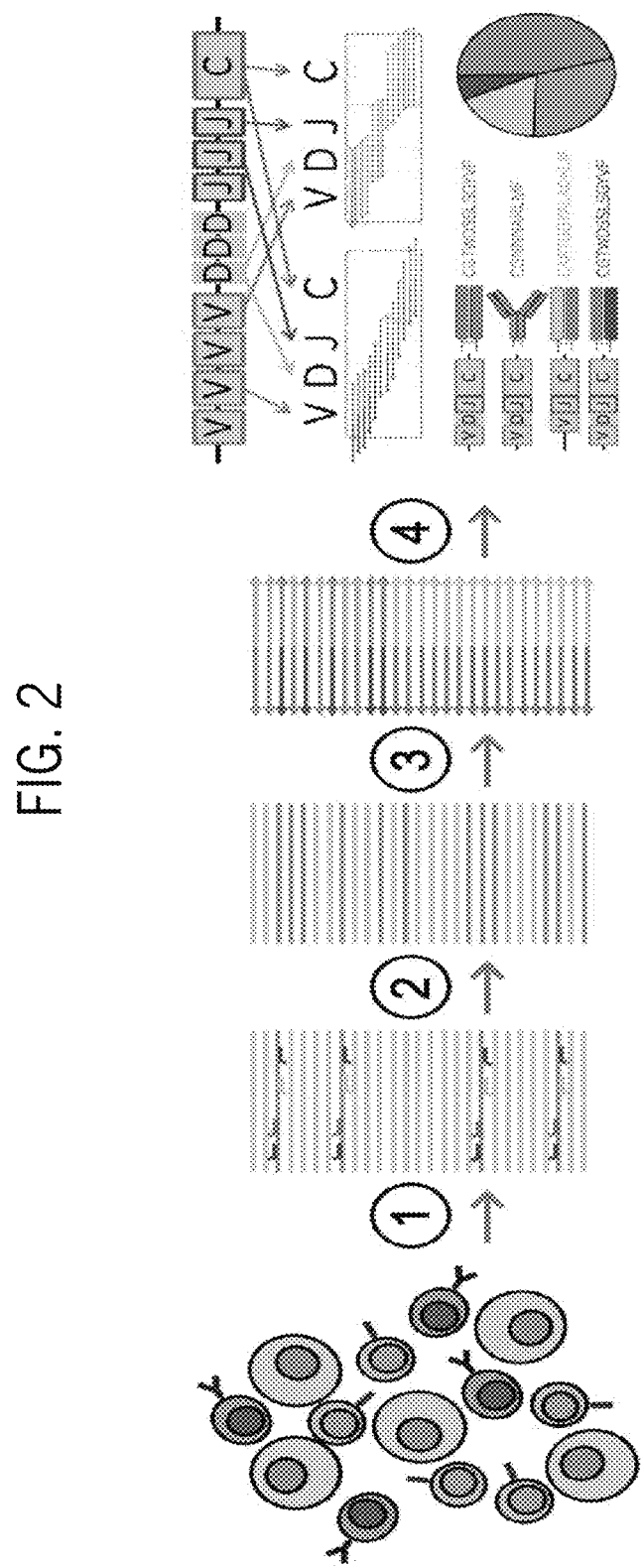
FIG. 2. Is a schematic of novel hybrid-capture approach to immune profiling. 1) Tumor sampling-RNA is isolated from formalin-fixed, paraffin-embedded primary tumor samples. Samples harbor a broad spectrum of lymphocyte infiltration, largely dependent on sample tissue origin. 2) TCR/BCR transcript enrichment—specially designed and optimized hybrid-capture probe pools target genes for seven lymphocyte receptors (TCR-α, TCR-β, TCR-γ, TCR-δ, Ig-Heavy, Ig-κ, and Ig-λ) to enrich immune receptors in RNA-seq output without compromising downstream transcriptomic analysis. 3) RNA-sequencing—a state of the art RNA-seq platform (for an example of an RNA-seq platform, see U.S. patent application Ser. No. 16/657,804, titled "Data Based Cancer Research and Treatment Systems and Methods", and filed Oct. 18, 2019 and U.S. patent application Ser. No. 17/112,877, titled "Systems and Methods for Automating RNA Expression Calls in a Cancer Prediction Pipeline", and filed Dec. 4, 1920) provides transcriptomic analysis of tumor samples. TCR/BCR reads enriched by the application of rep-seq probes do not exceed 2% total reads in 95% of RNA-seq runs. 4) Repertoire-sequencing analysis—RNA-seq data is processed using a rep-seq bioinformatics pipeline (in one example, the rep-seq bioinformatics pipeline includes open-source rep-seq software TRUST4, see https://github.com/liulab-dfci/TRUST4). Candidate TCR/BCR reads are aligned against IMGT reference allele sequences and hypervariable complementarity-determining region 3 (CDR3) sequence clonotypes. CDR3 gene assignments and relative abundances are quantified. Rd. 2 discloses SEQ ID NOS 176-178 and 176, respectively, in order of appearance.

Several experiments were performed leading to a configuration of TCR/BCR probes that can be successfully used in an RNAseq assay. Brief descriptions of such experiments are presented below, and a schematic of the method is shown in FIG. 2.

First, two sets of TCR/BCR probes were designed. Design 1 included all TCR/BCR probes in a single tube. Several attempts to optimize this configuration, including omitting certain probes from the pool, and changing the concentration of the probes in the pool relative to the concentration of the whole exome panel probes, were performed, however, in each case, results were deemed unacceptable. Design 2 included dividing the probes into 4 groups: TCR non-constant, TCR constant, BCR non-constant, BCR constant. Then, probes for each group were selected, resulting in a final configuration for each group as follows:

I. "BCR constant"—45 probes

II. "BCR non-constant"—893 probes

III. "TCR constant"—18 probes

IV. "TCR non-constant"—650 probes

TCR/BCR probe concentrations relative to each other and relative to the exome probes were also evaluated. Exome probes were tested at 25 attomole/probe/capture. Ratios noted below reference the relative concentrations to the exome. For example 10× spike means a final amount of 250 attomole/probe/capture (with exome at 25 attomole/probe/capture). In various embodiments, probes designed to target a whole human exome may be hybridized with DNA or RNA molecules. When the probes are hybridized with RNA molecules, the molecules in the library may be referred to as a human transcriptome.

| FINAL CONDITIONS Exome | Ratio to main panel main panel | Final amount (amole/probe/ capture) 25 |
|---|---|---|
| BCR Constant Region Probes | 0.1:1 | 2.5 |
| BCR Non-Constant Region Probes | 0.25:1 | 6.25 |
| TCR Constant Region Probes | 10:1 | 250 |
| TCR Non-Constant Region Probes | 10:1 | 250 |

We have leveraged specially designed probes to integrate repertoire-sequencing (rep-seq) into a high-volume RNA-seq workflow. The methods disclosed herein can capture a snapshot of immune receptor repertoire without compromising transcriptome analysis.

Example 2

Sequencing Results

In this example, TCR and BCR sequences in a blood specimen collected from a patient having B cell lymphoma were analyzed according to the systems and methods disclosed herein.

Methods

Sample Preparation (Including Enrichment with TCR/BCR Hybrid Capture Probes Obtained According to the Methods of Example 1):

RNA was quantified using Quant-it Ribogreen RNA assay (ThermoFisher Scientific, P/N R11490), and qualified using Fragment Analyzer High Sens RNA Analysis Kit (Agilent Technologies, P/N DNF-472-1000). RNA was normalized to 10 ng/uL in 10 uL starting volume and then subjected to heat and chemical fragmentation, with variable parameters to yield similar sized fragments from RNA inputs with different starting size distributions. Library preparation was performed using an off the shelf kit (KAPA RNA HyperPrep Kit for Illumina, P/N KK8544) with IDT unique dual indexed (UDI) unique molecular identifier (UMI) adapters. This involved first-strand synthesis using a reverse transcriptase (RT) enzyme to create first strand cDNA followed by treatment with RNAse to degrade RNA, and DNA polymerase to accomplish second-strand synthesis to create double stranded cDNA. IDT UDI-UMI adapters were ligated to cDNA and the adapter-ligated libraries were cleaned using a magnetic bead-based method (Roche Diagnostics, P/N KK8002). The libraries were amplified with high fidelity, low-bias PCR using primers complementary to adapter sequences. Amplified libraries were subjected to magnetic bead based clean-up (Axygen, P/N MAG-PCR-CL-250) to eliminate unused primers, and quantity was assessed. Prior to hybridization, samples were normalized by library mass and multiplexed into pools of 6-8 samples per capture pool. Library hybridization and capture was conducted using the xGen Exome Research Panel v2 probe set with supplemental custom designed probes, including the TCR/BCR probes derived by the method in step A, along with xGen Universal Blockers (Integrated DNA Technologies, P/N 1075475) and xGen Hybridization and Wash Kit (Integrated DNA Technologies, P/N 1080584). The enriched targets were amplified using the KAPA HiFi HotStart ReadyMix and primers (Roche Diagnostics, P/N KK2621) and underwent an additional magnetic bead based clean-up. Quantity and quality of the final library was assessed and success was determined based on a calculated molarity incorporating both quantification and qualification measurements.

Sequencing: Amplified target-captured libraries were sequenced to an average of 50 million reads on an Illumina NovaSeq 6000 System using patterned flow cell technology.

Analysis: RNA-sequencing data in the form of FASTQ files containing read pairs were subjected to repertoire sequencing analysis using TRUST4v1.0.0 software. TRUST4v1.0.0 was run with no modifications, per the developer's instructions, where FASTQ files containing read pairs were used as input and the human IMGT reference sequence files provided with the software were used to generate quantitative data related to TCR and BCR clonotypes (productive, non-productive and partial) identified by the software. The tabulated clonotype report generated by TRUST4 was used to calculate Shanon entropy for productive clonotypes in each immune receptor chain (IGH, IGK, IGL, TRA, TRB, TRG and TRD). TRUST4 report columns and additional non-statistical annotations are combined into a final data table with column descriptions itemized below.

Results 1,957 clonotypes of expanded B cells and T cells were detected in the specimen, and 1,074 of those detected clonotypes were determined to be productive sequences (for example, they did not include a stop codon, were not out of frame, were not partial sequences, etc.).

Table 6 is a table showing the top ten most abundant sequences (for example, sequences associated with the largest number of supporting sequence reads). Each column represents a clone. The closer a column is to the left, the more raw abundance (for example, supporting, detected sequence reads) is associated with that clone. Clones demonstrating a greater degree of expansion are closer to the left. In this example, the first (left-most) IGH CDR3 is ~25% of IGH productive clonotypes by abundance (see the "receptor_productive_frequency" row). The complete results are included as a separate table in Appendix I of U.S. Provisional Application Nos. 63/013,130, 63/084,459, and 63/201,020. The most frequent clones may be assumed to represent expanded populations of B cells or T cells. In this case, the expanded populations of B cells may be analyzed to track the B cell lymphoma to detect progression, response to treatment, MRD, etc. In one embodiment, the TCR/BCR sequencing methods disclosed herein are utilized on multiple specimens collected from the patient at different times in order to track disease over time.

The following are titles and descriptions of the rows in the appendix, as an example of the variety of data that may comprise TCR/BCR immune repertoire sequencing data associated with each CDR3 sequence or clonotype:

a. count—integer number of read fragments supporting clonotype (for example, the number of read fragments aligning to a clonotype reference sequence)
b. frequency—clonotype frequency within BCRs or TCRs
c. CDR3nt—CDR3 nucleotide sequence
d. CDR3aa—CDR3 amino acid sequence (if sequence is non-productive, '_' indicates a STOP codon; 'out_of_frame' indicates a frameshift mutation, or 'partial' indicates a partial sequence)
e. V-V gene clonotype assignment called {formatted as gene*allele} ("null" indicates no gene called) (may comprise a V gene family, V gene, and/or V allele)
f. D-D gene clonotype assignment {gene*allele} called (null if no gene called or not applicable to receptor) (may comprise a D gene family, D gene, and/or D allele)
g. J-J gene clonotype assignment {gene*allele} called (null if no gene called) (may comprise a J gene family, J gene, and/or J allele)

h. C-C gene clonotype assignment {gene} (no allele info returned for C genes) called (null if no gene called)
i. Receptor [type]—{'IGH','IGK','IGL','TRA','TRB','TRG','TRD','mixed',}(in some examples, mixed may be alpha/delta TCR)
j. productive_status—{'in','partial','out_of_frame','internal_stop'} (in=in-frame/productive, partial is a partial sequence, out_of_frame means the sequence is frame shifted and is not expected to be productive, internal_stop means that the sequence has a stop codon and is not expected to be productive)
k. receptor_frequency—clonotype frequency by receptor (for the receptor type)
l. receptor_productive_frequency—productive clonotype frequency within all productive receptor clonotypes
m. V_gene_family—(e.g. IGLV3-25*03→IGLV3)
n. V_gene—(e.g. IGLV3-25*03→IGLV3-25)
o. V_allele—(e.g. IGLV3-25*03→03)
p. D_gene_family
q. D_gene
r. D_allele
s. J_gene_family
t. J_gene
u. J_allele
v. IGH_isotype—null if not called/applicable, otherwise: {'A16','A2','D','E','G1','G2','G3','G4','M'}
w. has_CDR3nt_twin—"True" entered if there are duplicates of this clonotype's nt sequence in the repertoire
x. has_CDR3aa_twin—"True" entered if there are duplicates of this clonotype's aa sequence in the repertoire In various embodiments, the clonotype frequency and/or gene clonotype assignments may be determined by a TCR or BCR sequence assembly algorithm included in the systems and methods described herein.

TABLE 6

| count | 315 | 311 | 229 | 225 | 220 | 187 | 183 | 173 | 170 | 170 |
|---|---|---|---|---|---|---|---|---|---|---|
| frequency | 0.183 | 0.068 | 0.058 | 0.055 | 0.055 | 0.041 | 0.045 | 0.042 | 0.042 | 0.042 |
| CDR3 nt | TGTGC GAGA GAAG AGGTC AGGG ATGGA TCGTA TTACG ATTTT TGGAG TGGTT ACCCC TACCC GGAAT ACTAC TACTA CTACA TGGAC GTCTG G | TGC GCC AGC CAA GTA GCG GGA CCC TAC GAG TAC TTC | TGT CAG CAT CGT GGC AAC CGG CCC ACT TTC | TGT GGT TCT AAC GAC TAC AAG CTC AGC TTT | TGC CAA CAG TAT AAT TAT TCT CGG AGT TTT | TGC AGT GCT AGA AGA CTA GCG GGA CTT AGC ACA GAT ACG CAG TAT TTT | TGT GTC TTA TAA CAC CGA CAA GCT CAT CTT T | TGT GTG GAT AGC AAC TAT CAG TTA ATC TGG | TGT TGA GCA AAT CAT TAT AGT GTT TCT TCT GGT TCT GCA AGG CAA CTG ACC TTT | TGT GTG ATC AAA GCT GCA GGC AAC AAG CTA ACT TTT |
| CDR3 aa | CAREE VRDGS YYDF WSGYP YPEYY YYYM DVW | CAS SQV AGP YEQ YF | CQH RGN RPTF | CGS NDY KLS F | CQQ YNS YSR SF | CSA RRL AGG LST DTQ YF | partial | partial | C_A NHS VSS GSA RQL TF | CVI KAA GNK LTF |
| V | IGHV3-21*01 | TRBV4-1*01 | IGKV3-11*01 | TRAVI7*01 | IGKV1-5*03 | TRBV20-1*02 | TRAV8-6*01 | TRAV3*01 | TRAV24*01 | TRAV19*01 |
| D | IGHD3-3*01 | TRBD2*02 | | | | TRBD2*02 | | | | |
| J | IGHJ6*04 | TRBJ2-7*01 | IGKJ4*01 | TRAJ20*01 | IGKJ2*03 | TRBJ2-3*01 | TRAJ34*01 | TRAJ33*01 | TRAJ22*01 | TRAJ17*01 |
| C | IGHA1 | TRBC | IGKC | TRAC | IGKC | TRBC | TRA | TRAC | TRAC | TRA |
| receptor | IGH | TRB | IGK | TRA | IGK | TRB | TRA | TRA | TRA | TRA |
| productive_status | in | in | in | in | in | in | partial | partial | internal_stop | in |
| receptor_frequency | 0.185 | 0.068 | 0.094 | 0.055 | 0.090 | 0.041 | 0.045 | 0.043 | 0.042 | 0.042 |
| receptor_productive_frequency | 0.254 | 0.115 | 0.107 | 0.131 | 0.103 | 0.069 | | | | 0.099 |
| V_gene_family | IGHV3 | TRBV4 | IGKV3 | TRAV17 | IGKV1 | TRBV20 | TRAV8 | TRAV3 | TRAV24 | TRAV19 |

TABLE 6-continued

| | | | | | | | | | | |
|---|---|---|---|---|---|---|---|---|---|---|
| V_gene | IGHV3-21 | TRBV4-1 | IGKV3-11 | TRAV17 | IGKV1-5 | TRBV20-1 | TRAV8-6 | TRAV3 | TRAV24 | TRAV19 |
| V_allele | 01 | 01 | 01 | 01 | 03 | 02 | 01 | 01 | 01 | 01 |
| D_gene_family | IGHD3 | TRBD2 | | | | TRBD2 | | | | |
| D_gene | IGHD3-3 | TRBD2 | | | | TRBD2 | | | | |
| D_allele | 01 | 02 | | | | 02 | | | | |
| J_gene_family | IGHJ6 | TRBJ2 | IGKJ4 | TRAJ20 | IGKJ2 | TRBJ2 | TRAJ34 | TRAJ33 | TRAJ22 | TRAJ17 |
| J_gene | IGHJ6 | TRBJ2-7 | IGKJ4 | TRAJ20 | IGKJ2 | TRBJ2-3 | TRAJ34 | TRAJ33 | TRAJ22 | TRAJ17 |
| J allele | 04 | 01 | 01 | 01 | 03 | 01 | 01 | 01 | 01 | 01 |
| IGH_isotype | A1 | | | | | | | | | |
| has_CDR3nt_twin | False | False | False | False | False | False | False | False | False | False |
| has_CDR3aa_twin | False | False | True | False | True | False | False | False | False | False |

Example 3

TCR/BCR Sequence Database and Uses Thereof

In this example, a reference dataset may be generated or an existing reference dataset may be selected. The data may be de-identified data. The data may have protected health information (PHI) removed. The reference dataset can include TCR/BCR sequencing data associated with annotated clinical documentation as well as additional NGS-based outputs (including but not limited to, patient HLA type or matched NGS DNA/RNA sequencing, viral/pathogen sequencing, whole exome or targeted panel sequencing of patient specimen(s)). Clinical documentation may include: disease characterization and duration, severity of symptoms or disease (for example, disease associated with infection by the pathogen(s)), symptom descriptions and/or severity ratings, therapy or therapies (for example, a cancer therapy such as an immunotherapy, or a vaccine) and duration and outcome, time between start and/or end of disease and sample collection, sample collection site/specimen information (for example, saliva, blood, mucus, nasal/anterior nares swab, nasopharyngeal swab, nylon flocked swabs, spun polyester swabs, nasopharyngeal aspirate, bronchoalveolar lavage, specimens collected in Mawls tubes or Longhorn Primerstore MTM tubes, nasopharyngeal/nasal/nares or other specimens collected in viral transport medium/VTM, fecal, etc.), infection status for one or more pathogens as determined by one or more diagnostic assays (for example, PCR-based, isothermal nucleic acid amplification-based, NGS-based, serology-based, array/microarray/array card/openarray plate/FilmArray/etc., ELISA, ELISpot, FluoroSpot, antigen-based, rapid antigen testing, or other molecular assay), etc. HLA data may be used to further annotate or contextualize the TCR sequence data. For example, certain combinations of TCR sequences and HLA types may be incompatible, implying that certain TCR sequences may be expected in the context of certain HLA types. For example, for patients missing a TCR sequence that would be expected in the context of exposure to a specific pathogen, the absence of that sequence may be expected if the patient does not have HLA types that are compatible with that TCR sequence.

This reference dataset may be mined to identify TCR or BCR sequences that are enriched in patients that are responding to or have recently recovered from disease caused by a specific pathogen or combination of pathogens. For example, see Emerson, R., DeWitt, W., Vignali, M. et al. Immunosequencing identifies signatures of cytomegalovirus exposure history and HLA-mediated effects on the T cell repertoire. Nat Genet 49, 659-665 (2017). https://doi.org/10.1038/ng.3822, the contents of which are incorporated by reference herein in their entirety for all purposes.

The mining may include the use of machine learning clustering techniques on the TCR/BCR sequence database. Example methods include detecting a pathogen-associated TCR or BCR sequence in data from patients having a particular cancer type. These sequences could be used as a biomarker, an indication for prescribing checkpoint inhibitors or predicting response to IO. Cross-reactivity means the sequence could be present in a higher percentage of patients, especially if the infection by the pathogen is common, so these are more likely to be the first sequences discovered that are common to many patients.

The systems and methods could be used to detect receptor sequences that are generated in response to one disease state, but are cross reactive and can be used as adoptive cell therapy for another. For example, influenza infection or vaccine, or SARS-CoV-2 infection or vaccine can give rise to a receptor sequence that then attacks cancer cells (see https://onlinelibrary.wiley.com/doi/10.1111/bj h.17116).

In one example, the patients have non-small cell lung cancer (NSCLC) and a viral-associated TCR sequence. TCRbeta chains were grouped into affinity groups (based on similar amino acid structure). Certain viral associated TCRs cross react with cancer antigens (for patients having the same HLA). (see Cell press immunity paper "Global analysis of shared T cell specificities inhuman non-small cell lung cancer enables HLA inference and antigen discovery" Chiou et al https://sciencedirect.com/science/article/pii/S1074761321000 807).

Subsequent observation of these TCR and BCR sequences in a patient can then be analyzed by a predictive model trained on the reference dataset or a subset of the reference dataset (for example, only records having data deemed relevant to the prediction, including data associated with a known negative or positive status or numeric score related to the prediction target or category of prediction) to calculate a likelihood of the patient having an infection status, exposure history, and/or potential protection or resistance to infection associated with any of the TCR and/or BCR sequences, where the associations may be based on associations or trends captured in the reference dataset.

The reference dataset may also be analyzed to find associations between the severity of disease and various genetic, immunological, or clinical factors or characteristics. For example, factors may include alleles or variants associated with the ABO blood type gene, the gene located on chromosome 9q34.2, immunological genes, genes located on chromosomes 3 or 6, HLA genes, etc., immunological characteristics, clinical data/status (age, history of cardiac disease, diabetic, blood sugar levels, hypertension, obesity, asthma, COPD, etc.), and/or the presence of specific TCR and/or BCR sequences.

The TCR and/or BCR sequences may have been generated in response to the pathogen that causes the disease or in response to another pathogen. For example, if the disease is COVID-19, SARS, or MERS, the TCR or BCR may have been generated in response to OC43, HKU1, 229E, and NL63 coronaviruses and may cross-react with SARS-CoV-2, SARS-CoV-1, MERS, etc.

By way of example, immunological characteristics associated with severe COVID-19 disease may include any of the following: large populations of activated CD4 T cells, little or no circulating follicular helper T Cells (cTfh), activated and/or exhausted populations of CD8 T cells, little or no TEMRA-like cells, T-bet+ cells (including plasmablast cells), Ki67+ cells (including plasmablast cells), memory B cells, strong or Tbetbright effector-like CD8 T cell responses, weak CD4 T cell responses, reduced lymphocyte response, strong plasmablast response without large populations of activated cTfh, or failed T or B cell responses. (see Mathew et al, Science 4 Sep. 2020: Vol. 369, Issue 6508, the contents of which are incorporated herein by reference in their entirety for all purposes).

By way of example, immunological characteristics associated with mild or asymptomatic COVID-19 may include any of the following: SARS-CoV-2 specific T cell responses (for example, targeting internal viral proteins, viral surface proteins, viral nucleocapsid, viral membrane, or viral spike protein); durable functioning memory T cell responses; T cells expressing CD38, HLA-DR, Ki-67, PD-1 (or other inhibitory receptors), CCR7, CD127, CD45RA, and/or TCF1; SARS-CoV-2-specific IgG; inflammatory markers (for example, in patient plasma). (see Sekine et al, Robust T cell immunity in convalescent individuals with asymptomatic or mild COVID-19, Cell (2020), doi: https://doi.org/10.1016/j.cell.2020.08.017, the contents of which are incorporated herein in their entirety for all purposes).

Accordingly, in some embodiments, the reference TCR/BCR sequence dataset may be analyzed to find associations between, for example, immunological characteristics and/or clinical characteristics (including diagnosis) associated with severe, mild or asymptomatic COVID-19. Such information can then be used to provide or to confirm a diagnosis, to predict disease severity, and predict therapeutic efficacy, for example.

Example 4

Coronavirus Specific TCR/BCR Sequences

In this example, a coronavirus cohort (for example, data collected from a group of patients having a coronavirus infection or exposure and/or negative controls known to have been unexposed to or unaffected by coronavirus for a specified amount of time immediately before their specimens were collected) may be analyzed. A coronavirus cohort may be assembled from a reference dataset, for example the reference dataset described in Example 2, especially a subset of the dataset where the patients have a known or inferred coronavirus exposure status. Coronavirus may include any individual coronavirus that infects humans (for example, SARS-CoV-1, SARS-CoV-2, MERS-CoV, Coronavirus HKU1, Coronavirus NL63, Coronavirus 229E, Coronavirus OC43, etc.), or a combination thereof.

The cohort or reference dataset may be used to determine which TCR and/or BCR sequences are associated with coronavirus infection or exposure. For coronavirus associated TCR sequences, the systems and methods may control for HLA types as described in Example 1. For example, the method may assume that the top 5 or 10 HLA alleles in the population of interest are present in all patients unless the HLA types of the patient are known.

The quantity, presence or absence of these TCR and/or BCR sequences in a patient may be used to predict the patient's exposure to a coronavirus (for example, including the use of a predictive model trained on the reference dataset in Example 1, a subset of that dataset, or another dataset), the likelihood that the patient will have mild symptoms or severe symptoms if exposed to a coronavirus, and/or to measure the patient's response to a vaccine. It would be possible to determine whether the presence of those TCRs and/or BCRs afforded protection from (or susceptibility to) severe COVID symptoms, which could then be used to stratify subjects based on their potential risk of complications following SARS-CoV-2 (or other coronavirus) infection.

The analysis may also be used to predict which TCR and/or BCR sequences associated with a coronavirus exposure are cross-protective against SARS-CoV-2 (or another coronavirus), to measure prevalence of certain sequences across population, or for a trial design to determine if a TCR-HLA combination is protective or associated with a certain symptom severity level.

Example 5

Predicting Pathogen and/or Disease Susceptibility of a Patient

In this example, a specimen from a patient may be analyzed for TCR and/or BCR sequences according to the methods disclosed above. The patient may be having respiratory infection and/or flu-like symptoms without a specific diagnosis as to which respiratory infection is the cause of the symptoms The detected TCR and/or BCR sequences may be analyzed by a predictive model trained by a reference dataset, for example the dataset described in Example 2, to predict the most likely pathogen causing the symptoms, and/or the likelihood that the patient will have mild disease or severe disease (for example, the patient's disease susceptibility). In various embodiments, the patient's COVID-19 status (infected or not infected with SARS-CoV-2) is unknown. In another embodiment, the patient has a COVID-19 diagnosis and/or previous positive result from a SARS-CoV-2 diagnostic assay.

A specimen from the patient may also be analyzed for evidence of the presence of a pathogen (for example, by the assay(s) listed in Example 1). The pathogens screened by the assay(s) may include any pathogen commonly associated with respiratory infection and/or flu-like symptoms, for example, SARS-CoV-1, SARS-CoV-2, MERS-CoV, Coronavirus HKU1, Coronavirus NL63, Coronavirus 229E, Coronavirus OC43, Influenza A, Influenza A H1, Influenza A H1-2009, Influenza A H1N1, Influenza A H3, Influenza B, Influenza C, Parainfluenza virus 1, Parainfluenza virus 2, Parainfluenza virus 3, Parainfluenza virus 4, Rhinovirus/Enterovirus, Adenovirus, Respiratory Syncytial Virus, Respiratory Syncytial Virus A, Respiratory Syncytial Virus B, Human Metapneumovirus, Bocavirus, Human Bocavirus, *Chlamydophila pneumoniae, Mycoplasma pneumoniae, Legionella pneumophila, Bordetella, Bordetella holmesii, Bordetella pertussis, Streptococcus pneumoniae, Coxiella burnetii, Staphylococcus aureus, Klebsiella pneumoniae, Moraxella catarrhalis, Haemophilus influenzae, Pneumocystis jirovecii, Enterovirus* D68, Epstein-Barr virus (EBV), Mumps, Measles, Cytomegalovirus, Human herpesvirus 6 (HHV-6), Varicella zoster virus (VZV), Parechovirus, etc.

Example 6

Assessing Response to Therapy—Vaccine

In this example, specimen(s) from either a vaccine trial subject or a patient receiving a vaccine in another context may be analyzed for TCR and/or BCR sequences according to the methods disclosed above to assess the patient's response to the vaccine and the patient's disease susceptibility to the disease associated with the vaccine (for example, the disease that the vaccine is designed to prevent, attenuate, or ameliorate) or another disease.

A reference dataset as described in Example 2 may be used to determine which TCR and/or BCR sequences are associated with a response to a vaccine. The presence or absence of these TCR/BCR sequences and additional statistics or results associated with TCR/BCR sequences in the patient may be used to predict the degree of disease susceptibility of the patient. Additional clinical or molecular data as described in the previous examples may also be factored into the disease susceptibility prediction.

The report may include detected TCR/BCR sequences, predicted disease susceptibility, the basis or bases for the predicted disease susceptibility, and other related information.

In one embodiment, the specimen is collected after the vaccine is administered to the subject. In another embodiment, multiple specimens are collected from the patient, including a first specimen collected before the vaccine is administered to the patient and a second specimen collected after the vaccine is administered to the patient. In another embodiment, multiple doses of the vaccine are administered to the patient and a specimen may be collected after each dose of vaccine is administered.

Example 7

T Cell Clonal Expansion and Estimates of Clonality within Repertoires in Various Cancers Introduction The level of immune cell infiltration into a tumor is due to a variety of factors, for example: the level of immunogenicity of the tumor, the type of tissue where the tumor has arisen, the degree by which immune cells are able to physically move through the tumor stromal material, or metabolically repressive and hypoxic nature of solid tumors. However, the level of immune filtration may be characteristic among similar tumor types, with brain tumors having characteristically low immune filtration, and lung and skin malignancies having characteristically high infiltration. Tumors of different origins may also have more or fewer distinct clones of lymphocytes present within the tumor microenvironment. Lymphomas and leukemias present unique cases, because the malignant T or B cells may arise from a single clone. Thus, samples from patients suffering from lymphoma may have a very few T cell receptor (TCR) or B cell receptor (BCR) clones represented in their immune profile. In summary, sequencing a variety of tumor samples of different cellular origin, and developing immune profiles, provides valuable insight into the effectiveness of a particular immune profiling assay. Developing immune profiles from a variety of malignancies allows for an unbiased evaluation of the novel hybrid-capture approach described herein for application to real-world diagnostic challenges.

Methods

Sample preparation and sequencing were performed as described in Example 2, above.

Analysis: The analysis was performed as described above for Example 2 (gene expression RUO infiltration analysis is known in the art and is described, for example at https://www.worldscientific.com/doi/abs/10.1142/9789813279827_0026 and also described in (published) patent app. no. 16/533,676 incorporated herein by reference.

Results

Figure 7:
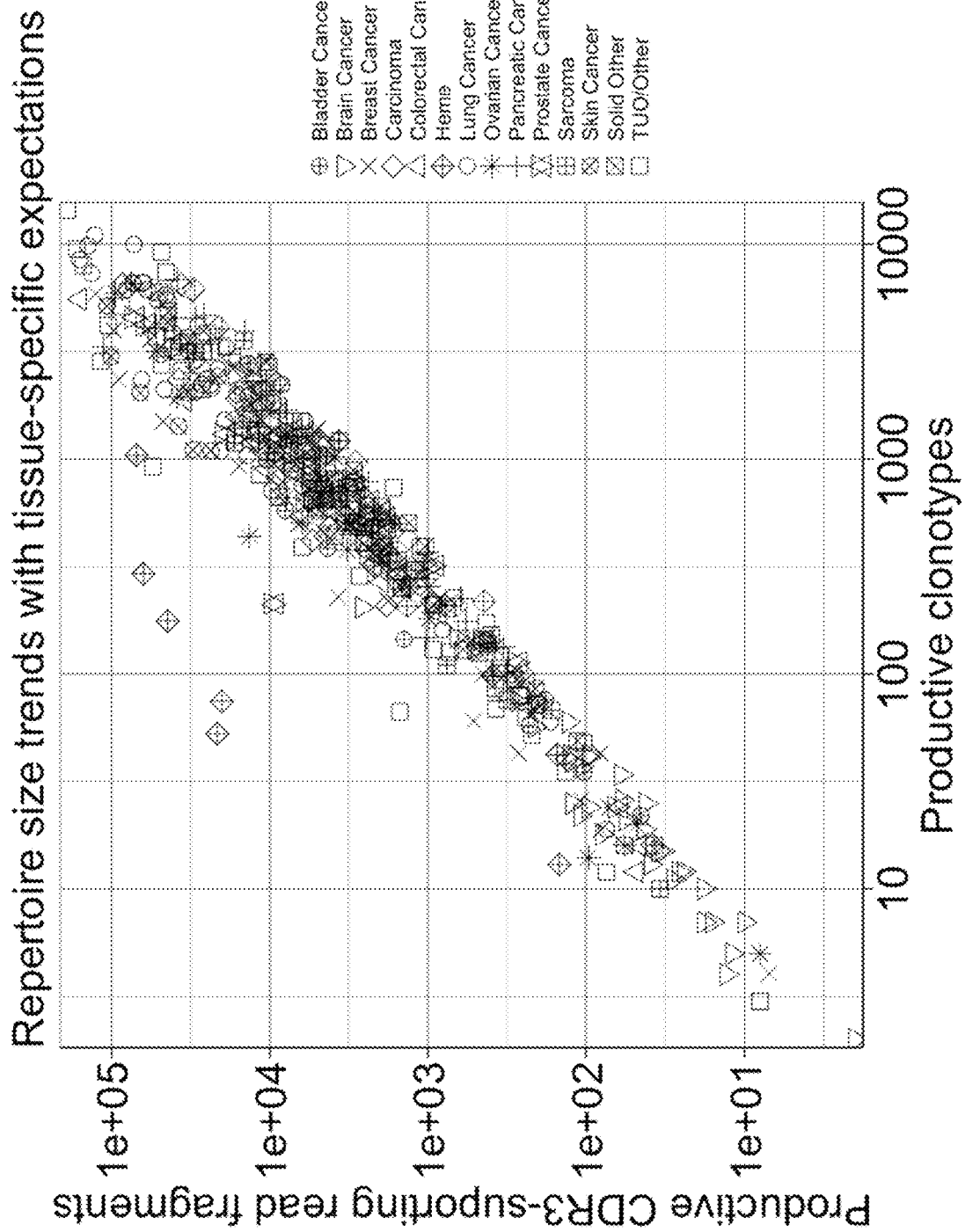
FIG. 7. is a scatter-plot showing the productive clonotypes vs. the CDR3-supporting read fragments from 501 human cancer samples analyzed using the novel hybrid-capture immune profiling approach. Each datapoint represents data from one sample, where the cancer type associated with the sample is represented by a particular color/shape combination (see legend). The x-axis represents the number of productive clonotypes detected in each sample and the y-axis represents number of CDR3 supporting sequence read fragments (sequence read fragments having a portion that maps to a CDR3 locus) detected.
Figure 8:
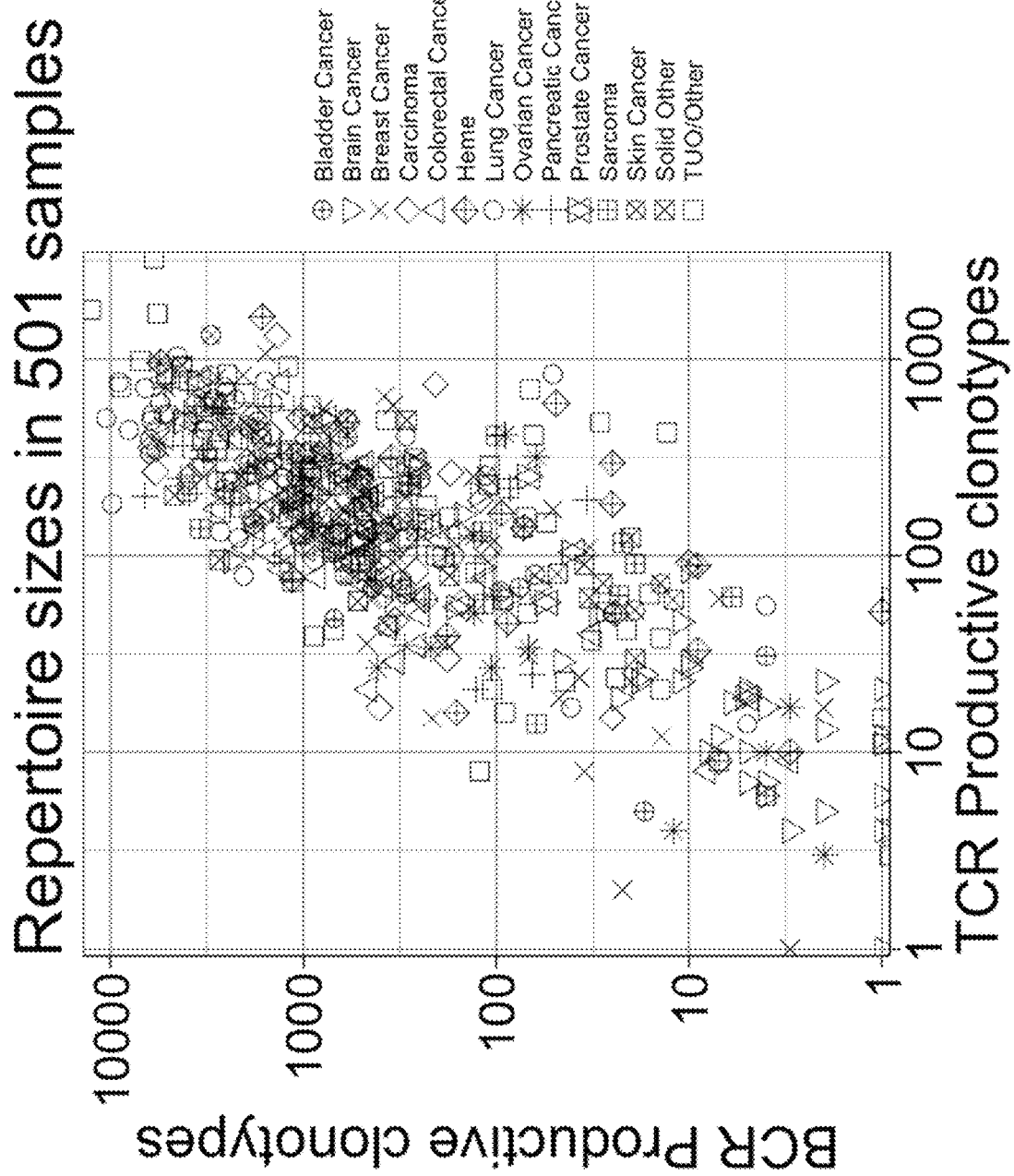
FIG. 8. Repertoires generated from 501 tumor transcriptomes demonstrate broad distribution of clonotypic richness. Total productive clonotypes (excluding CDR3 sequences with partial alignments, frameshifts and internal stop codons) for BCRs (Ig-heavy, -κ, and -λ) and TCRs (TCR-α, TCR-β, TCR-γ, and TCR-δ).
Figure 9:
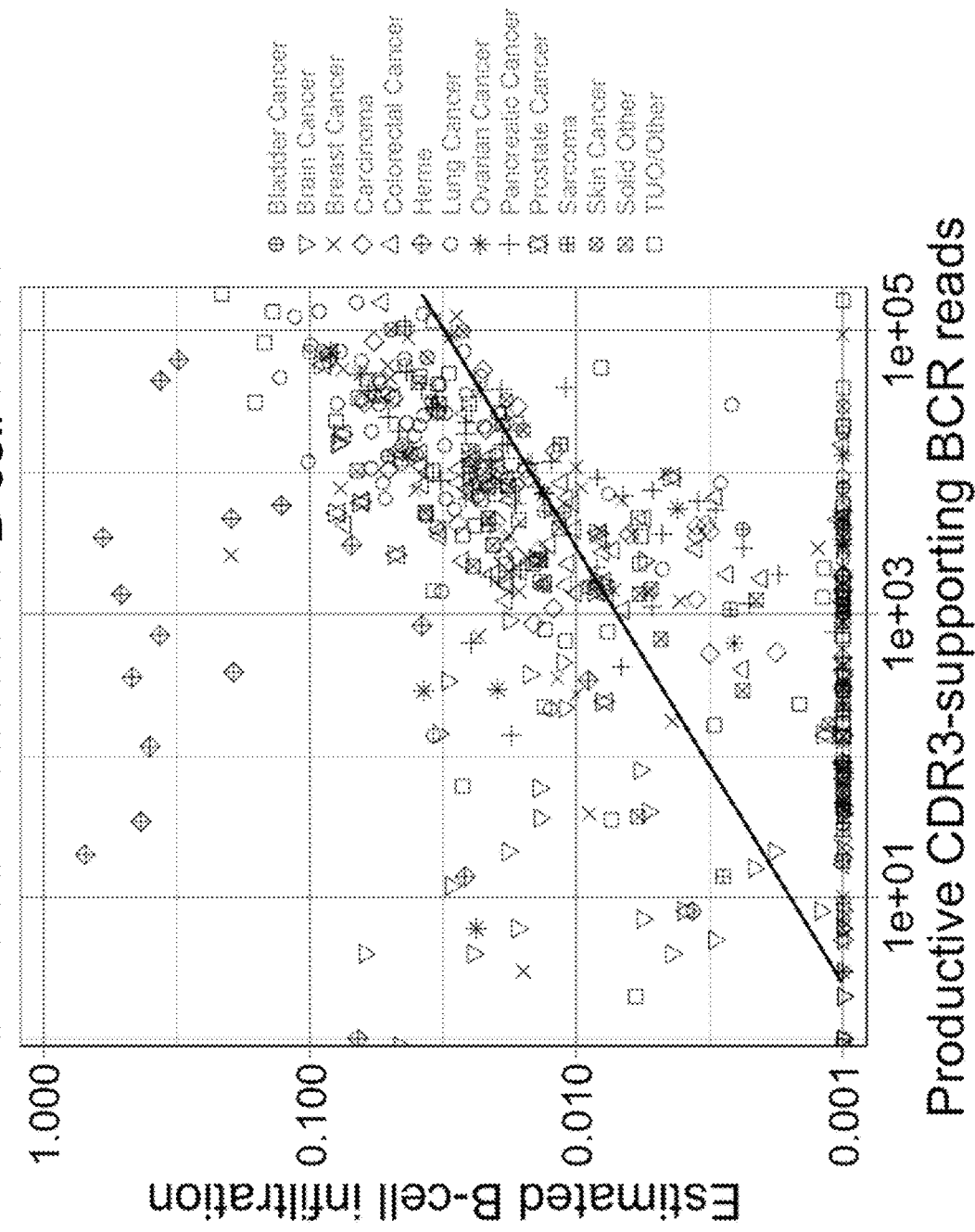
FIG. 9. Repertoires generated from 501 tumor transcriptomes demonstrate broad distribution of clonotypic richness. Gene expression-based estimations (published patent application Ser. No. 16/533,676 incorporated herein by reference and PMID: 30864330) for B-cells (y-axis) correlate with clonotype yield (reads supporting productive CDR3s, x-axis) for respective receptors (one-tailed Pearson—95% CI). Samples with infiltration estimations at or below 0.001 are displayed at that value.
Figure 10:
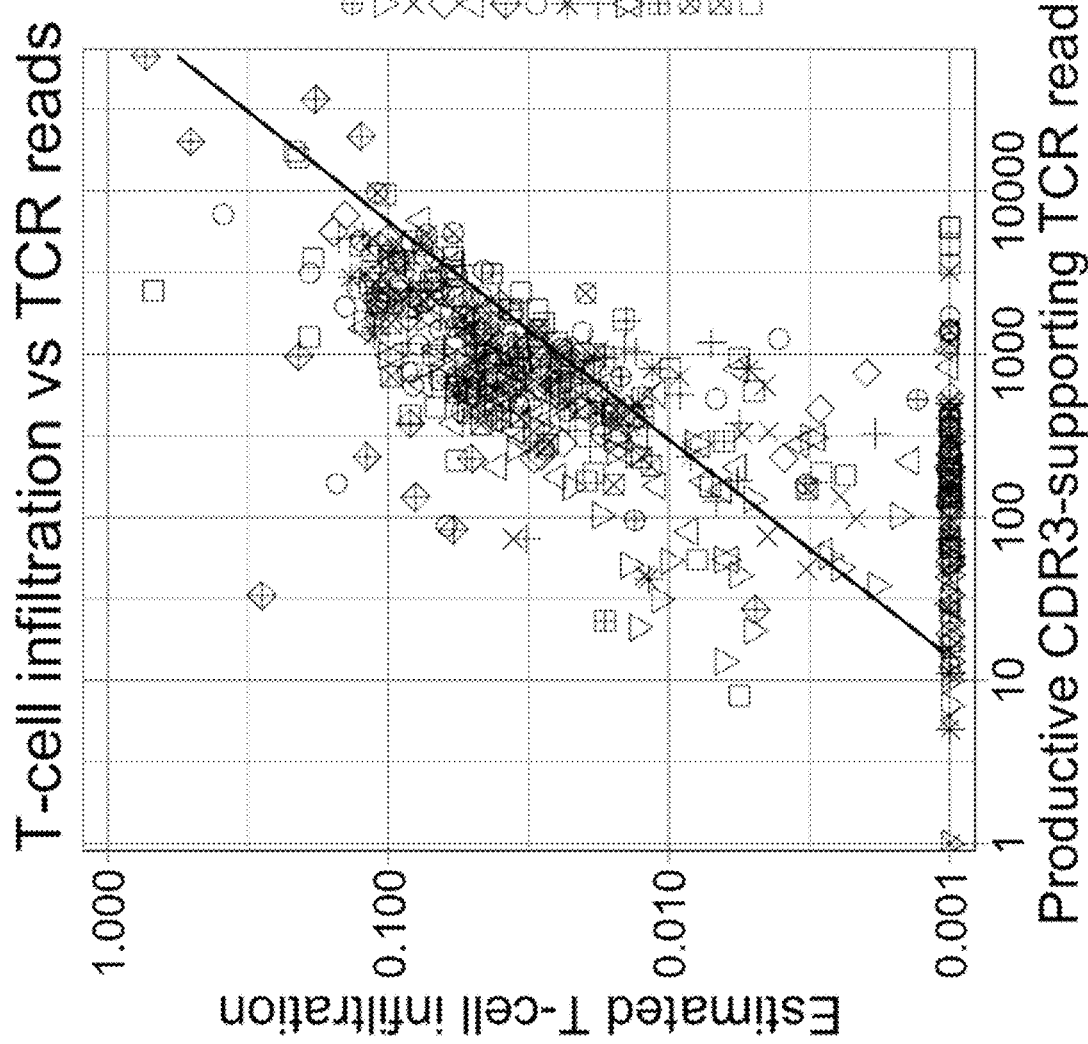
FIG. 10. Repertoires generated from 501 tumor transcriptomes demonstrate broad distribution of clonotypic richness. Gene expression-based estimations (published patent application Ser. No. 16/533,676 incorporated herein by reference and PMID: 30864330) for CD4/CD8 T cells (y-axis) correlate with clonotype yield (reads supporting productive CDR3s, x-axis) for respective receptors (one-tailed Pearson—95% CI). Samples with infiltration estimations at or below 0.001 are displayed at that value.

We hypothesized that the novel hybrid-capture approach disclosed herein would provide accurate and efficient sampling of immune profiles. To test this hypothesis, RNA samples were derived from 501 individuals, cDNA libraries were prepared, and the novel hybrid-capture probe approach described herein was used to isolate sequences. Sequencing produced an average of about 20,000 reads per sample for each of the 501 samples sequenced. Sequencing data was plotted with productive clonotypes on the X axis and CDR3-supporting read fragments on the Y axis to demonstrate the average number of clonotypes present in the tumor sample (FIG. 7). Consistent with other reports, brain tumor samples (solid blue circles) revealed few productive clonotypes, whereas lung tumor samples showed significant infiltration of diverse lymphocyte clonotypes. Furthermore, immune cell profiles demonstrated broad clonal richness (FIG. 8) In addition, productive T and B cell reads correlated with estimated T and B cell infiltration into the tumor (FIGS. 9, 10). These data support the hypothesis that the novel hybrid-capture approach can be used to efficiently collect valuable immune profiling data from a variety of tumor types, especially where repertoire yields recapitulate tissue-specific expectations for lymphocyte infiltration.

Figure 11:
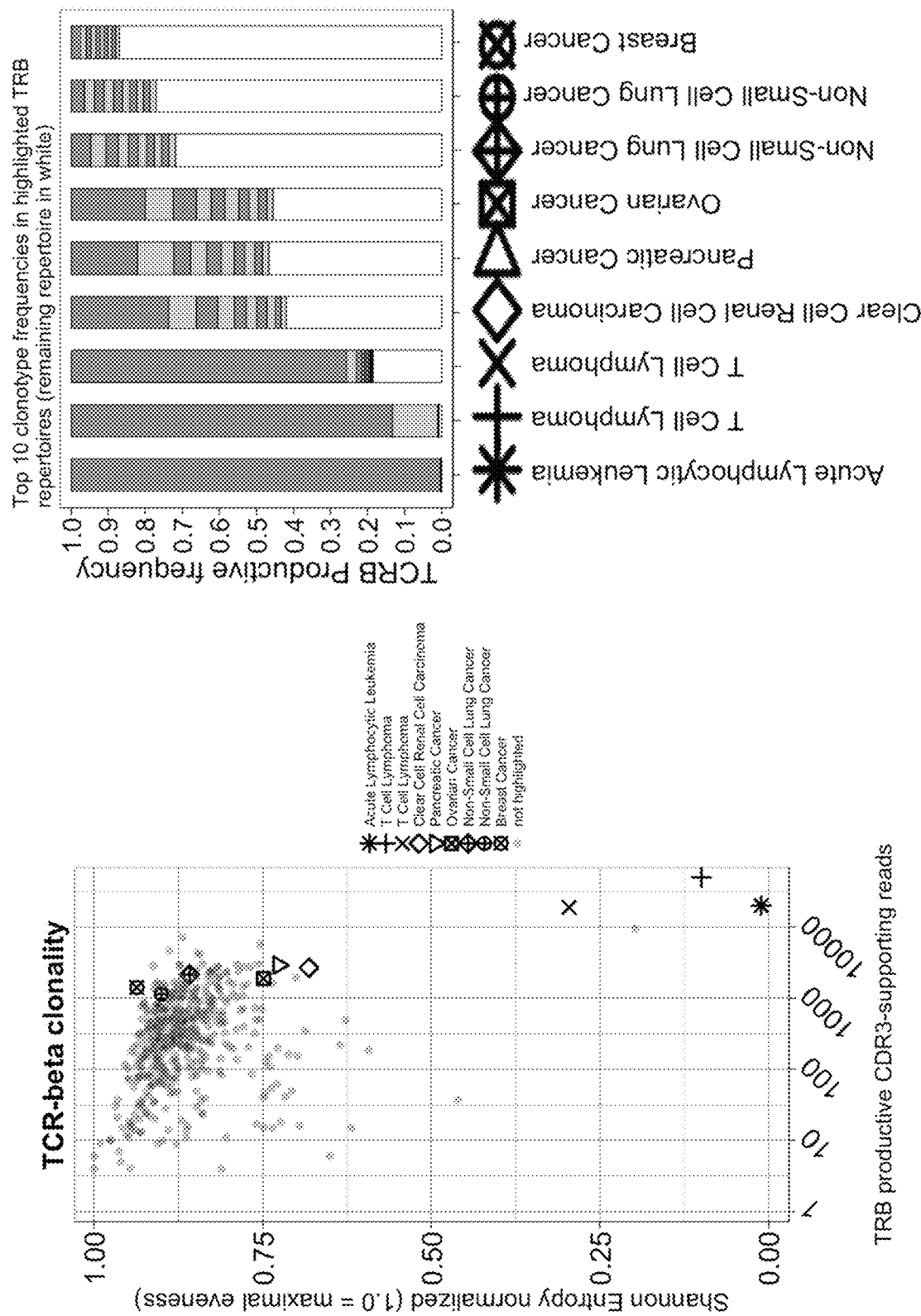
FIG. 11. (Left) is a scatter-plot showing the number of TCR Beta productive clonotypes vs. the normalized Shannon entropy within each immune profile from 501 human cancer samples that were sequenced using the novel hybrid-capture approach disclosed herein. A higher normalized Shannon entropy is correlated with increased diversity in clonotypes within the sample. 9 example repertoires were selected (indicated by asterisks, color coded by cancer type of the sample; asterisks, from bottom to top, in order are: Red-acute lymphocytic leukemia, Orange-T cell lymphoma, Yellow-T cell lymphoma, Turquoise-Clear cell renal cell carcinoma, Indigo-pancreatic cancer, Purple-ovarian cancer, Light green-non-small cell lung cancer, Green-non-small cell lung cancer, Black-breast cancer). (Right) Expansion of top 10 clonotypes in selected TRB repertoires. The productive receptor frequency for the top ten clonotypes are displayed (each color represents one of the top ten clonotypes and the remaining repertoire is shown in grey).

Next, immune profiles from hematological malignancies were further analyzed. Hematological cancers often consist of few clonotypes due to the clonal nature of tumor cell expansion. Therefore, we hypothesized that the novel hybrid-capture approach would reveal few clones in the samples derived from leukemia and lymphoma, while revealing many clones in other tumor types. Shannon entropy was normalized against the theoretical maximum evenness for a given repertoire size to represent clonal distributions for each receptor. This provided a measure to evaluate the expected versus the observed diversity of clonotypes in each sample. Samples derived from T cell lymphoma or leukemia demonstrated low normalized Shannon entropy while, for example, samples derived from melanoma, breast cancer, or oropharyngeal cancers demonstrated high normalized Shannon entropy (FIG. 11, left panel). Further resolution of relative frequencies for the top 10 most productive TCRBeta (TRB) clonotypes are displayed FIG. 11, right panel. Therefore, these data support the hypothesis that the novel hybrid-capture assay described herein efficiently isolates and amplifies sequences that are highly relevant to making clinical diagnostic decisions. Indeed, applying the novel hybrid-capture assay described herein to a diverse set of tumor samples demonstrated that the assay is effective at capturing a diverse landscape of immune infiltration and repertoire differences that reflect known biological trends.

Example 8

B Cell Lymphoma Case Study: Demonstrating Anti-CD19 CAR Detection in a Patient

Introduction

Chimeric antigen receptor (CAR) technology leverages synthetic biological approaches to treat disease in an antigen specific manner. CARs are designed to function as "replacement" T cell receptors directed to an antigen of choice. Therefore, T cells may be isolated from a patient, transduced with the CAR, and administered as an autologous transplant. CARs are constructed from the antigen recognition domain of an antibody (scFv) and various intracellular signaling domains. When a CAR binds to cognate antigen, the signaling domains on the intracellular portion transduce a signal similar to native T cell receptor, along with co-stimulatory signals, activating the effector functions of the CAR T cell. Successful and durable CAR T cell treatment depends on engraftment and persistence of the CAR T cells in the patient. Thus, technology that can detect the presence and state of CAR T cells in a patient longitudinally, would aid in the ability of a health care practitioner to make informed decisions regarding treatment.

Methods

Subject sample preparation and sequencing were performed as described in Example 2.

Analysis was performed as previously described (no special analysis was required to prepare data for detection of this CAR's CDR3 amino acid sequence in the rep-seq data.

Subject History

The subject was diagnosed with B-cell lymphoma in 2015. Initial treatment with rituximab lead to complete remission of disease. Disease recurred in 2017 prompting a second treatment with rituximab, again leading to complete remission. The subject again experienced disease recurrence in 2019 and underwent treatment with anti-CD19 CAR (Axicabtagene ciloleucel), leading to complete remission. The subject again experienced recurrence in 2020 and was placed on rituximab and anti-CD79b monoclonal antibody treatment. Subject samples were collected 1 year post-treatment with anti-CD19 CAR. At this time, malignant cells were CD19+, CD20− by flow cytometry.

Results

Figure 12:
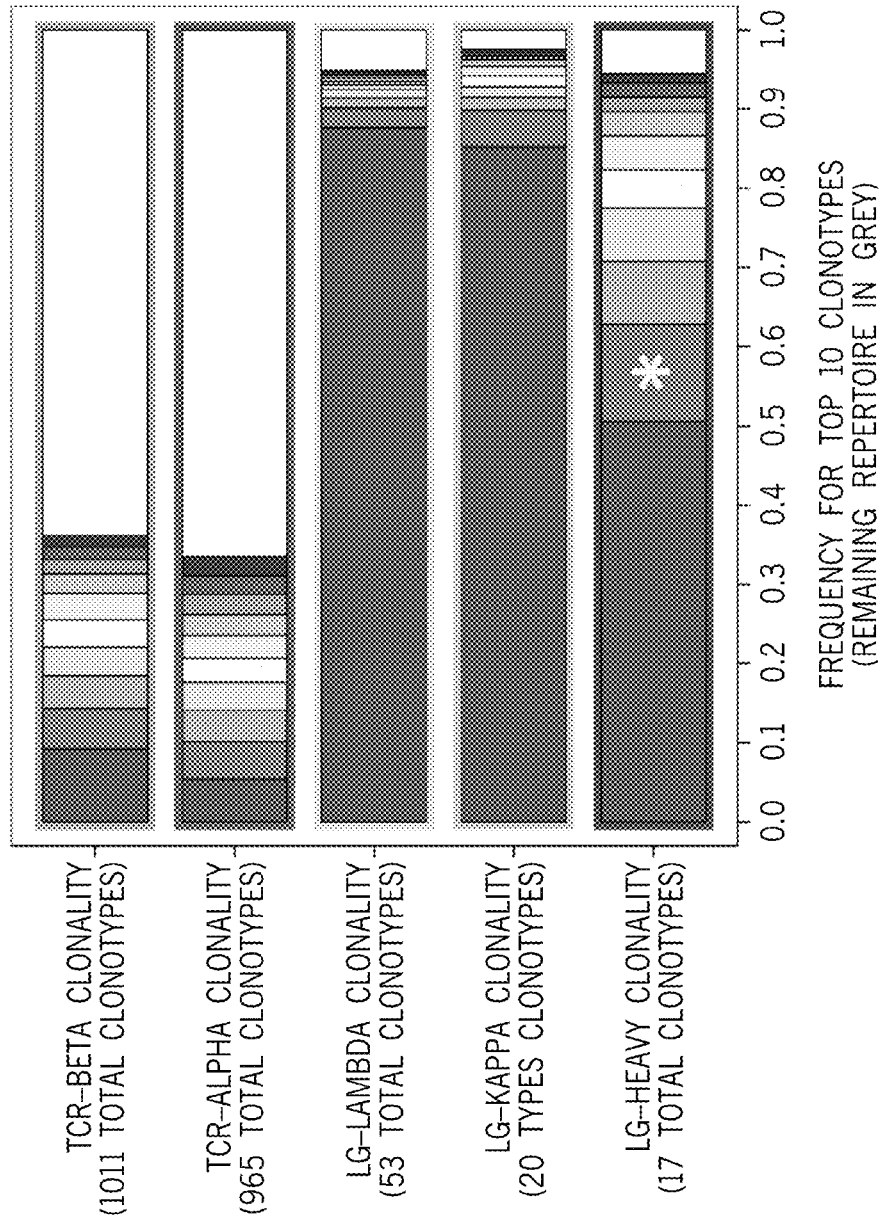
FIG. 12. Is a bar graph showing the frequency of the top 10 clonotypes in an individual with B-cell lymphoma who has been previously treated with anti-CD19 CAR. Yellow asterisk indicates clonotype that represent reads aligned to the heavy chain of chimeric antigen receptor.

We hypothesized that the novel hybrid capture and sequencing approach disclosed herein would efficiently and accurately detect CAR T cell engraftment. Therefore, to test this hypothesis we developed an immune profile for a subject that had undergone successful anti-CD19 CAR treatment, but had experienced subsequent recurrence. The anti-CD19 CAR axicabtagene ciloleucel utilizes the FMC63 scFv as an ectodomain to detect CD19. In various embodiments, any CAR sequence could be detected by using the systems and methods disclosed herein. Though the IGHJ4 heavy chain is derived from mouse, the high sequence homology between human and mouse in this region should allow detection using the novel hybrid-capture approach designed, in this example, for human application. In various embodiments additional probes specific to the desired CAR sequence could be added to the systems and methods disclosed herein to increase the number of sequencing reads corresponding to the CAR sequence. Immune profiling revealed an overall repertoire ~60% of the size of similar B-cell lymphoma repertoires. Furthermore, T cells were highly represented in the subject's repertoire (FIG. 12). One interpretation of this result is that extensive rituximab treatment has reduced the B cell repertoire. Notably, this approach allowed for detection of 20/164 IGH-aligned reads to be mapped to the anti-CD19 CAR (FIG. 12, yellow asterisk). Thus, these data demonstrate that the novel hybrid-capture approach efficiently and accurately detects anti-CD19 CAR scFv sequences in a subject.

Example 9

COVID 19 Case Study: Demonstrating the Rep-Seq Data Compatibility with External Data-Detection of Putative SARS-CoV-2 Specific TCRs Found in COVID-19 Patients Introduction Antigen-specific immune cell repertoires contain potentially vital information of the immunological history of a subject. For example, a subject's T and B cell repertoire reflects their exposure to pathogens. Furthermore, circulating antibodies directed to pathogens may wane over time. In contrast, pathogen-specific T cells may persist indefinitely. Therefore, sequencing a subject's immune repertoire and developing an immune profile may be a more efficient and accurate way of determining exposure than, for example, serology testing.

The pandemic caused by SARS-CoV-2 has led to incredible loss of life and hardship for individuals around the world. However, in response to the pandemic, unprecedented effort and resources have been allocated to immunological research. Through these efforts, immune repertoires have been obtained from individuals that have been infected with SARS-CoV-2 and made publicly available. Therefore, immune profiles created using the novel hybrid-capture approach disclosed herein can be made from individuals that have been infected with SARS-CoV-2 and validated to externally produced data.

Methods

Sample preparation, sequencing, and analysis were performed as previously described.

Results

Figure 13:
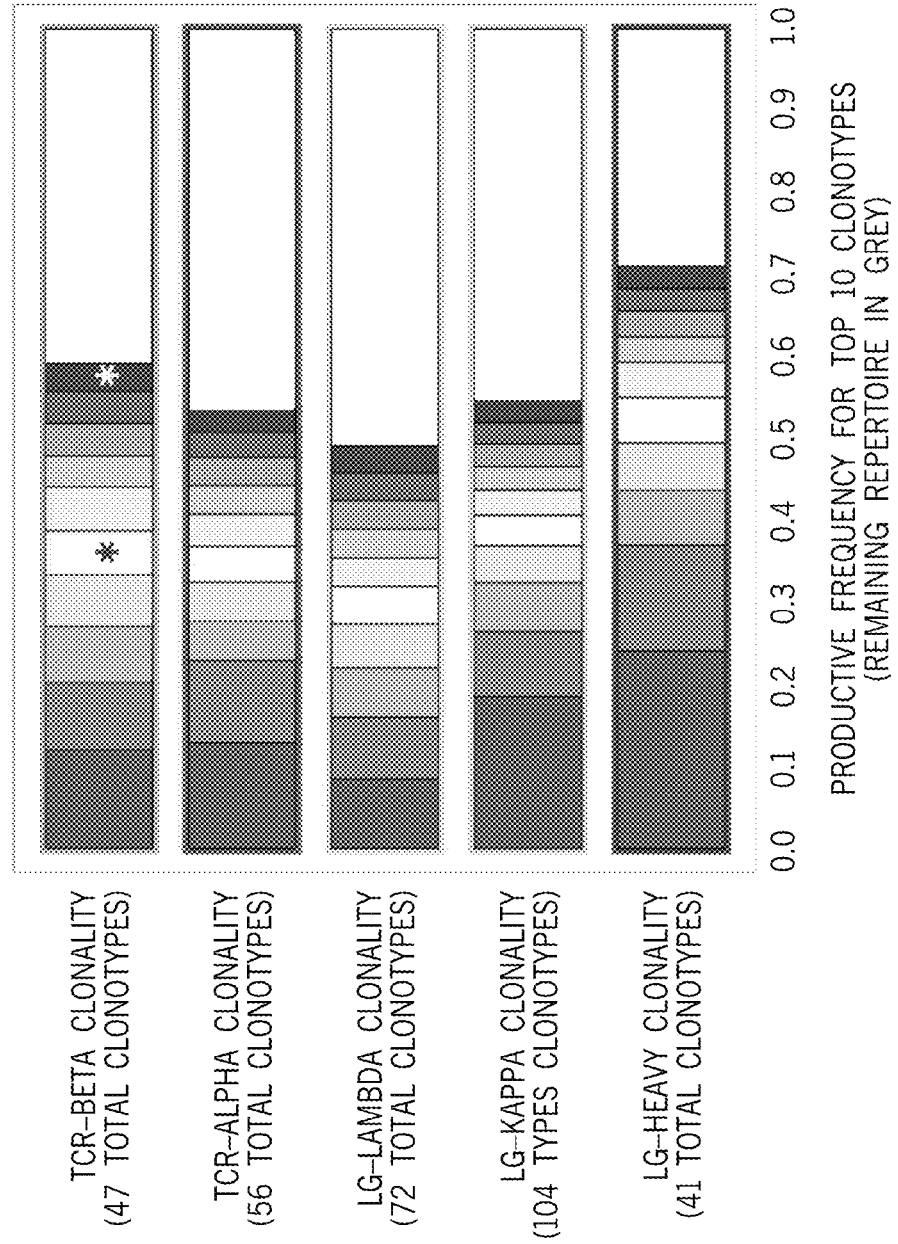
FIG. 13. Is a bar graph showing the productive frequency for the top 10 clonotypes assayed using the novel hybrid-capture approach from an individual that has been infected with SARS-CoV-2. The data were then compared to a database of putative SARS-CoV-2 reactive TCR B clonotypes. Yellow and purple asterisks indicate clonotypes matched to MIRA assay data, indicating that these clonotypes are likely SARS-CoV-2 specific.

The novel hybrid-capture approach disclosed herein efficiently produces high quality immune profiles from patient samples. To test the hypothesis that the novel hybrid-capture approach could detect pathogen-specific TCR sequences, we developed an immune profile from an individual that had been infected with SARS-CoV-2. The immune profiling revealed 47 and 56 TCR beta and alpha clonotypes, respectively. Next, we compared the TCR beta clonotypes to a publicly available database of SARS-CoV-2 specific TCR beta clonotypes developed using multiplexed identification of T cell receptors antigen assay (MIRA) (PMID: 32793896). This repository contains 160,000 TCR beta clonotypes with affinity for SARS-CoV-2 peptides and can be considered a positive control panel for SARS-CoV-2 exposure and/or infection. Intriguingly, four TCR beta clonotypes were matches for clonotypes discovered by MIRA assay (FIG. 13). The four CDR3 reads that matched MIRA assay data were the following: CASSIGVNTEAFF (SEQ ID NO: 186) (11 reads, found in 509 COVID-19+ repertoires, FIG. 13—purple asterisk), CASSLSGGPYNEQFF (SEQ ID NO: 187) (7 reads, found in 30 COVID-19+ repertoires, FIG. 13—yellow asterisk), CASSSGIQPQHF (SEQ ID NO: 188) (not detected in 500 COVID19− validation samples), and CASSVSYEQYF (SEQ ID NO: 189) (not detected in 500 COVID19− validation samples). These data support the hypothesis that the novel hybrid-capture approach described herein efficiently and accurately allows for the identification of immune profiles (TCR/BCR profiles) of individuals that have been infected with a pathogen, for example SARS-CoV-2.

Example 10

In one example, a TCR/BCR profile may be generated for a patient suffering from colorectal cancer. The patient may also harbor a KRAS P12D alteration, and an HLA C08.02 allele known to present this altered KRAS peptide. The TCR/BCR profile may be analyzed for CDR3 sequences likely to recognize the altered KRAS peptide.

Subject sample preparation and sequencing may be performed as described in Example 2. Analysis may be performed as previously described in Example 2.

The novel hybrid capture approach described in the current application may be used to develop an immune profile for an individual suffering from colorectal cancer. In some embodiments, the patient harbors a KRAS P12D mutation. In further embodiments, the patient harbors the HLA C08.02 allele, which is known to present the mutated KRAS peptide as a neoantigen. Therefore, in some embodiments, the immune profile developed from the individual harboring the aforementioned KRAS mutation and specific HLA allele C08.02 contains TCR clonotypes that recognize the KRAS neoantigen created by the P12D mutation in KRAS. In some embodiments, these clonotype sequences may be used to select lymphocyte clones for generation of patient-specific precision medicine therapies. In some embodiments, the putative neoantigen specific clonotypes derived from patient immune profiles may be used to assemble a database of such clonotypes. In some embodiments, the database of neoantigen-associated clonotypes may be further used in comparison to patients with unknown mutational status of KRAS. In some embodiments, the database of neoantigen-associated clonotypes may be used to diagnose patients with KRAS P12D mutation based on their immune profile, in addition to or without requiring a biopsy and an additional sequencing step.

In some embodiments, the immune profile developed from the patient suffering from colorectal cancer may be used to select the appropriate therapy to treat the tumor. In further embodiments, the therapy chosen to treat the colorectal cancer based on the immune profile is selected from the following: a cytotoxic chemotherapy, a targeted therapy, for example a Janus kinase inhibitor, or an immunotherapy. In some embodiments, the immunotherapy chosen is selected from the group consisting of: checkpoint blockade therapy, CAR T cell therapy, CAR M therapy, cancer vaccine, or other immune oncological modality.

In some embodiments, the results of the TCR/BCR profiling of the colorectal cancer patient may be used to prepare a report that details the most abundant T cell and B cell clones. In some embodiments, the top ten most abundant clones may be displayed. The most abundant clones may be assumed to represent expanded populations of B cells or T cells. In one embodiment, the TCR/BCR sequencing methods disclosed herein are utilized on multiple specimens collected from the patient at different times in order to track disease over time.

Example 11

In one example, a TCR/BCR profile may be generated for a patient having non-small cell lung cancer (NSCLC) and an EGFR mutation. The TCR/BCR profile may be analyzed for CDR3 sequences likely to recognize peptides encoded by the mutated EGFR gene.

Subject sample preparation and sequencing may be performed as described in Example 2. Analysis may be performed as previously described in Example 2.

The novel hybrid capture approach described in the current application may be used in conjunction with sequencing to develop an immune profile for an individual suffering from non-small cell lung cancer. In some embodiments, the patient harbors a mutation in EGFR. In some embodiments, an immune profile developed from the individual harboring EGFR mutation contains TCR clonotypes that recognize the EGFR neoantigen. In some embodiments, these clonotype sequences may be used to select lymphocyte clones for generation of patient-specific precision medicine therapies. In some embodiments, the putative neoantigen specific clonotypes derived from patient immune profiles may be used to assemble a database of such clonotypes. In some embodiments, the database of neoantigen-associated clonotypes may be further used in comparison to patients with unknown mutational status of EGFR. In some embodiments, the database of neoantigen-associated clonotypes may be used to diagnose patients with EGFR mutation based on their immune profile, in addition to or without requiring a biopsy and an additional sequencing step.

In some embodiments, the immune profile developed from the patient suffering from non-small cell lung cancer may be used to select the appropriate therapy to treat the tumor. In further embodiments, the therapy chosen to treat the colorectal cancer based on the immune profile is selected from the following: a cytotoxic chemotherapy, a targeted therapy, for example a Janus kinase inhibitor, or an immunotherapy. In some embodiments, the immunotherapy chosen is selected from the group consisting of: checkpoint blockade therapy, CAR T cell therapy, CAR M therapy, a cancer vaccine, or other immune oncological modality.

In some embodiments, the results of the TCR/BCR profiling of the NSCLC patient may be used to prepare a report that details the most abundant T cell and B cell clones. In some embodiments, the top ten most abundant clones may be displayed. The most abundant clones may be assumed to represent expanded populations of B cells or T cells. In one embodiment, the TCR/BCR sequencing methods disclosed herein are utilized on multiple specimens collected from the patient at different times in order to track disease over time.

The invention claimed is:

1. A method of determining the TCR/BCR profile of a patient who has COVID-19 or another disease, the method comprising:
   a) isolating RNA from a sample from the patient;
   b) enriching the isolated RNA for TCR/BCR genes using a set of TCR/BCR hybrid-capture probes and enriching for a targeted whole transcriptome panel using a set of hybrid-capture probes;
   c) determining the sequence of the RNA of (b) to generate sequencing data; and
   d) analyzing the sequencing data to determine the TCR/BCR profile of the patient,
   wherein the set of TCR/BCR hybrid-capture probes comprises a first pool comprising TCR constant region probes, a second pool comprising TCR non-constant region probes, a third pool comprising BCR constant region probes, a fourth pool comprising BCR non-constant region probes, and wherein a fifth pool comprises the transcriptome hybrid-capture probes.

2. The method of claim 1, wherein the ratio of the first pool, second pool, third pool, and fourth pool within the set is 1:2.5:100:100.

3. The method of claim 1, wherein the ratio of the first pool, second pool, third pool, fourth pool, and fifth pool within the set is 1:2.5:100:100:10.

4. The method of claim 3, wherein 2% or less of the reads in the sequencing data map to TCR/BCR genes.

5. The method of claim 1, wherein the sample is a blood sample.

6. The method of claim 1, further comprising comparing the patient's TCR/BCR profile to a SARS-CoV-2 TCR/BCR positive control profile; determining whether the patient has been exposed to SARS CoV-2; and treating the patient if the determining indicates exposure to SARS-CoV-2.

7. A method of determining SARS CoV-2 exposure in a patient, comprising:
   a) isolating RNA from a sample from the patient;
   b) enriching the isolated RNA for TCR/BCR genes using a set of TCR/BCR hybrid-capture probes and enriching for a targeted whole transcriptome panel using a set of transcriptome hybrid-capture probes;
   c) determining the sequence of the RNA of (b) to generate sequencing data; and
   d) analyzing the sequencing data to determine the TCR/BCR profile of the patient; and
   e) comparing the TCR/BCR profile of the patient to a positive control to determine SARS-CoV-2 exposure;
   wherein the set of TCR/BCR hybrid-capture probes comprises a first pool comprising TCR constant region probes, a second pool comprising TCR non-constant region probes, a third pool comprising BCR constant region probes, and a fourth pool comprising BCR non-constant region probes, and wherein a fifth pool comprises the transcriptome hybrid-capture probes.

8. The method of claim 7, wherein the ratio of the first pool, second pool, third pool, and fourth pool within the set is 1:2.5:100:100.

9. The method of claim 7, wherein the ratio of the first pool, second pool, third pool, fourth pool, and fifth pool within the set is 1:2.5:100:100:10.

10. The method of claim 9, wherein 2% or less of the reads in the sequencing data map to TCR/BCR genes.

11. The method of claim 7, wherein the sample is a blood sample.

12. The method of claim 7, wherein the patient has been exposed to or is suspected to have been exposed to SARS-CoV-2.

13. The method of claim 12, wherein the patient is experiencing flu-like symptoms or symptoms associated with a respiratory disease.

14. The method of claim 13, further comprising treating the patient for SARS-CoV-2 exposure, if the patient is determined to have been exposed to SARS-CoV-2.

15. A method of identifying TCR/BCR non-constant region sequences that are enriched in a cohort of patients with COVID-19 or other disease, the method comprising:
   a) isolating RNA from a sample from each patient in the cohort;
   b) enriching the isolated RNA for TCR/BCR genes using a set of TCR/BCR hybrid-capture probes and enriching for a targeted whole transcriptome panel using a set of transcriptome hybrid-capture probes;
   c) determining the sequence of the RNA of (b) to generate sequencing data;
   d) analyzing the sequencing data to determine the TCR/BCR profile of the patients in the cohort; and
   e) identifying TCR/BCR non-constant region sequences that are enriched in the cohort as compared to a control group without the disease or condition,
   wherein the set of hybrid-capture probes comprises a first pool of TCR constant region probes, a second pool of TCR non-constant region probes, a third pool of BCR constant region probes, and a fourth pool of BCR non-constant region probes, and wherein a fifth pool comprises the transcriptome hybrid-capture probes.

16. The method of claim 15, wherein the ratio of the first pool, second pool, third pool, and fourth pool within the set is 1:2.5:100:100.

17. The method of claim 15, wherein the ratio of the first pool, second pool, third pool, fourth pool, and fifth pool within the set is 1:2.5:100:100:10.

18. The method of claim 17, wherein 2% or less of the reads in the sequencing data map to TCR/BCR genes.

19. The method of claim 15, wherein the sample is a blood sample.

20. A method of determining the TCR/BCR profile of a patient, the method comprising:
   a) isolating RNA from a sample from the patient;
   b) enriching the isolated RNA for TCR/BCR genes using a set of TCR/BCR hybrid-capture probes and enriching for a targeted whole transcriptome panel using a set of transcriptome hybrid-capture probes;
   c) sequencing the enriched RNA of (b) to generate sequencing data; and
   d) analyzing the sequencing data to determine the TCR/BCR profile of the patient, wherein the set of TCR/BCR hybrid-capture probes comprises a first pool comprising BCR constant region probes, a second pool comprising BCR non-constant region probes, a third pool comprising TCR constant region probes, and a fourth pool comprising TCR non-constant region probes, wherein the ratio of the transcriptome hybrid-capture probes, first pool, second pool, third pool, and fourth pool is 10:1:2.5:100:100, wherein 2% or less of the reads in the sequencing data map to TCR/BCR genes, wherein the sample is a blood sample.

* * * * *

SEQUENCE LISTING

```
<160> NUMBER OF SEQ ID NOS: 192

<210> SEQ ID NO 1
<211> LENGTH: 15
<212> TYPE: PRT
<213> ORGANISM: Severe acute respiratory syndrome coronavirus 2

<400> SEQUENCE: 1

Asp Asp Gln Ile Gly Tyr Tyr Arg Arg Ala Thr Arg Arg Ile Arg
1               5                   10                  15

<210> SEQ ID NO 2
<211> LENGTH: 15
<212> TYPE: PRT
<213> ORGANISM: Severe acute respiratory syndrome coronavirus 2

<400> SEQUENCE: 2

Lys Ala Tyr Asn Val Thr Gln Ala Phe Gly Arg Arg Gly Pro Glu
1               5                   10                  15

<210> SEQ ID NO 3
<211> LENGTH: 15
<212> TYPE: PRT
<213> ORGANISM: Severe acute respiratory syndrome coronavirus 2

<400> SEQUENCE: 3
```

```
Leu Ile Arg Gln Gly Thr Asp Tyr Lys His Trp Pro Gln Ile Ala
1               5                   10                  15

<210> SEQ ID NO 4
<211> LENGTH: 15
<212> TYPE: PRT
<213> ORGANISM: Severe acute respiratory syndrome coronavirus 2

<400> SEQUENCE: 4

Trp Pro Gln Ile Ala Gln Phe Ala Pro Ser Ala Ser Ala Phe Phe
1               5                   10                  15

<210> SEQ ID NO 5
<211> LENGTH: 15
<212> TYPE: PRT
<213> ORGANISM: Severe acute respiratory syndrome coronavirus 2

<400> SEQUENCE: 5

Ser Trp Phe Thr Ala Leu Thr Gln His Gly Lys Glu Asp Leu Lys
1               5                   10                  15

<210> SEQ ID NO 6
<211> LENGTH: 20
<212> TYPE: PRT
<213> ORGANISM: Severe acute respiratory syndrome coronavirus 2

<400> SEQUENCE: 6

Met Lys Asp Leu Ser Pro Arg Trp Tyr Phe Tyr Tyr Leu Gly Thr Gly
1               5                   10                  15

Pro Glu Ala Gly
            20

<210> SEQ ID NO 7
<211> LENGTH: 20
<212> TYPE: PRT
<213> ORGANISM: Severe acute respiratory syndrome coronavirus 2

<400> SEQUENCE: 7

Gly Met Glu Val Thr Pro Ser Gly Thr Trp Leu Thr Tyr Thr Gly Ala
1               5                   10                  15

Ile Lys Leu Asp
            20

<210> SEQ ID NO 8
<211> LENGTH: 15
<212> TYPE: PRT
<213> ORGANISM: Severe acute respiratory syndrome coronavirus 2

<400> SEQUENCE: 8

Arg Val Glu Ser Ser Ser Lys Leu Trp Ala Gln Cys Val Gln Leu
1               5                   10                  15

<210> SEQ ID NO 9
<211> LENGTH: 15
<212> TYPE: PRT
<213> ORGANISM: Severe acute respiratory syndrome-related coronavirus

<400> SEQUENCE: 9

Asp Asp Gln Ile Gly Tyr Tyr Arg Arg Ala Thr Arg Arg Val Arg
1               5                   10                  15

<210> SEQ ID NO 10
<211> LENGTH: 15
<212> TYPE: PRT
```

```
<213> ORGANISM: Severe acute respiratory syndrome-related coronavirus

<400> SEQUENCE: 10

Lys Gln Tyr Asn Val Thr Gln Ala Phe Gly Arg Arg Gly Pro Glu
1               5                   10                  15

<210> SEQ ID NO 11
<211> LENGTH: 15
<212> TYPE: PRT
<213> ORGANISM: Severe acute respiratory syndrome-related coronavirus

<400> SEQUENCE: 11

Ser Trp Phe Thr Ala Leu Thr Gln His Gly Lys Glu Glu Leu Arg
1               5                   10                  15

<210> SEQ ID NO 12
<211> LENGTH: 20
<212> TYPE: PRT
<213> ORGANISM: Severe acute respiratory syndrome-related coronavirus

<400> SEQUENCE: 12

Met Lys Glu Leu Ser Pro Arg Trp Tyr Phe Tyr Tyr Leu Gly Thr Gly
1               5                   10                  15

Pro Glu Ala Ser
            20

<210> SEQ ID NO 13
<211> LENGTH: 20
<212> TYPE: PRT
<213> ORGANISM: Severe acute respiratory syndrome-related coronavirus

<400> SEQUENCE: 13

Gly Met Glu Val Thr Pro Ser Gly Thr Trp Leu Thr Tyr His Gly Ala
1               5                   10                  15

Ile Lys Leu Asp
            20

<210> SEQ ID NO 14
<211> LENGTH: 15
<212> TYPE: PRT
<213> ORGANISM: Severe acute respiratory syndrome coronavirus 2

<400> SEQUENCE: 14

Asn Arg Tyr Phe Arg Leu Thr Leu Gly Val Tyr Asp Tyr Leu Val
1               5                   10                  15

<210> SEQ ID NO 15
<211> LENGTH: 15
<212> TYPE: PRT
<213> ORGANISM: Severe acute respiratory syndrome coronavirus 2

<400> SEQUENCE: 15

Lys His Phe Tyr Trp Phe Phe Ser Asn Tyr Leu Lys Arg Arg Val
1               5                   10                  15

<210> SEQ ID NO 16
<211> LENGTH: 15
<212> TYPE: PRT
<213> ORGANISM: Severe acute respiratory syndrome coronavirus 2

<400> SEQUENCE: 16

Pro Leu Asn Ser Ile Ile Lys Thr Ile Gln Pro Arg Val Glu Lys
1               5                   10                  15
```

```
<210> SEQ ID NO 17
<211> LENGTH: 15
<212> TYPE: PRT
<213> ORGANISM: Severe acute respiratory syndrome coronavirus 2

<400> SEQUENCE: 17

Leu Met Ile Glu Arg Phe Val Ser Leu Ala Ile Asp Ala Tyr Pro
1               5                   10                  15

<210> SEQ ID NO 18
<211> LENGTH: 15
<212> TYPE: PRT
<213> ORGANISM: Severe acute respiratory syndrome coronavirus 2

<400> SEQUENCE: 18

Glu Phe Tyr Ala Tyr Leu Arg Lys His Phe Ser Met Met Ile Leu
1               5                   10                  15

<210> SEQ ID NO 19
<211> LENGTH: 15
<212> TYPE: PRT
<213> ORGANISM: Severe acute respiratory syndrome coronavirus 2

<400> SEQUENCE: 19

Asn His Asn Phe Leu Val Gln Ala Gly Asn Val Gln Leu Arg Val
1               5                   10                  15

<210> SEQ ID NO 20
<211> LENGTH: 15
<212> TYPE: PRT
<213> ORGANISM: Severe acute respiratory syndrome coronavirus 2

<400> SEQUENCE: 20

Arg Glu Glu Ala Ile Arg His Val Arg Ala Trp Ile Gly Phe Asp
1               5                   10                  15

<210> SEQ ID NO 21
<211> LENGTH: 15
<212> TYPE: PRT
<213> ORGANISM: Severe acute respiratory syndrome coronavirus 2

<400> SEQUENCE: 21

Thr Phe Lys Val Ser Ile Trp Asn Leu Asp Tyr Ile Ile Asn Leu
1               5                   10                  15

<210> SEQ ID NO 22
<211> LENGTH: 15
<212> TYPE: PRT
<213> ORGANISM: Severe acute respiratory syndrome coronavirus 2

<400> SEQUENCE: 22

Asn Val Asn Arg Phe Asn Val Ala Ile Thr Arg Ala Lys Val Gly
1               5                   10                  15

<210> SEQ ID NO 23
<211> LENGTH: 15
<212> TYPE: PRT
<213> ORGANISM: Severe acute respiratory syndrome coronavirus 2

<400> SEQUENCE: 23

Leu Arg Lys His Phe Ser Met Met Ile Leu Ser Asp Asp Ala Val
1               5                   10                  15

<210> SEQ ID NO 24
```

```
<211> LENGTH: 15
<212> TYPE: PRT
<213> ORGANISM: Severe acute respiratory syndrome-related coronavirus

<400> SEQUENCE: 24

Asn Arg Phe Cys Lys Cys Thr Leu Gly Val Tyr Asp Phe Cys Val
1               5                   10                  15

<210> SEQ ID NO 25
<211> LENGTH: 15
<212> TYPE: PRT
<213> ORGANISM: Severe acute respiratory syndrome-related coronavirus

<400> SEQUENCE: 25

Lys Ser Phe Ser Thr Phe Glu Ser Ala Tyr Met Pro Ile Ala Asp
1               5                   10                  15

<210> SEQ ID NO 26
<211> LENGTH: 15
<212> TYPE: PRT
<213> ORGANISM: Severe acute respiratory syndrome-related coronavirus

<400> SEQUENCE: 26

Pro Cys Pro Ser Ile Leu Lys Val Ile Asp Gly Gly Lys Ile Trp
1               5                   10                  15

<210> SEQ ID NO 27
<211> LENGTH: 15
<212> TYPE: PRT
<213> ORGANISM: Severe acute respiratory syndrome-related coronavirus

<400> SEQUENCE: 27

Ile Leu Leu Glu Arg Tyr Val Ser Leu Ala Ile Asp Ala Tyr Pro
1               5                   10                  15

<210> SEQ ID NO 28
<211> LENGTH: 15
<212> TYPE: PRT
<213> ORGANISM: Severe acute respiratory syndrome-related coronavirus

<400> SEQUENCE: 28

Asp Phe Tyr Gly Tyr Leu Gln Lys His Phe Ser Met Met Ile Leu
1               5                   10                  15

<210> SEQ ID NO 29
<211> LENGTH: 15
<212> TYPE: PRT
<213> ORGANISM: Severe acute respiratory syndrome-related coronavirus

<400> SEQUENCE: 29

Leu His Asn Phe Ser Ile Ile Ser Gly Thr Ala Phe Leu Gly Val
1               5                   10                  15

<210> SEQ ID NO 30
<211> LENGTH: 15
<212> TYPE: PRT
<213> ORGANISM: Severe acute respiratory syndrome-related coronavirus

<400> SEQUENCE: 30

Arg Asp Phe Ala Met Arg His Val Arg Gly Trp Leu Gly Met Asp
1               5                   10                  15

<210> SEQ ID NO 31
<211> LENGTH: 15
<212> TYPE: PRT
```

```
<213> ORGANISM: Severe acute respiratory syndrome-related coronavirus

<400> SEQUENCE: 31

Asn Asp Lys Ile Thr Glu Phe Gln Leu Asp Tyr Ser Ile Asp Val
1               5                   10                  15

<210> SEQ ID NO 32
<211> LENGTH: 15
<212> TYPE: PRT
<213> ORGANISM: Severe acute respiratory syndrome-related coronavirus

<400> SEQUENCE: 32

Asn Ala Asn Arg Phe Asn Val Ala Ile Thr Arg Ala Lys Lys Gly
1               5                   10                  15

<210> SEQ ID NO 33
<211> LENGTH: 15
<212> TYPE: PRT
<213> ORGANISM: Severe acute respiratory syndrome-related coronavirus

<400> SEQUENCE: 33

Leu Gln Lys His Phe Ser Met Met Ile Leu Ser Asp Asp Ser Val
1               5                   10                  15

<210> SEQ ID NO 34
<211> LENGTH: 15
<212> TYPE: PRT
<213> ORGANISM: Severe acute respiratory syndrome-related coronavirus

<400> SEQUENCE: 34

Asn Ser Val Phe Arg Met Pro Met Gly Val Tyr Asn Tyr Lys Ile
1               5                   10                  15

<210> SEQ ID NO 35
<211> LENGTH: 15
<212> TYPE: PRT
<213> ORGANISM: Severe acute respiratory syndrome-related coronavirus

<400> SEQUENCE: 35

Asn His Val Leu Trp Leu Phe Ser Tyr Cys Arg Lys Ile Gly Val
1               5                   10                  15

<210> SEQ ID NO 36
<211> LENGTH: 15
<212> TYPE: PRT
<213> ORGANISM: Severe acute respiratory syndrome-related coronavirus

<400> SEQUENCE: 36

Pro Ser Asn Ser Ile Val Cys Arg Phe Asp Thr Arg Val Leu Asn
1               5                   10                  15

<210> SEQ ID NO 37
<211> LENGTH: 15
<212> TYPE: PRT
<213> ORGANISM: Severe acute respiratory syndrome-related coronavirus

<400> SEQUENCE: 37

Leu Leu Ile Glu Arg Phe Val Ser Leu Ala Ile Asp Ala Tyr Pro
1               5                   10                  15

<210> SEQ ID NO 38
<211> LENGTH: 15
<212> TYPE: PRT
<213> ORGANISM: Severe acute respiratory syndrome-related coronavirus
```

```
<400> SEQUENCE: 38

Glu Tyr Tyr Glu Phe Leu Cys Lys His Phe Ser Met Met Ile Leu
1               5                   10                  15

<210> SEQ ID NO 39
<211> LENGTH: 15
<212> TYPE: PRT
<213> ORGANISM: Severe acute respiratory syndrome-related coronavirus

<400> SEQUENCE: 39

Phe Tyr Gly Pro Tyr Arg Asp Ala Gln Val Val Gln Leu Pro Val
1               5                   10                  15

<210> SEQ ID NO 40
<211> LENGTH: 15
<212> TYPE: PRT
<213> ORGANISM: Severe acute respiratory syndrome-related coronavirus

<400> SEQUENCE: 40

Lys Asp Glu Ala Ile Lys Arg Val Arg Gly Trp Val Gly Phe Asp
1               5                   10                  15

<210> SEQ ID NO 41
<211> LENGTH: 15
<212> TYPE: PRT
<213> ORGANISM: Severe acute respiratory syndrome-related coronavirus

<400> SEQUENCE: 41

Leu Glu Arg Val Ser Leu Trp Asn Tyr Gly Lys Pro Ile Asn Leu
1               5                   10                  15

<210> SEQ ID NO 42
<211> LENGTH: 15
<212> TYPE: PRT
<213> ORGANISM: Severe acute respiratory syndrome-related coronavirus

<400> SEQUENCE: 42

Asn Val Asn Arg Phe Asn Val Ala Ile Thr Arg Ala Lys Lys Gly
1               5                   10                  15

<210> SEQ ID NO 43
<211> LENGTH: 15
<212> TYPE: PRT
<213> ORGANISM: Severe acute respiratory syndrome-related coronavirus

<400> SEQUENCE: 43

Leu Cys Lys His Phe Ser Met Met Ile Leu Ser Asp Asp Gly Val
1               5                   10                  15

<210> SEQ ID NO 44
<211> LENGTH: 15
<212> TYPE: PRT
<213> ORGANISM: Severe acute respiratory syndrome-related coronavirus

<400> SEQUENCE: 44

Asn Arg Phe Phe Lys Cys Thr Met Gly Val Tyr Asp Phe Lys Val
1               5                   10                  15

<210> SEQ ID NO 45
<211> LENGTH: 15
<212> TYPE: PRT
<213> ORGANISM: Severe acute respiratory syndrome-related coronavirus

<400> SEQUENCE: 45
```

Gly His Phe Asn Glu Glu Phe Tyr Asn Phe Leu Arg Leu Arg Gly
1               5                   10                  15

<210> SEQ ID NO 46
<211> LENGTH: 15
<212> TYPE: PRT
<213> ORGANISM: Severe acute respiratory syndrome-related coronavirus

<400> SEQUENCE: 46

Leu Leu Ser Ser Leu Thr Leu Thr Val Lys Phe Val Val Glu Ser
1               5                   10                  15

<210> SEQ ID NO 47
<211> LENGTH: 15
<212> TYPE: PRT
<213> ORGANISM: Severe acute respiratory syndrome-related coronavirus

<400> SEQUENCE: 47

Val Leu Leu Glu Arg Tyr Val Ser Leu Ala Ile Asp Ala Tyr Pro
1               5                   10                  15

<210> SEQ ID NO 48
<211> LENGTH: 15
<212> TYPE: PRT
<213> ORGANISM: Severe acute respiratory syndrome-related coronavirus

<400> SEQUENCE: 48

Asp Tyr Tyr Gly Tyr Leu Arg Lys His Phe Ser Met Met Ile Leu
1               5                   10                  15

<210> SEQ ID NO 49
<211> LENGTH: 15
<212> TYPE: PRT
<213> ORGANISM: Severe acute respiratory syndrome-related coronavirus

<400> SEQUENCE: 49

Leu His Asn Phe Ser Val Ser His Asn Gly Val Phe Leu Gly Val
1               5                   10                  15

<210> SEQ ID NO 50
<211> LENGTH: 15
<212> TYPE: PRT
<213> ORGANISM: Severe acute respiratory syndrome-related coronavirus

<400> SEQUENCE: 50

Arg Asp Phe Ala Ile Arg Asn Val Arg Gly Trp Leu Gly Met Asp
1               5                   10                  15

<210> SEQ ID NO 51
<211> LENGTH: 15
<212> TYPE: PRT
<213> ORGANISM: Severe acute respiratory syndrome-related coronavirus

<400> SEQUENCE: 51

Leu Phe Thr Asn Ser Ile Leu Met Leu Asp Lys Gln Gly Gln Leu
1               5                   10                  15

<210> SEQ ID NO 52
<211> LENGTH: 15
<212> TYPE: PRT
<213> ORGANISM: Severe acute respiratory syndrome-related coronavirus

<400> SEQUENCE: 52

Asn Val Asn Arg Phe Asn Leu Ala Ile Thr Arg Ala Lys Lys Gly
1               5                   10                  15

```
<210> SEQ ID NO 53
<211> LENGTH: 15
<212> TYPE: PRT
<213> ORGANISM: Severe acute respiratory syndrome-related coronavirus

<400> SEQUENCE: 53

Leu Arg Lys His Phe Ser Met Met Ile Leu Ser Asp Asp Gly Val
1               5                   10                  15

<210> SEQ ID NO 54
<211> LENGTH: 15
<212> TYPE: PRT
<213> ORGANISM: Severe acute respiratory syndrome-related coronavirus

<400> SEQUENCE: 54

Asn Ser Leu Phe Arg Met Pro Leu Gly Val Tyr Asn Tyr Lys Ile
1               5                   10                  15

<210> SEQ ID NO 55
<211> LENGTH: 15
<212> TYPE: PRT
<213> ORGANISM: Severe acute respiratory syndrome-related coronavirus

<400> SEQUENCE: 55

Asn His Ala Phe Trp Val Phe Ser Tyr Cys Arg Lys Leu Gly Thr
1               5                   10                  15

<210> SEQ ID NO 56
<211> LENGTH: 15
<212> TYPE: PRT
<213> ORGANISM: Severe acute respiratory syndrome-related coronavirus

<400> SEQUENCE: 56

Pro Leu Leu Glu Asn Ile Asp Tyr Phe Asn Met Arg Arg Ala Lys
1               5                   10                  15

<210> SEQ ID NO 57
<211> LENGTH: 15
<212> TYPE: PRT
<213> ORGANISM: Severe acute respiratory syndrome-related coronavirus

<400> SEQUENCE: 57

Glu Tyr Tyr Glu Phe Leu Asn Lys His Phe Ser Met Met Ile Leu
1               5                   10                  15

<210> SEQ ID NO 58
<211> LENGTH: 15
<212> TYPE: PRT
<213> ORGANISM: Severe acute respiratory syndrome-related coronavirus

<400> SEQUENCE: 58

Asn Asp Val Ala Phe Val Ser Thr Phe Asn Val Leu Gln Asp Val
1               5                   10                  15

<210> SEQ ID NO 59
<211> LENGTH: 15
<212> TYPE: PRT
<213> ORGANISM: Severe acute respiratory syndrome-related coronavirus

<400> SEQUENCE: 59

Lys Glu Glu Ala Val Lys Arg Val Arg Ala Trp Val Gly Phe Asp
1               5                   10                  15
```

```
<210> SEQ ID NO 60
<211> LENGTH: 15
<212> TYPE: PRT
<213> ORGANISM: Severe acute respiratory syndrome-related coronavirus

<400> SEQUENCE: 60

Tyr Gln Lys Val Phe Arg Val Tyr Leu Ala Tyr Ile Lys Lys Leu
1               5                   10                  15

<210> SEQ ID NO 61
<211> LENGTH: 15
<212> TYPE: PRT
<213> ORGANISM: Severe acute respiratory syndrome-related coronavirus

<400> SEQUENCE: 61

Asn Val Asn Arg Phe Asn Val Ala Ile Thr Arg Ala Arg Lys Gly
1               5                   10                  15

<210> SEQ ID NO 62
<211> LENGTH: 15
<212> TYPE: PRT
<213> ORGANISM: Severe acute respiratory syndrome-related coronavirus

<400> SEQUENCE: 62

Leu Asn Lys His Phe Ser Met Met Ile Leu Ser Asp Asp Gly Val
1               5                   10                  15

<210> SEQ ID NO 63
<211> LENGTH: 9
<212> TYPE: PRT
<213> ORGANISM: Severe acute respiratory syndrome coronavirus 2

<400> SEQUENCE: 63

Tyr Leu Gln Pro Arg Thr Phe Leu Leu
1               5

<210> SEQ ID NO 64
<211> LENGTH: 9
<212> TYPE: PRT
<213> ORGANISM: Severe acute respiratory syndrome coronavirus 2

<400> SEQUENCE: 64

Val Leu Asn Asp Ile Leu Ser Arg Leu
1               5

<210> SEQ ID NO 65
<211> LENGTH: 9
<212> TYPE: PRT
<213> ORGANISM: Severe acute respiratory syndrome coronavirus 2

<400> SEQUENCE: 65

Thr Leu Asp Ser Lys Thr Gln Ser Leu
1               5

<210> SEQ ID NO 66
<211> LENGTH: 9
<212> TYPE: PRT
<213> ORGANISM: Severe acute respiratory syndrome coronavirus 2

<400> SEQUENCE: 66

Lys Ile Ala Asp Tyr Asn Tyr Lys Leu
1               5

<210> SEQ ID NO 67
<211> LENGTH: 9
```

```
-continued

<212> TYPE: PRT
<213> ORGANISM: Severe acute respiratory syndrome coronavirus 2

<400> SEQUENCE: 67

Arg Leu Asp Lys Val Glu Ala Glu Val
1               5

<210> SEQ ID NO 68
<211> LENGTH: 9
<212> TYPE: PRT
<213> ORGANISM: Severe acute respiratory syndrome coronavirus 2

<400> SEQUENCE: 68

Arg Leu Gln Ser Leu Gln Thr Tyr Val
1               5

<210> SEQ ID NO 69
<211> LENGTH: 9
<212> TYPE: PRT
<213> ORGANISM: Severe acute respiratory syndrome coronavirus 2

<400> SEQUENCE: 69

Leu Leu Phe Asn Lys Val Thr Leu Ala
1               5

<210> SEQ ID NO 70
<211> LENGTH: 9
<212> TYPE: PRT
<213> ORGANISM: Severe acute respiratory syndrome coronavirus 2

<400> SEQUENCE: 70

His Leu Met Ser Phe Pro Gln Ser Ala
1               5

<210> SEQ ID NO 71
<211> LENGTH: 9
<212> TYPE: PRT
<213> ORGANISM: Severe acute respiratory syndrome coronavirus 2

<400> SEQUENCE: 71

Val Val Phe Leu His Val Thr Tyr Val
1               5

<210> SEQ ID NO 72
<211> LENGTH: 9
<212> TYPE: PRT
<213> ORGANISM: Severe acute respiratory syndrome coronavirus 2

<400> SEQUENCE: 72

Phe Ile Ala Gly Leu Ile Ala Ile Val
1               5

<210> SEQ ID NO 73
<211> LENGTH: 9
<212> TYPE: PRT
<213> ORGANISM: Severe acute respiratory syndrome coronavirus 2

<400> SEQUENCE: 73

Ser Pro Arg Arg Ala Arg Ser Val Ala
1               5

<210> SEQ ID NO 74
<211> LENGTH: 9
<212> TYPE: PRT
<213> ORGANISM: Severe acute respiratory syndrome coronavirus 2
```

-continued

<400> SEQUENCE: 74

Gly Pro Lys Lys Ser Thr Asn Leu Val
1               5

<210> SEQ ID NO 75
<211> LENGTH: 9
<212> TYPE: PRT
<213> ORGANISM: Severe acute respiratory syndrome coronavirus 2

<400> SEQUENCE: 75

Thr Pro Ile Asn Leu Val Arg Asp Leu
1               5

<210> SEQ ID NO 76
<211> LENGTH: 9
<212> TYPE: PRT
<213> ORGANISM: Severe acute respiratory syndrome coronavirus 2

<400> SEQUENCE: 76

Glu Pro Val Leu Lys Gly Val Lys Leu
1               5

<210> SEQ ID NO 77
<211> LENGTH: 9
<212> TYPE: PRT
<213> ORGANISM: Severe acute respiratory syndrome coronavirus 2

<400> SEQUENCE: 77

Gln Pro Thr Glu Ser Ile Val Arg Phe
1               5

<210> SEQ ID NO 78
<211> LENGTH: 9
<212> TYPE: PRT
<213> ORGANISM: Severe acute respiratory syndrome coronavirus 2

<400> SEQUENCE: 78

Phe Pro Gln Ser Ala Pro His Gly Val
1               5

<210> SEQ ID NO 79
<211> LENGTH: 9
<212> TYPE: PRT
<213> ORGANISM: Severe acute respiratory syndrome coronavirus 2

<400> SEQUENCE: 79

Ile Pro Thr Asn Phe Thr Ile Ser Val
1               5

<210> SEQ ID NO 80
<211> LENGTH: 9
<212> TYPE: PRT
<213> ORGANISM: Severe acute respiratory syndrome coronavirus 2

<400> SEQUENCE: 80

Leu Pro Pro Ala Tyr Thr Asn Ser Phe
1               5

<210> SEQ ID NO 81
<211> LENGTH: 9
<212> TYPE: PRT
<213> ORGANISM: Severe acute respiratory syndrome coronavirus 2

<400> SEQUENCE: 81

Lys Pro Phe Glu Arg Asp Ile Ser Thr
1               5

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ala Ala Pro His Cys Ser Gly Gly Ser Cys Leu Asp Ala Phe Asp Ile
1               5                   10                  15

<210> SEQ ID NO 83
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Ala Ala Pro His Cys Ser Gly Gly Ser Cys Tyr Asp Ala Phe Asp Ile
1               5                   10                  15

<210> SEQ ID NO 84
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ala Ala Asn His Cys Ser Gly Gly Ser Cys Tyr Asp Gly Phe Asp Ile
1               5                   10                  15

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Ala Pro Tyr Cys Ser Gly Gly Ser Cys Asn Asp Ala Phe Asp Ile
1               5                   10                  15

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Ala Pro His Cys Ser Ser Thr Ser Cys Phe Asp Ala Phe Asp Ile
1               5                   10                  15

<210> SEQ ID NO 87
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 87

Ala Ala Pro Tyr Cys Ser Gly Gly Ser Cys Ser Asp Ala Phe Asp Ile
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Arg Asp Gly Ile Val Asp Thr Ala Met Val Thr Trp Phe Asp Tyr
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Arg Asp Gly Ile Gln Gly Met Ala Thr Thr Tyr Trp Phe Asp Tyr
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Arg Asp Gly Ile Val Asp Thr Ala Leu Val Thr Trp Phe Asp Tyr
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Arg Asp Ser Asp Val Asp Thr Ser Met Val Thr Trp Phe Asp Tyr
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Arg Asp Ser Asp Val Asp Thr Ala Met Val Thr Trp Phe Asp Tyr
1               5                   10                  15
```

```
<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gln Gln Tyr Gly Ser Ser Pro Trp Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Gln Tyr Gly Ser Ser Pro Trp Met
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Gln Tyr Gly Asn Ser Pro Trp Thr
1               5

<210> SEQ ID NO 96
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Gln Ser Tyr Ser Thr Pro Pro Trp Thr
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gln Gln Ser Tyr Asn Thr Pro Pro Trp Thr
1               5                   10

<210> SEQ ID NO 98
<211> LENGTH: 373
<212> TYPE: DNA
<213> ORGANISM: Homo sapiens

<400> SEQUENCE: 98
gaggtgcagc tggtggagtc tgggggaggc gtggtccagc ctggggaggtc cctgagactc    60
```

```
tcctgtgcag cctctggatt caccttcagt atctatggca tgcactgggt ccgccaggct    120
ccaggcaagg ggctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaagagggg    300
agaccatctg atattgtagt ggtggtggcc tttgactact ggggccaggg aaccctggtc    360
accgtctcct cag                                                       373
```

<210> SEQ ID NO 99
<211> LENGTH: 352
<212> TYPE: DNA
<213> ORGANISM: Homo sapiens

<400> SEQUENCE: 99

```
gaggtgcagc tggtggagtc tggaggaggc ttgatccagc ctggggggtc cctgagactc     60
tcctgtgcag cctctgggtt caccgtcagt agcaactaca tgagctgggt ccgccaggct    120
ccagggaagg ggctggagtg ggtctcagtt atttatagcg gtggtagcac atactacgca    180
gactccgtga agggccgatt caccatctcc agagacaatt ccaagaacac gctgtatctt    240
caaatgaaca gcctgagagc cggggacacg gccgtgtatt actgtgcgag ggattacggt    300
gacttctact ttgactactg gggccaggga accctggtca ccgtctcctc ag            352
```

<210> SEQ ID NO 100
<211> LENGTH: 384
<212> TYPE: DNA
<213> ORGANISM: Homo sapiens

<400> SEQUENCE: 100

```
caggtgcagc tggtgcagtc tggggctgag gtgaagaagc ctggggcctc agtgaaggtc     60
tcctgcaagg cttctggata caccttcacc ggctactata tgcactgggt gcgacaggcc    120
cctggacaag ggcttgagtg gatgggatgg atcaaccctc tcagtggtgg cacaaactat    180
gcacagaagt tccagggcag ggtcaccatg accagggaca cgtccatcag cacagcctac    240
atggagctga gcaggctgag atctgacgac acggccgtgt attactgtgc gagcccagca    300
tcacgtggat atagtggcta cgatcatggg tactactact acatggacgt ctggggcaaa    360
gggaccacgg tcaccgtctc ctca                                            384
```

<210> SEQ ID NO 101
<211> LENGTH: 370
<212> TYPE: DNA
<213> ORGANISM: Homo sapiens

<400> SEQUENCE: 101

```
caggtgcagc tggtgcagtc tgggcctgag gtgaagaagc ctgggacctc agtgaaggtc     60
tcctgcaagg cttctggatt cacctttact agctctgctg tgcagtgggt gcgacaggct    120
cgtggacaac gccttgagtg gataggatgg atcgtcgttg cagtggtaa cacaaactac    180 gcacagaagt tccaggaaag agtcaccatt accagggaca tgtccacaag cacagcctac    240
atggagctga gcagcctgag atccgaggac acggccgtgt attactgtgc ggctccccat    300
tgtagcggtg gtagctgcct tgatgctttt gatatctggg gccaagggac aatggtcacc    360
gtctcttcag                                                            370
```

<210> SEQ ID NO 102

```
<211> LENGTH: 375
<212> TYPE: DNA
<213> ORGANISM: Homo sapiens

<400> SEQUENCE: 102
caggtgcagc tggtggagtc tgggggaggc ttggtcaagc ctggagggtc cctgagactc      60
tcctgtgcag cctctggatt catcttcagt gactactgca tgagctggat ccgccgggct     120
ccagggaagg ggctggaatg gctttcatat attagtaata gtggtaccac cagatactac     180
gcagactctg tgaagggccg attcaccatc tccagggaca acggcaggaa ctcactgtat     240
ctgcaaatgg acagcctgag cgccgaagac acggccgttt attactgtgc gagaaggggg     300
gacggtagca gctcgatcta ctactacaac tacatggacg tctggggcaa agggaccacg     360
gtcaccgtct cctca                                                      375

<210> SEQ ID NO 103
<211> LENGTH: 361
<212> TYPE: DNA
<213> ORGANISM: Homo sapiens

<400> SEQUENCE: 103
gaggtgcagc tggtggagtc tgggggaggc gtggtccagc ctggagggtc cctgagactc      60
tcctgtgcag cctctggatt caccttcagt agctatggca tgcactgggt ccgccaggct     120
ccaggcaagg ggctggagtg ggtgacagtt atttcatatg atggaaggaa taatactact     180
gcagactccg tgaagggccg attcaccatc tccagagaca actccaagaa cacgctgtat     240
ctgcaaatga acagcctgag agctgaggac acggctgtgt attactgtgc gagagaattc     300
ggtgaccccg agtggtactt tgactactgg ggccagggaa ccctggtcac cgtctcctca     360
g                                                                    361

<210> SEQ ID NO 104
<211> LENGTH: 367
<212> TYPE: DNA
<213> ORGANISM: Homo sapiens

<400> SEQUENCE: 104
caggtgcagc tggtgcagtc tggggctgag gtgaagaagc ctggggcctc agtgaaggtc      60
tcctgcatgg cttctggata caccttcacc ggctactata tgcactgggt gcgacaggcc     120
cctggacaag gcttgagtg gatgggatgg atcaaccct acagtggtgg cacaaactat     180
gcacagaagt tcagggcag ggtcaccatg accaggaca cgtccatcag cacagcctac     240
atggagctga gcaggctgag atctgacgac acggccgtgt attactgtgc gagagactcc     300
ccatttagtg ctttaggggc ctccaatgac tactggggcc agggaaccct ggtcaccgtc     360
tcctcag                                                              367

<210> SEQ ID NO 105
<211> LENGTH: 370
<212> TYPE: DNA
<213> ORGANISM: Homo sapiens

<400> SEQUENCE: 105
gaggtgcagc tggtggagtc tgggggaggc gtggtccagc ctggagggtc cctgagactc      60
tcctgtgcag cctctggatt caccttcagt agctatgcta tgcactgggt ccgccaggct     120
ccagccaagg ggctggagtg ggtggcagtt atattatatg atggaagcgg taaatactac     180
gcagactccg tgaagggccg attcaccatc tccagagaca attccaagaa cacgttgtat     240
```

```
ctgcaaatga acagcctgag agctgaggac acggctgtgt attactgtgc gagagacggg    300
atcgtggata cagctctggt tacgtggttt gactactggg gccagggaac cctggtcacc    360
gtctcctcag                                                           370
```

<210> SEQ ID NO 106
<211> LENGTH: 414
<212> TYPE: DNA
<213> ORGANISM: Homo sapiens

<400> SEQUENCE: 106

```
caggtgcagc tggtgcagtc tggggctgag gtgaagaagc ctgggtcctc ggtgaaggtc    60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagggaat    300
cgactacttt attgtagtag taccagctgc tatctagatg cggttaggca ggggtactac    360
tactactact acatggacgt ctggggcaaa gggaccacgg tcaccgtctc ctca          414
```

<210> SEQ ID NO 107
<211> LENGTH: 382
<212> TYPE: DNA
<213> ORGANISM: Homo sapiens

<400> SEQUENCE: 107

```
gaggtgcagc tggtggagtc tgggggaggc gtggtccagc ctgggaggtc cctgagactc    60
tcctgtgcag cctctggatt cacccttcagt agatatggca tgcactgggt ccgccaggct    120
ccaggcaagg ggctggagtg ggtggcagtt atatcatatg atggaagtaa taatactat     180 gcagactccg tgaagggccg attcaccatc tccagagaca attccaagaa cacgctgtat    240
ctgcaaatga acagcctgag agctgaggac acggctgtgt attactgtgc gaaagtgacc    300
gccccttatt gtagtggtgg tagctgctac ggaggtaact ttgactactg ggccaggga    360 accctggtca ccgtctcctc ag                                            382
```

<210> SEQ ID NO 108
<211> LENGTH: 379
<212> TYPE: DNA
<213> ORGANISM: Homo sapiens

<400> SEQUENCE: 108

```
gaagtgcagc tggtggagtc tgggggaggc ttggtacagc ctggcaggtc cctgagactc    60
tcctgtgcag cctctggatt caccttgat gattatgcca tgcactgggt ccggcaagct    120
ccagggaagg gcctggagtg ggtctcaggt attagttgga atagtggtac cataggctat    180
gcggactctg tgaagggccg attcaccatc tccagagaca cgccaagaa ctccctgtat    240 ctgcaaatga acagtctgag agctgaggac acggcttttt attactgtgc aaaagcgggc    300
gtaaggggta tagcagcagc tggtcccgac ctcaacttcg accactgggg ccagggaacc    360
ctggtcaccg tctcctcag                                                379
```

<210> SEQ ID NO 109
<211> LENGTH: 364
<212> TYPE: DNA
<213> ORGANISM: Homo sapiens

<400> SEQUENCE: 109

```
gaggtgcagc tggtggagtc tgggggaggc gtggtccagc ctgggaggtc cctgagactc    60
tcctgtgcag cctctggatt caccttcagt aactatgcta tacactgggt ccgccaggct   120
ccaggcaagg gctggagtg gtggcagtt atatcatatg atggaagcaa taaatactac    180
gcagactccg tgaagggccg attcaccatc tccagagaca attccaagaa cacgctgtat   240
ctgcaaatga acagcctgag agctgaggac acggctgtgt attactgtgc gagagatttt   300
gacgatagtt cgttctgggc gtttgactac tggggccagg aaccctggt caccgtctcc   360
tcag                                                                364
```

<210> SEQ ID NO 110
<211> LENGTH: 361
<212> TYPE: DNA
<213> ORGANISM: Homo sapiens

<400> SEQUENCE: 110

```
caggtgcagc tggtgcagtc tggggctgag gtgaagaagc ctggggcctc agtgaaggtt    60
tcctgcaagg catctggata caccttcacc agttactata tgcactgggt gcgacaggcc   120
cctggacaag gcttgagtg gatgggaata atcaaccta gtggtggtag cacaagctac    180
gcacagaagt tccagggcag agtcaccatg accagggaca cgtccacgag cacagtctac   240
atggagctga gcagcctgag atctgaggac acggccgtgt attactgtgc tagagtgccc   300
cgtgagggga ccccagggtt cgaccccgg ggccagggaa ccctggtcac cgtctcctca   360
g                                                                  361
```

<210> SEQ ID NO 111
<211> LENGTH: 370
<212> TYPE: DNA
<213> ORGANISM: Homo sapiens

<400> SEQUENCE: 111

```
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagtt   300
tggcaatact atgatagtag tggttccttt gactactggg gccagggaac cctggtcacc   360
gtctcctcag                                                         370
```

<210> SEQ ID NO 112
<211> LENGTH: 124
<212> TYPE: PRT
<213> ORGANISM: Homo sapiens

<400> SEQUENCE: 112

```
Glu Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Ser Ile Tyr
             20                  25                  30

Gly Met His Trp Val Arg Gln Ala Pro Gly Lys Gly Leu Glu Trp Val
         35                  40                  45

Ala Val Ile Ser Tyr Asp Gly Ser Asn Lys Tyr Tyr Ala Asp Ser Val
     50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Glu Gly Arg Pro Ser Asp Ile Val Val Val Ala Phe Asp
            100                 105                 110

Tyr Trp Gly Gln Gly Thr Leu Val Thr Val Ser Ser
        115                 120

<210> SEQ ID NO 113
<211> LENGTH: 117
<212> TYPE: PRT
<213> ORGANISM: Homo sapiens

<400> SEQUENCE: 113

Glu Val Gln Leu Val Glu Ser Gly Gly Gly Leu Ile Gln Pro Gly Gly
  1               5                  10                  15

Ser Leu Arg Leu Ser Cys Ala Ala Ser Gly Phe Thr Val Ser Ser Asn
                 20                  25                  30

Tyr Met Ser Trp Val Arg Gln Ala Pro Gly Lys Gly Leu Glu Trp Val
             35                  40                  45

Ser Val Ile Tyr Ser Gly Gly Ser Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Gly Asp Thr Ala Val Tyr Tyr Cys Ala
                 85                  90                  95

Arg Asp Tyr Gly Asp Phe Tyr Phe Asp Tyr Trp Gly Gln Gly Thr Leu
            100                 105                 110

Val Thr Val Ser Ser
        115

<210> SEQ ID NO 114
<211> LENGTH: 128
<212> TYPE: PRT
<213> ORGANISM: Homo sapiens

<400> SEQUENCE: 114

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Tyr
                 20                  25                  30

Tyr Met His Trp Val Arg Gln Ala Pro Gly Gln Gly Leu Glu Trp Met
             35                  40                  45

Gly Trp Ile Asn Pro Ile Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Ser Pro Ala Ser Arg Gly Tyr Ser Gly Tyr Asp His Gly Tyr Tyr
            100                 105                 110

Tyr Tyr Met Asp Val Trp Gly Lys Gly Thr Thr Val Thr Val Ser Ser
        115                 120                 125

<210> SEQ ID NO 115
```

<211> LENGTH: 123
<212> TYPE: PRT
<213> ORGANISM: Homo sapiens

<400> SEQUENCE: 115

Gln Val Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Val Gln Trp Val Arg Gln Ala Arg Gly Gln Arg Leu Glu Trp Ile
        35                  40                  45

Gly Trp Ile Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Pro His Cys Ser Gly Gly Ser Cys Leu Asp Ala Phe Asp Ile
            100                 105                 110

Trp Gly Gln Gly Thr Met Val Thr Val Ser Ser
        115                 120

<210> SEQ ID NO 116
<211> LENGTH: 125
<212> TYPE: PRT
<213> ORGANISM: Homo sapiens

<400> SEQUENCE: 116

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Cys Met Ser Trp Ile Arg Arg Ala Pro Gly Lys Gly Leu Glu Trp Leu
        35                  40                  45

Ser Tyr Ile Ser Asn Ser Gly Thr Thr Arg Tyr Tyr Ala Asp Ser Val
    50                  55                  60

Lys Gly Arg Phe Thr Ile Ser Arg Asp Asn Gly Arg Asn Ser Leu Tyr
65                  70                  75                  80

Leu Gln Met Asp Ser Leu Ser Ala Glu Asp Thr Ala Val Tyr Tyr Cys
                85                  90                  95

Ala Arg Arg Gly Asp Gly Ser Ser Ile Tyr Tyr Tyr Asn Tyr Met
            100                 105                 110

Asp Val Trp Gly Lys Gly Thr Thr Val Thr Val Ser Ser
        115                 120                 125

<210> SEQ ID NO 117
<211> LENGTH: 120
<212> TYPE: PRT
<213> ORGANISM: Homo sapiens

<400> SEQUENCE: 117

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

```
Thr Val Ile Ser Tyr Asp Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Gly Asp Pro Glu Trp Tyr Phe Asp Tyr Trp Gly Gln
                100                 105                 110

Gly Thr Leu Val Thr Val Ser Ser
            115                 120

<210> SEQ ID NO 118
<211> LENGTH: 122
<212> TYPE: PRT
<213> ORGANISM: Homo sapiens

<400> SEQUENCE: 118

Gln Val Gln Leu Val Gln Ser Gly Ala Glu Val Lys Lys Pro Gly Ala
1               5                   10                  15

Ser Val Lys Val Ser Cys Met Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Ser Pro Phe Ser Ala Leu Gly Ala Ser Asn Asp Tyr Trp
                100                 105                 110

Gly Gln Gly Thr Leu Val Thr Val Ser Ser
            115                 120

<210> SEQ ID NO 119
<211> LENGTH: 123
<212> TYPE: PRT
<213> ORGANISM: Homo sapiens

<400> SEQUENCE: 119

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Ala Lys Gly Leu Glu Trp Val
            35                  40                  45

Ala Val Ile Leu Tyr Asp Gly Ser Gly Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Val Asp Thr Ala Leu Val Thr Trp Phe Asp Tyr
                100                 105                 110

Trp Gly Gln Gly Thr Leu Val Thr Val Ser Ser
            115                 120
```

<210> SEQ ID NO 120
<211> LENGTH: 138
<212> TYPE: PRT
<213> ORGANISM: Homo sapiens

<400> SEQUENCE: 120

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Asn Arg Leu Leu Tyr Cys Ser Ser Thr Ser Cys Tyr Leu
            100                 105                 110

Asp Ala Val Arg Gln Gly Tyr Tyr Tyr Tyr Tyr Met Asp Val Trp
        115                 120                 125

Gly Lys Gly Thr Thr Val Thr Val Ser Ser
    130                 135

<210> SEQ ID NO 121
<211> LENGTH: 127
<212> TYPE: PRT
<213> ORGANISM: Homo sapiens

<400> SEQUENCE: 121

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Thr Ala Pro Tyr Cys Ser Gly Gly Ser Cys Tyr Gly Gly
            100                 105                 110

Asn Phe Asp Tyr Trp Gly Gln Gly Thr Leu Val Thr Val Ser Ser
        115                 120                 125

<210> SEQ ID NO 122
<211> LENGTH: 126
<212> TYPE: PRT
<213> ORGANISM: Homo sapiens

<400> SEQUENCE: 122

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr

```
            20                  25                  30
Ala Met His Trp Val Arg Gln Ala Pro Gly Lys Gly Leu Glu Trp Val
            35                  40                  45

Ser Gly Ile Ser Trp Asn Ser Gly Thr Ile Gly Tyr Ala Asp Ser Val
        50                  55                  60

Lys Gly Arg Phe Thr Ile Ser Arg Asp Asn Ala Lys Asn Ser Leu Tyr
 65                 70                  75                  80

Leu Gln Met Asn Ser Leu Arg Ala Glu Asp Thr Ala Phe Tyr Tyr Cys
                85                  90                  95

Ala Lys Ala Gly Val Arg Gly Ile Ala Ala Gly Pro Asp Leu Asn
            100                 105                 110

Phe Asp His Trp Gly Gln Gly Thr Leu Val Thr Val Ser Ser
        115                 120                 125
```

<210> SEQ ID NO 123
<211> LENGTH: 121
<212> TYPE: PRT
<213> ORGANISM: Homo sapiens

<400> SEQUENCE: 123

```
Glu Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Asn Tyr
            20                  25                  30

Ala Ile His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Asp Phe Asp Asp Ser Ser Phe Trp Ala Phe Asp Tyr Trp Gly
            100                 105                 110

Gln Gly Thr Leu Val Thr Val Ser Ser
            115                 120
```

<210> SEQ ID NO 124
<211> LENGTH: 120
<212> TYPE: PRT
<213> ORGANISM: Homo sapiens

<400> SEQUENCE: 124

```
Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
 65                 70                  75                  80

Met Glu Leu Ser Ser Leu Arg Ser Glu Asp Thr Ala Val Tyr Tyr Cys
                85                  90                  95

Ala Arg Val Pro Arg Glu Gly Thr Pro Gly Phe Asp Pro Trp Gly Gln
```

```
                100             105             110
Gly Thr Leu Val Thr Val Ser Ser
        115             120

<210> SEQ ID NO 125
<211> LENGTH: 123
<212> TYPE: PRT
<213> ORGANISM: Homo sapiens

<400> SEQUENCE: 125

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Val Trp Gln Tyr Tyr Asp Ser Ser Gly Ser Phe Asp Tyr
            100                 105                 110

Trp Gly Gln Gly Thr Leu Val Thr Val Ser Ser
        115                 120

<210> SEQ ID NO 126
<211> LENGTH: 322
<212> TYPE: DNA
<213> ORGANISM: Homo sapiens

<400> SEQUENCE: 126
gacatccagt tgacccagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctcggac gttcggccaa    300
gggaccaagg tggaaatcaa ac                                              322

<210> SEQ ID NO 127
<211> LENGTH: 325
<212> TYPE: DNA
<213> ORGANISM: Homo sapiens

<400> SEQUENCE: 127
gaaattgtgt tgacgcagtc tccaggcacc ctgtctttgt ctccagggga aagagccacc     60
ctctcctgca gggccagtca gagtgttagc agcacctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcacctag gacttttggc    300
cagggaccag ctggagat caaac                                             325

<210> SEQ ID NO 128
```

```
<211> LENGTH: 322
<212> TYPE: DNA
<213> ORGANISM: Homo sapiens

<400> SEQUENCE: 128
gccatccgga tgacccagtc tccatcctcc ctgtctgcat ctgtaggaga cagagtcacc        60
atcacttgcc aggcgagtca ggacattagc aactatttaa attggtatca gcagaaacca       120
gggaaagccc ctaagctcct gatctacgat gcatccaatt tggaaacagg ggtcccatca       180
aggttcagtg gaagtggatc tgggacagat tttactttca ccatcagcag cctgcagcct       240
gaagatattg caacatatta ctgtcaacag tatgataatc tccctatcac cttcggccaa       300
gggacacgac tggagattaa ac                                                322

<210> SEQ ID NO 129
<211> LENGTH: 325
<212> TYPE: DNA
<213> ORGANISM: Homo sapiens

<400> SEQUENCE: 129
gaaattgtgt tgacgcagtc tccaggcacc ctgtctttgt ctccagggga aagagccacc        60
ctctcctgca gggccagtca gagtgttaga agcagctact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtatggta gctcaccgtg acgttcggc       300 caagggacca aggtggaaat caaac                                              325

<210> SEQ ID NO 130
<211> LENGTH: 331
<212> TYPE: DNA
<213> ORGANISM: Homo sapiens

<400> SEQUENCE: 130
cagtctgtgc tgactcagcc accctcagcg tctgggaccc ccggacagag ggtcaccgtc        60
tcttgttctg gaagcagctc caacatcgga agcaatactg taaactggta ccagcagctc       120
ccaggaacgg cccccaaact cctcatctat agtaataatc agcggccctc aggggtccct       180
gaccgattct ctggctccaa gtctggcacc tcagcctccc tggccatcag tgggctccag       240
tctgaggatg aggctgatta tttctgtgca gcatgggatg acagcctgaa tggtccggta       300
ttcggcggag ggaccaagct gaccgtccta g                                       331

<210> SEQ ID NO 131
<211> LENGTH: 319
<212> TYPE: DNA
<213> ORGANISM: Homo sapiens

<400> SEQUENCE: 131
gacatccaga tgacccagtc tccttccacc ctgtctgcat ctgtaggaga cagagtcacc        60
atcacttgcc gggccaatca gagtattagt agctggttgg cctggtatca gcagaaacca       120
gggaaagccc ctaagctcct gatctataag gcgtctagtt tagaaagtgg ggtcccatca       180
aggttcagcg gcagtggatc tgggacagaa ttcactctca ccatcagcag cctgcagcct       240
gatgattttg caacttatta ctgccaacag tataatagtt attggacgtt cggccaaggg       300
accaaggtgg aaatcaaac                                                    319
```

<210> SEQ ID NO 132
<211> LENGTH: 331
<212> TYPE: DNA
<213> ORGANISM: Homo sapiens

<400> SEQUENCE: 132

```
cagtctgccc tgactcagcc tccctccgcg tccgggtctc ctggacagtc agtcaccatc      60
tcctgcactg gaaccagcag tgacgttggt ggttataact atgtctcctg gtaccaacag     120
cacccaggca aagcccccaa actcatgatt tatgaggtca gtaagcggcc ctcaggggtc     180
cctgatcgct tctctggctc caagtctggc aacacggcct ccctgaccgt ctctgggctc     240
caggctgagg atgaggctga gtattactgc agctcagatg caggcagcaa caatgtggta     300
ttcggcggag ggaccaagct gaccgtccta g                                    331
```

<210> SEQ ID NO 133
<211> LENGTH: 325
<212> TYPE: DNA
<213> ORGANISM: Homo sapiens

<400> SEQUENCE: 133

```
gacatccagt tgacccagtc tccatcctcc ctgtctgcat ctgtaggaga cagagtcacc      60
atcacttgcc gggcaagtca gagcattagc acctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcaacag agttacagta cccctccgtg gacgttcggc     300
caagggacca aggtggagat caaac                                            325
```

<210> SEQ ID NO 134
<211> LENGTH: 322
<212> TYPE: DNA
<213> ORGANISM: Homo sapiens

<400> SEQUENCE: 134

```
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcccctcac tttcggcgga     300
gggaccaagg tggagatcaa ac                                               322
```

<210> SEQ ID NO 135
<211> LENGTH: 322
<212> TYPE: DNA
<213> ORGANISM: Homo sapiens

<400> SEQUENCE: 135

```
gccatccgga tgacccagtc tccatcctcc ctgtctgcat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagcg gaagtggatc tgggacagat tttactttca ccatcaacag cctgcagcct     240
gaagatattg caacatatta ctgtcaacag tatgataatc tccctcctac tttcggcgga     300
gggaccaagg tggagatcaa ac                                               322
```

<210> SEQ ID NO 136
<211> LENGTH: 310
<212> TYPE: DNA
<213> ORGANISM: Homo sapiens

<400> SEQUENCE: 136

```
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtatcacct cggccaagg gacacgactg      300
gagattaaac                                                            310
```

<210> SEQ ID NO 137
<211> LENGTH: 325
<212> TYPE: DNA
<213> ORGANISM: Homo sapiens

<400> SEQUENCE: 137

```
gacatccagt tgacccagtc tccatcctcc ctgtctgcgt ctgtaggaga cagagtcacc      60
atcacttgcc gggcaagtca gagcattcgc agctatttaa attggtatca acagaaacca     120
gggaaagccc ctaagctcct gatctatgct gcatccagtt tgcaaagtgg ggtcccttca     180
aggttcagtg gcagtggatc tgggacagat ttcactctca ccatcagcag tctgcaacct     240
gatgattttg caacttacta ctgtcaacag agttacagta cccctccggc cacttttggc     300
caggggacca agctggagat caaac                                           325
```

<210> SEQ ID NO 138
<211> LENGTH: 325
<212> TYPE: DNA
<213> ORGANISM: Homo sapiens

<400> SEQUENCE: 138

```
tcctatgagc tgacacagcc accctcagtg tcagtggccc caggaaagac ggccaggatt      60
acctgtgggg aaaacaacat tggaagtaaa agtgtgcact ggtaccagca gaagccaggc     120
caggcccctg tgctggtcat ctattatgat agcgaccggc cctcagggat ccctgagcga     180
ttctctggct ccaactctgg gaacacggcc accctgacca tcaacagggt cgaagccggg     240
gatgaggccg actattactg tcaggtgtgg gatagtagta gtgatcatgt ggtattcggc     300
ggagggacca agctgaccgt cctag                                           325
```

<210> SEQ ID NO 139
<211> LENGTH: 337
<212> TYPE: DNA
<213> ORGANISM: Homo sapiens

<400> SEQUENCE: 139

```
gatattgtga tgactcagtc tccactctcc ctgcccgtca cccctggaga gccggcctcc      60
atctcctgca ggtctagtca gagcctcctg catagtaatg gatacaacta tttggattgg     120
tacctgcaga agccagggca gtctccacag ctcctgatct atttgggttc taatcgggcc     180
tccggggtcc ctgacaggtt cagtggcagt ggatcaggca cagatttac actgaaaatc     240
agcagagtgg aggctgagga tgttggggtt tattactgca tgcaagctct acaaactcca     300
ttcactttcg gccctgggac caaagtggat atcaaac                              337
```

```
<210> SEQ ID NO 140
<211> LENGTH: 107
<212> TYPE: PRT
<213> ORGANISM: Homo sapiens

<400> SEQUENCE: 140

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
                85                  90                  95

Thr Phe Gly Gln Gly Thr Lys Val Glu Ile Lys
            100                 105

<210> SEQ ID NO 141
<211> LENGTH: 108
<212> TYPE: PRT
<213> ORGANISM: Homo sapiens

<400> SEQUENCE: 141

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Leu Glu Ile Lys
            100                 105

<210> SEQ ID NO 142
<211> LENGTH: 107
<212> TYPE: PRT
<213> ORGANISM: Homo sapiens

<400> SEQUENCE: 142

Ala Ile Arg Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60
```

```
Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Asn Leu Pro Ile
                 85                  90                  95

Thr Phe Gly Gln Gly Thr Arg Leu Glu Ile Lys
            100                 105
```

<210> SEQ ID NO 143
<211> LENGTH: 108
<212> TYPE: PRT
<213> ORGANISM: Homo sapiens

<400> SEQUENCE: 143

```
Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Arg Ser Ser
                 20                  25                  30

Tyr Leu Ala Trp Tyr Gln Gln Lys Pro Gly Gln Ala Pro Arg Leu Leu
             35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

Trp Thr Phe Gly Gln Gly Thr Lys Val Glu Ile Lys
            100                 105
```

<210> SEQ ID NO 144
<211> LENGTH: 110
<212> TYPE: PRT
<213> ORGANISM: Homo sapiens

<400> SEQUENCE: 144

```
Gln Ser Val Leu Thr Gln Pro Pro Ser Ala Ser Gly Thr Pro Gly Gln
  1               5                  10                  15

Arg Val Thr Val Ser Cys Ser Gly Ser Ser Ser Asn Ile Gly Ser Asn
                 20                  25                  30

Thr Val Asn Trp Tyr Gln Gln Leu Pro Gly Thr Ala Pro Lys Leu Leu
             35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Phe Cys Ala Ala Trp Asp Asp Ser Leu
                 85                  90                  95

Asn Gly Pro Val Phe Gly Gly Gly Thr Lys Leu Thr Val Leu
            100                 105                 110
```

<210> SEQ ID NO 145
<211> LENGTH: 106
<212> TYPE: PRT
<213> ORGANISM: Homo sapiens

<400> SEQUENCE: 145

```
Asp Ile Gln Met Thr Gln Ser Pro Ser Thr Leu Ser Ala Ser Val Gly
  1               5                  10                  15

Asp Arg Val Thr Ile Thr Cys Arg Ala Asn Gln Ser Ile Ser Ser Trp
```

```
                    20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Trp Thr
                85                  90                  95

Phe Gly Gln Gly Thr Lys Val Glu Ile Lys
            100                 105

<210> SEQ ID NO 146
<211> LENGTH: 110
<212> TYPE: PRT
<213> ORGANISM: Homo sapiens

<400> SEQUENCE: 146

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Asp Ala Gly Ser
                85                  90                  95

Asn Asn Val Val Phe Gly Gly Gly Thr Lys Leu Thr Val Leu
            100                 105                 110

<210> SEQ ID NO 147
<211> LENGTH: 108
<212> TYPE: PRT
<213> ORGANISM: Homo sapiens

<400> SEQUENCE: 147

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Ser Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Trp Thr Phe Gly Gln Gly Thr Lys Val Glu Ile Lys
            100                 105

<210> SEQ ID NO 148
<211> LENGTH: 107
<212> TYPE: PRT
```

<213> ORGANISM: Homo sapiens

<400> SEQUENCE: 148

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 149
<211> LENGTH: 107
<212> TYPE: PRT
<213> ORGANISM: Homo sapiens

<400> SEQUENCE: 149

Ala Ile Arg Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Asn Ser Leu Gln Pro
65                  70                  75                  80

Glu Asp Ile Ala Thr Tyr Tyr Cys Gln Gln Tyr Asp Asn Leu Pro Pro
                85                  90                  95

Thr Phe Gly Gly Gly Thr Lys Val Glu Ile Lys
            100                 105

<210> SEQ ID NO 150
<211> LENGTH: 103
<212> TYPE: PRT
<213> ORGANISM: Homo sapiens

<400> SEQUENCE: 150

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ile Thr Phe Gly Gln
                85                  90                  95

```
Gly Thr Arg Leu Glu Ile Lys
            100
```

<210> SEQ ID NO 151
<211> LENGTH: 108
<212> TYPE: PRT
<213> ORGANISM: Homo sapiens

<400> SEQUENCE: 151

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Asp Asp Phe Ala Thr Tyr Tyr Cys Gln Gln Ser Tyr Ser Thr Pro Pro
                85                  90                  95

Ala Thr Phe Gly Gln Gly Thr Lys Leu Glu Ile Lys
            100                 105
```

<210> SEQ ID NO 152
<211> LENGTH: 108
<212> TYPE: PRT
<213> ORGANISM: Homo sapiens

<400> SEQUENCE: 152

```
Ser Tyr Glu Leu Thr Gln Pro Pro Ser Val Ser Val Ala Pro Gly Lys
1               5                   10                  15

Thr Ala Arg Ile Thr Cys Gly Glu Asn Asn Ile Gly Ser Lys Ser Val
            20                  25                  30

His Trp Tyr Gln Gln Lys Pro Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Asn Arg Val Glu Ala Gly
65                  70                  75                  80

Asp Glu Ala Asp Tyr Tyr Cys Gln Val Trp Asp Ser Ser Ser Asp His
                85                  90                  95

Val Val Phe Gly Gly Gly Thr Lys Leu Thr Val Leu
            100                 105
```

<210> SEQ ID NO 153
<211> LENGTH: 112
<212> TYPE: PRT
<213> ORGANISM: Homo sapiens

<400> SEQUENCE: 153

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45
```

```
Pro Gln Leu Leu Ile Tyr Leu Gly Ser Asn Arg Ala Ser Gly Val Pro
        50                  55                  60
Asp Arg Phe Ser Gly Ser Gly Ser Gly Thr Asp Phe Thr Leu Lys Ile
 65                  70                  75                  80
Ser Arg Val Glu Ala Glu Asp Val Gly Val Tyr Tyr Cys Met Gln Ala
                 85                  90                  95
Leu Gln Thr Pro Phe Thr Phe Gly Pro Gly Thr Lys Val Asp Ile Lys
            100                 105                 110
```

<210> SEQ ID NO 154
<211> LENGTH: 93
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 154
tgtgcgagag aagaggtcag ggatggatcg tattacgatt tttggagtgg ttaccctac    60 ccggaatact actactacta catggacgtc tgg                                93

<210> SEQ ID NO 155
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 155

```
Cys Ala Arg Glu Glu Val Arg Asp Gly Ser Tyr Tyr Asp Phe Trp Ser
 1               5                  10                  15
Gly Tyr Pro Tyr Pro Glu Tyr Tyr Tyr Tyr Met Asp Val Trp
            20                  25                  30
```

<210> SEQ ID NO 156
<211> LENGTH: 42
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 156
tgcgccagca gccaagtagc gggaccctac gagcagtact tc                      42

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 157

```
Cys Ala Ser Ser Gln Val Ala Gly Pro Tyr Glu Gln Tyr Phe
 1               5                  10
```

<210> SEQ ID NO 158
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

```
<400> SEQUENCE: 158
tgtcagcatc gtggcaaccg gcccactttc                                          30

<210> SEQ ID NO 159
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Cys Gln His Arg Gly Asn Arg Pro Thr Phe
1               5                   10

<210> SEQ ID NO 160
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tgtggttcta acgactacaa gctcagcttt                                          30

<210> SEQ ID NO 161
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Cys Gly Ser Asn Asp Tyr Lys Leu Ser Phe
1               5                   10

<210> SEQ ID NO 162
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tgccaacagt ataatagtta ttctcggagt ttt                                      33

<210> SEQ ID NO 163
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Cys Gln Gln Tyr Asn Ser Tyr Ser Arg Ser Phe
1               5                   10

<210> SEQ ID NO 164
<211> LENGTH: 51
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 164
tgcagtgcta aagactagc gggaggactt agcacagata cgcagtattt t          51

<210> SEQ ID NO 165
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Cys Ser Ala Arg Arg Leu Ala Gly Gly Leu Ser Thr Asp Thr Gln Tyr
1               5                   10                  15
Phe

<210> SEQ ID NO 166
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 166
tgtgtcttat aacaccgaca agctcatctt t                               31

<210> SEQ ID NO 167
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
tgtgtggata gcaactatca gttaatctgg                                 30

<210> SEQ ID NO 168
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
tgttgagcaa atcatagtgt ttcttctggt tctgcaaggc aactgacctt t          51

<210> SEQ ID NO 169
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Ala Asn His Ser Val Ser Ser Gly Ser Ala Arg Gln Leu Thr Phe
1               5                   10                  15

<210> SEQ ID NO 170
<211> LENGTH: 36

-continued

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 170
tgtgtgatca aagctgcagg caacaagcta actttt                                  36

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Cys Val Ile Lys Ala Ala Gly Asn Lys Leu Thr Phe
1               5                   10

<210> SEQ ID NO 172
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Cys Ala Ser Leu Pro Tyr Asp Tyr Ile Trp Arg Asn Tyr Arg His Met
1               5                   10                  15

Thr Glu Tyr Phe Asp Tyr Trp
            20

<210> SEQ ID NO 173
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Cys Ala Arg Asp Met Gly Leu Ala Thr Ala Gly Gly Ile Asp Tyr Trp
1               5                   10                  15

<210> SEQ ID NO 174
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Cys Gln Gln Tyr Asn Ile Tyr Pro Tyr Thr Phe
1               5                   10

<210> SEQ ID NO 175
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

```
Cys Gln Val Trp Asp Ser Ser Asp His Val Val Phe
1               5                   10
```

<210> SEQ ID NO 176
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

```
Cys Gly Thr Trp Asp Ser Ser Leu Ser Gly Tyr Val Phe
1               5                   10
```

<210> SEQ ID NO 177
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

```
Cys Gly Asn Asn Asn Ala Arg Leu Met Phe
1               5                   10
```

<210> SEQ ID NO 178
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

```
Cys Ala Arg Thr Gly Gly Tyr Ala Leu Ala Asp Lys Leu Ile Phe
1               5                   10                  15
```

<210> SEQ ID NO 179
<211> LENGTH: 284
<212> TYPE: DNA
<213> ORGANISM: Homo sapiens

<400> SEQUENCE: 179

```
gcccagtcgg tgacccagct tggcagccac gtctctgtct ctgaaggagc cctggttctg      60
ctgaggtgca actactcatc gtctgttcca ccatatctct tctggtatgt gcaataccCC     120
aaccaaggac tccagcttct cctgaagtac acatcagcgg ccaccctggt taaaggcatc     180
aacggttttg aggctgaatt taagaagagt gaaacctcct tccacctgac gaaaccctca     240
gcccatatga gcgacgcggc tgagtacttc tgtgctgtga gtga                       284
```

<210> SEQ ID NO 180
<211> LENGTH: 284
<212> TYPE: DNA
<213> ORGANISM: Homo sapiens

<400> SEQUENCE: 180

```
gcccagtcgg tgacccagct tggcagccac gtctctgtct ctgaaggagc cctggttctg      60
ctgaggtgca actactcatc gtctgttcca ccatatctct tctggtatgt gcaataccCC     120
aaccaaggac tccagcttct cctgaagtac acatcagcgg ccaccctggt taaaggcatc     180
aacggttttg aggctgaatt taagaagagt gaaacctcct tccacctgac aaaaccctca     240
```
gcccatatga gcgacgcggc tgagtacttc tgtgctgtga gtga                284

<210> SEQ ID NO 181
<211> LENGTH: 276
<212> TYPE: DNA
<213> ORGANISM: Homo sapiens

<400> SEQUENCE: 181
gcccagtcgg tgacccagct tggcagccac gtctctgtct ctgagggagc cctggttctg    60
ctgaggtgca actactcatc gtctgttcca ccatatctct tctggtatgt gcaatacccc   120
aaccaaggac tccagcttct cctgaagtac acaacagggg ccaccctggt taaaggcatc   180
aacggttttg aggctgaatt taagaagagt gaaacctcct tccacctgac gaaaccctca   240
gcccatatga gcgacgcggc tgagtacttc tgtgct                            276

<210> SEQ ID NO 182
<211> LENGTH: 284
<212> TYPE: DNA
<213> ORGANISM: Homo sapiens

<400> SEQUENCE: 182
gcccagtcgg tgacccagct tggcagccac gtctctgtct ctgaacgagc cctggttctg    60
ctgaggtgca actactcatc gtctgttcca ccatatctct tctggtatgt gcaatacccc   120
aaccaaggac tccagcttct cctgaagtac acatcagcgg ccaccctggt taaaggcatc   180
aacggttttg aggctgaatt taagaagagt gaaacctcct tccacctgac gaaaccctca   240
gcccatatga gcgacgcggc tgagtacttc tgtgctgtga gtga                   284

<210> SEQ ID NO 183
<211> LENGTH: 284
<212> TYPE: DNA
<213> ORGANISM: Homo sapiens

<400> SEQUENCE: 183
gcccagtcgg tgacccagct tggcagccac gtctctgtct ctgaaggagc cctggttctg    60
ctgaggtgca actactcatc gtctgttcca ccatatctct tctggtatgt gcaatacccc   120
aaccaaggac tccagcttct cctgaagtac acatcagcgg ccaccctggt taaaggaatc   180
aacggttttg aggctgaatt taagaagagt gaaacctcct tccacctgac gaaaccctca   240
gcccatatga gcgacgcggc tgagtacttc tgtgctgtga gtga                   284

<210> SEQ ID NO 184
<211> LENGTH: 218
<212> TYPE: DNA
<213> ORGANISM: Homo sapiens

<400> SEQUENCE: 184
ggtgcaactc actactgctg tccaccaata ctcttctggt atgtgcaata ccccaaccaa    60
ggactccagc ttctcctgaa gtacacatca gcggccaccc tggttaaagg catcaacggt   120
tttgaggctg aatttaagaa gagtgaaacc tccttccacc tgacgaaacc cgcagcccat   180
atgagcgacg cggctgagta cttctgtgct gtgagtga                          218

<210> SEQ ID NO 185
<211> LENGTH: 197
<212> TYPE: DNA
<213> ORGANISM: Homo sapiens -continued

<400> SEQUENCE: 185

```
gttgaaccat atctcttctg gtatgtgcaa tacccaacc aaggactcca gcttctcctg      60
aagtacacaa cagggggccac cctggttaaa ggcatcaacg gttttgaggc tgaatttaaa    120
aagagtgaaa cctccttcca cctgacgaaa ccctcagccc atatgaccga cccggctgag    180
tacttctgtg ctgtgag                                                     197
```

<210> SEQ ID NO 186
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Cys Ala Ser Ser Ile Gly Val Asn Thr Glu Ala Phe Phe
1               5                   10

<210> SEQ ID NO 187
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Cys Ala Ser Ser Leu Ser Gly Gly Pro Tyr Asn Glu Gln Phe Phe
1               5                   10                  15

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Cys Ala Ser Ser Ser Gly Ile Gln Pro Gln His Phe
1               5                   10

<210> SEQ ID NO 189
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Cys Ala Ser Ser Val Ser Tyr Glu Gln Tyr Phe
1               5                   10

<210> SEQ ID NO 190
<211> LENGTH: 15
<212> TYPE: PRT
<213> ORGANISM: Severe acute respiratory syndrome-related coronavirus

<400> SEQUENCE: 190

Leu Ile Arg Gln Gly Thr Asp Tyr Lys His Trp Pro Gln Ile Ala
1               5                   10                  15

<210> SEQ ID NO 191

-continued

```
<211> LENGTH: 15
<212> TYPE: PRT
<213> ORGANISM: Severe acute respiratory syndrome-related coronavirus

<400> SEQUENCE: 191

Trp Pro Gln Ile Ala Gln Phe Ala Pro Ser Ala Ser Ala Phe Phe
1               5                   10                  15

<210> SEQ ID NO 192
<211> LENGTH: 15
<212> TYPE: PRT
<213> ORGANISM: Severe acute respiratory syndrome-related coronavirus

<400> SEQUENCE: 192

Arg Val Glu Ser Ser Ser Lys Leu Trp Ala Gln Cys Val Gln Leu
1               5                   10                  15
```